(12) United States Patent
So et al.

(10) Patent No.: US 10,573,820 B2
(45) Date of Patent: Feb. 25, 2020

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: KiHo So, Cheonan-si (KR); Daesung Kim, Yongin-si (KR); Yun Suk Lee, Seongnam-si (KR); Dae Hwan Oh, Cheonan-si (KR); Hyoung Keun Park, Chuncheon-si (KR); Yeon Hee Choi, Cheonan-si (KR); Gyu min Lee, Cheonan-si (KR)

(73) Assignee: Duk San Neolux Co., Ltd., Cheonan-si, Chungcheongnam-do (KR)

( * ) Notice: Subject to any disclaimer, the term of this patent is extended or adjusted under 35 U.S.C. 154(b) by 273 days.

(21) Appl. No.: 15/735,737

(22) PCT Filed: May 18, 2016

(86) PCT No.: PCT/KR2016/005275
§ 371 (c)(1),
(2) Date: Dec. 12, 2017

(87) PCT Pub. No.: WO2016/200070
PCT Pub. Date: Dec. 15, 2016

(65) Prior Publication Data
US 2018/0182972 A1    Jun. 28, 2018

(30) Foreign Application Priority Data

Jun. 12, 2015   (KR) .................. 10-2015-0083505

(51) Int. Cl.
*H01L 51/50*   (2006.01)
*H01L 51/00*   (2006.01)
(Continued)

(52) U.S. Cl.
CPC ........ *H01L 51/0061* (2013.01); *C07C 211/60* (2013.01); *C07D 209/86* (2013.01);
(Continued)

(58) Field of Classification Search
None
See application file for complete search history.

(56) References Cited

U.S. PATENT DOCUMENTS

2008/0124573 A1   5/2008   Negishi
2012/0217492 A1*  8/2012   Kim ..................... C07D 209/80
                                                    257/40

FOREIGN PATENT DOCUMENTS

KR    10-2011-0129766 A    12/2011
KR    10-2013-0096334 A    8/2013
(Continued)

OTHER PUBLICATIONS

Chinese Office Action for corresponding CN Patent Application No. 201680034231.1, dated Aug. 2, 2019, seven pages.

*Primary Examiner* — Gregory D Clark
(74) *Attorney, Agent, or Firm* — Vorys, Sater, Seymour and Pease LLP; Mih Suhn Koh

(57) ABSTRACT

Provided are a compound represented by Formula 1, and an organic electric element comprising a first electrode, a second electrode, and an organic material layer formed between the first electrode and the second electrode, wherein the organic material layer comprises the compound represented by Formula 1, and the driving voltage of an organic electronic device can be lowered, and the luminous efficiency, color purity and life time of an organic electronic device can be improved by comprising the compound represented by Formula 1 in the organic material layer.

9 Claims, 1 Drawing Sheet

(51) Int. Cl.
    *C07D 333/76*     (2006.01)
    *C07D 409/12*     (2006.01)
    *C09K 11/06*     (2006.01)
    *C07D 209/86*     (2006.01)
    *C07D 307/91*     (2006.01)
    *C07D 405/12*     (2006.01)
    *C07D 409/14*     (2006.01)
    *C07D 495/04*     (2006.01)
    *C07D 209/88*     (2006.01)
    *C07C 211/60*     (2006.01)

(52) U.S. Cl.
    CPC ......... *C07D 209/88* (2013.01); *C07D 307/91* (2013.01); *C07D 333/76* (2013.01); *C07D 405/12* (2013.01); *C07D 409/12* (2013.01); *C07D 409/14* (2013.01); *C07D 495/04* (2013.01); *C09K 11/06* (2013.01); *H01L 51/006* (2013.01); *C07C 2603/18* (2017.05); *C07C 2603/26* (2017.05); *C07C 2603/40* (2017.05); *C07C 2603/94* (2017.05); *C09K 2211/1018* (2013.01); *C09K 2211/1022* (2013.01); *H01L 51/0003* (2013.01); *H01L 51/0004* (2013.01); *H01L 51/0054* (2013.01); *H01L 51/0058* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/508* (2013.01); *H01L 51/5012* (2013.01); *H01L 51/5056* (2013.01); *H01L 51/5088* (2013.01); *H01L 51/5092* (2013.01)

(56) References Cited

FOREIGN PATENT DOCUMENTS

| KR | 10-2014-0125576 A | 10/2014 |
| KR | 10-2014-0145428 A | 12/2014 |
| WO | 2011/055932 A2 | 5/2011 |

* cited by examiner

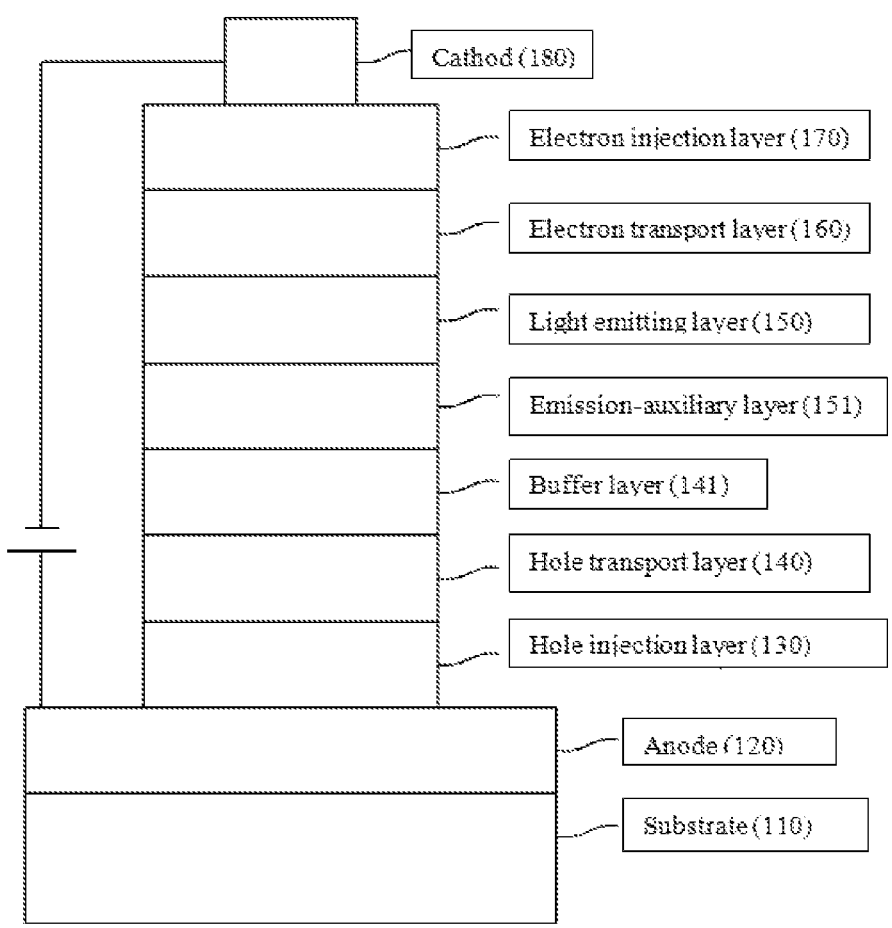

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0083505, filed on Jun. 12, 2015, which is hereby incorporated by reference for all purposes as if fully set forth herein. Further, this application claims the benefit of priority in countries other than U.S.A., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

In order to solve the problem of luminescence in the hole transport layer in recent organic electroluminescent devices, an emission-auxiliary layer must be present between the hole transport layer and the light emitting layer and it is time to develop different emission-auxiliary layers according to respective light emitting layers (R, G, B).

In general, an electron is transferred from an electron transport layer to a light emitting layer and a hole is transferred from a hole transport layer to the light emitting layer, as a result, an exciton is formed by the recombination of the electron and hole.

However, the material used for the hole transport layer has a low HOMO value and therefore has a low T1 value. As a result, the exciton generated in the light emitting layer is transferred to the hole transport layer, resulting in a charge unbalance in the light emitting layer and light is emitted at the interface of the hole transport layer.

When light is emitted at the interface of the hole transport layer, color purity and efficiency of the organic electronic device are lowered and the lifetime is shortened. Therefore, it is strongly desired to develop a light-emitting auxiliary layer material having a HOMO energy level between the HOMO energy level of the hole transport layer and the HOMO energy level of the light emitting layer, a high T1 value and a hole mobility within a proper driving voltage range (within a blue device driving voltage range of a full device).

However, this cannot be achieved simply by the structural properties of the core of an emission-auxiliary layer material. High efficiency and long lifespan of device can be achieved when the characteristics of the core and the sub-substituent and the proper combination of the emission-auxiliary layer and the hole transport layer and of the emission-auxiliary layer and the light-emitting layer are met.

On the other hand, it is required to develop a hole injection/transport layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element.

In addition, deposition is a main method of forming an OLED, and thus there is an actual need to develop a material that is durable to such a deposition method, that is, a highly heat-resistant material.

That is, it should be preceded that the materials consisting an organic material layer of the element, for example, a hole injection material, a hole transport material, a light emitting material, an electron transport material, an electron injection material, or the like, are supported by a stable and efficient material. However, such a stable and efficient organic material layer material for an organic electric element has not yet been fully developed. Accordingly, there is a continuous need to develop new materials for an organic material layer, particularly, it is strongly required to develop materials of the emission-auxiliary layer and the hole transport layer.

SUMMARY

In order to solve one or more of the above-mentioned problems in prior art, an aspect of the present invention is to provide a compound having efficient electron blocking ability and hole transport ability and allowing to improve luminous efficiency, to lower a driving voltage, to have a high heat-resistance, and to improve color purity and lifetime of the element, an organic electric element comprising the same, and an electronic device thereof.

In accordance with an aspect of the present invention, the compound represented by the following formula is provided. The following formula represents a compound in which core and two amine groups are bonded through a linking group, wherein the core is a form of a fluorene or carbazole fused with an aromatic ring, and at least one of $Ar^1$ to $Ar^4$ is the following formula 1a.

<Formula 1>

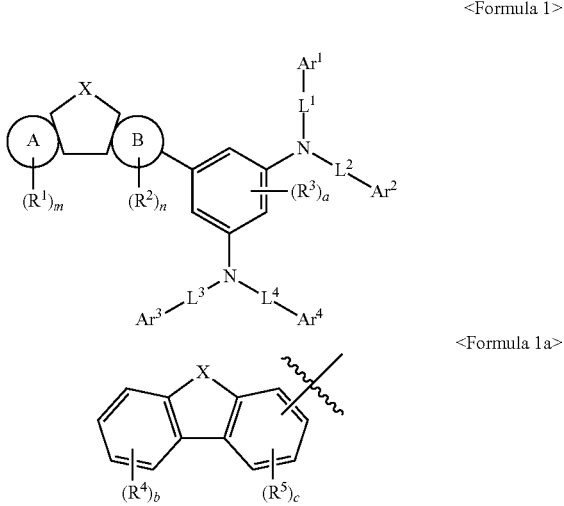

<Formula 1a>

In another aspect of the present invention, organic electric elements comprising the compound represented by the formula 1 above and electronic devices including the organic electric element are provided.

According to the embodiments of the present invention, by using a specific compound having a substituent which enhances the planity of a molecule, the limited type of an amine group bonded to the linking group, and the limited bonding position and number of amine groups as a material of the organic electric device, hole transport ability and thermal stability are improved, and the HOMO energy level and the high T1 value are easy to balance the charge in the light emitting layer. As a result, luminous efficiency, heat-resistance, and lifetime of the organic electric elements can be improved and a driving voltage of the organic electric elements can be lowered.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

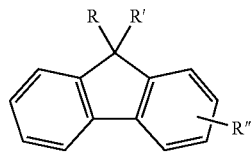

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

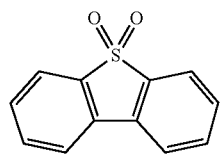 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence.

Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

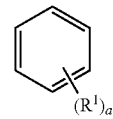

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

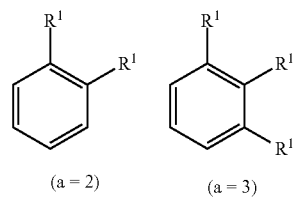

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an electron transport layer 160, an electron transport auxiliary layer, as a host or a dopant material of a light emitting layer 150, or as a material of a capping layer. For example, the inventive compound may be used as material of the light emitting layer 150, the hole transport layer 140, and/or the emission-auxiliary layer 151, preferably, as the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B).

On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

According to the present invention, energy levels and $T_1$ values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

<Formula 1>

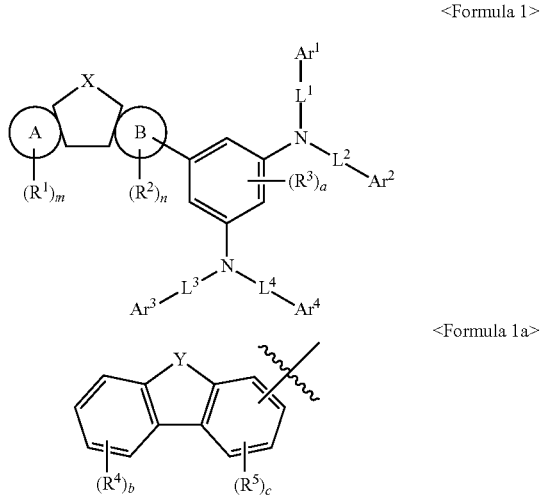

<Formula 1a>

In formula 1 above, each of symbols may be defined as follows.

In formula 1 above, X is $C(R^a)(R^b)$ or $N(R^c)$, wherein $R^a$ to $R^c$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, When $R^a$ to $R^c$ are an aryl group, $R^a$ to $R^c$ may be preferably $C_6$-$C_{30}$ aryl group, more preferably $C_6$-$C_{18}$ aryl group; when $R^a$ to $R^c$ are a heterocyclic group, $R^a$ to $R^c$ may be preferably $C_2$-$C_{30}$ heterocyclic group, more preferably $C_2$-$C_{12}$ heterocyclic group. For example, $R^a$ to $R^c$ may be each independently methyl, phenyl, biphenyl, naphthyl, terphenyl, fluorenyl, dibenzofuryl, dibenzothienyl or benzothienopyridyl and the like, and they may be each optionally further substituted with deuterium, methyl or phenyl.

In the above formula 1, A ring and B ring are each independently a $C_6$-$C_{18}$ aryl group, and the case where A ring and B ring are simultaneously $C_6$ aryl groups is excluded. Preferably, A ring and B ring may be each independently any one of the following Formulas.

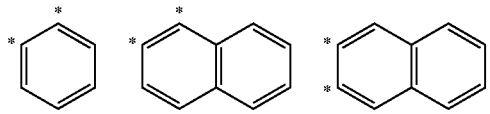

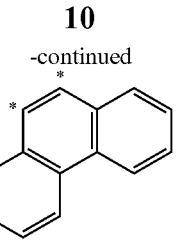

Wherein "*" indicates the position to be bonded.

On the other hand, it is preferable that at least one of A ring and B ring is $C_{10}$ aryl group, when X is $N(R^c)$.

In formula 1 above, $Ar^1$ to $Ar^4$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and it is preferable that at least one of $Ar^1$ to $Ar^4$ is Formula 1a.

When $Ar^1$ to $Ar^4$ are an aryl group, $Ar^1$ to $Ar^4$ may be preferably $C_6$-$C_{30}$ aryl group, more preferably $C_6$-$C_{18}$ aryl group; when $Ar^1$ to $Ar^4$ are a heterocyclic group, $Ar^1$ to $Ar^4$ may be preferably $C_2$-$C_{30}$ heterocyclic group, more preferably $C_2$-$C_{19}$ heterocyclic group. For example, $Ar^1$ to $Ar^4$ may be each independently methyl, ethenyl, methoxy, phenyl, biphenyl, naphthyl, terphenyl, phenanthrenyl, pyrenyl, fluoranthenyl, pyridyl, isoquinolyl, carbazolyl, benzocarbazolyl, dibenzothienyl, dibenzofuryl, benzothiocarbazolyl, indenocarbazolyl, dimethylfluorenyl, diphenylfuorenyl or spirobifluorenyl and the like, and they may be each optionally further substituted with deuterium, fluoro, methyl, ethenyl, methoxy, trimethylsilane, phenyl, naphtyl, pyridyl or fluorenyl.

In formula 1 above, $L^1$ to $L^4$ may be each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; and $C_2$-$C_{60}$ aliphatic hydrocarbon group, they (except for a single bond) may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

When $L^1$ to $L^4$ are an arylene group, they may be preferably a $C_6$-$C_{30}$ arylene group, more preferably $C_6$-$C_{10}$ arylene group; when $L^1$ to $L^4$ are a heterocyclic group, $L^1$ to $L^4$ may be preferably $C_2$-$C_{30}$ heterocyclic group, more preferably $C_2$-$C_{16}$ heterocyclic group. For example, $L^1$ to $L^4$ may be each independently single bond, phenylene, naphthylene, carbazole, benzocarbazole or dibenzofuran and the like, and they may be optionally further substituted with deuterium.

In formula 1 above, $R^1$ to $R^3$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, m is an integer of 0 to 8, n is an integer of 0 to 7, a is an integer of 0 to 3, when m, n and a are each an integer of 2 or more, a plurality of $R^1$ to a plurality of $R^3$ are each the same or different from each other.

When $R^1$ to $R^3$ are an aryl group, $R^1$ to $R^3$ may be preferably $C_6$-$C_{30}$ aryl group, more preferably $C_6$-$C_{12}$ aryl group; when $R^1$ to $R^3$ are a heterocyclic group, $R^1$ to $R^3$ may be preferably $C_2$-$C_{30}$ heterocyclic group, more preferably $C_2$-$C_8$ heterocyclic group. For example, $R^1$ to $R^3$ may be each independently cyano group, methyl, ethenyl, phenyl, naphthyl, biphenyl, or benzothienyl and the like.

In formula 1a, Y is independently S, O, $C(R^d)(R^e)$, or $N(R^f)$.

$R^d$ to $R^f$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group. Further, $R^d$ and $R^e$ may be linked to each other to form a spiro-compound together with carbon which they bond to.

When $R^d$ to $R^f$ are an aryl group, $R^d$ to $R^f$ may be preferably $C_6$-$C_{30}$ aryl group, more preferably $C_6$-$C_{12}$ aryl group. For example, $R^d$ to $R^f$ may be each independently methyl, phenyl, biphenyl, or fluorene and the like, and they may be optionally further substituted with methyl.

On the other hand, $R^d$ and $R^e$ may be linked to each other to form a spiro-compound together with carbon which they bond to.

In formula 1a, $R^4$ and $R^5$ may be each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group. Also, neighboring $R^4$s or neighboring $R^5$ may be linked to each other to form at least one of a ring, and $R^4$ and $R^5$ not forming a ring are each the same as defined above. b is an integer of 0 to 4, c is an integer of 0 to 3, and when b and c are each an integer of 2 or more, a plurality of $R^4$s and a plurality of $R^5$s may be each the same or different from each other.

When $R^4$ and $R^5$ are an aryl group, $R^4$ and $R^5$ may be preferably $C_6$-$C_{30}$ aryl group, more preferably $C_6$-$C_{12}$ aryl group. For example, $R^4$ and $R^5$ may be phenyl. Also, neighboring $R^4$s or neighboring $R^5$ may be optionally linked to each other to form $C_6$-$C_{20}$ saturated or unsaturated ring, and the carbon atom of saturated or unsaturated ring may be replaced by one or more heteroatoms selected from nitrogen, oxygen and sulfur. For example, the formed ring may be benzene, naphthalene, indole or benzothiophene and the like.

When $Ar^1$ to $Ar^4$, and $R^1$ to $R^5$ are each the aryl group, fluorenyl group, heterocyclic group, fused ring group, alkyl group, alkenyl group, alkynyl group, alkoxyl group, or aryloxy group, they may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when these substituents are adjacent, they may be linked each other to form a ring.

Specifically, Formula 1 above is represented by any one of Formulas 2 to 6 below. The following Formulas 2 to 6 correspond to the case where at least one of $Ar^1$ to $Ar^4$ is the above Formula 1a.

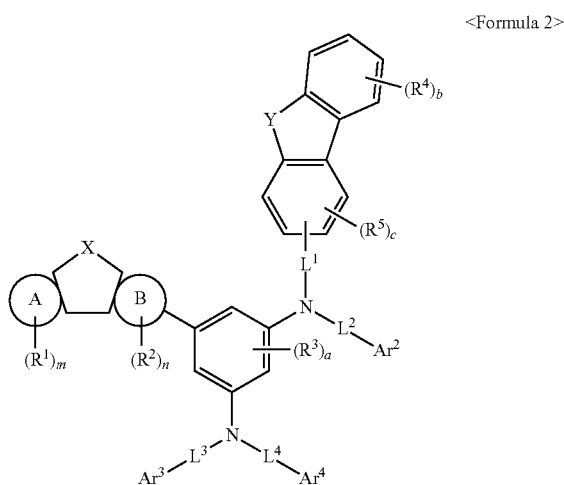

<Formula 2>

<Formula 3>
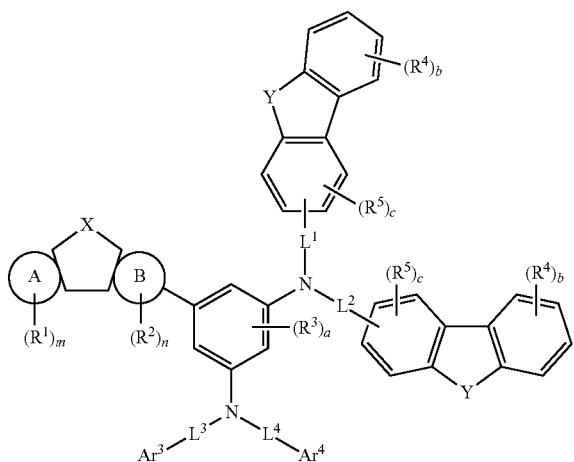
<Formula 4>
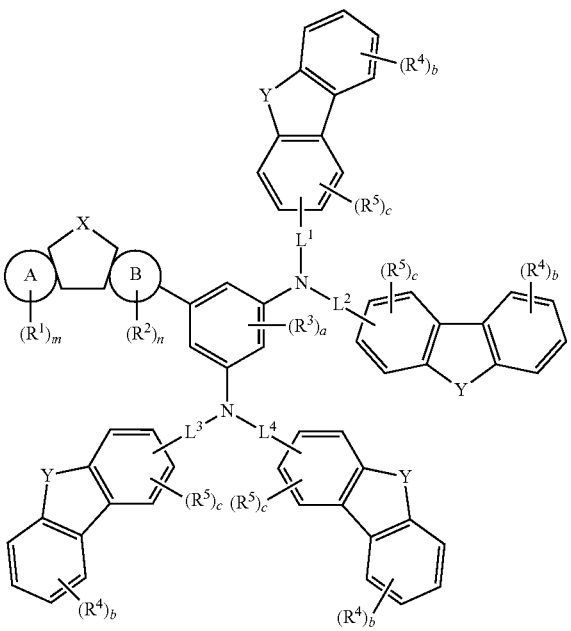
<Formula 5>
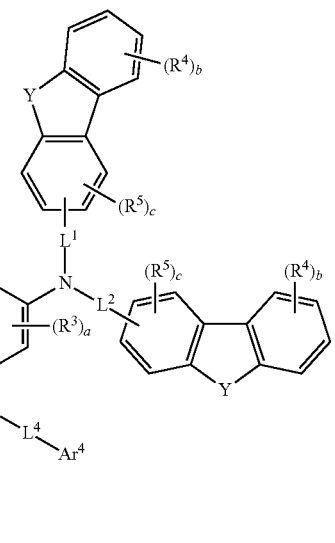
<Formula 6>
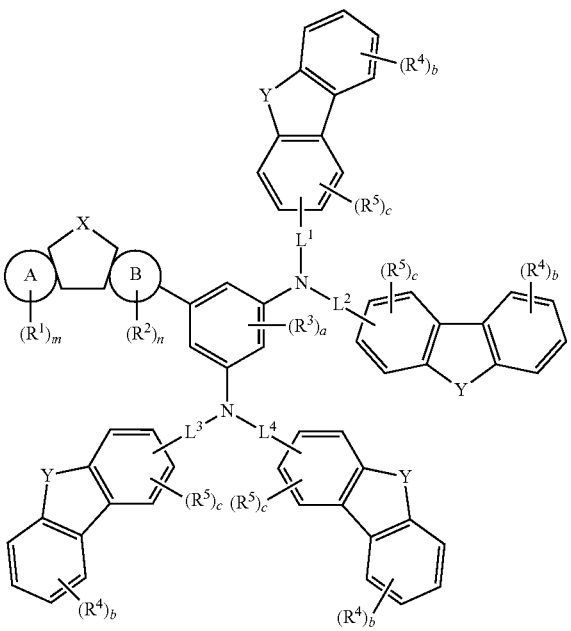
In Formulas 2 to 6, A ring, B ring, X, Y, $R^1$ to $R^5$, $Ar^2$ to $Ar^4$, $L^1$ to $L^4$, m, n, a, b and c are the same as defined in Formula 1 above.
Specifically, the compound represented by Formula 1 may be any one of the following compounds.

P-1
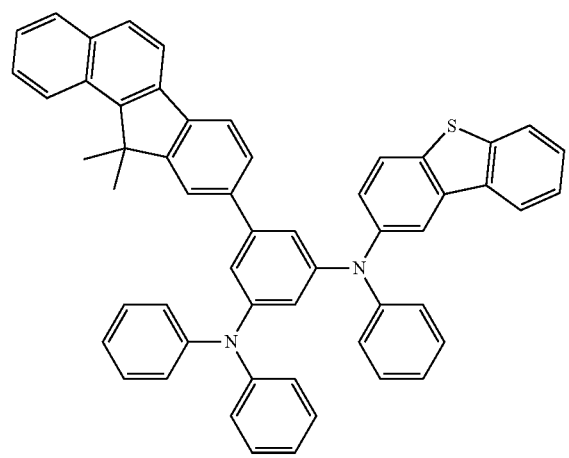
P-2
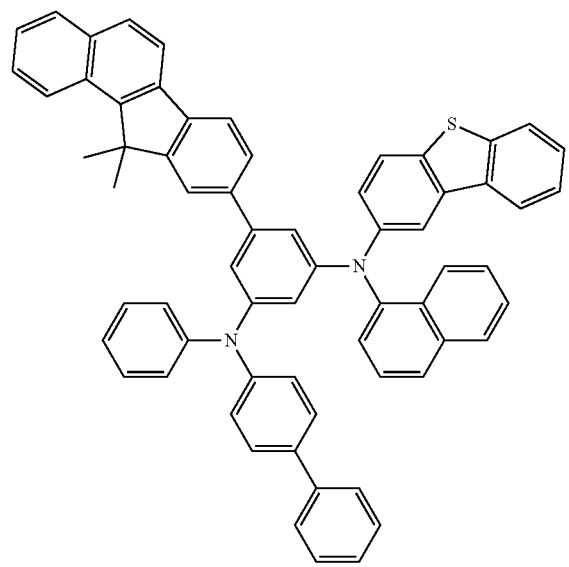
P-4
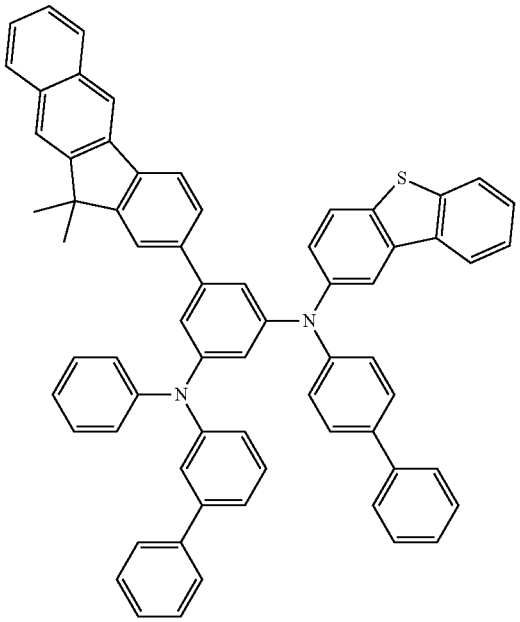
P-3
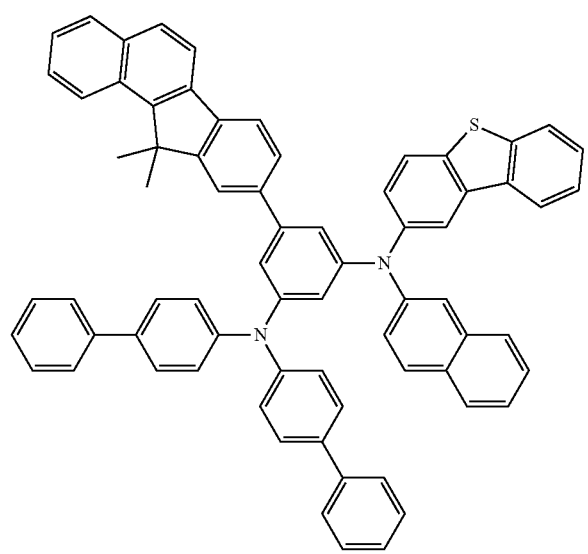
P-5
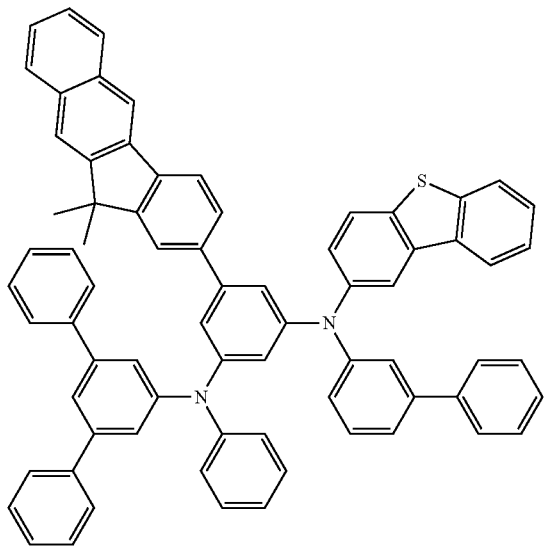

P-6
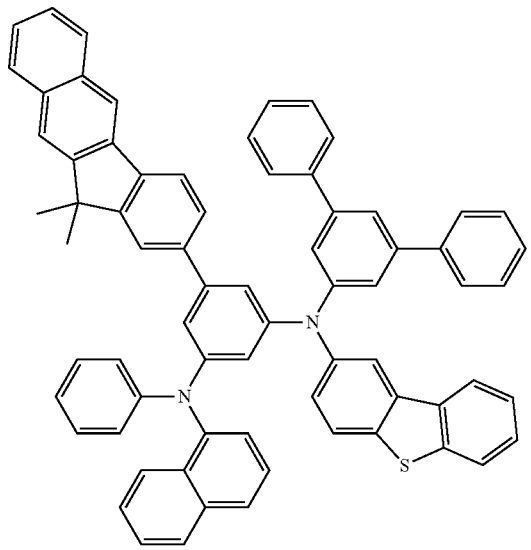
P-8
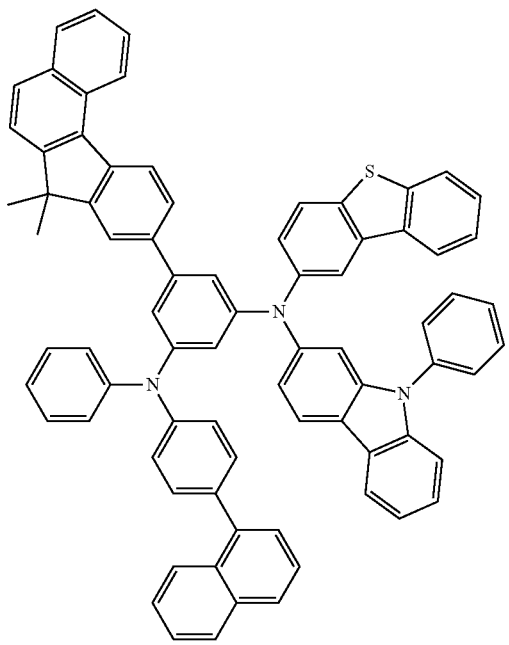
P-7
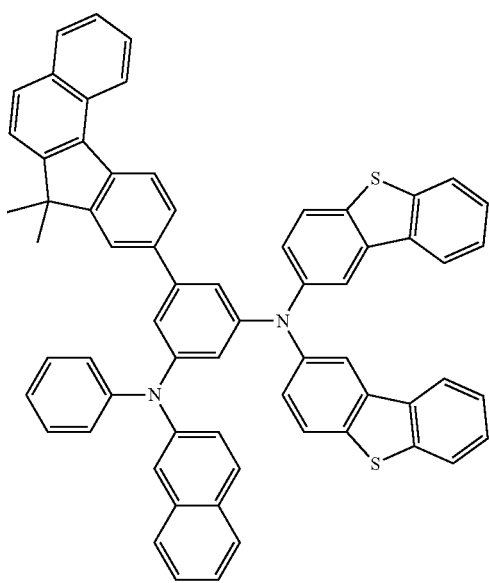
P-9
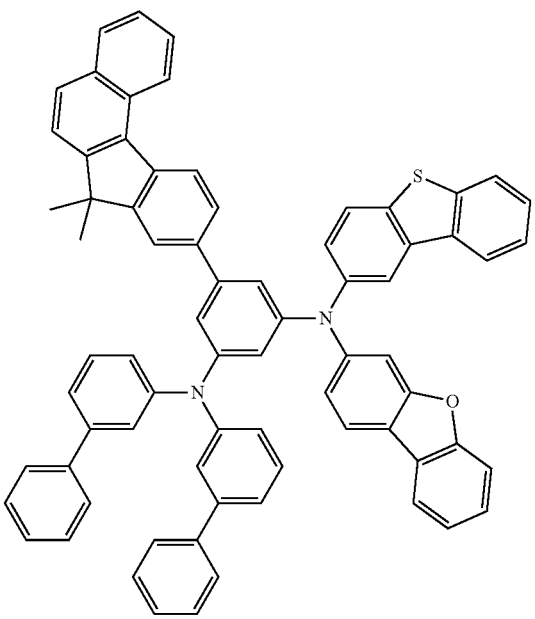

P-10
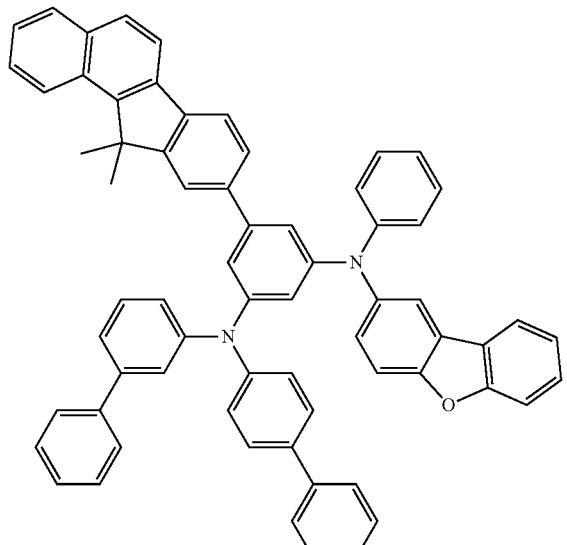
P-13
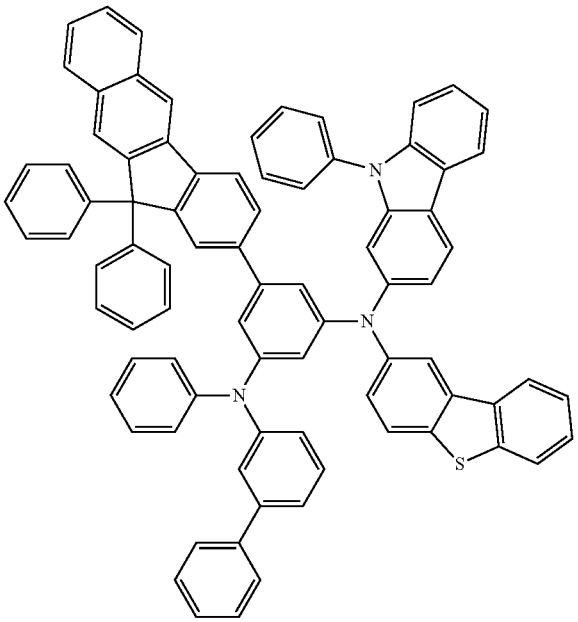
P-11
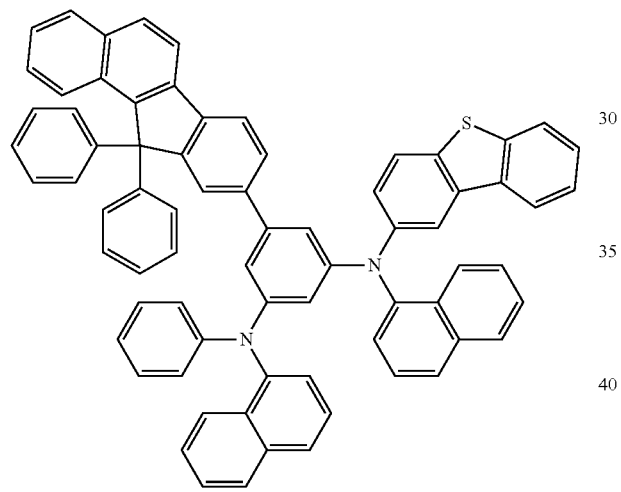
P-12
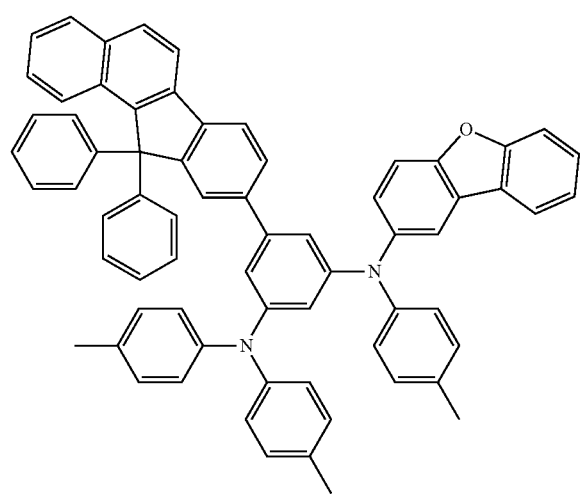
P-14
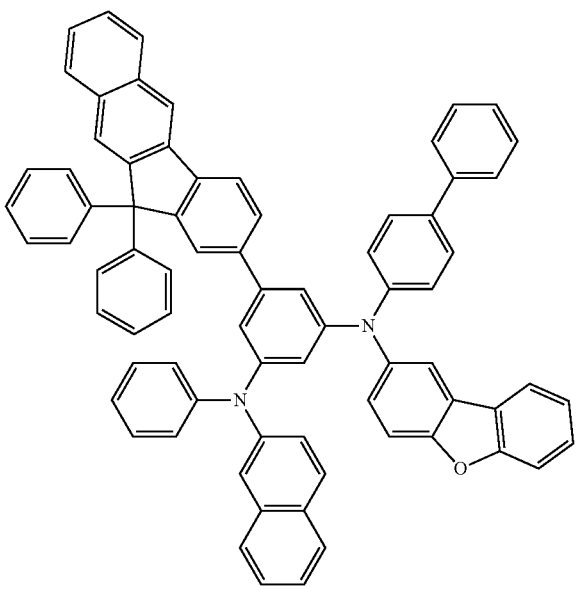

P-15
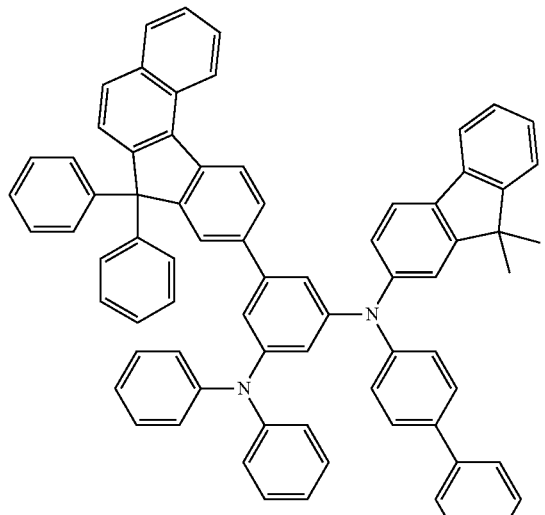
P-16
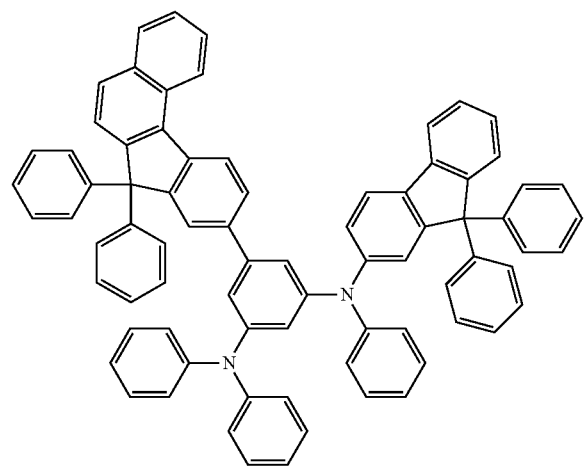
P-17
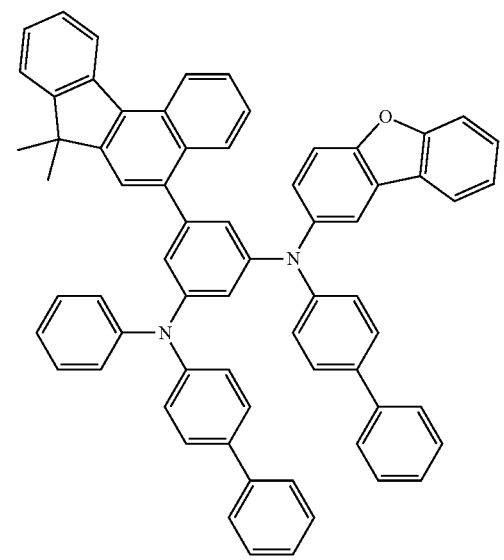
P-18
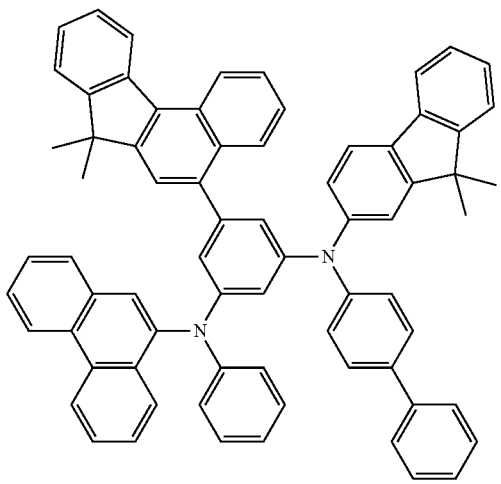
P-19
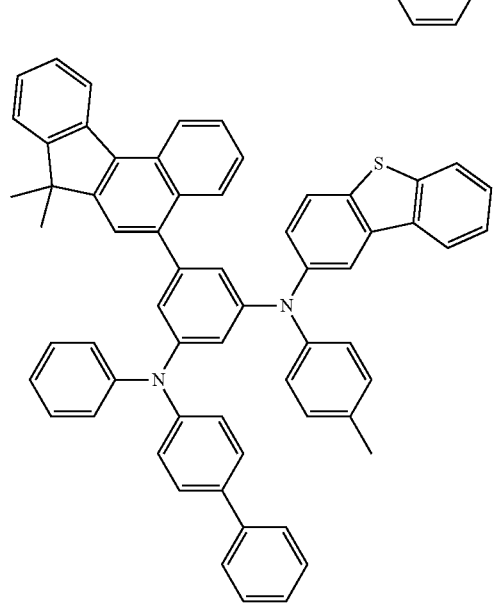
P-20
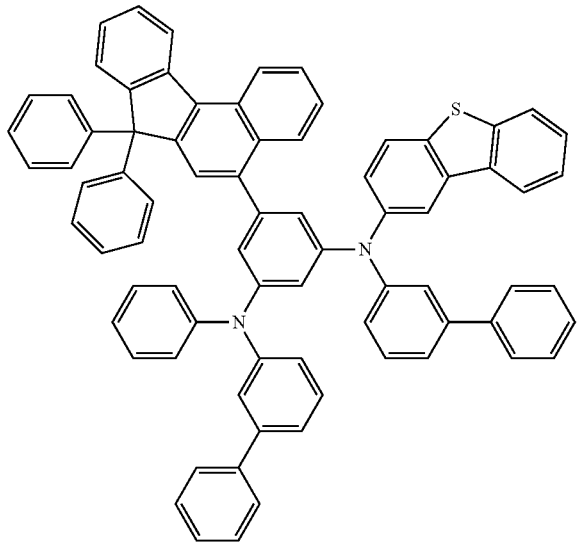

P-21
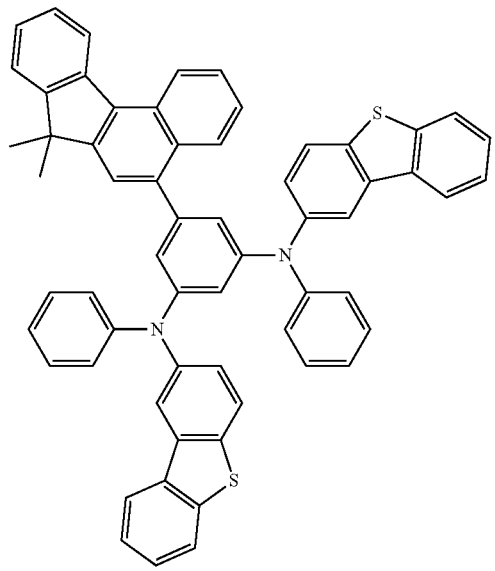
P-23
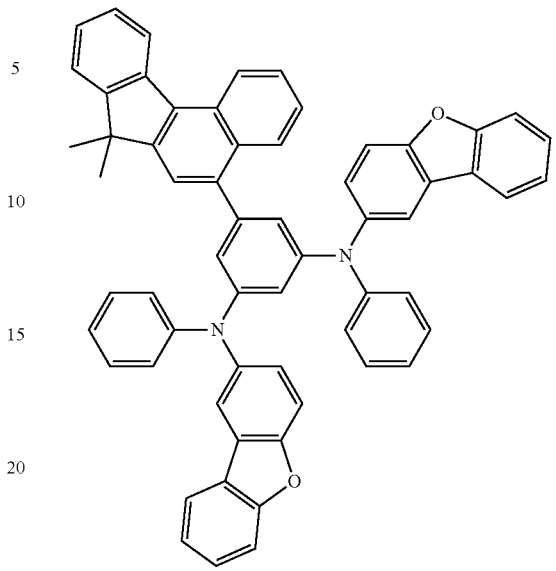
P-22
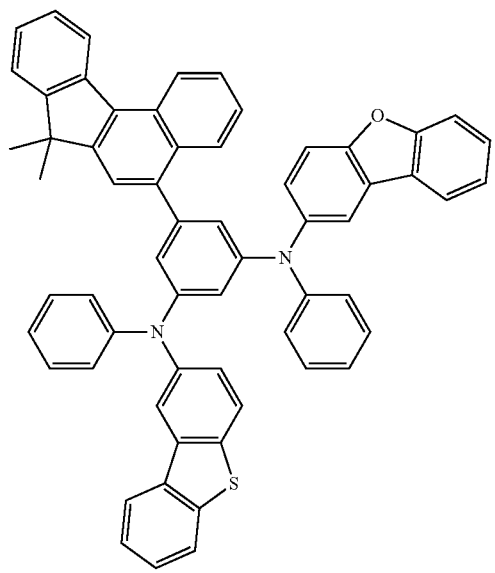
P-24
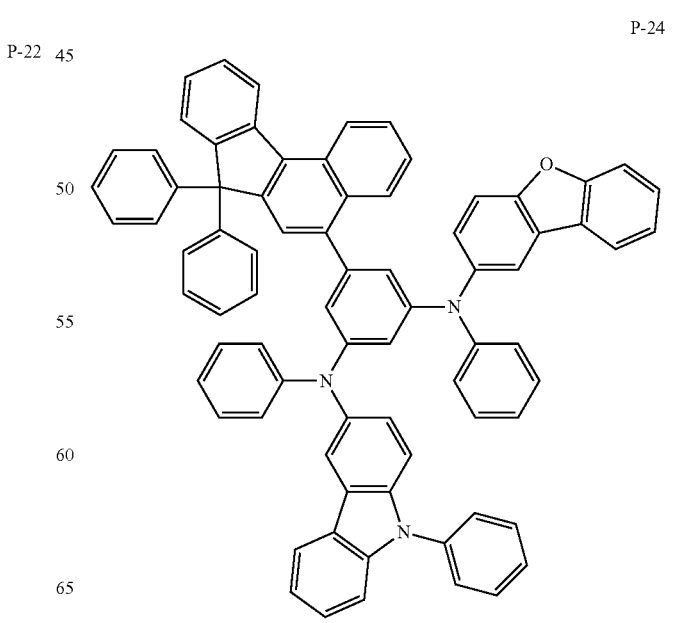

P-25
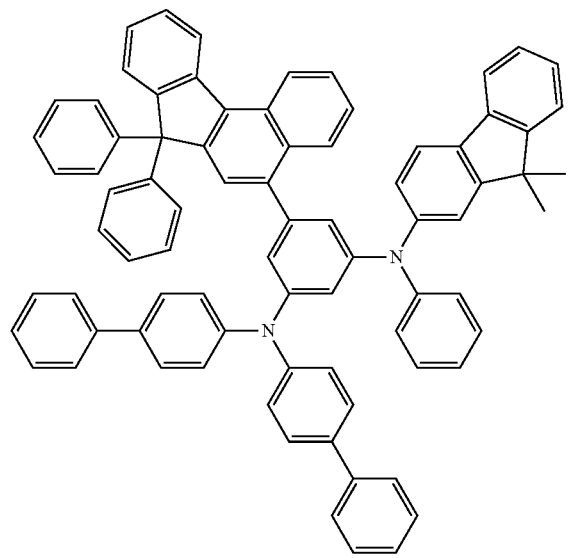
P-26
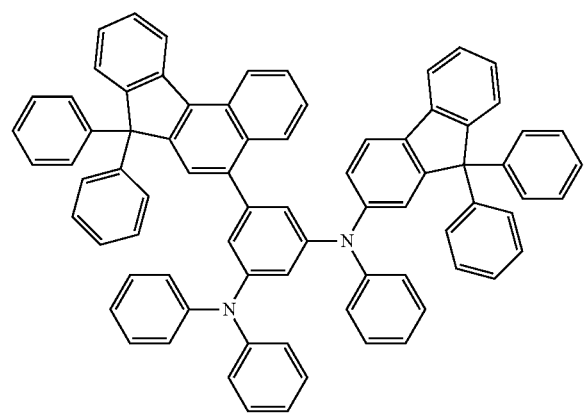
P-27
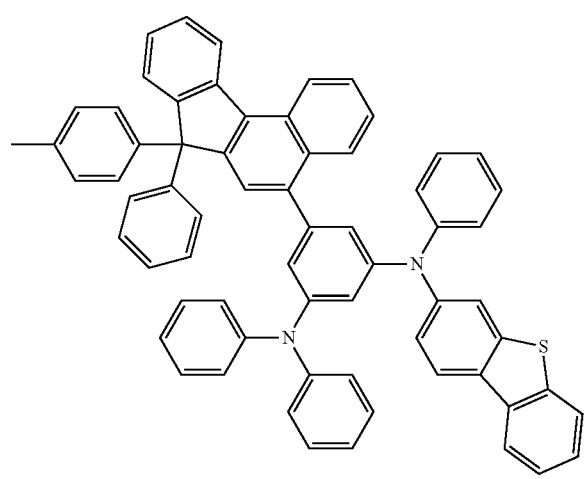
P-28
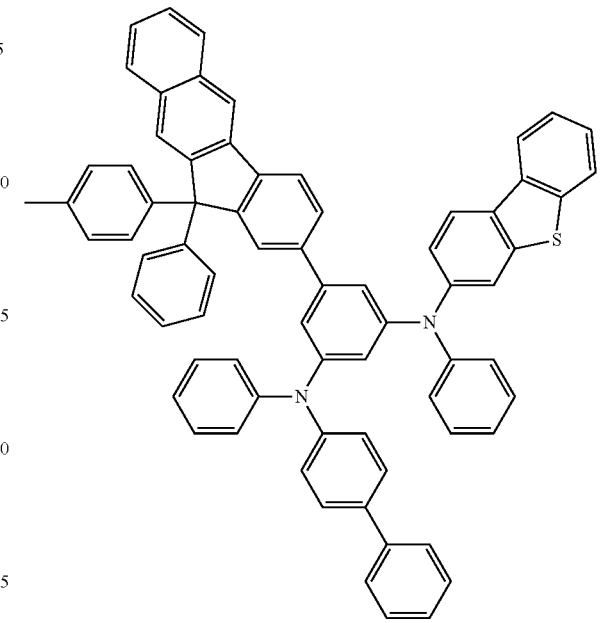
P-29
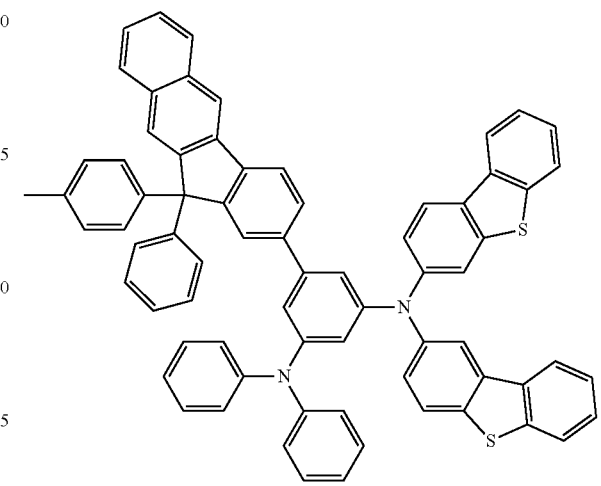
P-30

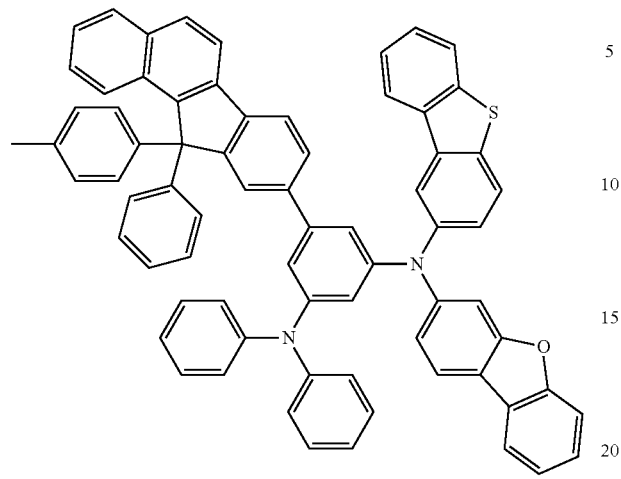
P-31
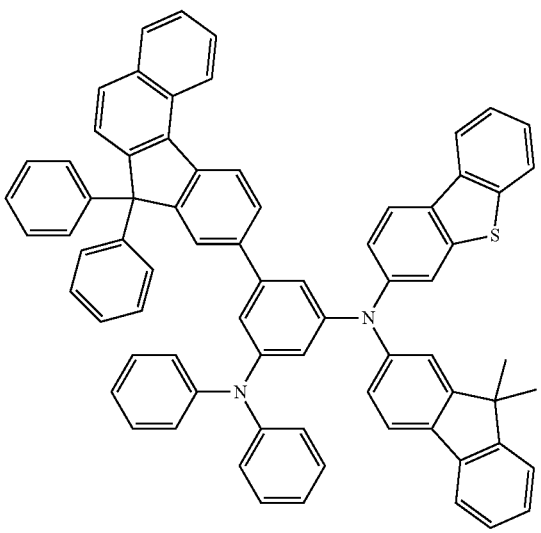
P-34
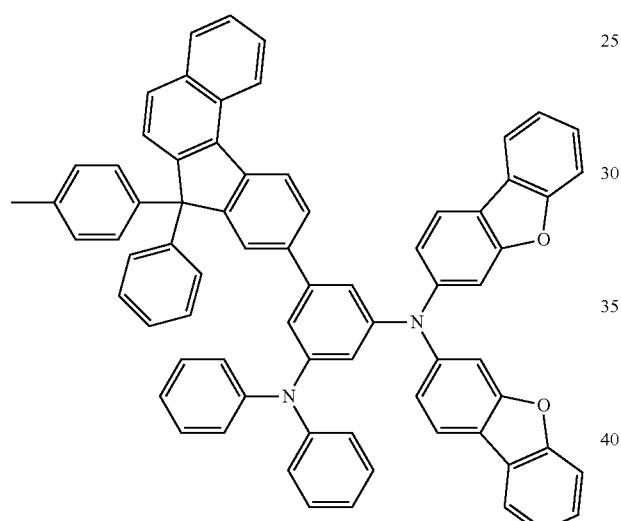
P-32
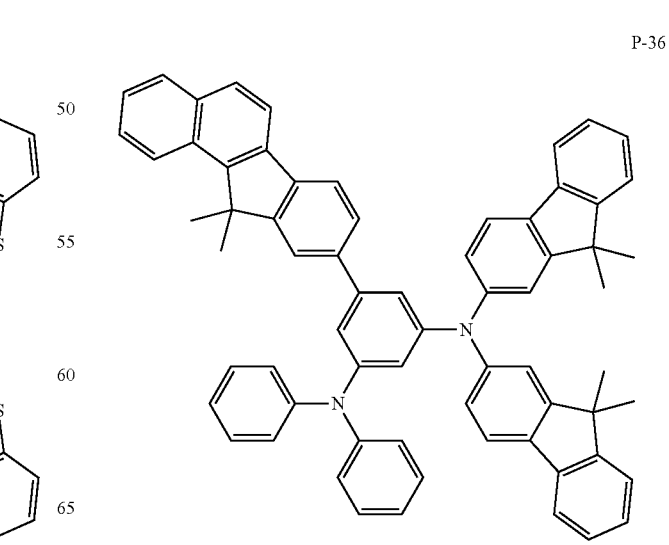
P-35
P-33
P-36

P-37
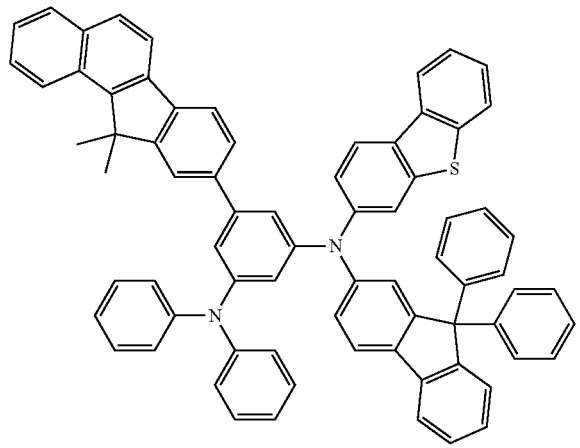
P-38
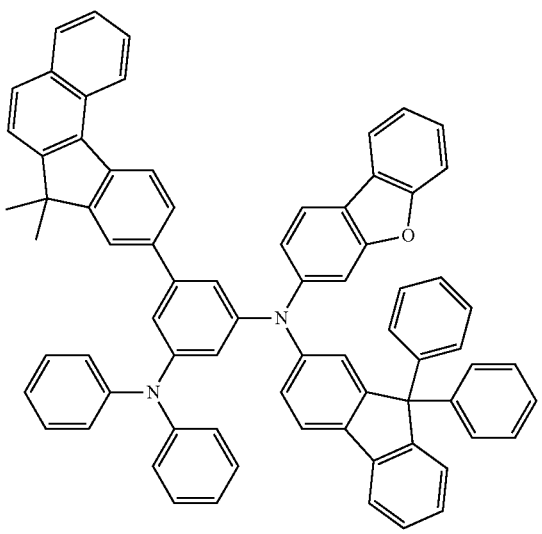
P-39
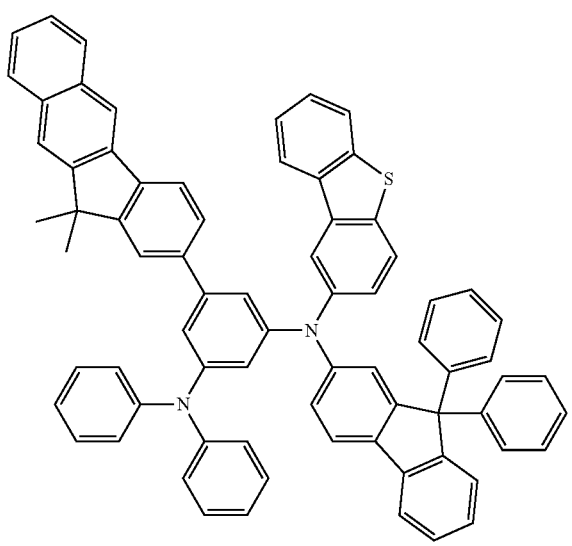
P-40
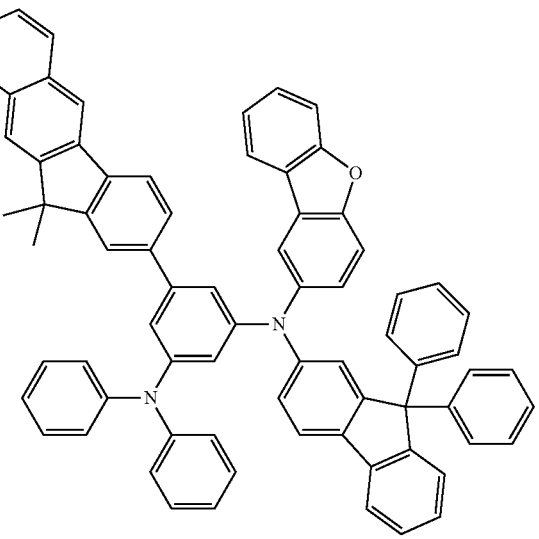
P-41
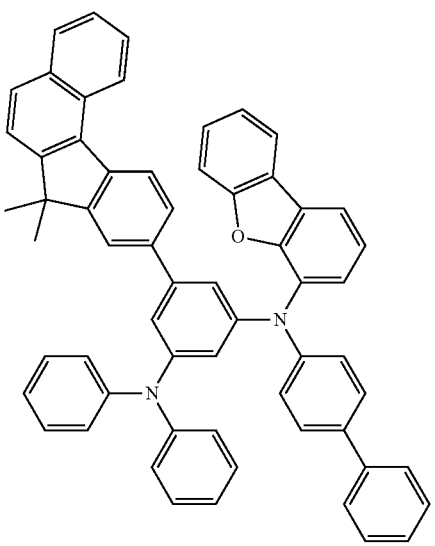
P-42
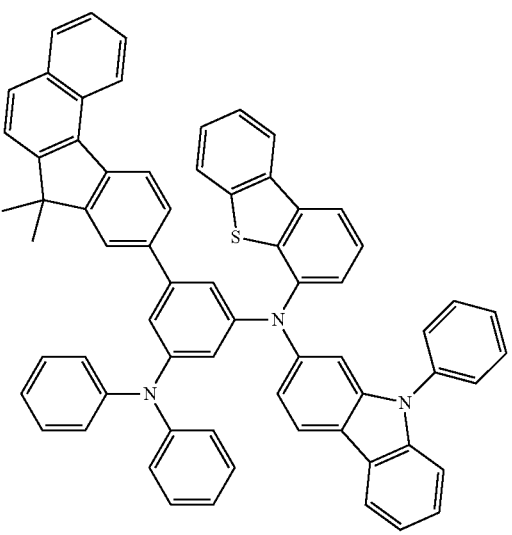

P-43
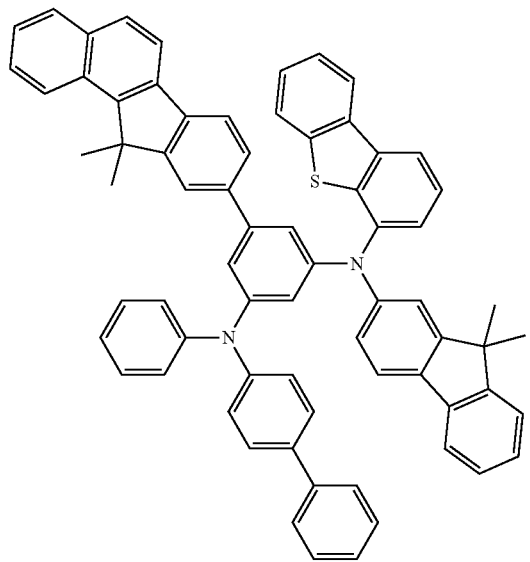
P-46
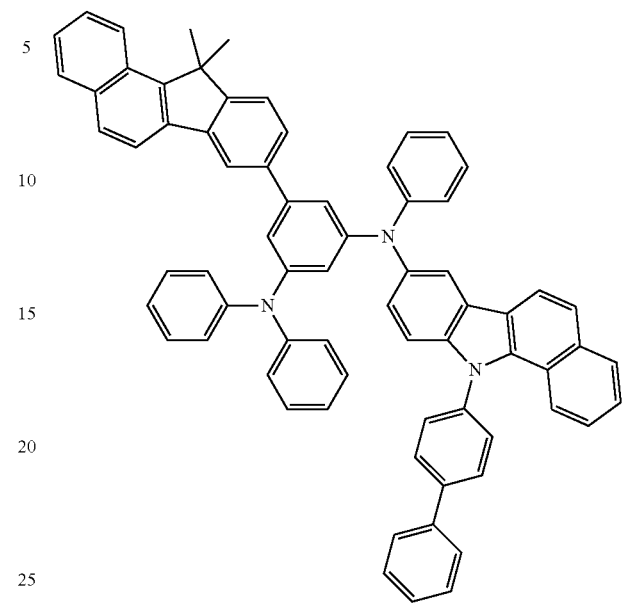
P-44
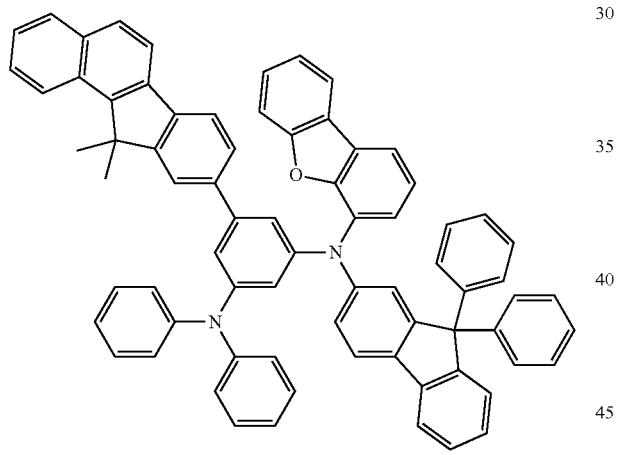
P-45
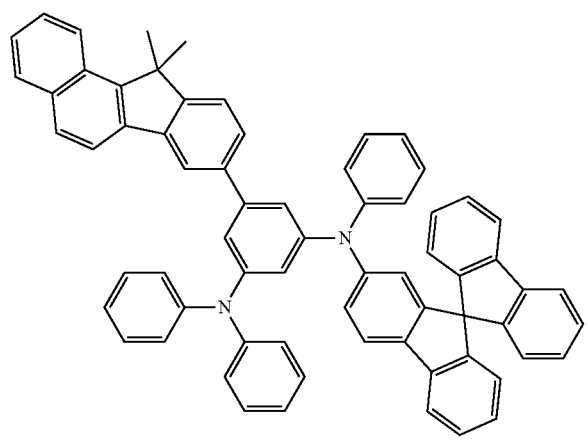
P-47
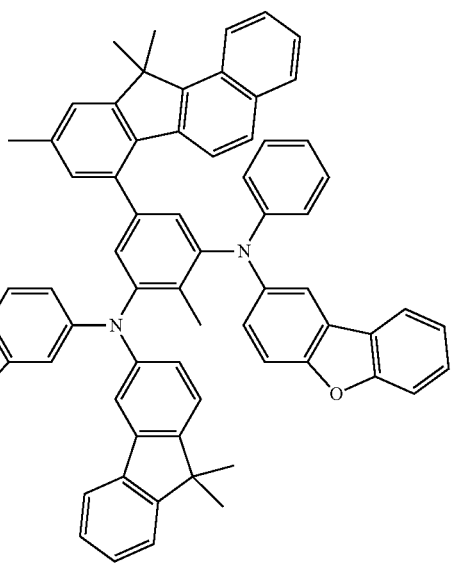

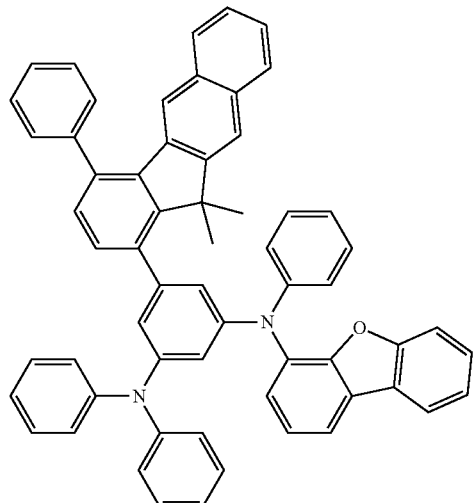
P-48
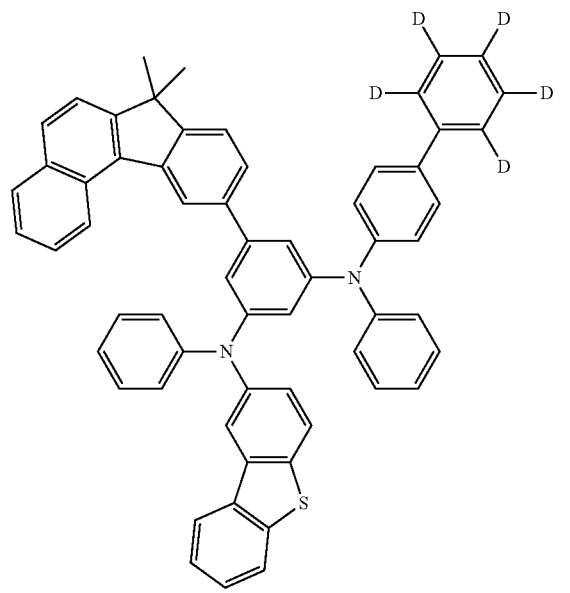
P-49
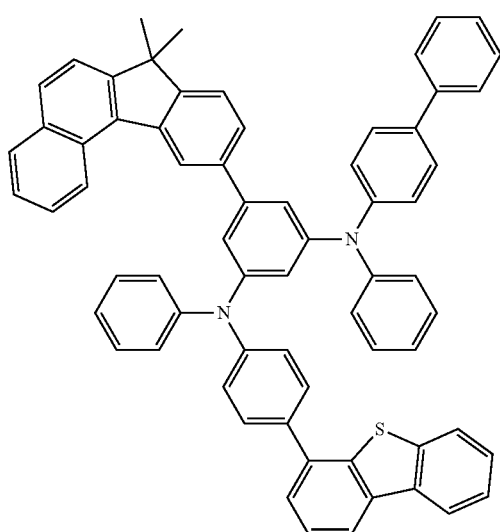
P-50
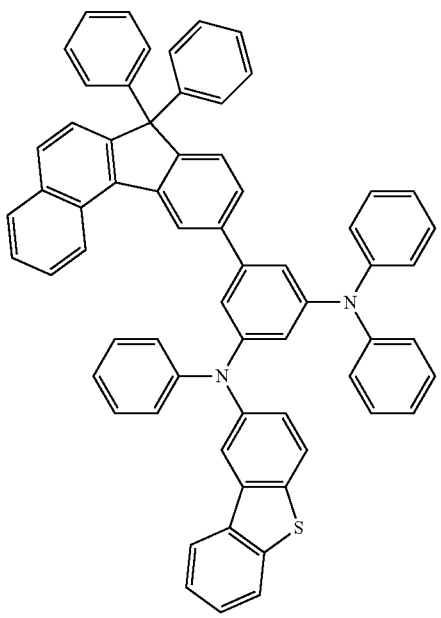
P-51
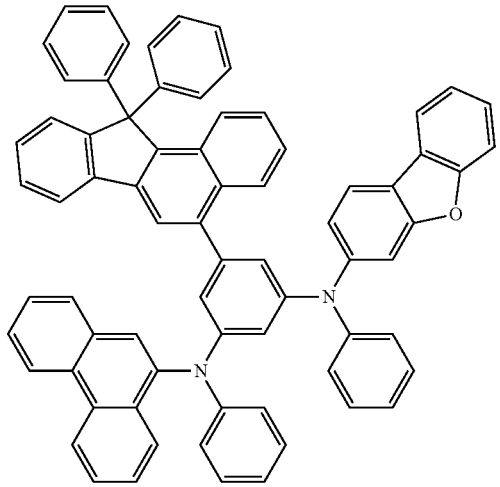
P-52

P-53
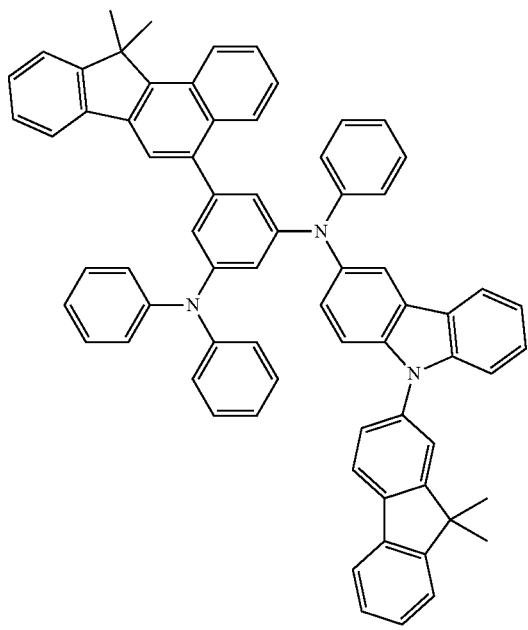
P-55
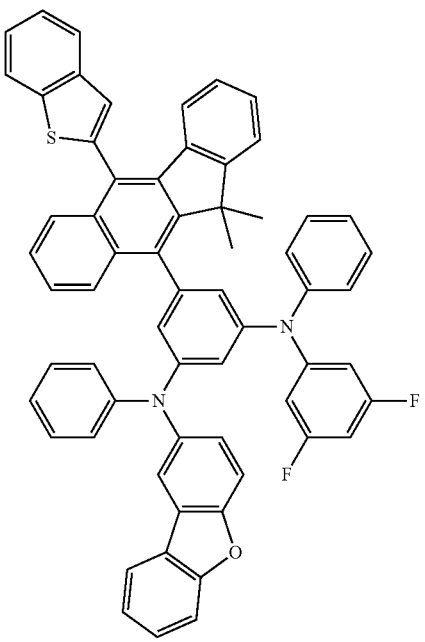
P-54
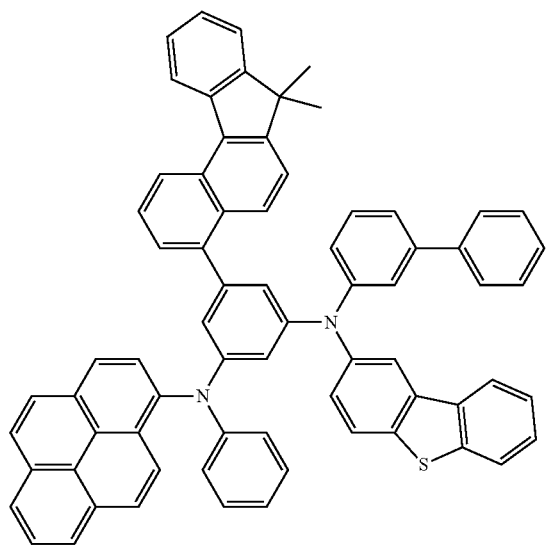
P-56
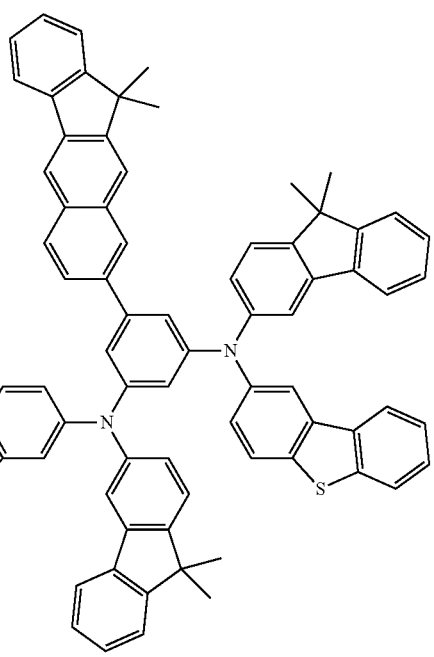

-continued
P-57
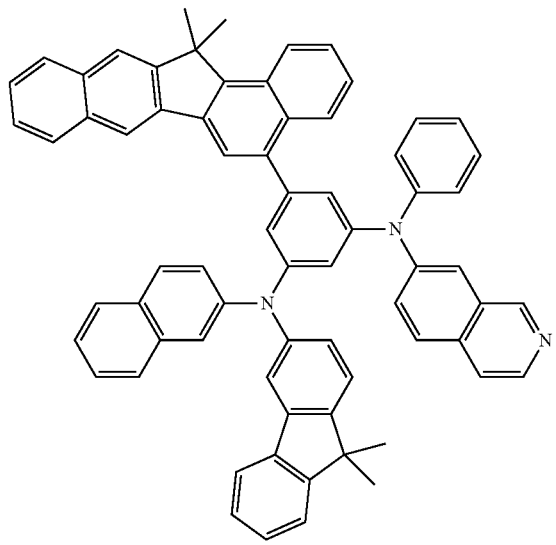
P-58
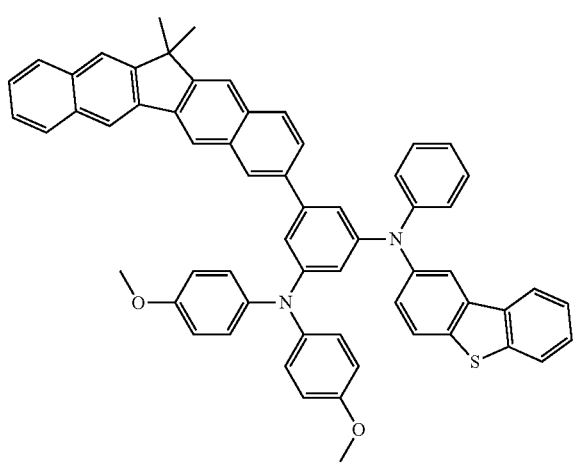
P-59
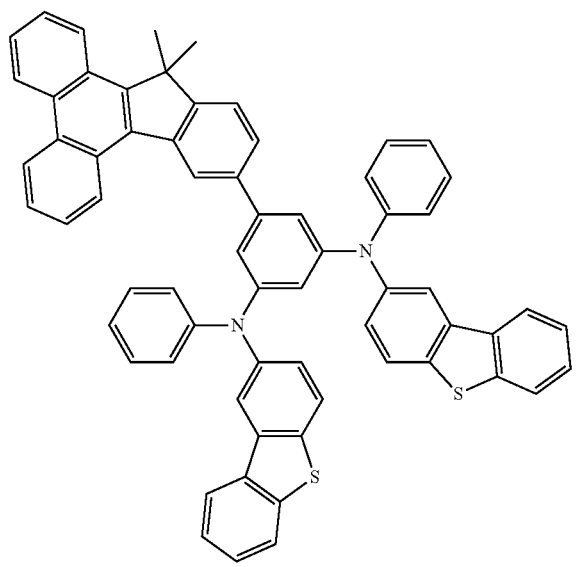
P-60
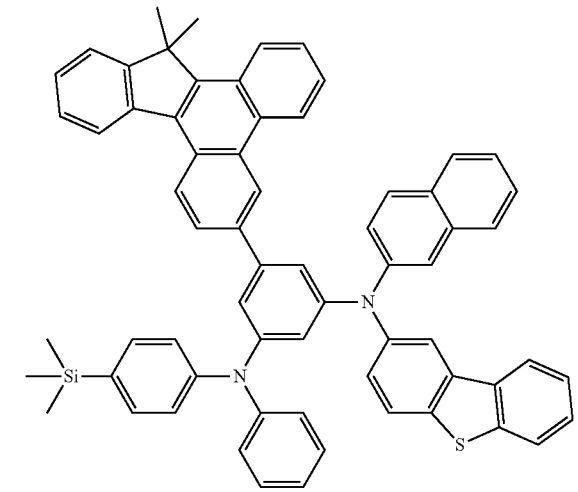
P-61
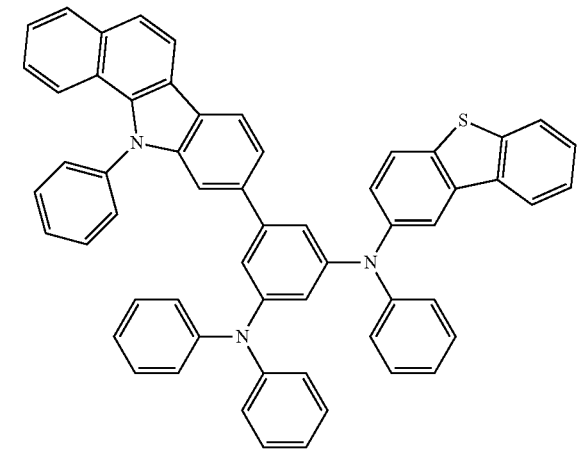
P-62
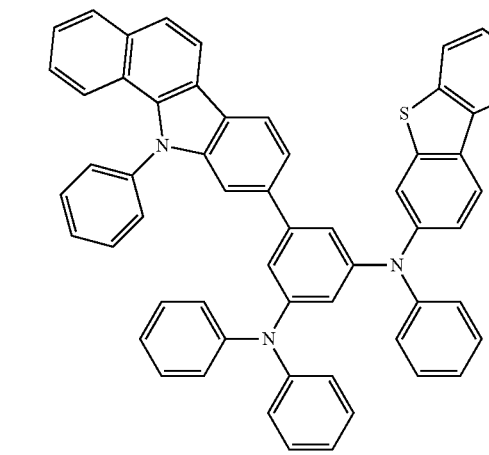

P-63
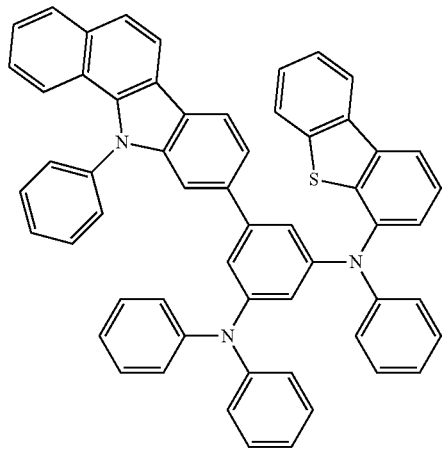
P-64
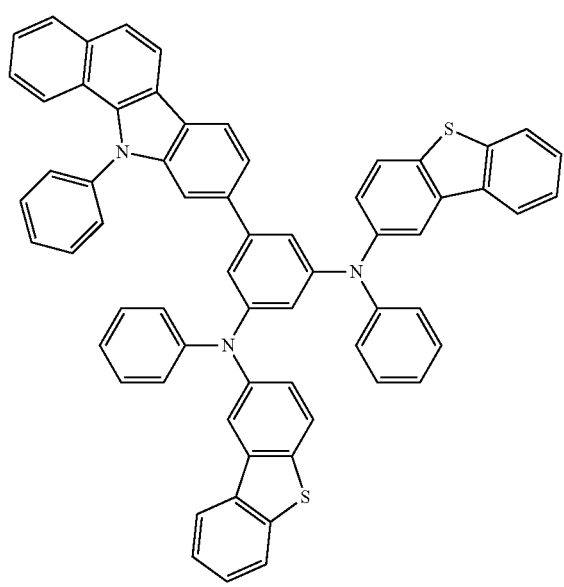
P-65
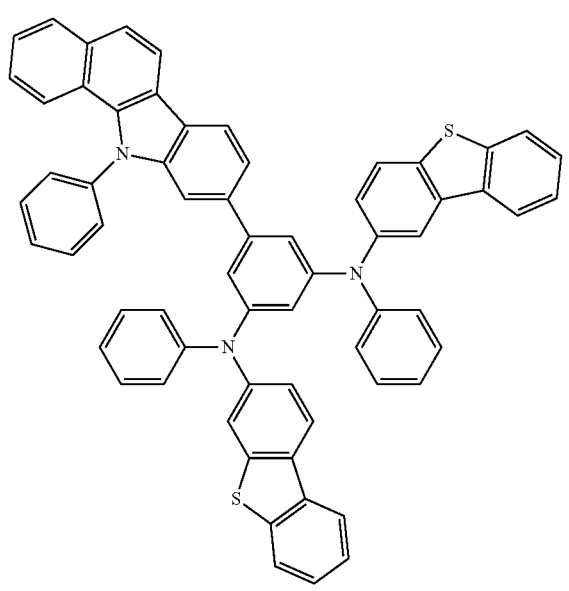
P-66
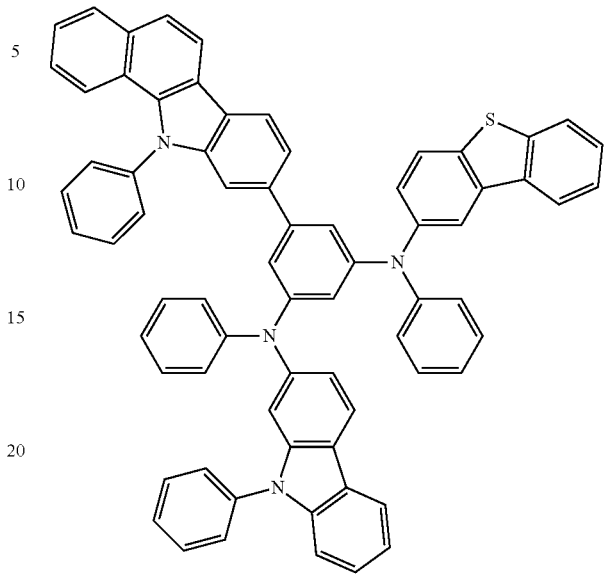
P-67
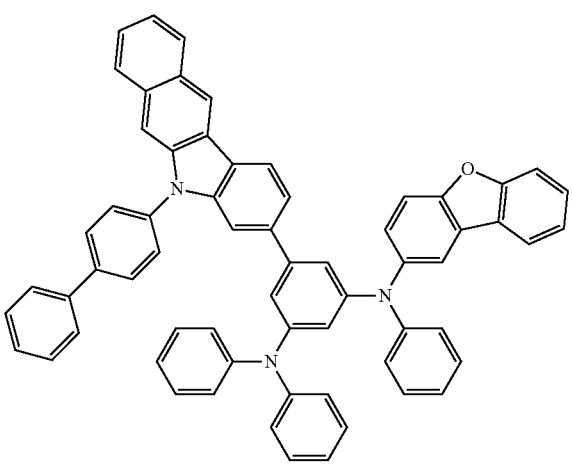

P-68
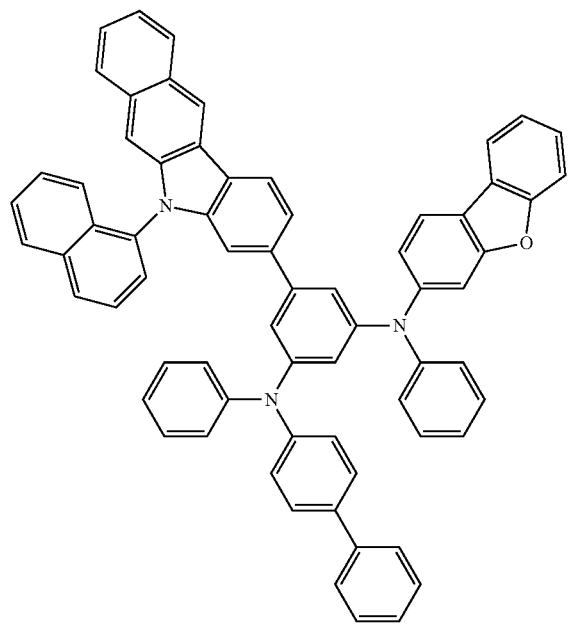
P-70
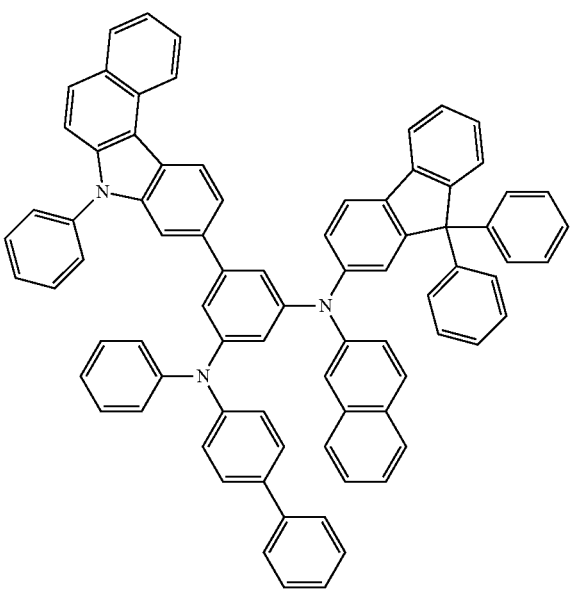
P-69
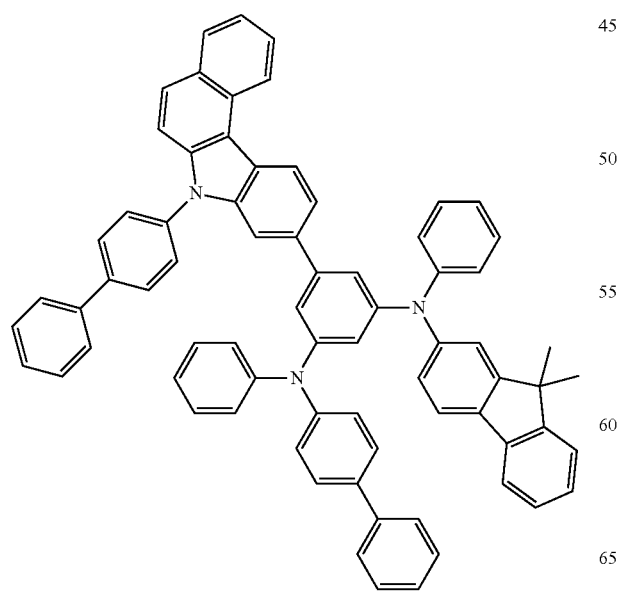
P-71
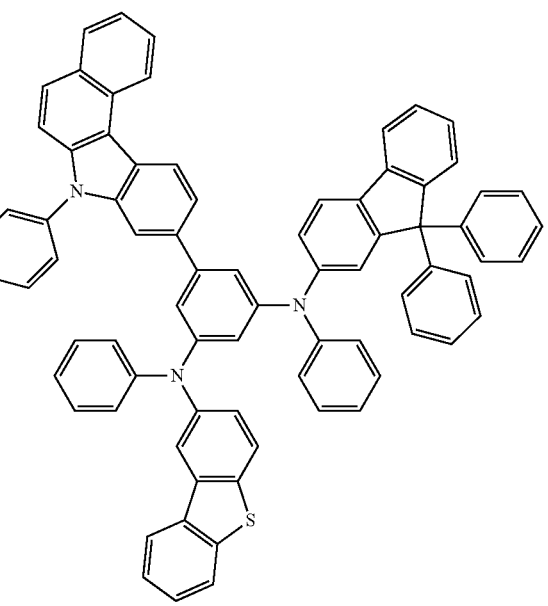

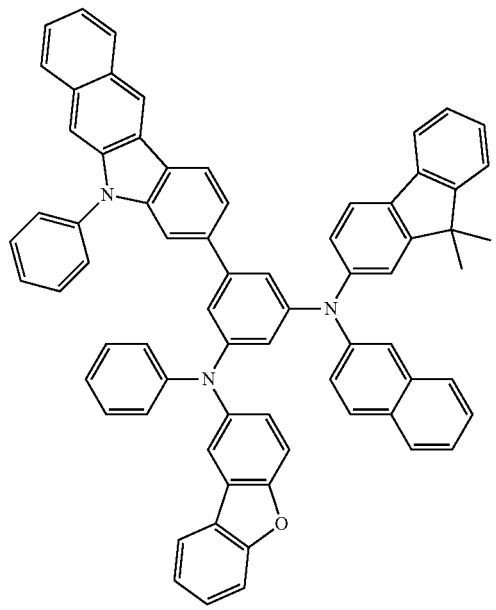
P-72
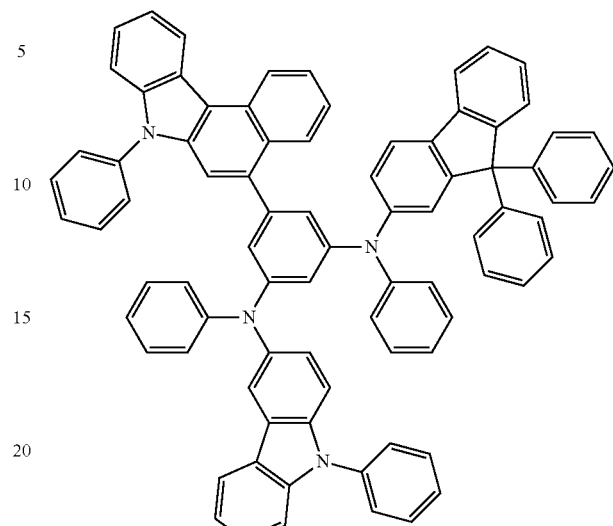
P-74
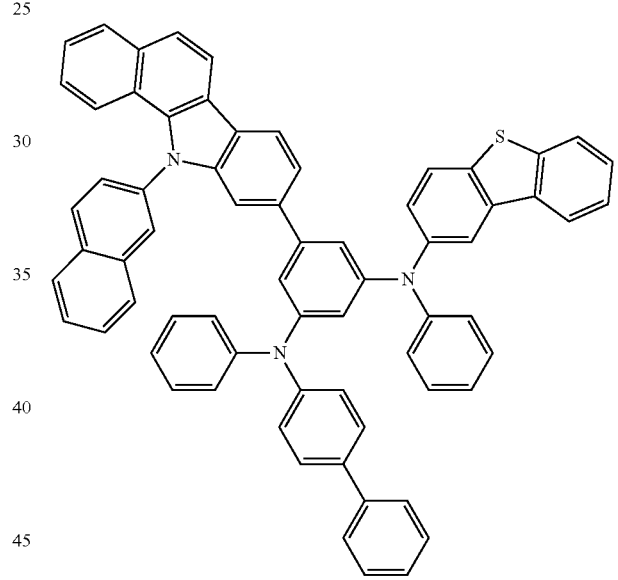
P-75
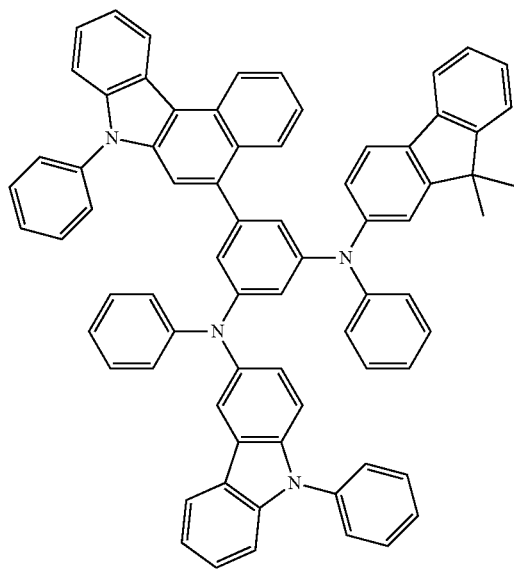
P-73
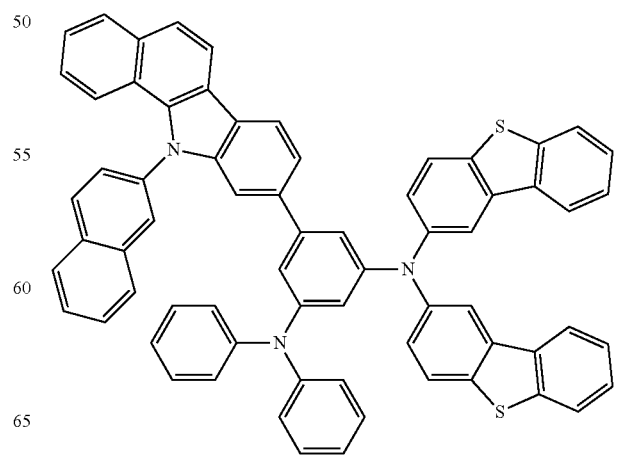
P-76

P-77
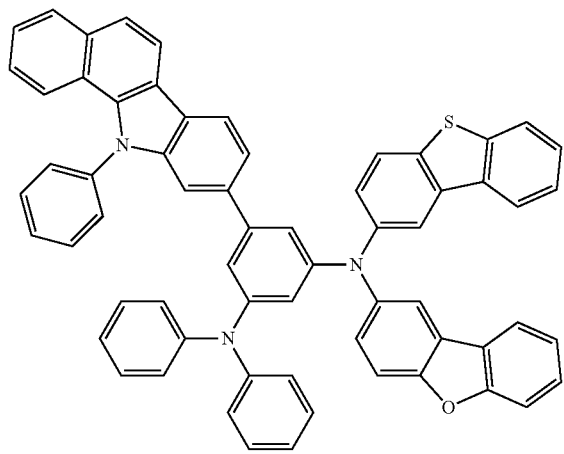
P-78
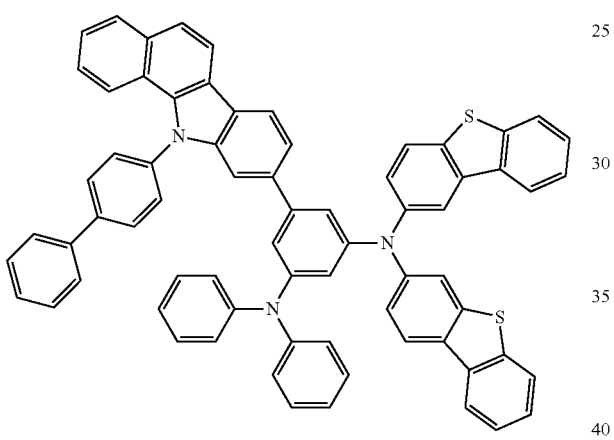
P-79
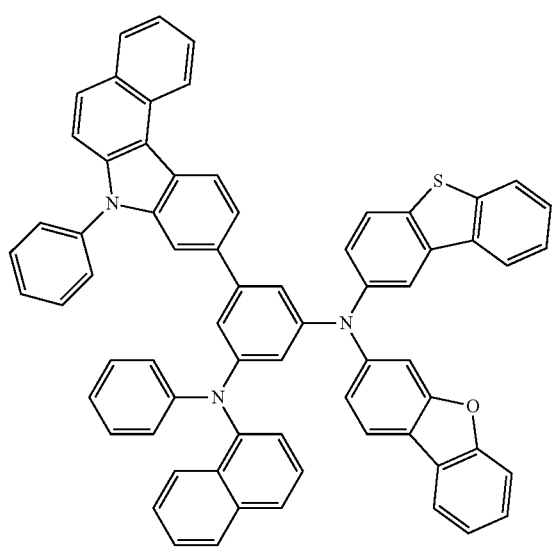
P-80
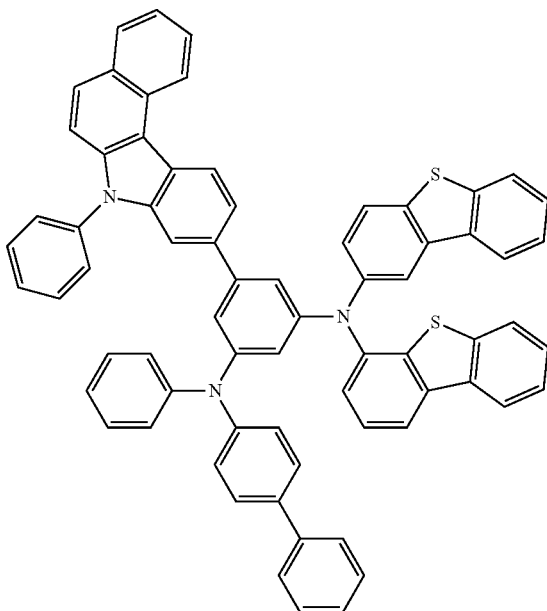
P-81
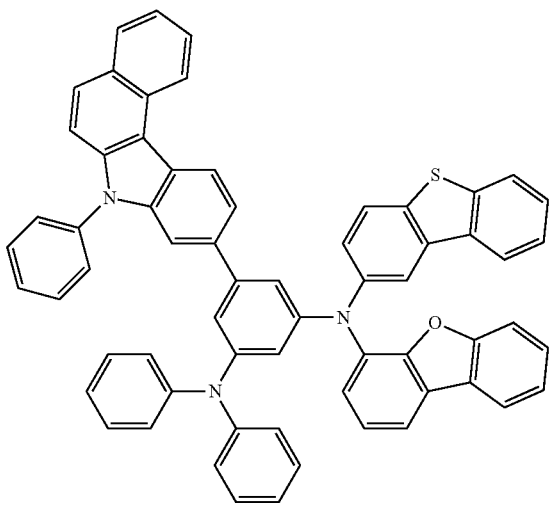

P-82
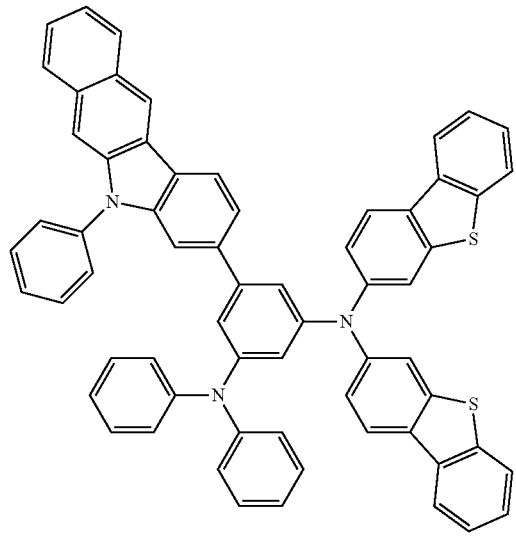
P-85
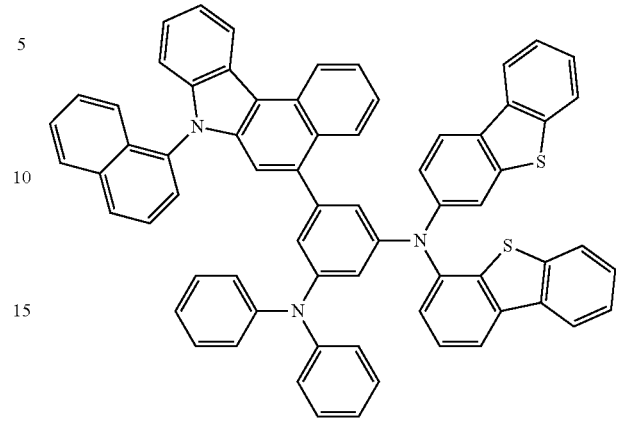
P-83
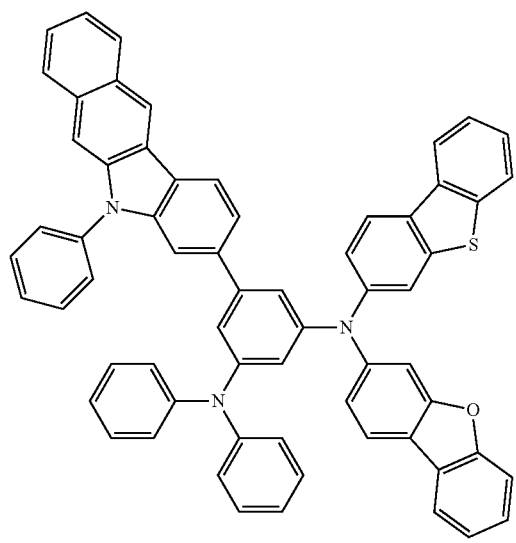
P-86
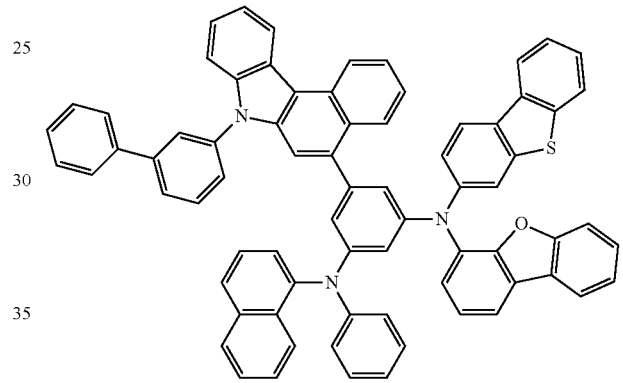
P-84
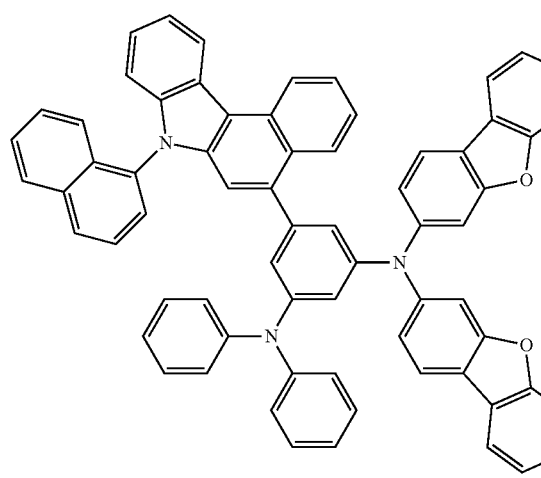
P-87
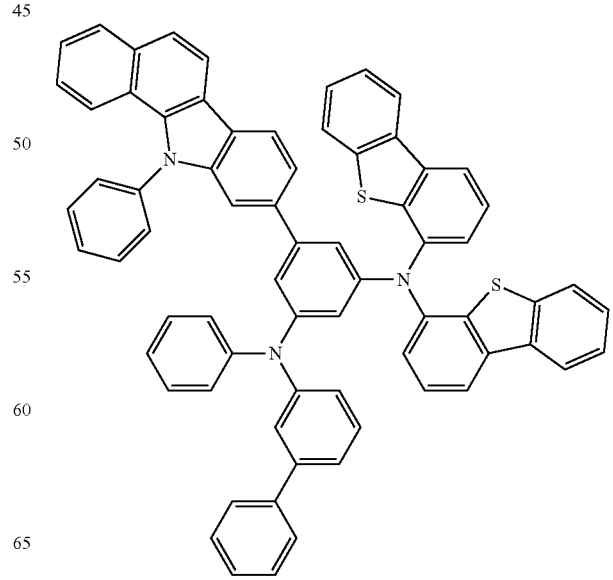

P-88
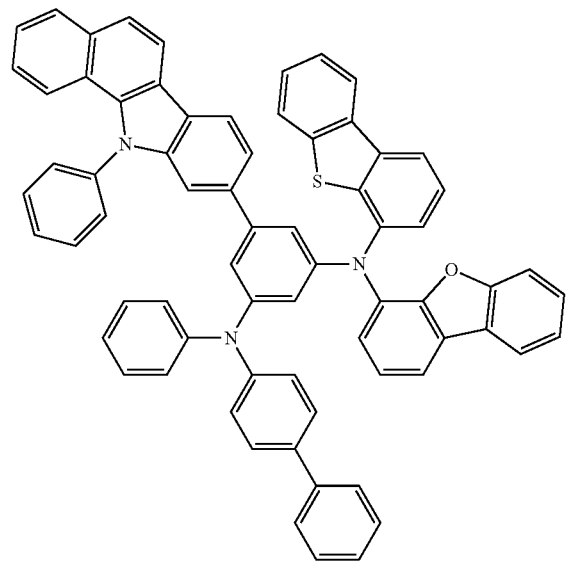
P-89
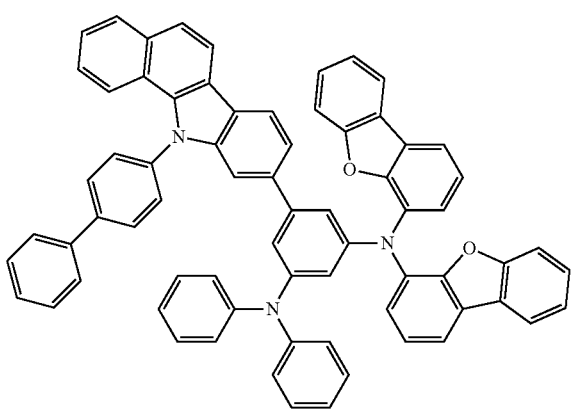
P-90
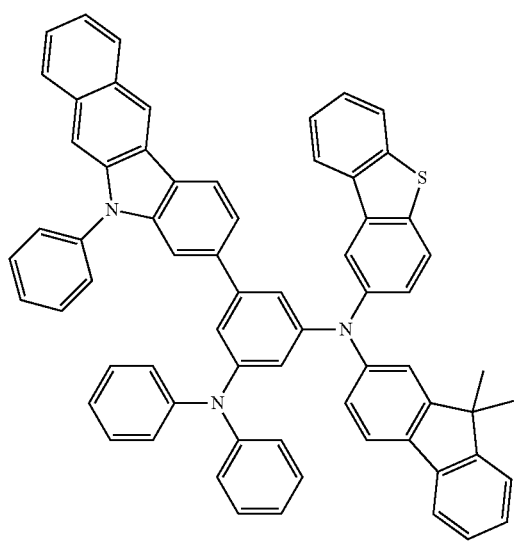
P-91
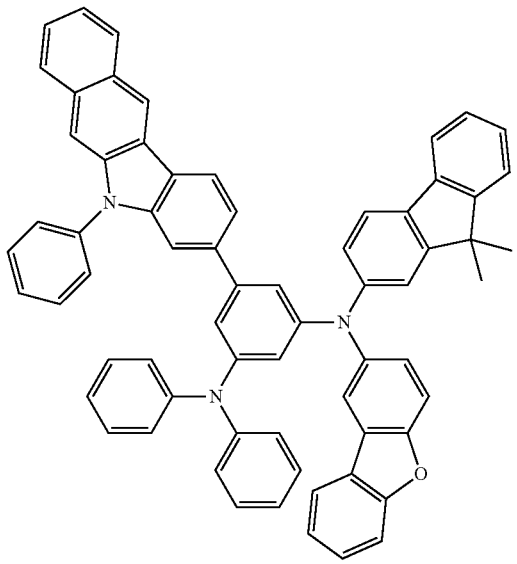
P-92
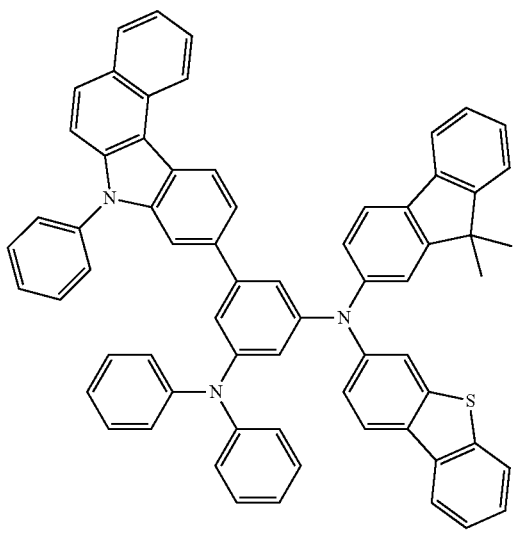

P-93
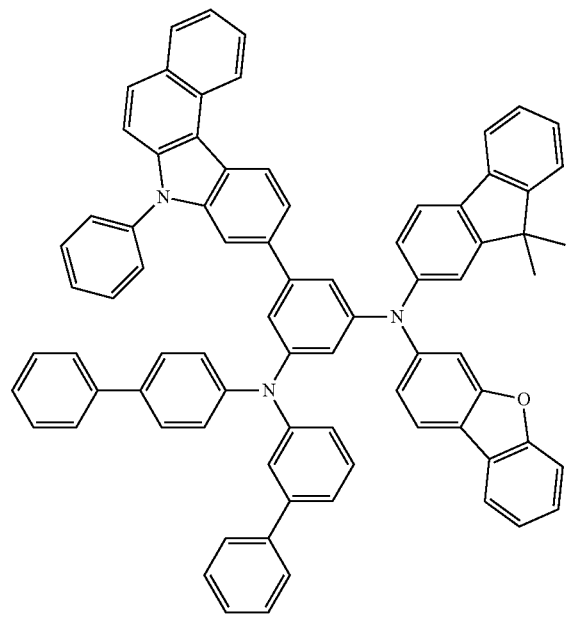
P-96
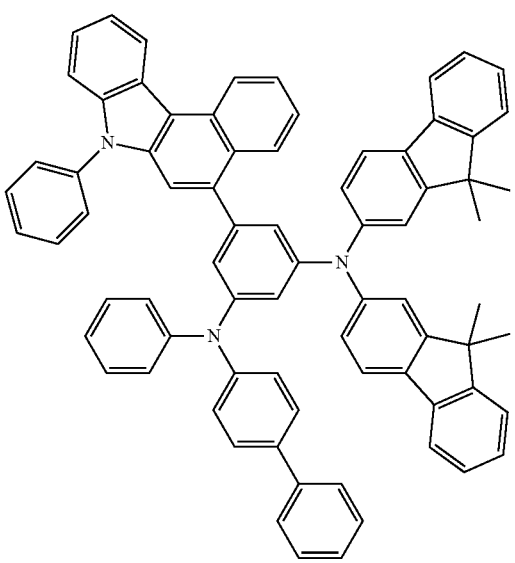
P-94
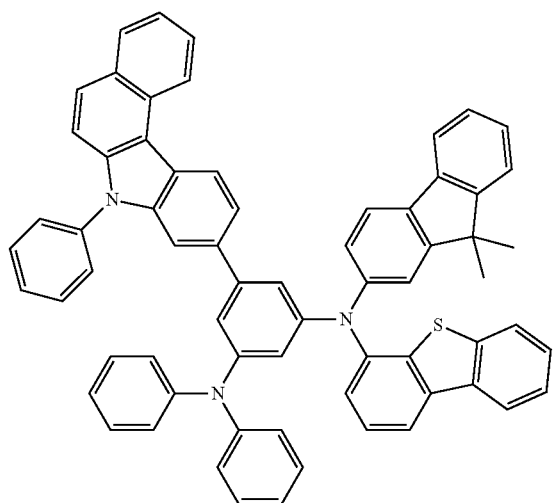
P-97
P-95
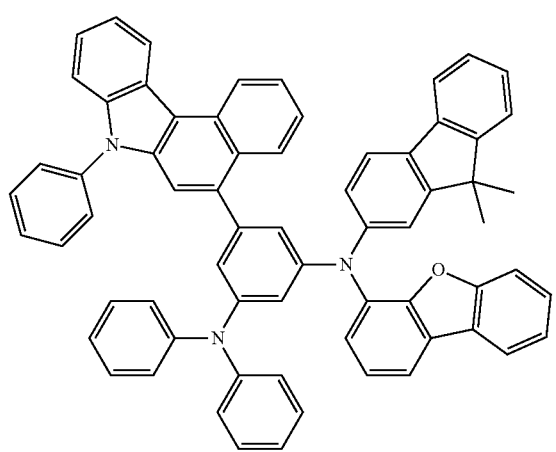
P-98
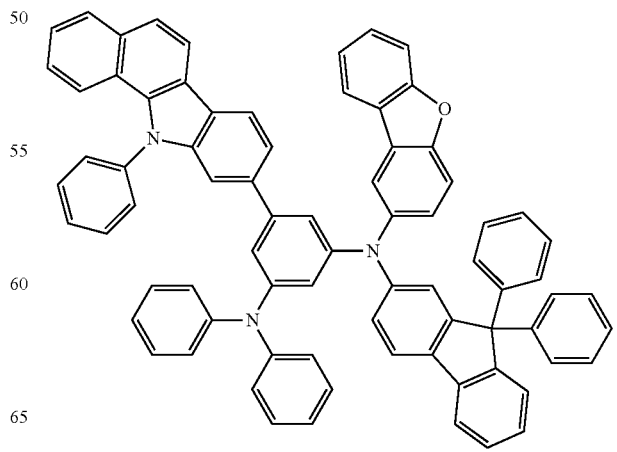

P-99
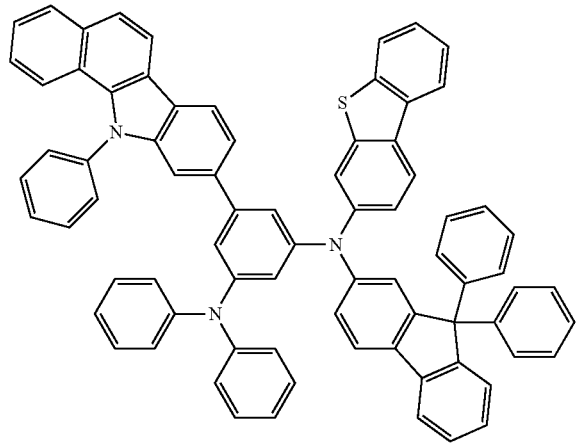
P-100
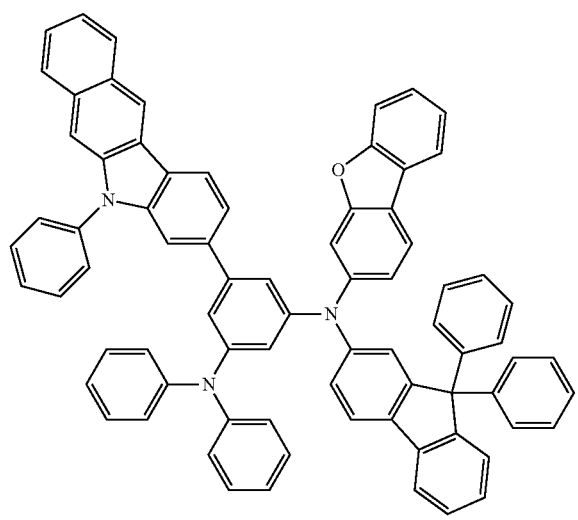
P-101
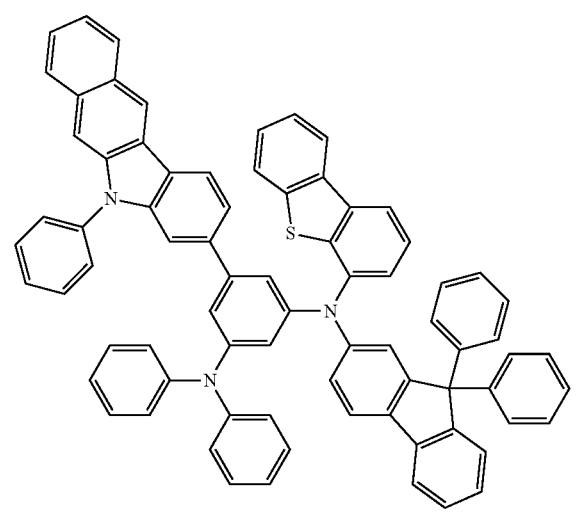
P-102
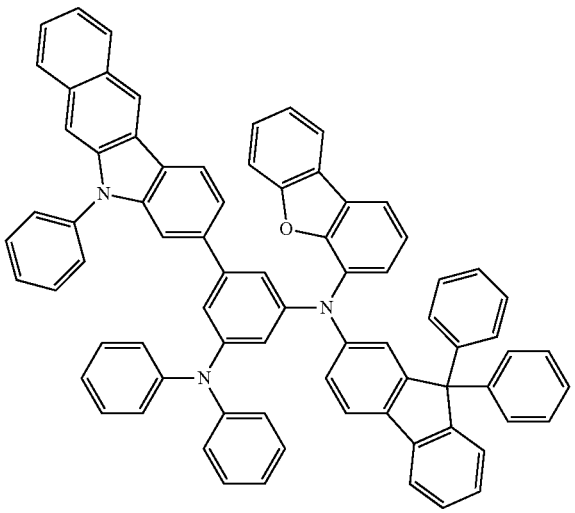
P-103
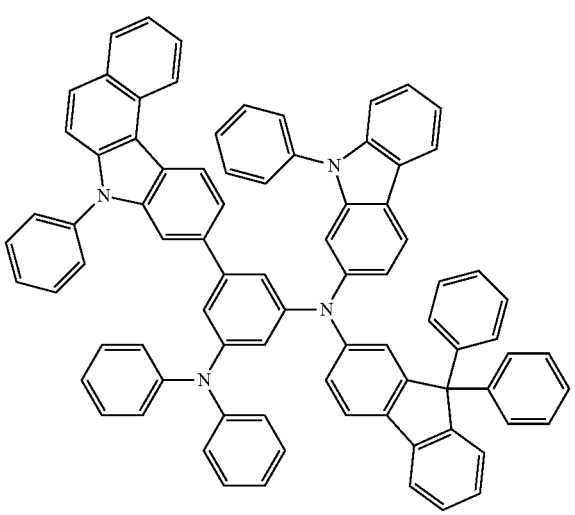
P-104
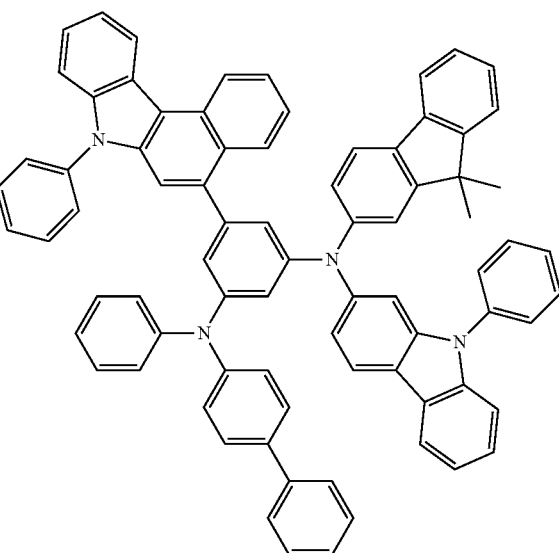

P-105
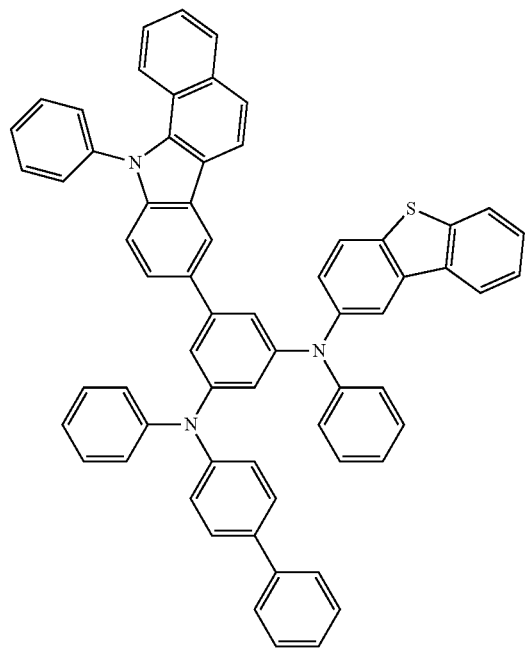
P-106
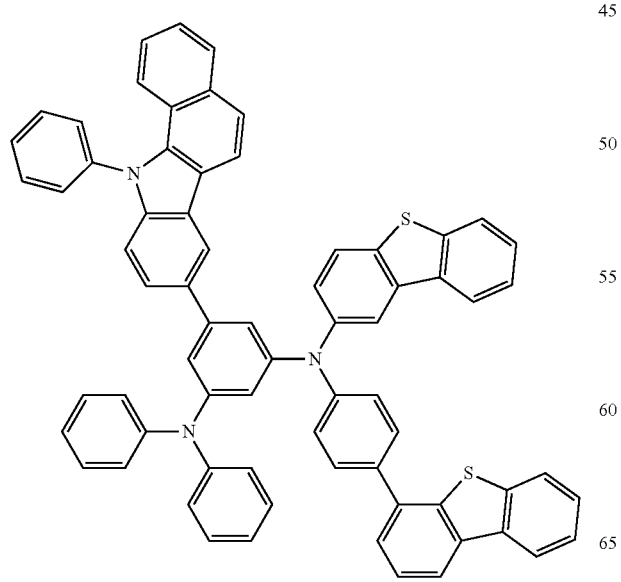
P-107
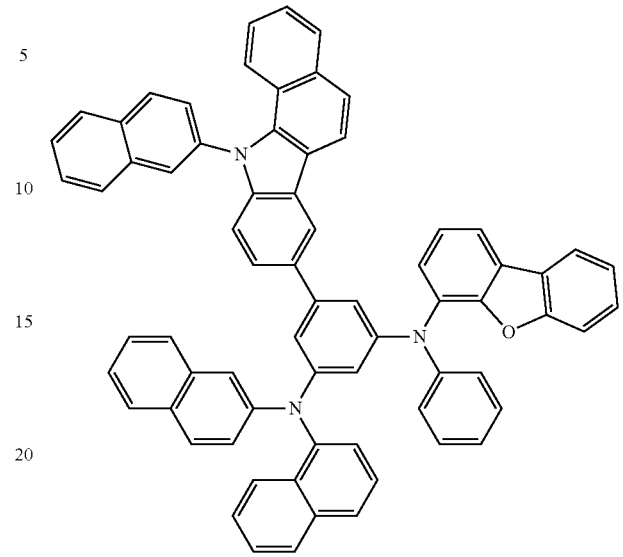
P-108
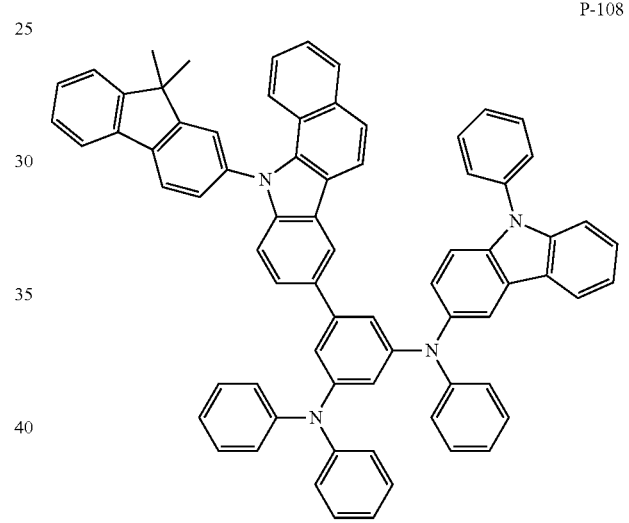
P-109
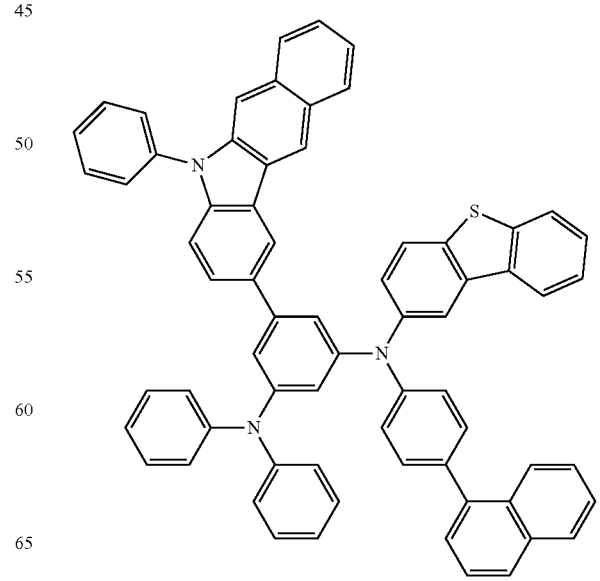

P-110
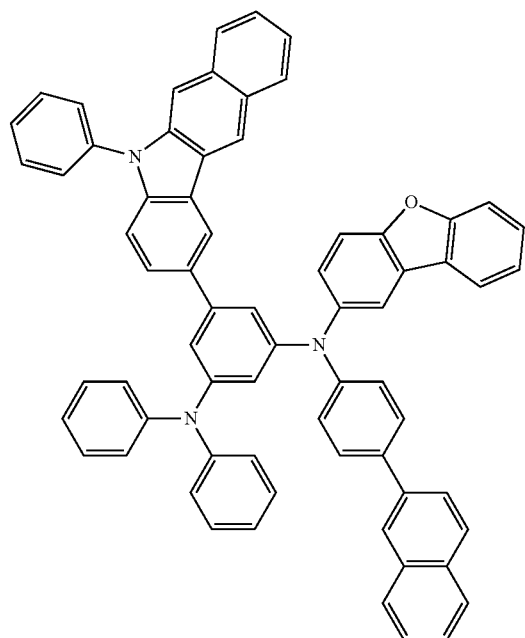
P-111
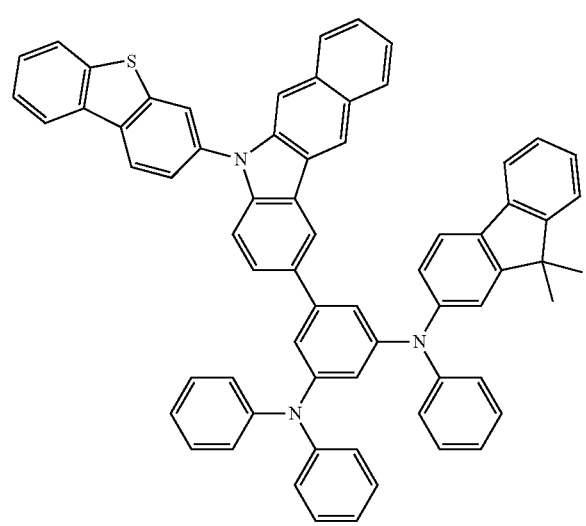
P-112
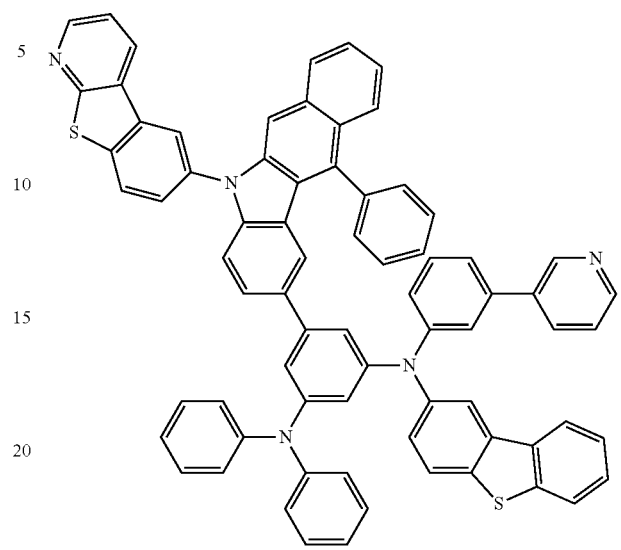
P-113
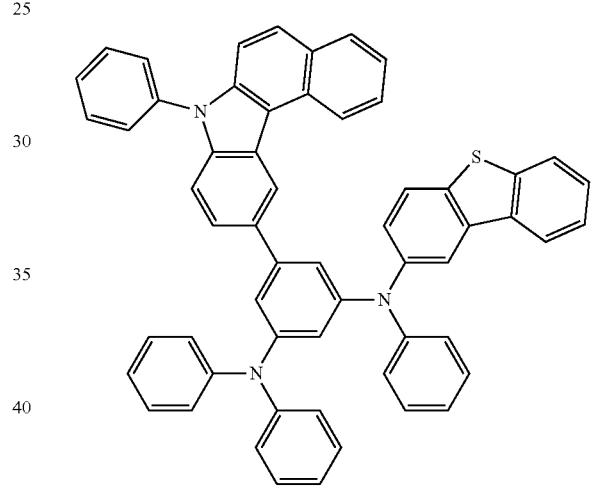
P-114
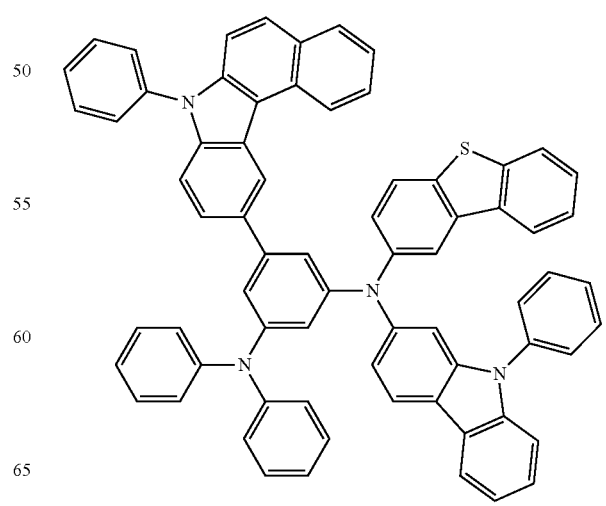

-continued
P-115
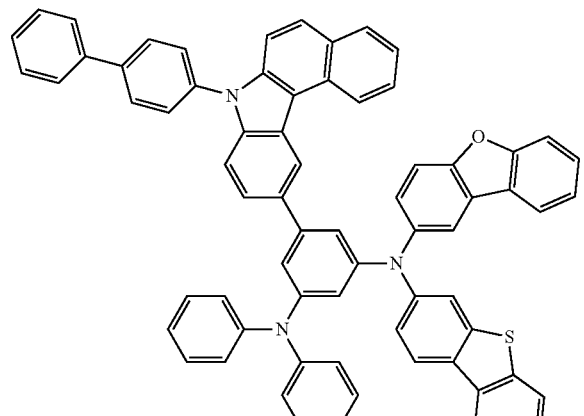
P-116
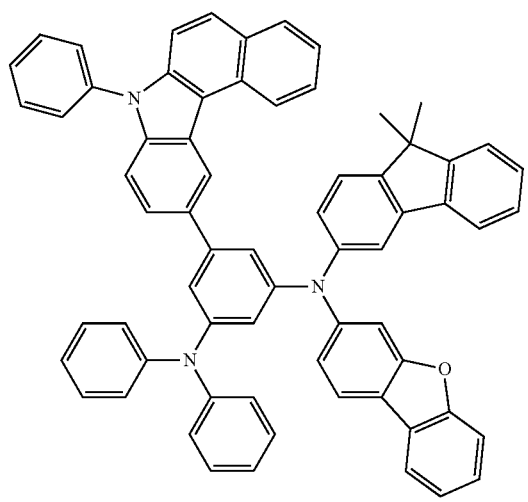
P-117
P-118
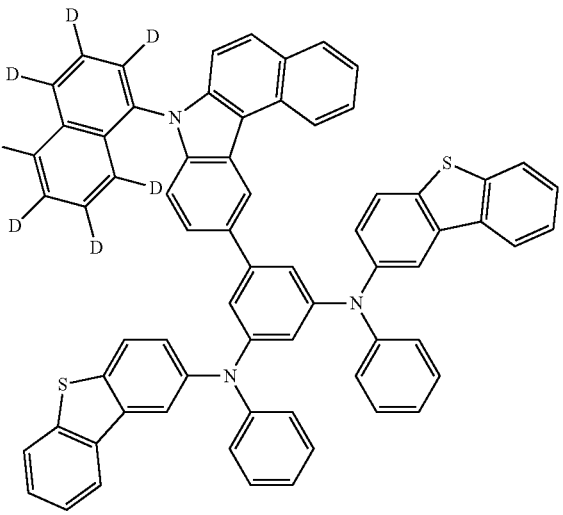
P-119
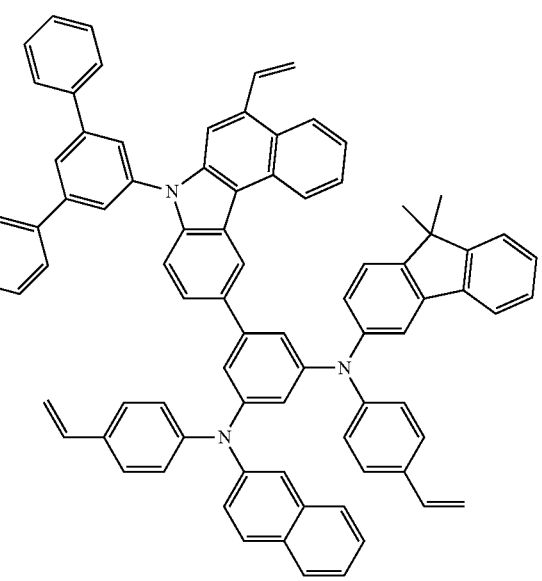

P-120
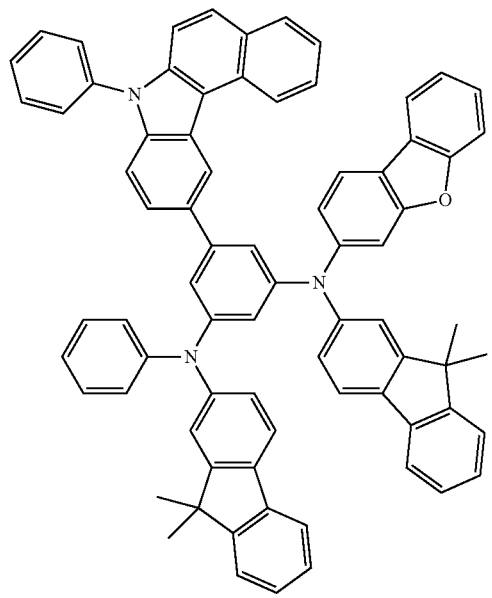
P-122
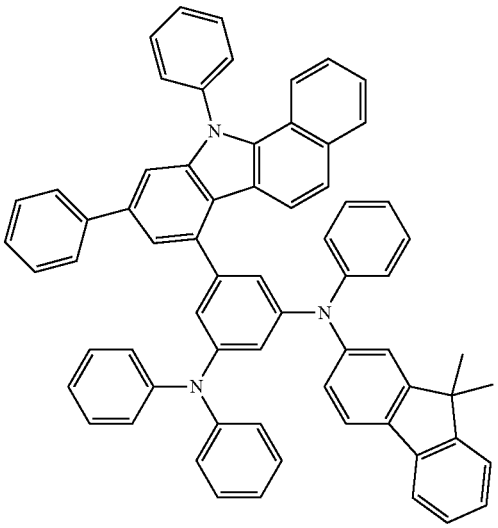
P-121
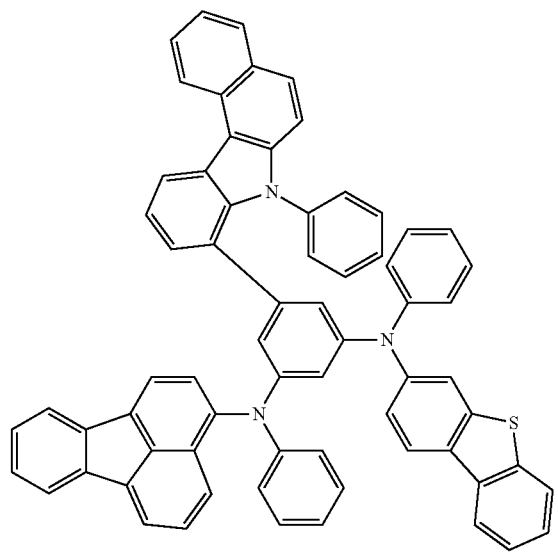
P-123
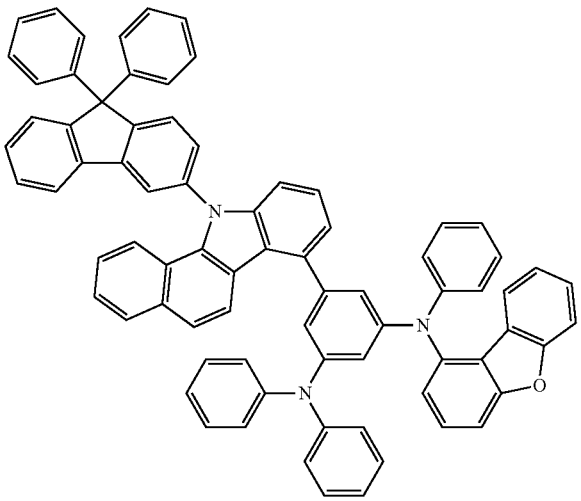

P-124
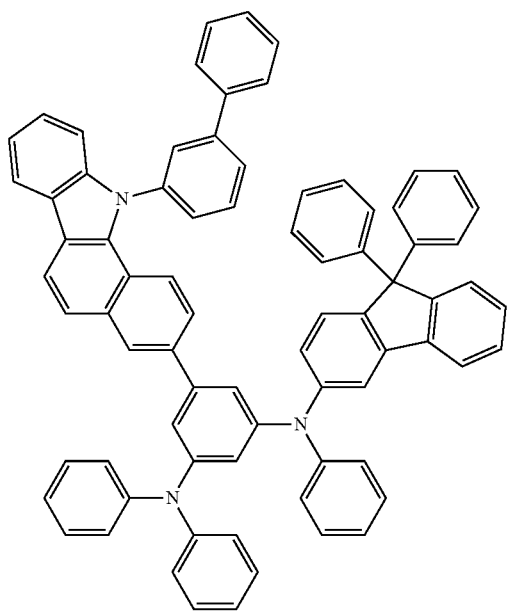
P-125
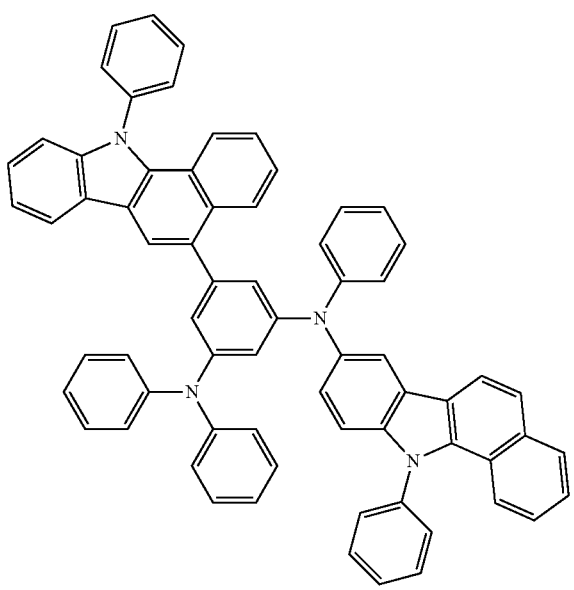
P-126
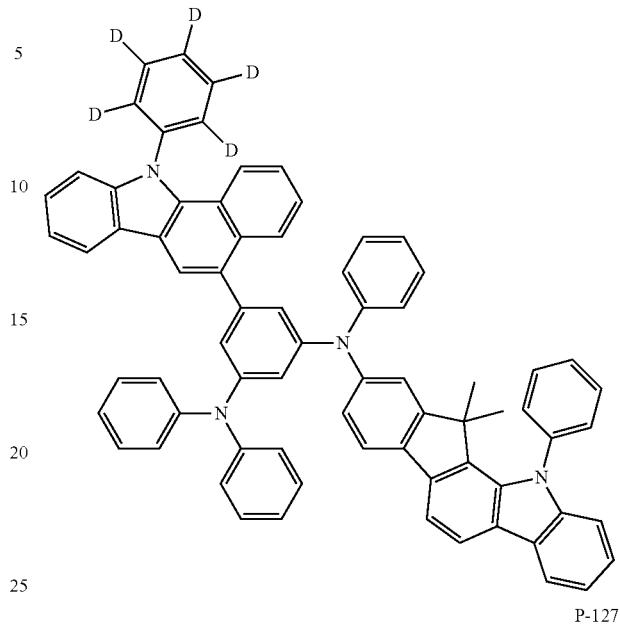
P-127
P-128
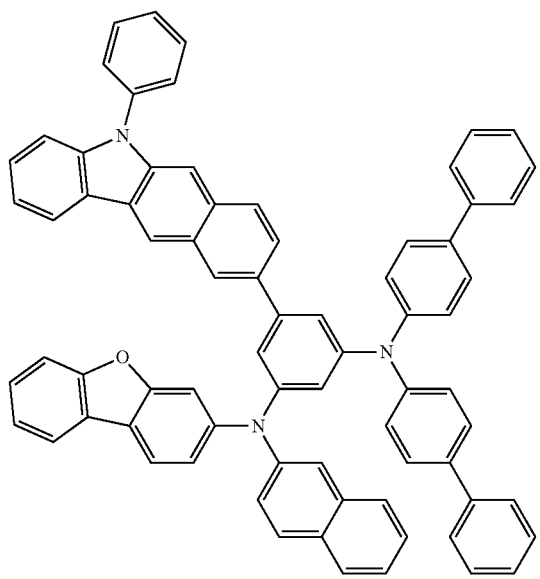

-continued
P-129
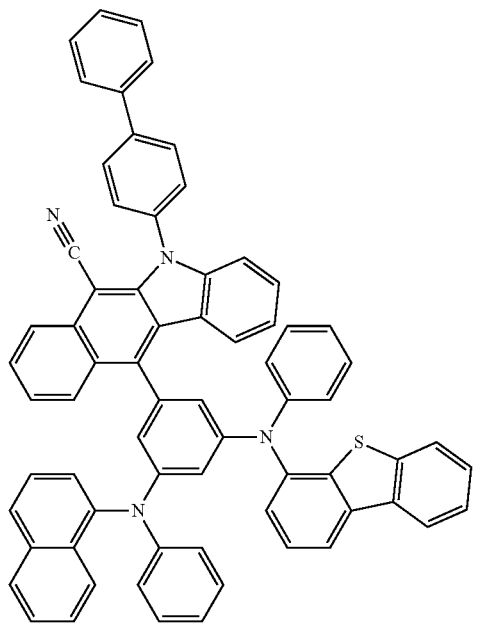
P-130
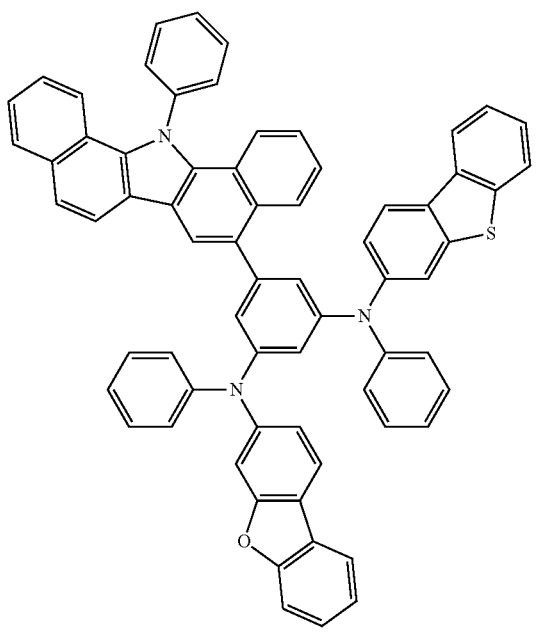
P-131
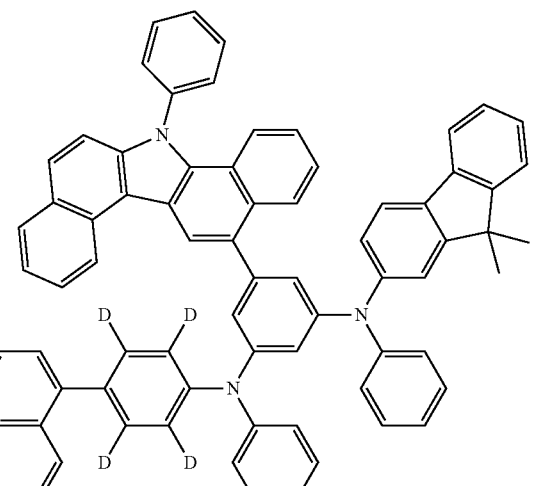
P-132
P-133

P-134

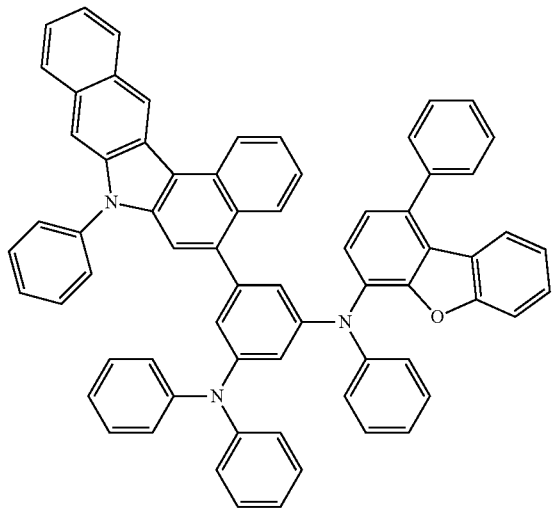

P-135

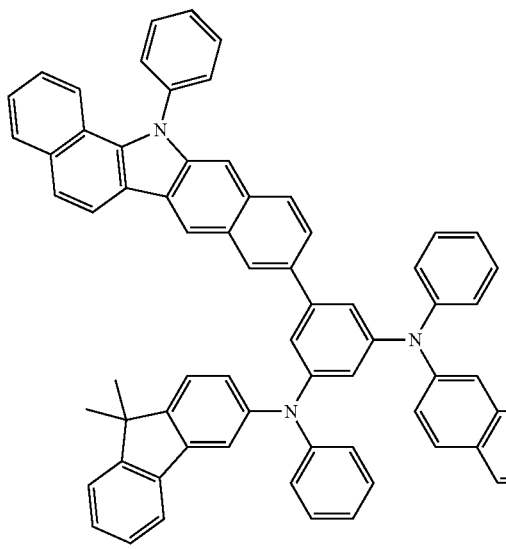

P-136

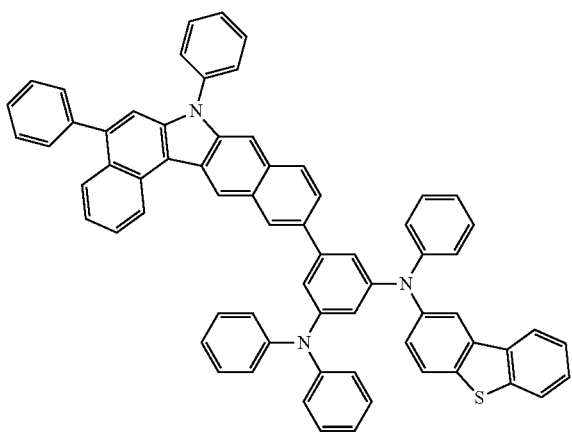

electrode. The organic material layer may comprise at least one layer of a hole injection layer, a hole transport layer, an emission-auxiliary layer, a light emitting layer, an electron transport-auxiliary layer, an electron transport layer and an electron injection layer, and at least one compound of the above compounds may be comprised in the organic material layer. That is, the organic material layer may be formed as a single compound or a mixture of two or more kinds represented by Formula 1. Preferably, a single compound or a mixture of two or more kinds may be comprised in a hole transport layer and/or an emission-auxiliary layer, or a hole transport layer and/or an emission-auxiliary layer may be formed by the compound.

Hereinafter, Synthesis method of the compound represented by Formula 1 according to one embodiment of the present invention and preparation method of an organic electric element will be described in detail by way of examples. However, the present invention is not limited to the following examples.

SYNTHESIS EXAMPLE

The compound (final products) represented by Formula 1 according to the present invention are synthesized by reacting Sub 1 and Sub 2 as shown in Reaction Scheme 1, but are not limited thereto.

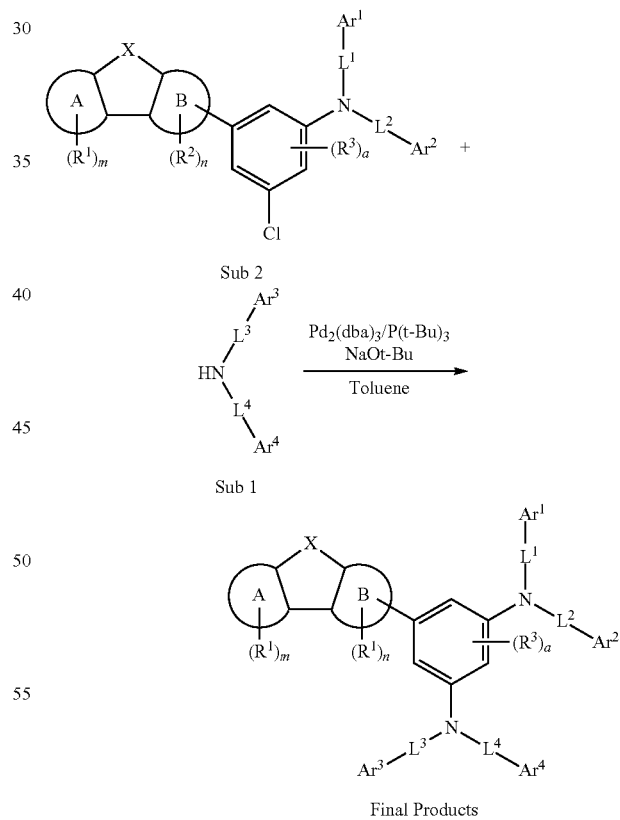

A ring, B ring, X, $R^1$ to $R^3$, $Ar^1$ to $Ar^4$, $L^1$ to $L^4$ and a are each identical as defined in formula 1 above.

I. Synthesis of Sub 1

Sub 1 of the Reaction Scheme 1 can be synthesized according to, but not limited to, the reaction route of the following Reaction Scheme 2.

In another aspect of the present invention, the present invention provides an organic electric element comprising a first electrode, a second electrode, and an organic material layer formed between the first electrode and the second <Reaction Scheme 2>

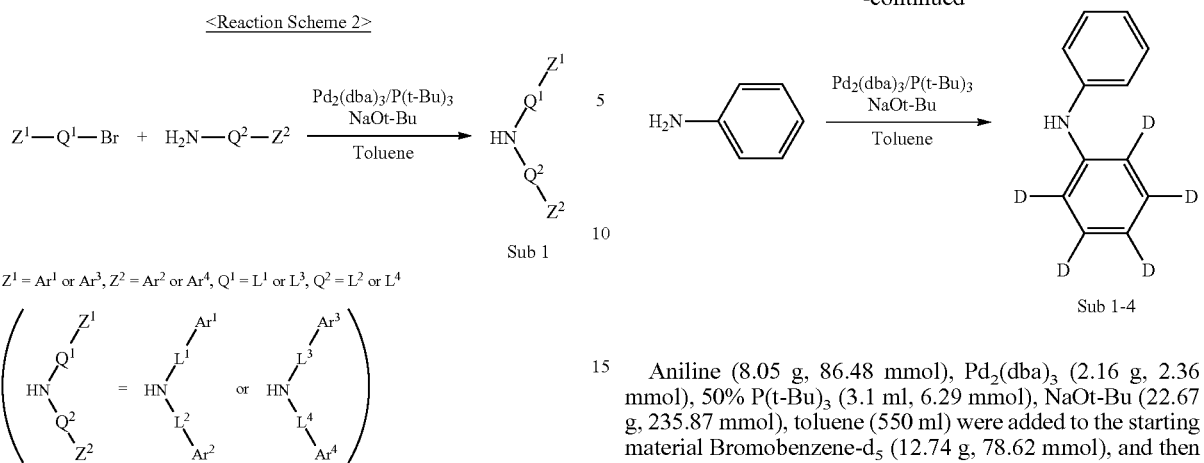

Sub 1

$Z^1 = Ar^1$ or $Ar^3$, $Z^2 = Ar^2$ or $Ar^4$, $Q^1 = L^1$ or $L^3$, $Q^2 = L^2$ or $L^4$

Synthesis Examples of compounds comprised in Sub 1 are as follows.

1. Synthesis Example of Sub 1-1

<Reaction Scheme 3>

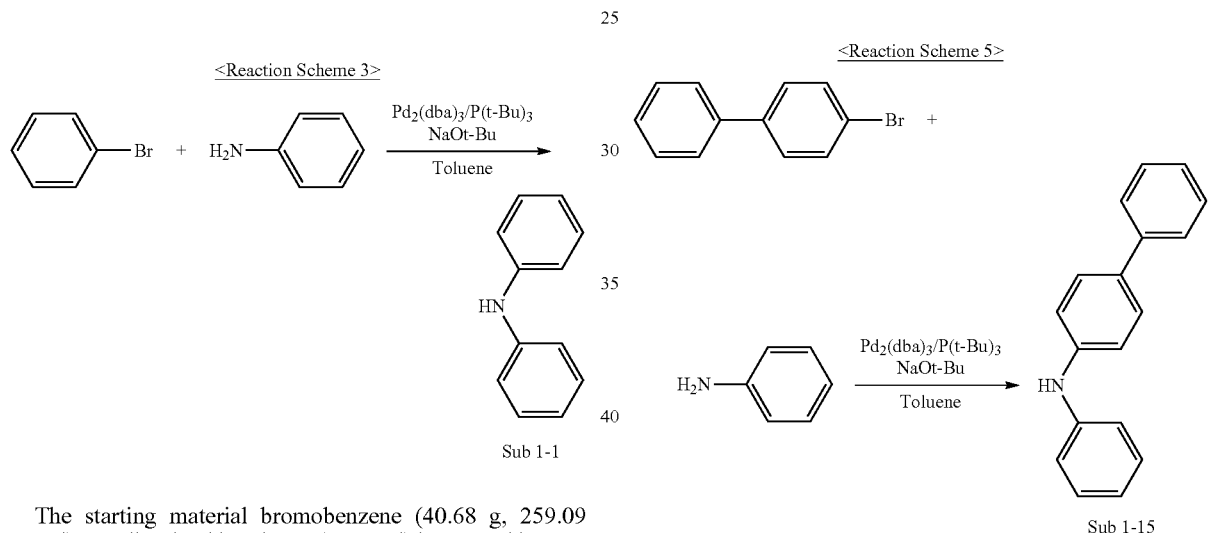

Sub 1-1

The starting material bromobenzene (40.68 g, 259.09 mmol) was dissolved in toluene (1360 ml) in a round bottom flask, and then aniline (26.54 g, 285.00 mmol), Pd$_2$(dba)$_3$ (7.12 g, 7.77 mmol), 50% P(t-Bu)$_3$ (10.1 ml, 20.73 mmol), NaOt-Bu (74.70 g, 777.28 mmol) were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 32.88 g (yield: 75%) of the product.

2. Synthesis Example of Sub 1-4

<Reaction Scheme 4>

Sub 1-4

Aniline (8.05 g, 86.48 mmol), Pd$_2$(dba)$_3$ (2.16 g, 2.36 mmol), 50% P(t-Bu)$_3$ (3.1 ml, 6.29 mmol), NaOt-Bu (22.67 g, 235.87 mmol), toluene (550 ml) were added to the starting material Bromobenzene-d$_5$ (12.74 g, 78.62 mmol), and then 10.82 g (yield: 79%) of the product was obtained by using the same manner as described above for the synthesis of Sub 1-1.

3. Synthesis Example of Sub 1-15

<Reaction Scheme 5>

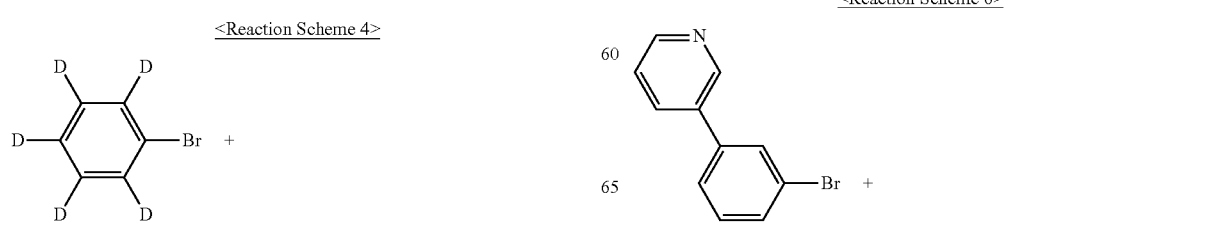

Sub 1-15

Aniline (10.39 g, 111.60 mmol), Pd$_2$(dba)$_3$ (2.79 g, 3.04 mmol), 50% P(t-Bu)$_3$ (4.0 ml, 8.12 mmol), NaOt-Bu (29.25 g, 304.38 mmol), toluene (710 ml) were added to the starting material 4-bromo-1,1'-biphenyl (23.65 g, 101.46 mmol), and then 20.66 g (yield: 83%) of the product was obtained by using the same manner as described above for the synthesis of Sub 1-1.

4. Synthesis Example of Sub 1-18

<Reaction Scheme 6>

-continued

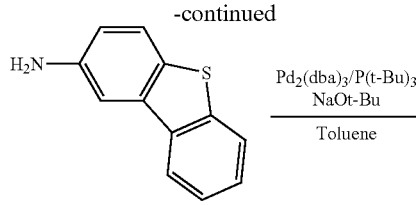

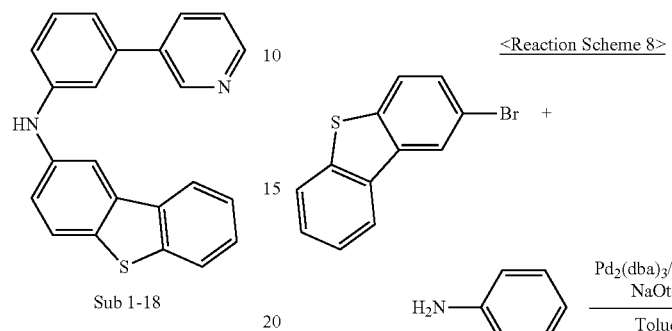

Sub 1-18

Dibenzo[b,d]thiophen-2-amine (9.86 g, 49.48 mmol), Pd$_2$(dba)$_3$ (1.24 g, 1.35 mmol), 50% P(t-Bu)$_3$ (1.8 ml, 3.60 mmol), NaOt-Bu (12.97 g, 134.95 mmol), toluene (315 ml) were added to the starting material 3-(3-bromophenyl)pyridine (10.53 g, 44.98 mmol), and then 11.26 g (yield: 71%) of the product was obtained by using the same manner as described above for the synthesis of Sub 1-1.

5. Synthesis Example of Sub 1-25

<Reaction Scheme 7>

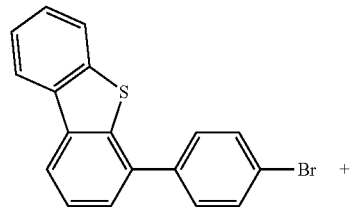

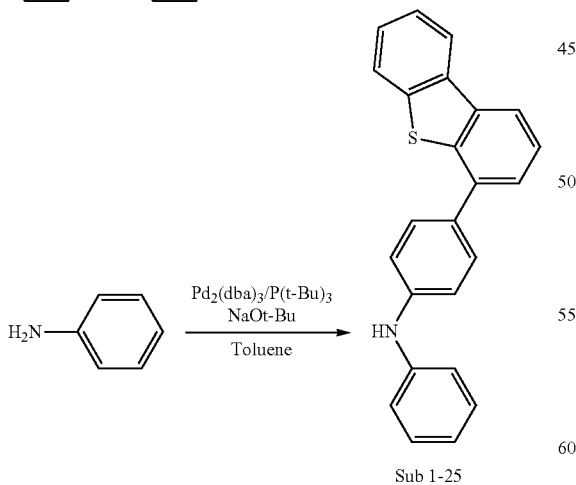

Sub 1-25

Aniline (3.80 g, 40.82 mmol), Pd$_2$(dba)$_3$ (1.02 g, 1.11 mmol), 50% P(t-Bu)$_3$ (1.4 ml, 2.97 mmol), NaOt-Bu (10.70 g, 111.33 mmol), toluene (260 ml) were added to the starting material 4-(4-bromophenyl)dibenzo[b,d]thiophene (12.59 g, 37.11 mmol), and then 10.43 g (yield: 80%) of the product was obtained by using the same manner as described above for the synthesis of Sub 1-1.

6. Synthesis Example of Sub 1-35

<Reaction Scheme 8>

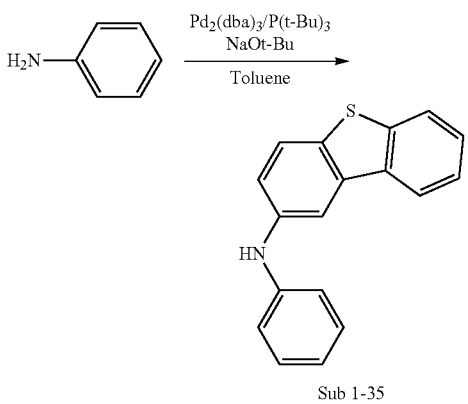

Sub 1-35

Aniline (14.84 g, 159.30 mmol), Pd$_2$(dba)$_3$ (3.98 g, 4.34 mmol), 50% P(t-Bu)$_3$ (5.6 ml, 11.59 mmol), NaOt-Bu (41.76 g, 434.47 mmol), toluene (760 ml) were added to the starting material 2-bromodibenzo[b,d]thiophene (38.11 g, 144.82 mmol), and then 30.71 g (yield: 77%) of the product was obtained by using the same manner as described above for the synthesis of Sub 1-1.

7. Synthesis Example of Sub 1-36

<Reaction Scheme 9>

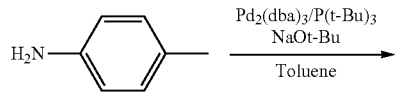

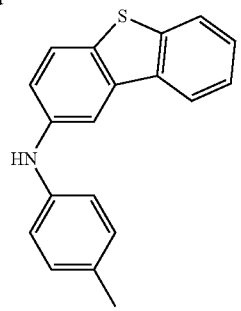

Sub 1-36 p-toluidine (5.62 g, 52.46 mmol), Pd₂(dba)₃ (1.31 g, 1.43 mmol), 50% P(t-Bu)₃ (1.9 ml, 3.82 mmol), NaOt-Bu (13.75 g, 143.07 mmol), toluene (335 ml) were added to the starting material 2-bromodibenzo[b,d]thiophene (12.55 g, 47.69 mmol), and then 10.21 g (yield: 74%) of the product was obtained by using the same manner as described above for the synthesis of Sub 1-1.

8. Synthesis Example of Sub 1-50

<Reaction Scheme 10>

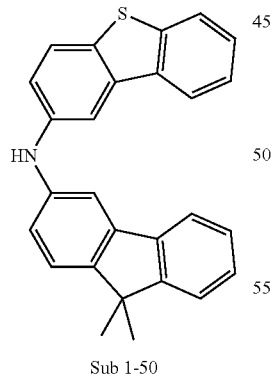

Sub 1-50

Dibenzo[b,d]thiophen-2-amine (17.52 g, 87.95 mmol), Pd₂(dba)₃ (2.20 g, 2.40 mmol), 50% P(t-Bu)₃ (3.1 ml, 6.40 mmol), NaOt-Bu (23.05 g, 239.85 mmol), toluene (560 ml) were added to the starting material 3-bromo-9,9-dimethyl-9H-fluorene (21.84 g, 79.95 mmol), and then 22.54 g (yield: 72%) of the product was obtained by using the same manner as described above for the synthesis of Sub 1-1.

9. Synthesis Example of Sub 1-63

<Reaction Scheme 11>

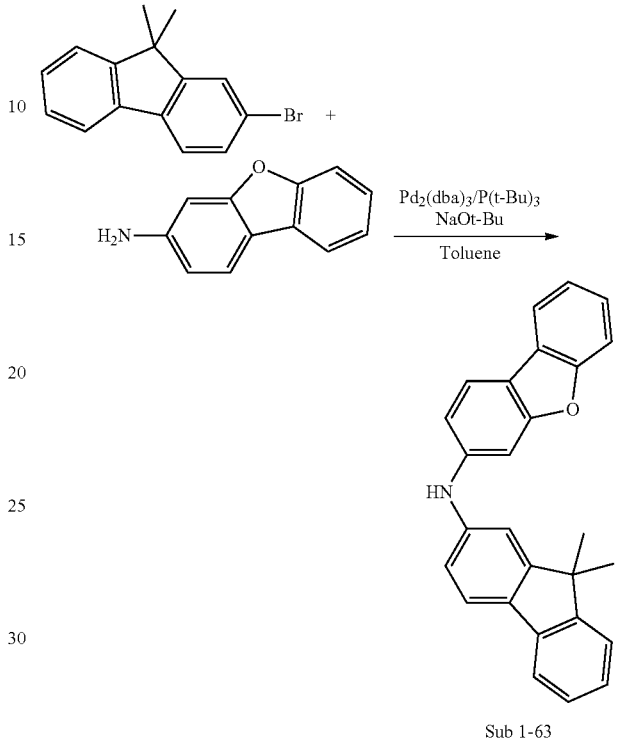

Sub 1-63

Dibenzo[b,d]furan-3-amine (7.69 g, 42.00 mmol), Pd₂(dba)₃ (1.05 g, 1.15 mmol), 50% P(t-Bu)₃ (1.5 ml, 3.05 mmol), NaOt-Bu (11.01 g, 114.54 mmol), toluene (270 ml) were added to the starting material 2-bromo-9,9-dimethyl-9H-fluorene (10.43 g, 38.18 mmol), and then 10.46 g (yield: 73%) of the product was obtained by using the same manner as described above for the synthesis of Sub 1-1.

10. Synthesis Example of Sub 1-78

<Reaction Scheme 12>

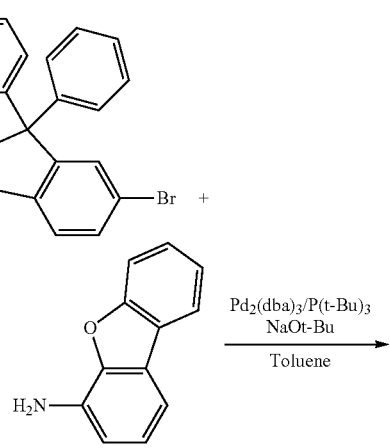

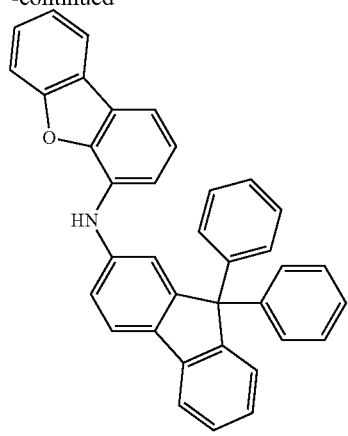

Sub 1-78

Dibenzo[b,d]furan-4-amine (6.15 g, 33.58 mmol), Pd$_2$(dba)$_3$ (0.84 g, 0.92 mmol), 50% P(t-Bu)$_3$ (1.2 ml, 2.44 mmol), NaOt-Bu (8.80 g, 91.59 mmol), toluene (215 ml) were added to the starting material 2-bromo-9,9-diphenyl-9H-fluorene (12.13 g, 30.53 mmol), and then 10.37 g (yield: 68%) of the product was obtained by using the same manner as described above for the synthesis of Sub 1-1.

11. Synthesis Example of Sub 1-80

<Reaction Scheme 13>

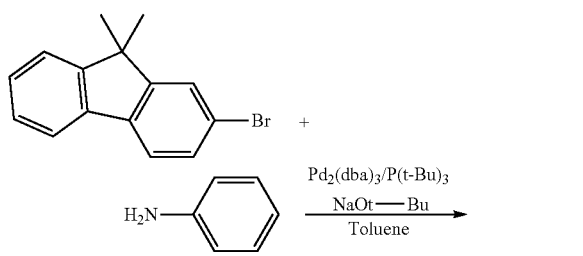

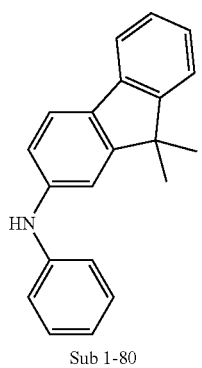

Sub 1-80

Aniline (4.69 g, 50.38 mmol), Pd$_2$(dba)$_3$ (1.26 g, 1.37 mmol), 50% P(t-Bu)$_3$ (1.8m, 3.66 mmol), NaOt-Bu (13.20 g, 137.39 mmol), toluene (320 ml) were added to the starting material 2-bromo-9,9-dimethyl-9H-fluorene (12.51 g, 45.80 mmol), and then 10.72 g (yield: 82%) of the product was obtained by using the same manner as described above for the synthesis of Sub 1-1.

12. Synthesis Example of Sub 1-93

<Reaction Scheme 14>

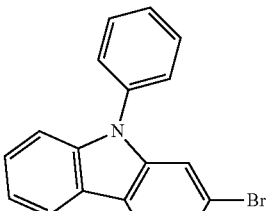

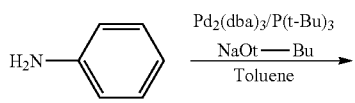

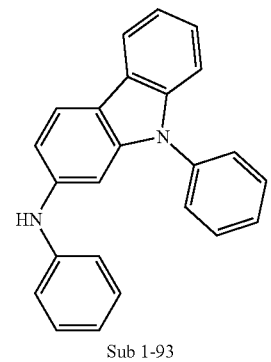

Sub 1-93

Aniline (4.68 g, 50.22 mmol), Pd$_2$(dba)$_3$ (1.25 g, 1.37 mmol), 50% P(t-Bu)$_3$ (1.8 ml, 3.65 mmol), NaOt-Bu (13.16 g, 136.96 mmol), toluene (320 ml) were added to the starting material 2-bromo-9-phenyl-9H-carbazole (14.71 g, 45.65 mmol), and then 10.99 g (yield: 72%) of the product was obtained by using the same manner as described above for the synthesis of Sub 1-1.

The compound belonging to Sub 1 may be, but not limited to, the following compounds, and Table 1 shows FD-MS (Field Desorption-Mass Spectrometry) values of compounds belonging to Sub 1.

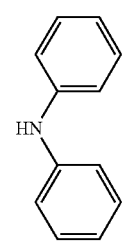

Sub 1-1

Sub 1-2
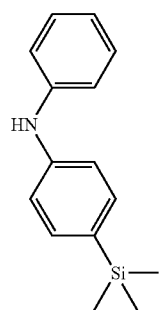
Sub 1-3
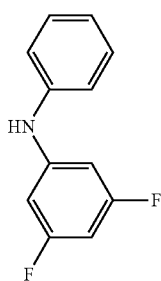
Sub 1-4
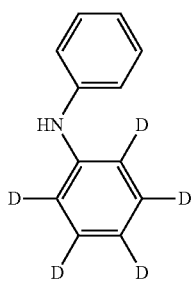
Sub 1-5
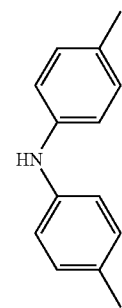
Sub 1-6
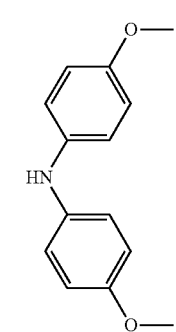
Sub 1-7
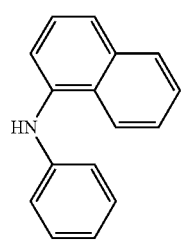
Sub 1-8
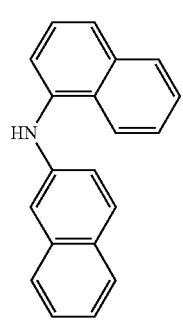
Sub 1-9
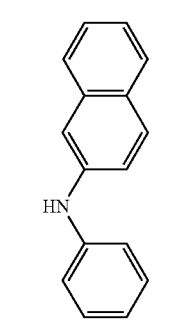
Sub 1-10
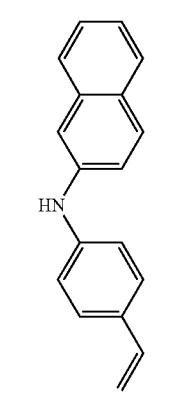
Sub 1-11

Sub 1-12
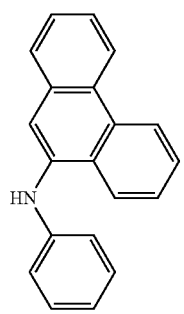
Sub 1-13
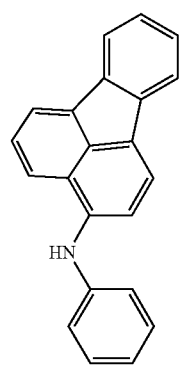
Sub 1-14
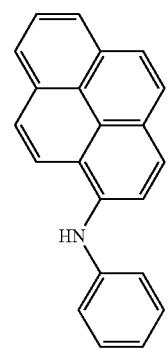
Sub 1-15
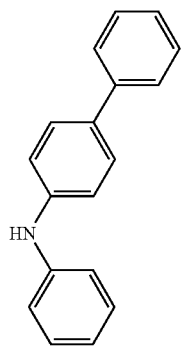
Sub 1-16
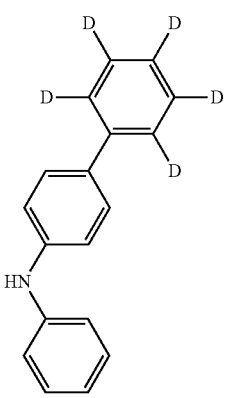
Sub 1-17
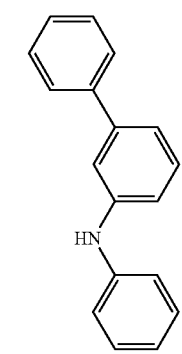
Sub 1-18
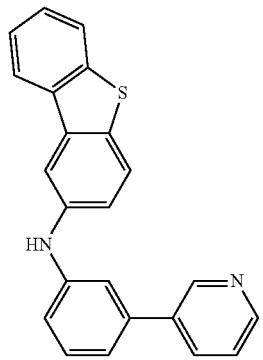
Sub 1-19
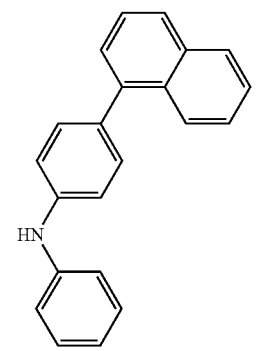

Sub 1-20
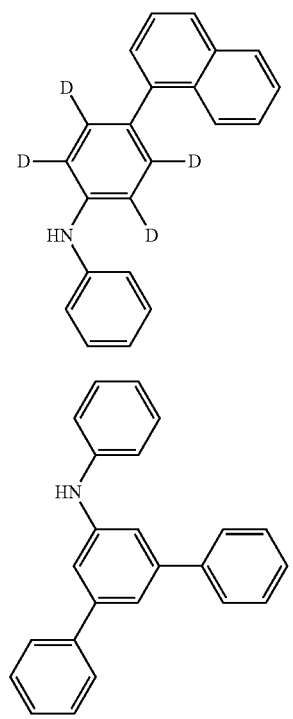
Sub 1-21
Sub 1-22
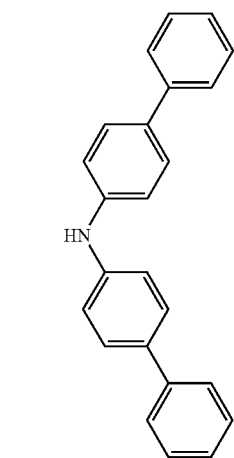
Sub 1-23
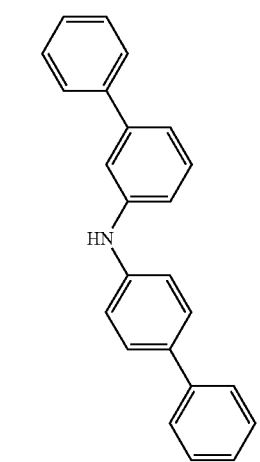
Sub 1-24
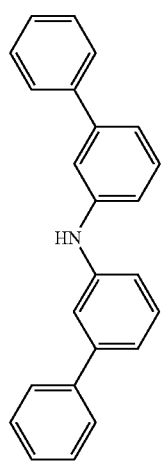
Sub 1-25
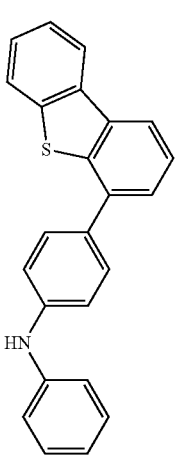
Sub 1-26
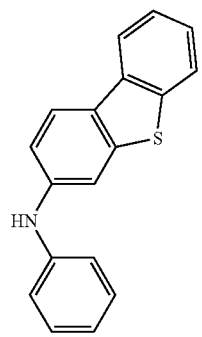

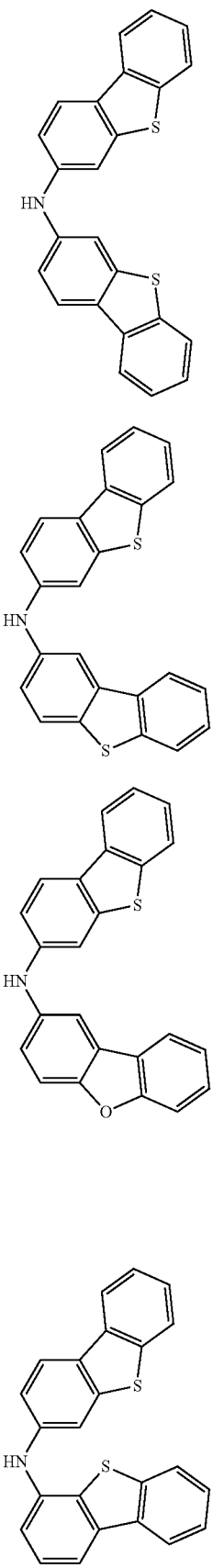
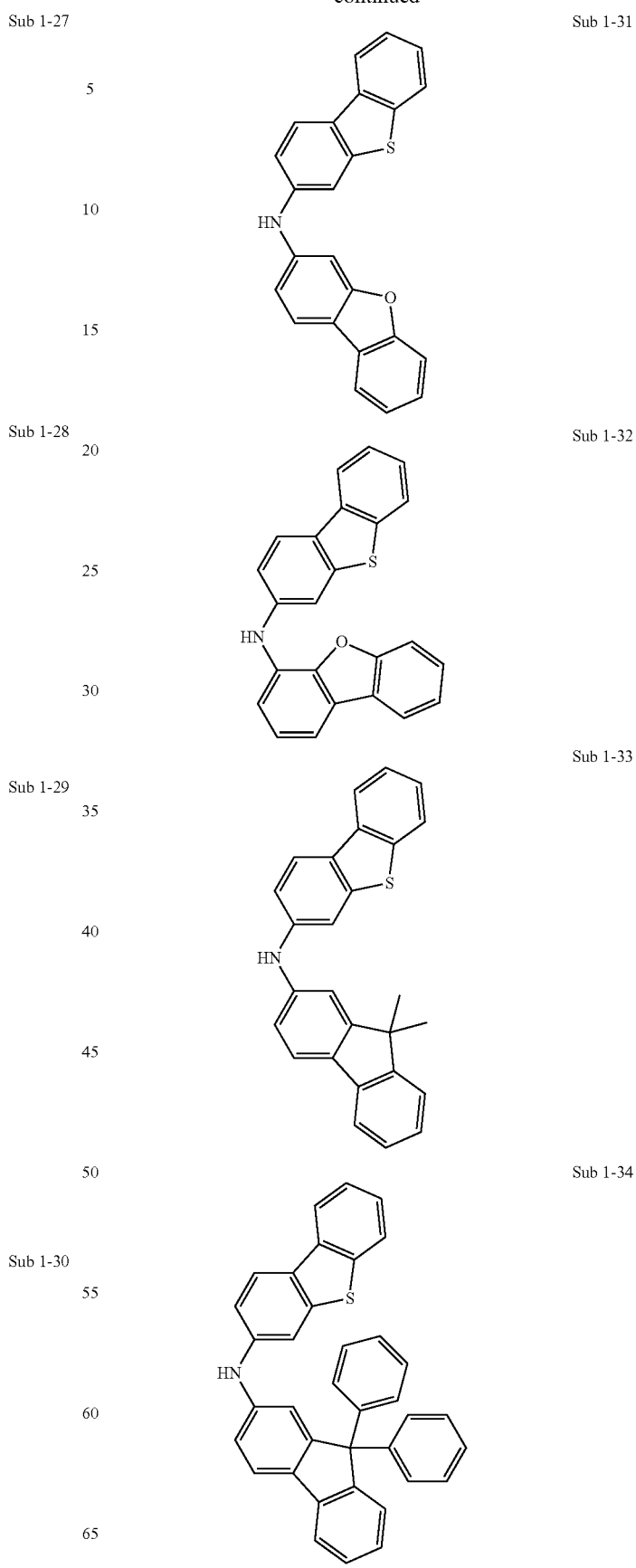

-continued
Sub 1-35
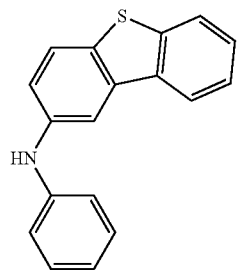
Sub 1-36
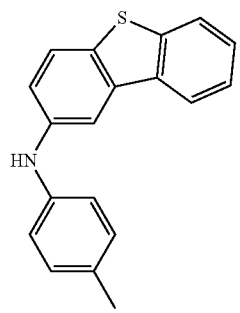
Sub 1-37
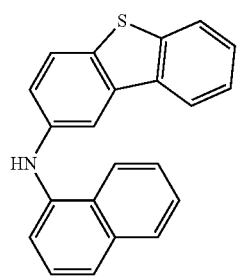
Sub 1-38
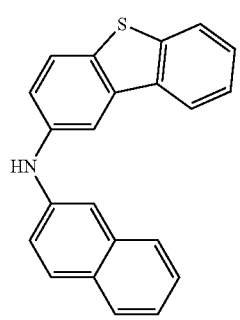
Sub 1-39
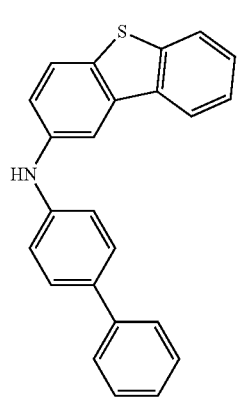
-continued
Sub 1-40
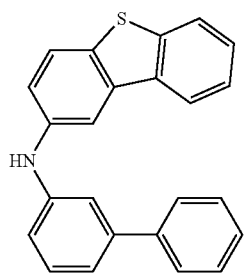
Sub 1-41
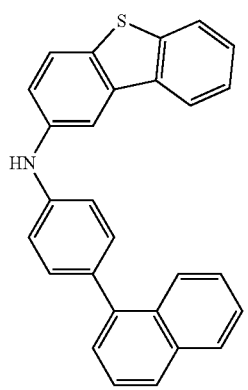
Sub 1-42
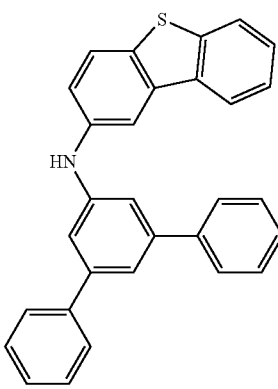
Sub 1-43
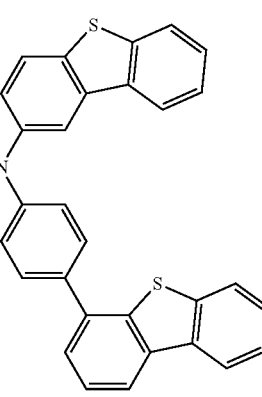

-continued
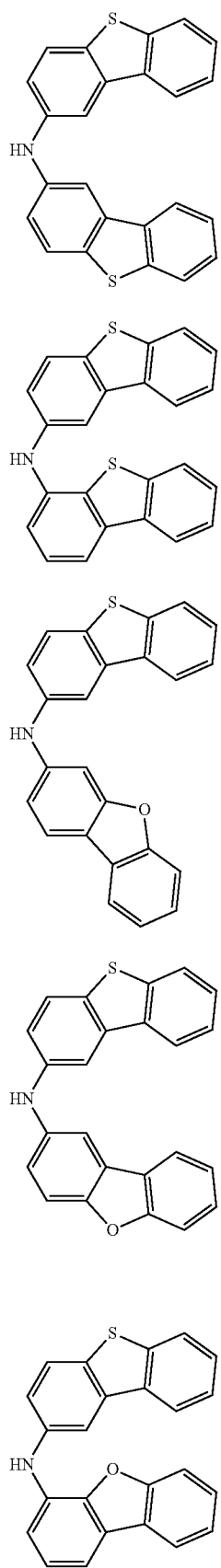
Sub 1-44
Sub 1-45
Sub 1-46
Sub 1-47
Sub 1-48
-continued
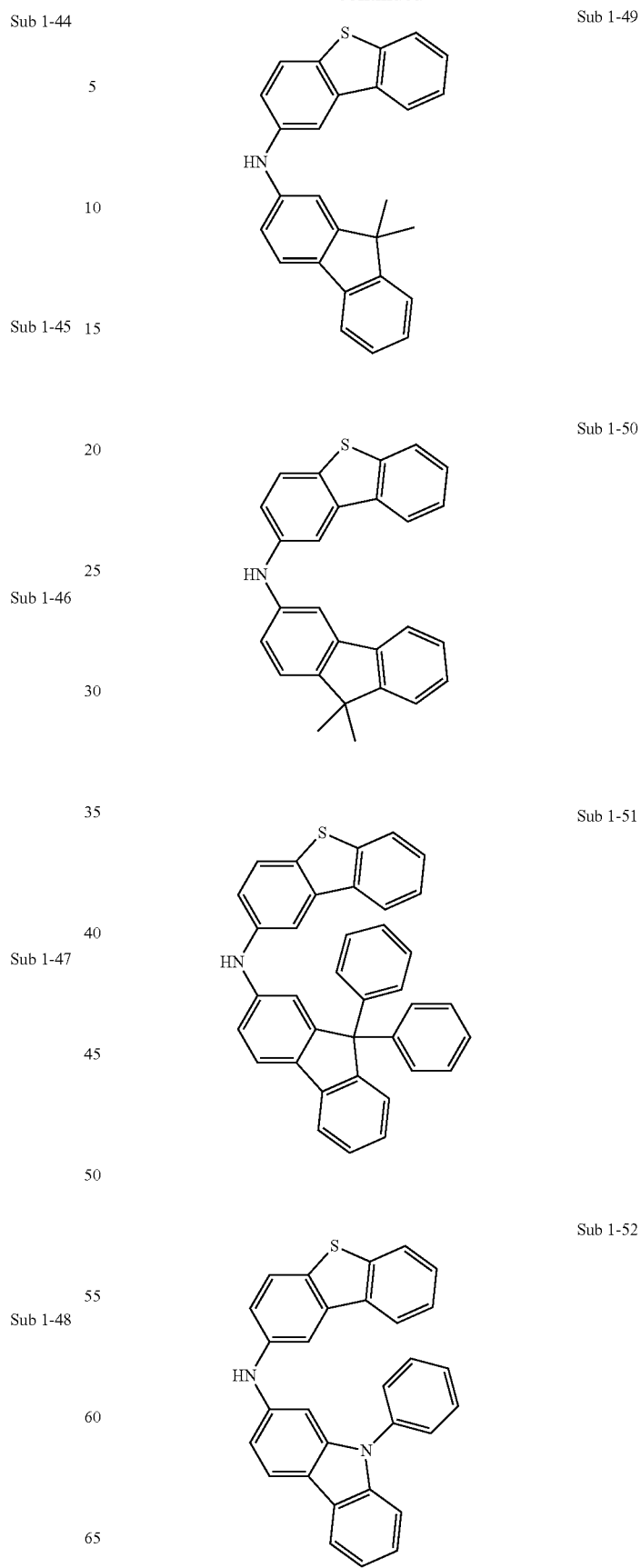
Sub 1-49
Sub 1-50
Sub 1-51
Sub 1-52

Sub 1-53
Sub 1-54
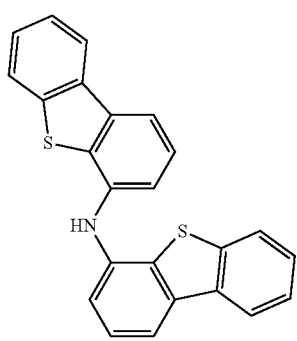
Sub 1-55
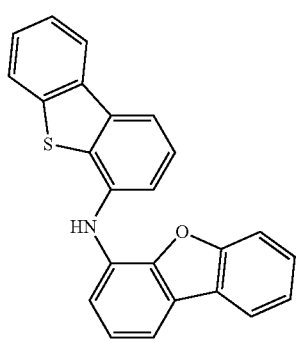
Sub 1-56
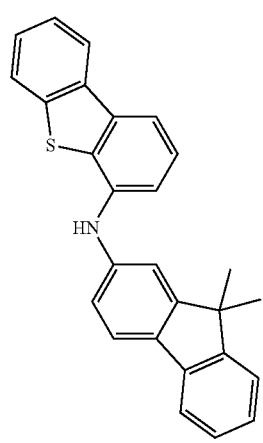
Sub 1-57
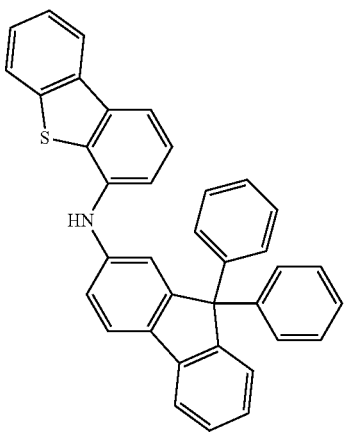
Sub 1-58
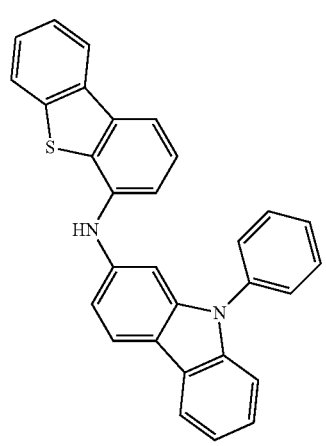
Sub 1-59
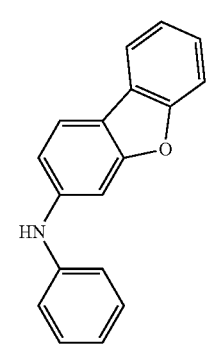
Sub 1-60
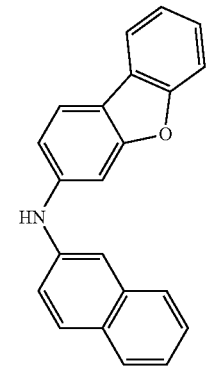

Sub 1-61
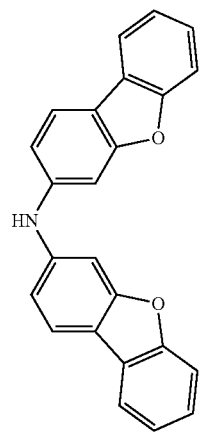
Sub 1-62
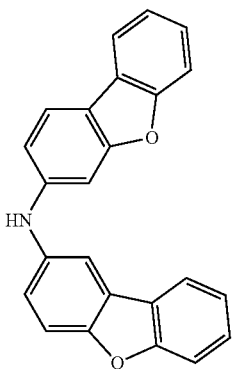
Sub 1-63
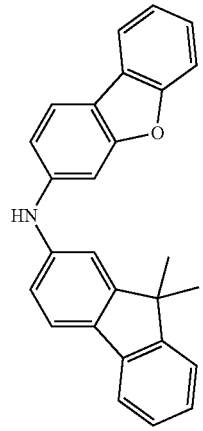
Sub 1-64
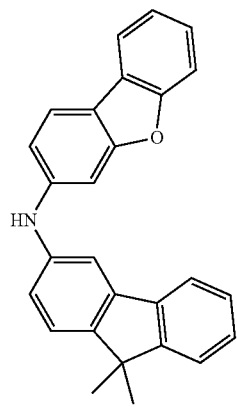
Sub 1-65
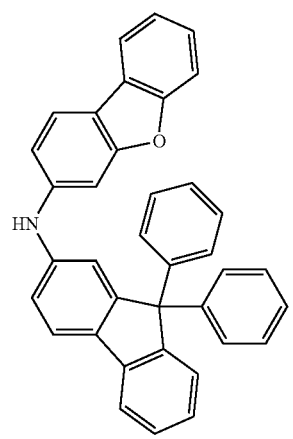
Sub 1-66
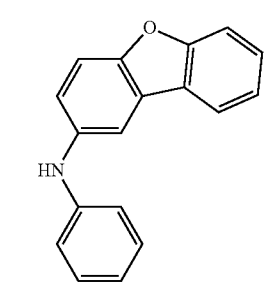
Sub 1-67
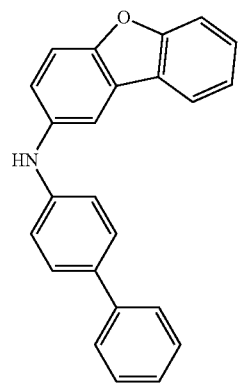
Sub 1-68

Sub 1-69
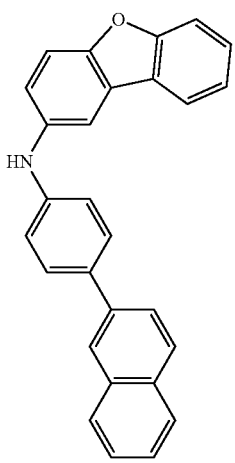
Sub 1-73
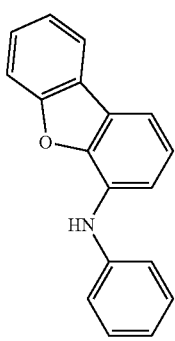
Sub 1-70
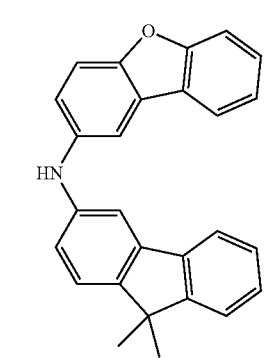
Sub 1-74
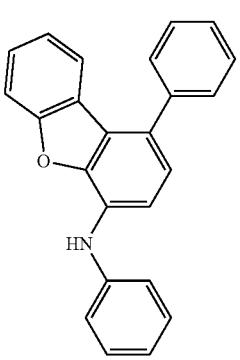
Sub 1-71
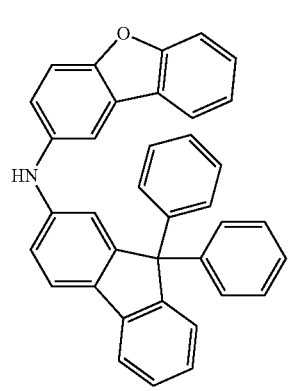
Sub 1-75
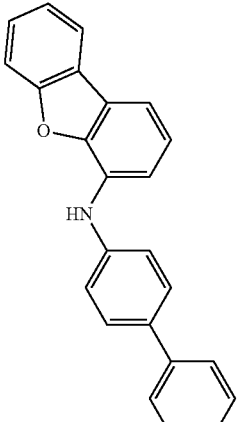
Sub 1-72
Sub 1-76
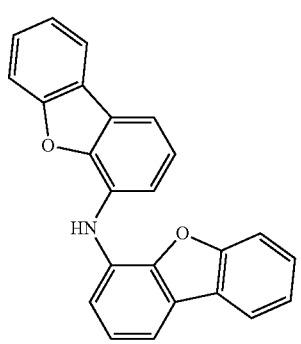

Sub 1-77
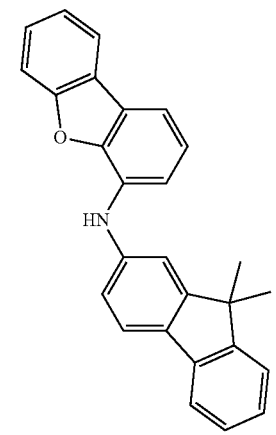
Sub 1-78
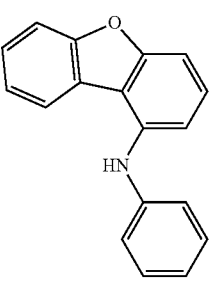
Sub 1-79
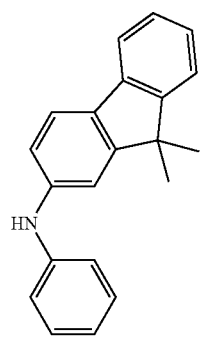
Sub 1-80
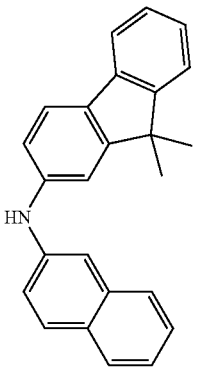
Sub 1-81
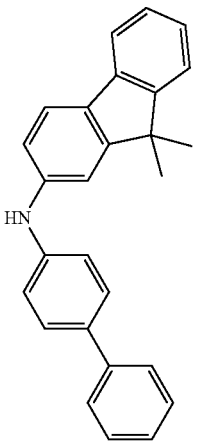
Sub 1-82
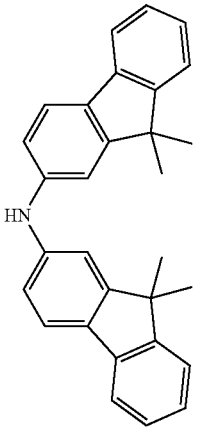
Sub 1-83
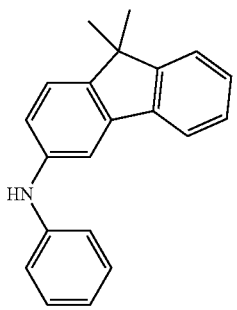
Sub 1-84

-continued
Sub 1-85
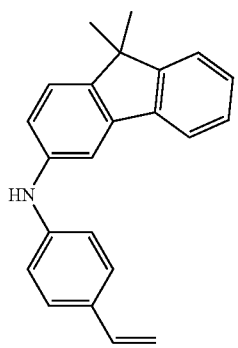
Sub 1-86
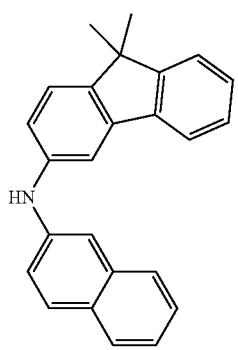
Sub 1-87
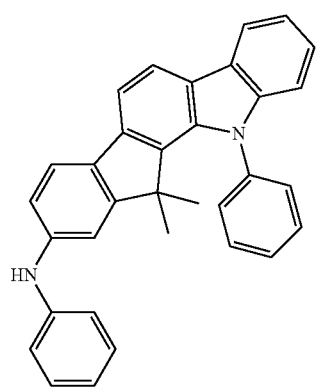
Sub 1-88
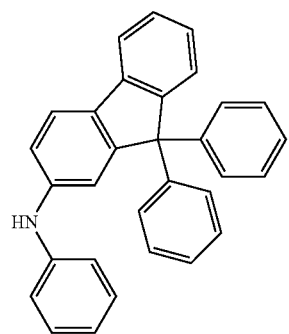
-continued
Sub 1-89
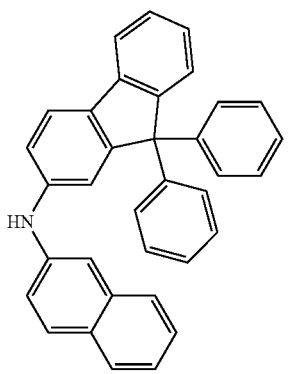
Sub 1-90
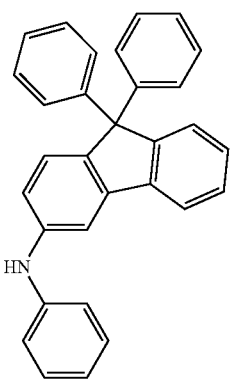
Sub 1-91
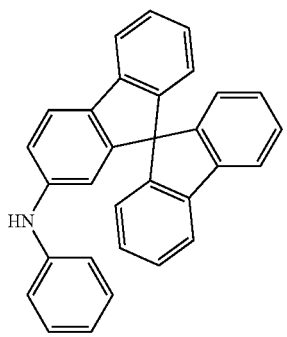
Sub 1-92
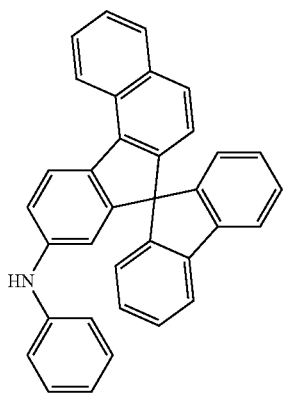

Sub 1-93
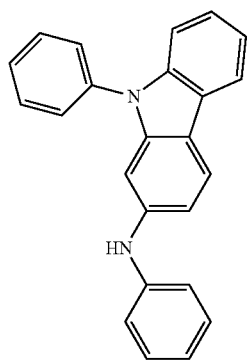
Sub 1-95
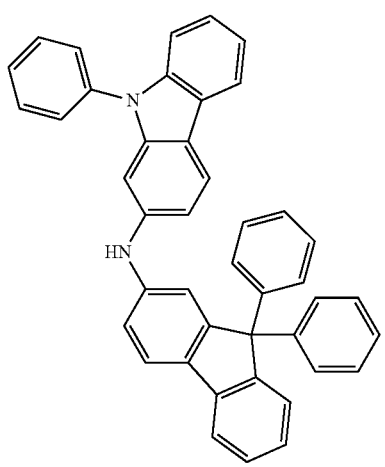
Sub 1-94
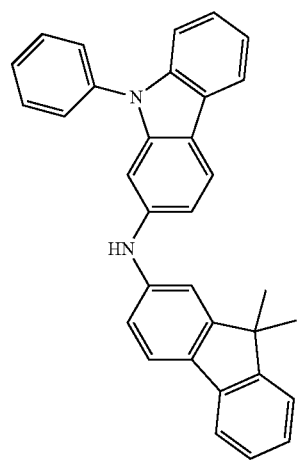
Sub 1-96
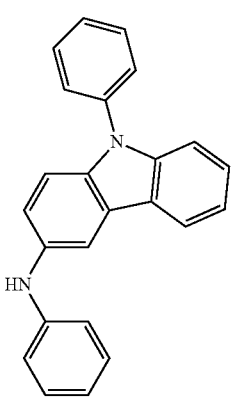

Sub 1-97
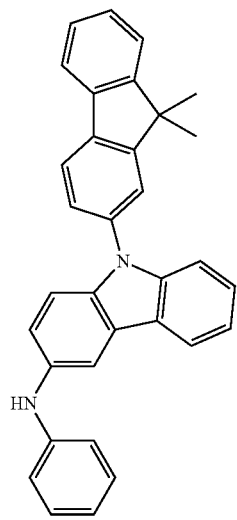
Sub 1-99
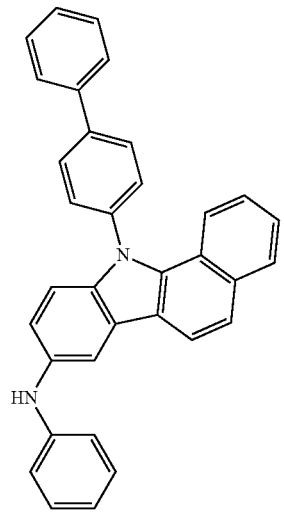
Sub 1-98
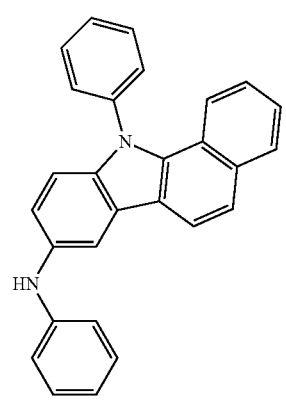
Sub 1-100
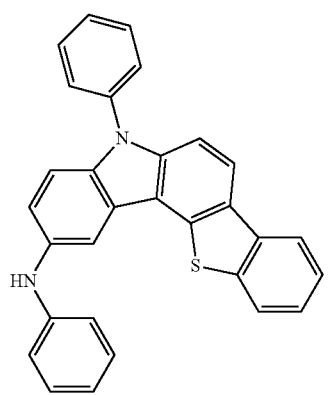

TABLE 1

| compound | FD-MS | compound | FD-MS |
|---|---|---|---|
| Sub 1-1 | m/z = 169.09($C_{12}H_{11}N$ = 169.22) | Sub 1-2 | m/z = 241.13($C_{15}H_{19}NSi$ = 241.40) |
| Sub 1-3 | m/z = 205.07($C_{12}H_9F_2N$ = 205.20) | Sub 1-4 | m/z = 174.12($C_{12}H_6D_5N$ = 174.25) |
| Sub 1-5 | m/z = 197.12($C_{14}H_{15}N$ = 197.28) | Sub 1-6 | m/z = 229.11($C_{14}H_{15}NO_2$ = 229.27) |
| Sub 1-7 | m/z = 219.10($C_{16}H_{13}N$ = 219.28) | Sub 1-8 | m/z = 269.12($C_{20}H_{15}N$ = 269.34) |
| Sub 1-9 | m/z = 219.10($C_{16}H_{13}N$ = 219.28) | Sub 1-10 | m/z = 245.12($C_{18}H_{15}N$ = 245.32) |
| Sub 1-11 | m/z = 220.10($C_{15}H_{12}N_2$ = 220.27) | Sub 1-12 | m/z = 269.12($C_{20}H_{15}N$ = 269.34) |
| Sub 1-13 | m/z = 293.12($C_{22}H_{15}N$ = 293.36) | Sub 1-14 | m/z = 293.12($C_{22}H_{15}N$ = 293.36) |
| Sub 1-15 | m/z = 245.12($C_{18}H_{15}N$ = 245.32) | Sub 1-16 | m/z = 250.15($C_{18}H_{10}D_5N$ = 250.35) |
| Sub 1-17 | m/z = 245.12($C_{18}H_{15}N$ = 245.32) | Sub 1-18 | m/z = 246.12($C_{17}H_{14}N_2$ = 246.31) |
| Sub 1-19 | m/z = 295.14($C_{22}H_{17}N$ = 295.38) | Sub 1-20 | m/z = 299.16($C_{22}H_{13}D_4N$ = 299.40) |
| Sub 1-21 | m/z = 321.15($C_{24}H_{19}N$ = 321.41) | Sub 1-22 | m/z = 321.15($C_{24}H_{19}N$ = 321.41) |
| Sub 1-23 | m/z = 321.15($C_{24}H_{19}N$ = 321.41) | Sub 1-24 | m/z = 321.15($C_{24}H_{19}N$ = 321.41) |
| Sub 1-25 | m/z = 351.11($C_{24}H_{17}NS$ = 351.46) | Sub 1-26 | m/z = 275.08($C_{18}H_{13}NS$ = 275.37) |
| Sub 1-27 | m/z = 381.06($C_{24}H_{15}NS_2$ = 381.51) | Sub 1-28 | m/z = 381.06($C_{24}H_{15}NS_2$ = 381.51) |
| Sub 1-29 | m/z = 381.06($C_{24}H_{15}NS_2$ = 381.51) | Sub 1-30 | m/z = 365.09($C_{24}H_{15}NOS$ = 365.45) |
| Sub 1-31 | m/z = 365.09($C_{24}H_{15}NOS$ = 365.45) | Sub 1-32 | m/z = 365.09($C_{24}H_{15}NOS$ = 365.45) |
| Sub 1-33 | m/z = 391.14($C_{27}H_{21}NS$ = 391.53) | Sub 1-34 | m/z = 515.17($C_{37}H_{25}NS$ = 515.67) |
| Sub 1-35 | m/z = 275.08($C_{18}H_{13}NS$ = 275.37) | Sub 1-36 | m/z = 289.09($C_{19}H_{15}NS$ = 289.39) |
| Sub 1-37 | m/z = 325.09($C_{22}H_{15}NS$ = 325.43) | Sub 1-38 | m/z = 325.09($C_{22}H_{15}NS$ = 325.43) |
| Sub 1-39 | m/z = 351.11($C_{24}H_{17}NS$ = 351.46) | Sub 1-40 | m/z = 351.11($C_{24}H_{17}NS$ = 351.46) |
| Sub 1-41 | m/z = 401.12($C_{28}H_{19}NS$ = 401.52) | Sub 1-42 | m/z = 427.14($C_{30}H_{21}NS$ = 427.56) |
| Sub 1-43 | m/z = 457.10($C_{30}H_{19}NS_2$ = 457.61) | Sub 1-44 | m/z = 381.06($C_{24}H_{15}NS_2$ = 381.51) |
| Sub 1-45 | m/z = 381.06($C_{24}H_{15}NS_2$ = 381.51) | Sub 1-46 | m/z = 365.09($C_{24}H_{15}NOS$ = 365.45) |
| Sub 1-47 | m/z = 365.09($C_{24}H_{15}NOS$ = 365.45) | Sub 1-48 | m/z = 365.09($C_{24}H_{15}NOS$ = 365.45) |
| Sub 1-49 | m/z = 391.14($C_{27}H_{21}NS$ = 391.53) | Sub 1-50 | m/z = 391.14($C_{27}H_{21}NS$ = 391.53) |
| Sub 1-51 | m/z = 515.17($C_{37}H_{25}NS$ = 515.67) | Sub 1-52 | m/z = 440.13($C_{30}H_{20}N_2S$ = 440.56) |
| Sub 1-53 | m/z = 275.08($C_{18}H_{13}NS$ = 275.37) | Sub 1-54 | m/z = 381.06($C_{24}H_{15}NS_2$ = 381.51) |
| Sub 1-55 | m/z = 365.09($C_{24}H_{15}NOS$ = 365.45) | Sub 1-56 | m/z = 391.14($C_{27}H_{21}NS$ = 391.53) |
| Sub 1-57 | m/z = 515.17($C_{37}H_{25}NS$ = 515.67) | Sub 1-58 | m/z = 440.13($C_{30}H_{20}N_2S$ = 440.56) |
| Sub 1-59 | m/z = 259.10($C_{18}H_{13}NO$ = 259.30) | Sub 1-60 | m/z = 309.12($C_{22}H_{15}NO$ = 309.36) |
| Sub 1-61 | m/z = 349.11($C_{24}H_{15}NO_2$ = 349.38) | Sub 1-62 | m/z = 349.11($C_{24}H_{15}NO_2$ = 349.38) |
| Sub 1-63 | m/z = 375.16($C_{27}H_{21}NO$ = 375.46) | Sub 1-64 | m/z = 375.16($C_{27}H_{21}NO$ = 375.46) |
| Sub 1-65 | m/z = 499.19($C_{37}H_{25}NO$ = 499.60) | Sub 1-66 | m/z = 259.10($C_{18}H_{13}NO$ = 259.30) |
| Sub 1-67 | m/z = 273.12($C_{19}H_{15}NO$ = 273.33) | Sub 1-68 | m/z = 335.13($C_{24}H_{17}NO$ = 335.40) |
| Sub 1-69 | m/z = 385.15($C_{28}H_{19}NO$ = 385.46) | Sub 1-70 | m/z = 375.16($C_{27}H_{21}NO$ = 375.46) |
| Sub 1-71 | m/z = 375.16($C_{27}H_{21}NO$ = 375.46) | Sub 1-72 | m/z = 499.19($C_{37}H_{25}NO$ = 499.60) |
| Sub 1-73 | m/z = 259.10($C_{18}H_{13}NO$ = 259.30) | Sub 1-74 | m/z = 335.13($C_{24}H_{17}NO$ = 335.40) |
| Sub 1-75 | m/z = 335.13($C_{24}H_{17}NO$ = 335.40) | Sub 1-76 | m/z = 349.11($C_{24}H_{15}NO_2$ = 349.38) |
| Sub 1-77 | m/z = 375.16($C_{27}H_{21}NO$ = 375.46) | Sub 1-78 | m/z = 499.19($C_{37}H_{25}NO$ = 499.60) |
| Sub 1-79 | m/z = 259.10($C_{18}H_{13}NO$ = 259.30) | Sub 1-80 | m/z = 285.15($C_{21}H_{19}N$ = 285.38) |
| Sub 1-81 | m/z = 335.17($C_{25}H_{21}N$ = 335.44) | Sub 1-82 | m/z = 361.18($C_{27}H_{23}N$ = 361.48) |
| Sub 1-83 | m/z = 401.21($C_{30}H_{27}N$ = 401.54) | Sub 1-84 | m/z = 285.15($C_{21}H_{19}N$ = 285.38) |
| Sub 1-85 | m/z = 311.17($C_{23}H_{21}N$ = 311.42) | Sub 1-86 | m/z = 335.17($C_{25}H_{21}N$ = 335.44) |
| Sub 1-87 | m/z = 450.21($C_{33}H_{26}N_2$ = 450.57) | Sub 1-88 | m/z = 409.18($C_{31}H_{23}N$ = 409.52) |
| Sub 1-89 | m/z = 459.20($C_{35}H_{25}N$ = 459.58) | Sub 1-90 | m/z = 409.18($C_{31}H_{23}N$ = 409.52) |
| Sub 1-91 | m/z = 407.17($C_{31}H_{21}N$ = 407.51) | Sub 1-92 | m/z = 457.18($C_{35}H_{23}N$ = 457.56) |
| Sub 1-93 | m/z = 334.15($C_{24}H_{18}N_2$ = 334.41) | Sub 1-94 | m/z = 450.21($C_{33}H_{26}N_2$ = 450.57) |
| Sub 1-95 | m/z = 574.24($C_{43}H_{30}N_2$ = 574.71) | Sub 1-96 | m/z = 334.15($C_{24}H_{18}N_2$ = 334.41) |
| Sub 1-97 | m/z = 450.21($C_{33}H_{26}N_2$ = 450.57) | Sub 1-98 | m/z = 384.16($C_{28}H_{20}N_2$ = 384.47) |
| Sub 1-99 | m/z = 460.19($C_{34}H_{24}N_2$ = 460.57) | Sub 1-100 | m/z = 440.13($C_{30}H_{20}N_2S$ = 440.56) |

II. Synthesis of Sub 2

Sub 2 of the Reaction Scheme 1 can be synthesized according to, but not limited to, the reaction route of the following Reaction Schemes 12 to 17.

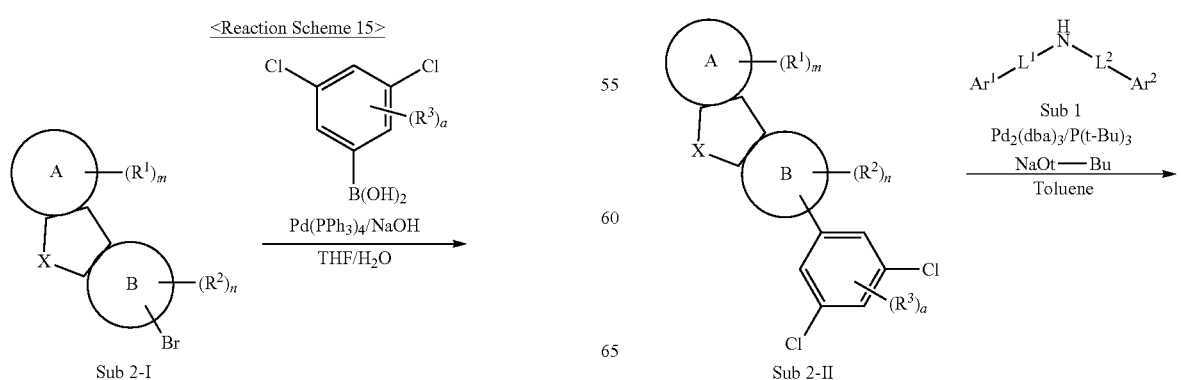

105
-continued
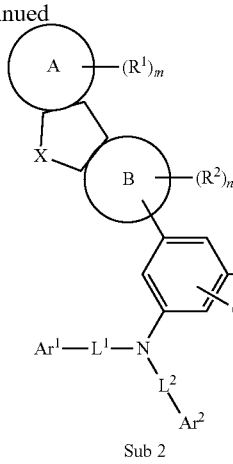
Sub 2
106
Synthesis Examples of compounds comprised in Sub 2 are as follows.
1. Synthesis Example of Sub 2-1
<Reaction Scheme 18>
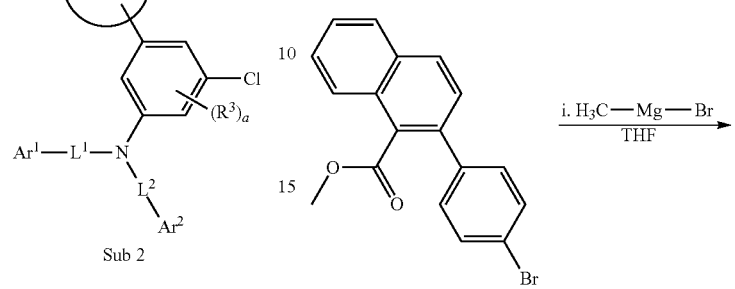
<Reaction Scheme 16>
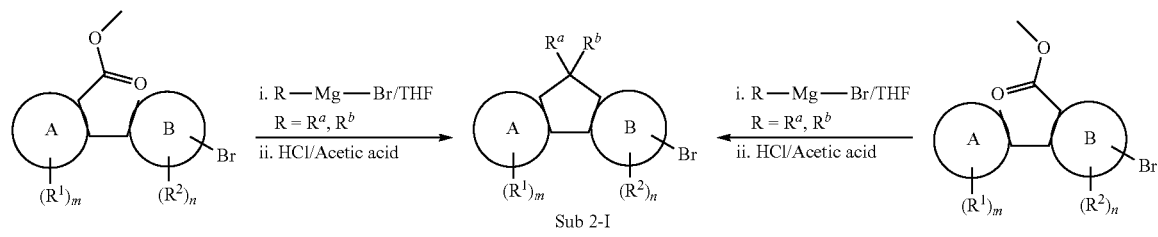
where X is $CR^aR^b$
<Reaction Scheme 17>
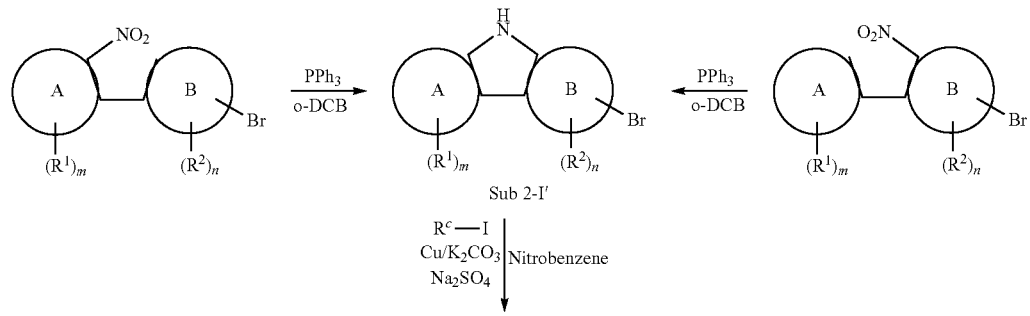
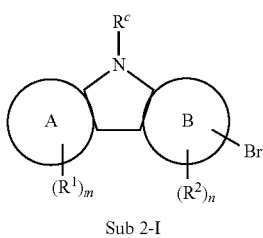
Sub 2-I
where X is $NR^c$

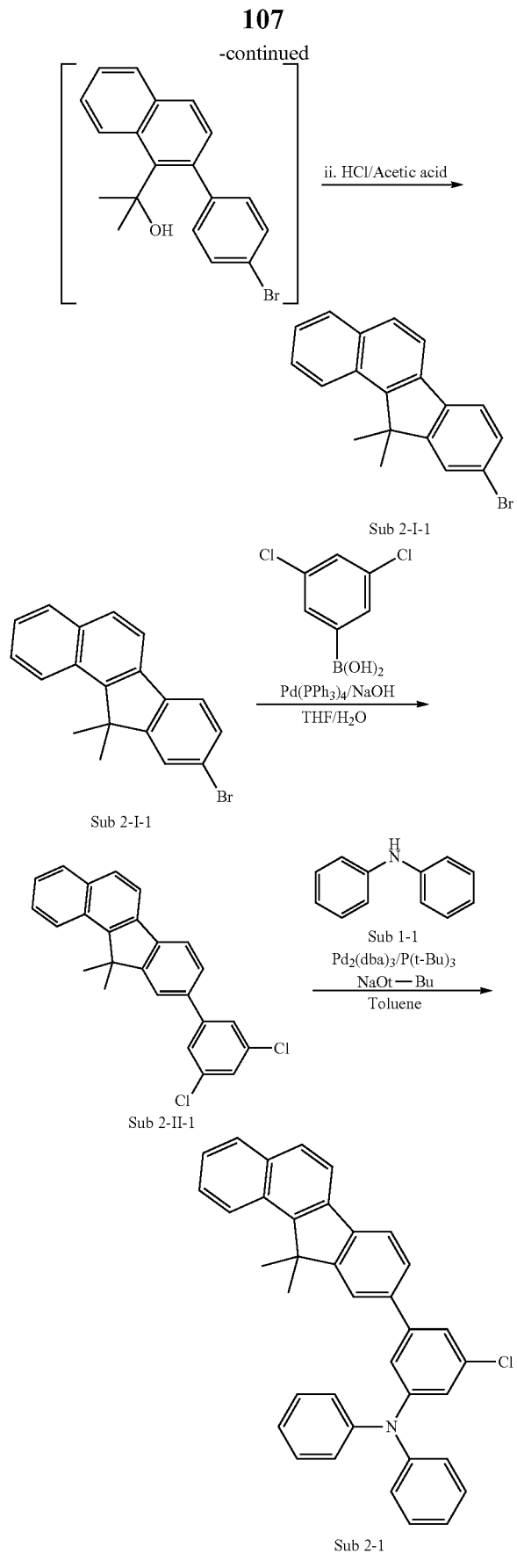

Sub 2-I-1

Sub 2-I-1

Sub 2-II-1

Sub 2-1

(1) Synthesis of Sub 2-I-1

The starting material methyl 2-(4-bromophenyl)-1-naphthoate (43.26 g, 126.79 mmol) was dissolved in THF (635 ml) in a round bottom flask, and then methylmagnesium bromide 1.0M in THF (507.2 ml, 507.15 mmol) was slowly dropped and stirred at a room temperature. When the reaction was completed, the reaction product was extracted with diethyl ether and water, and then, the organic layer was dried with $MgSO_4$ and concentrated to obtain an intermediate product. The intermediate product was dissolved in acetic acid solution (500 ml), HCl (10 ml) was added, and the mixture was refluxed. After completion of the reaction, water was added, and the resulting solid was filtered off under reduced pressure, and then washed with water and methanol to obtain 35.24 g (yield: 86% over two steps) of the product as a white powder.

(2) Synthesis of Sub 2-II-1

Sub 2-I-1 (25.67 g, 79.42 mmol) obtained in the above synthesis was dissolved in THF (260 ml) in a round bottom flask, and then, (3,5-dichlorophenyl)boronic acid (15.15 g, 79.42 mmol), $Pd(PPh_3)_4$ (2.75 g, 2.38 mmol), NaOH (9.53 g, 238.25 mmol), water (130 ml) were added and stirred at 80° C. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 23.81 g (yield: 77%) of the product.

(3) Synthesis of Sub 2-1

Sub 1-1 (6.90 g, 40.78 mmol) obtained in the above synthesis was dissolved in toluene (340 ml) in a round bottom flask, and then, Sub 2-II-1 (23.81 g, 61.16 mmol), $Pd_2(dba)_3$ (1.12 g, 1.22 mmol), 50% $P(t-Bu)_3$ (1.6 ml, 3.26 mmol), NaOt-Bu (11.76 g, 122.33 mmol) were added and stirred at 80° C. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 12.35 g (yield: 58%) of the product.

2. Synthesis Example of Sub 2-23

<Reaction Scheme 19>

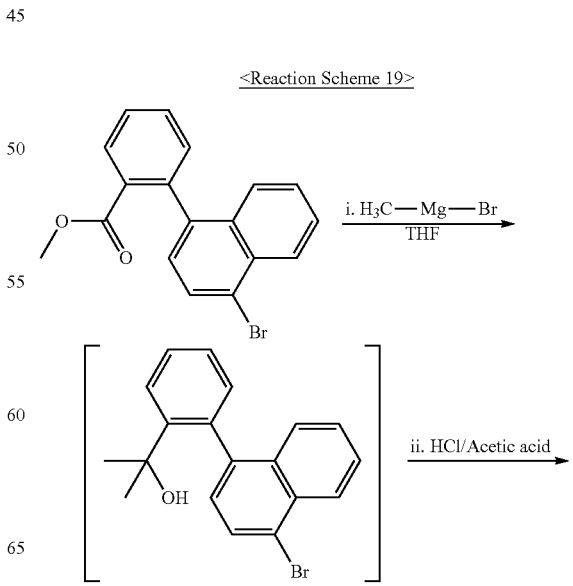

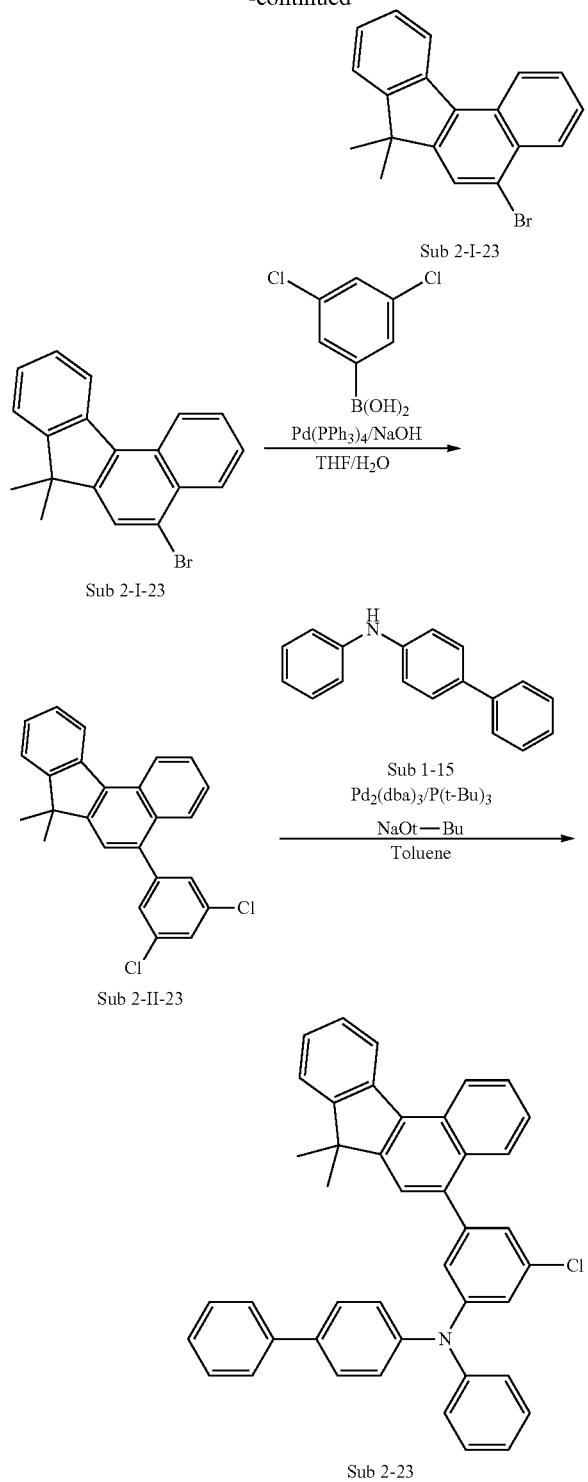

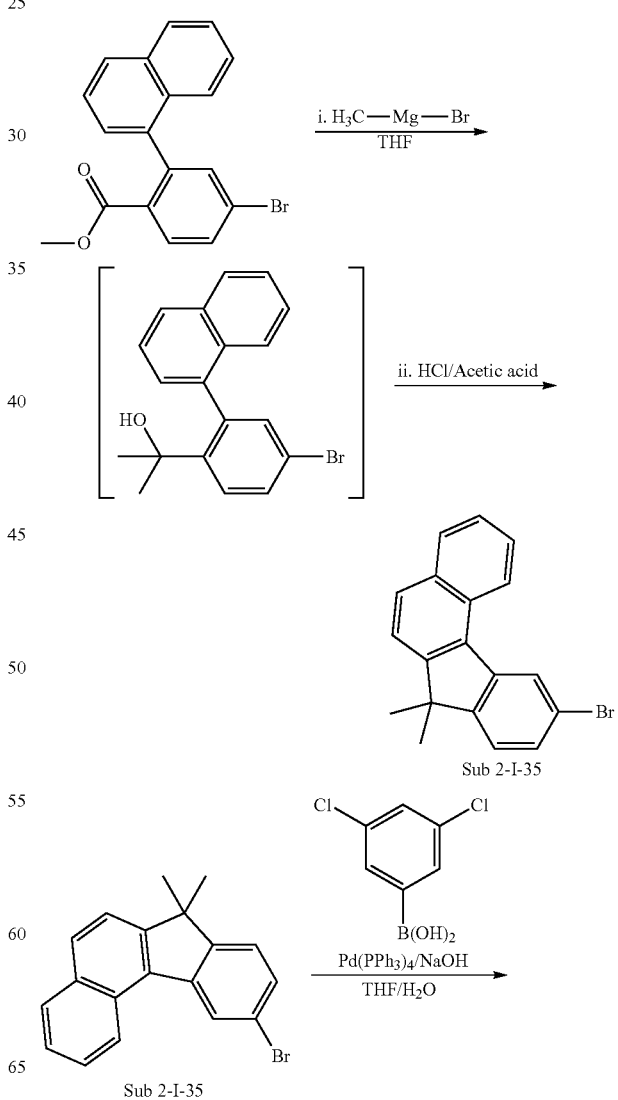

(1) Synthesis of Sub 2-I-23

An intermediate product was obtained by reacting the starting material methyl 2-(4-bromonaphthalen-1-yl)benzoate (42.62 g, 124.91 mmol), methylmagnesium bromide 1.0M in THF (499.6 ml, 499.65 mmol) and THF (625 ml), acetic acid solution (500 ml) and HCl (10 ml) were added. Then, 33.51 g (yield: 83% over two steps) of the product was obtained by using the same manner as described above for the synthesis of Sub 2-I-1.

(2) Synthesis of Sub 2-II-23

(3,5-dichlorophenyl)boronic acid (9.78 g, 51.26 mmol), Pd(PPh$_3$)$_4$ (1.78 g, 1.54 mmol), NaOH (6.15 g, 153.79 mmol), THF (170 ml), water (85 ml) were added to Sub 2-I-23 (16.57 g, 51.26 mmol) obtained in the above synthesis, and then 15.97 g (yield: 80%) of the product was obtained by using the same manner as described above for the synthesis of Sub 2-II-1.

(3) Synthesis of Sub 2-23

Sub 2-II-23 (15.97 g, 41.03 mmol), Pd$_2$(dba)$_3$ (0.75 g, 0.82 mmol), 50% P(t-Bu)$_3$ (1.1 ml, 2.19 mmol), NaOt-Bu (7.89 g, 82.06 mmol), toluene (230 ml) were added to Sub 1-15 (6.71 g, 27.35 mmol) obtained in the above synthesis, and then 10.31 g (yield: 63%) of the product was obtained by using the same manner as described above for the synthesis of Sub 2-1.

3. Synthesis Example of Sub 2-35

<Reaction Scheme 20>

4. Synthesis Example of Sub 2-37

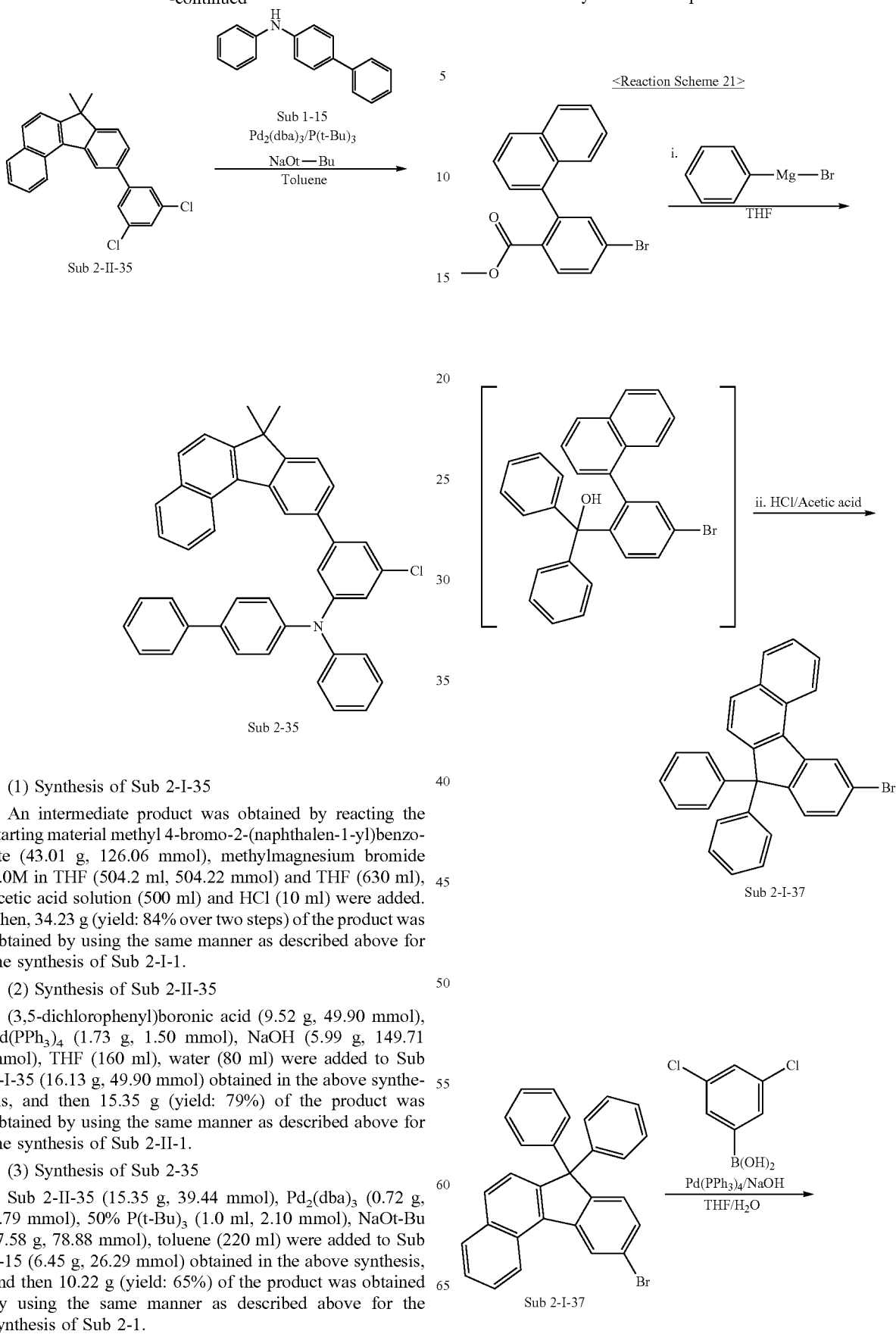

(1) Synthesis of Sub 2-I-35

An intermediate product was obtained by reacting the starting material methyl 4-bromo-2-(naphthalen-1-yl)benzoate (43.01 g, 126.06 mmol), methylmagnesium bromide 1.0M in THF (504.2 ml, 504.22 mmol) and THF (630 ml), acetic acid solution (500 ml) and HCl (10 ml) were added. Then, 34.23 g (yield: 84% over two steps) of the product was obtained by using the same manner as described above for the synthesis of Sub 2-I-1.

(2) Synthesis of Sub 2-II-35

(3,5-dichlorophenyl)boronic acid (9.52 g, 49.90 mmol), Pd(PPh$_3$)$_4$ (1.73 g, 1.50 mmol), NaOH (5.99 g, 149.71 mmol), THF (160 ml), water (80 ml) were added to Sub 2-I-35 (16.13 g, 49.90 mmol) obtained in the above synthesis, and then 15.35 g (yield: 79%) of the product was obtained by using the same manner as described above for the synthesis of Sub 2-II-1.

(3) Synthesis of Sub 2-35

Sub 2-II-35 (15.35 g, 39.44 mmol), Pd$_2$(dba)$_3$ (0.72 g, 0.79 mmol), 50% P(t-Bu)$_3$ (1.0 ml, 2.10 mmol), NaOt-Bu (7.58 g, 78.88 mmol), toluene (220 ml) were added to Sub 1-15 (6.45 g, 26.29 mmol) obtained in the above synthesis, and then 10.22 g (yield: 65%) of the product was obtained by using the same manner as described above for the synthesis of Sub 2-1.

113

-continued

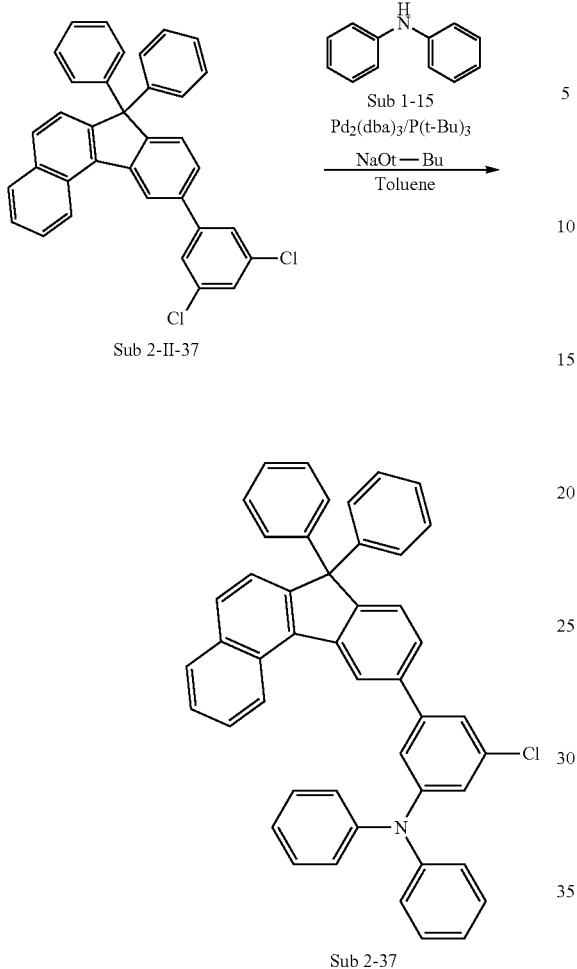

5. Synthesis Example of Sub 2-42

<Reaction Scheme 22>

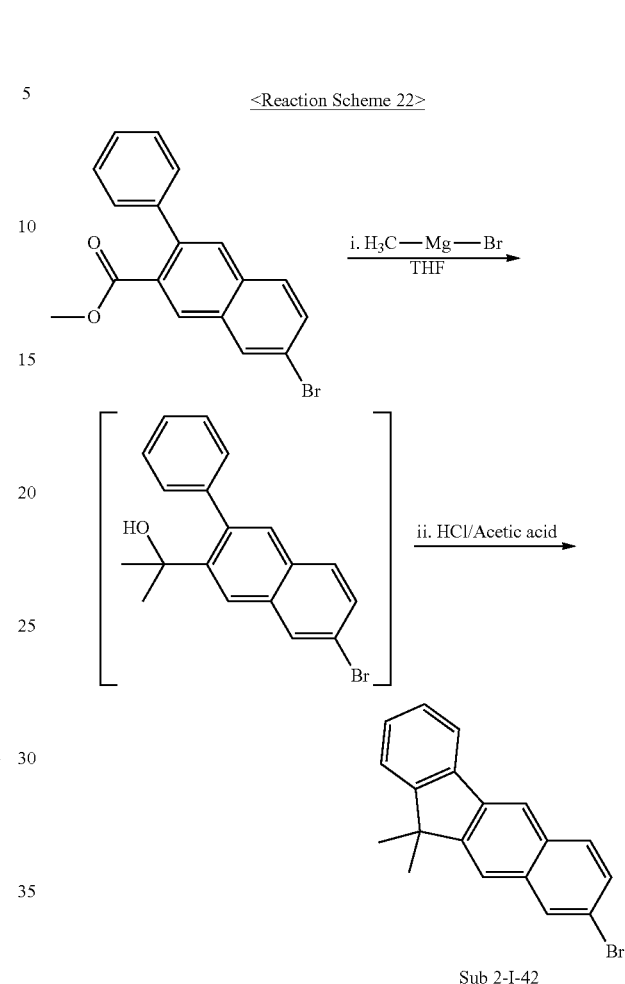

(1) Synthesis of Sub 2-I-37

An intermediate product was obtained by reacting the starting material methyl 4-bromo-2-(naphthalen-1-yl)benzoate (42.78 g, 125.38 mmol), phenylmagnesium bromide 1.0M in THF (501.5 ml, 501.52 mmol) and THF (630 ml), acetic acid solution (500 ml) and HCl (10 ml) were added. Then, 43.19 g (yield: 77% over two steps) of the product was obtained by using the same manner as described above for the synthesis of Sub 2-I-1.

(2) Synthesis of Sub 2-II-37

(3,5-dichlorophenyl)boronic acid (10.42 g, 54.61 mmol), Pd(PPh$_3$)$_4$ (1.89 g, 1.64 mmol), NaOH (6.55 g, 163.82 mmol), THF (180 ml), water (90 ml) were added to Sub 2-I-37 (24.43 g, 54.61 mmol) obtained in the above synthesis, and then 21.03 g (yield: 75%) of the product was obtained by using the same manner as described above for the synthesis of Sub 2-II-1.

(3) Synthesis of Sub 2-37

Sub 2-II-37 (21.03 g, 40.95 mmol), Pd$_2$(dba)$_3$ (0.75 g, 0.82 mmol), 50% P(t-Bu)$_3$ (1.1 ml, 2.18 mmol), NaOt-Bu (7.87 g, 81.91 mmol), toluene (230 ml) were added to Sub 1-1 (4.62 g, 27.30 mmol) obtained in the above synthesis, and then 10.76 g (yield: 61%) of the product was obtained by using the same manner as described above for the synthesis of Sub 2-1.

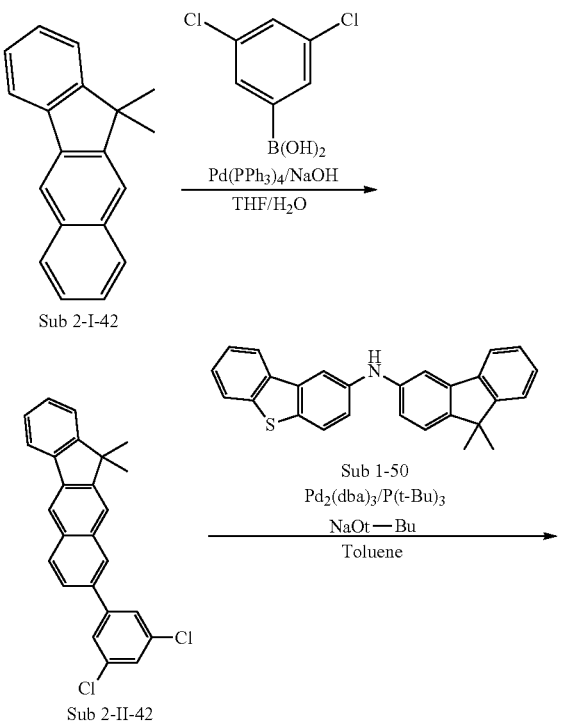

6. Synthesis Example of Sub 2-50

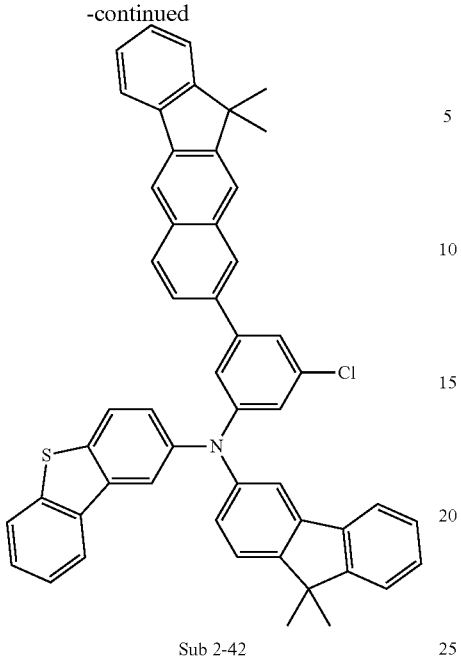

Sub 2-42

(1) Synthesis of Sub 2-I-42

An intermediate product was obtained by reacting the starting material methyl 7-bromo-3-phenyl-2-naphthoate (42.72 g, 125.21 mmol), methylmagnesium bromide 1.0M in THF (500.8 ml, 500.82 mmol) and THF (625 ml), acetic acid solution (500 ml) and HCl (10 ml) were added. Then, 31.97 g (yield: 79% over two steps) of the product was obtained by using the same manner as described above for the synthesis of Sub 2-I-1.

(2) Synthesis of Sub 2-II-42

(3,5-dichlorophenyl)boronic acid (10.53 g, 55.19 mmol), Pd(PPh$_3$)$_4$ (1.91 g, 1.66 mmol), NaOH (6.62 g, 165.58 mmol), THF (180 ml), water (90 ml) were added to Sub 2-I-42 (17.84 g, 55.19 mmol) obtained in the above synthesis, and then 15.26 g (yield: 71%) of the product was obtained by using the same manner as described above for the synthesis of Sub 2-II-1.

(3) Synthesis of Sub 2-42

Sub 2-II-42 (15.26 g, 39.19 mmol), Pd$_2$(dba)$_3$ (0.72 g, 0.78 mmol), 50% P(t-Bu)$_3$ (1.0 ml, 2.09 mmol), NaOt-Bu (7.53 g, 78.38 mmol), toluene (220 ml) were added to Sub 1-50 (10.23 g, 26.13 mmol) obtained in the above synthesis, and then 11.67 g (yield: 60%) of the product was obtained by using the same manner as described above for the synthesis of Sub 2-1.

<Reaction Scheme 23>

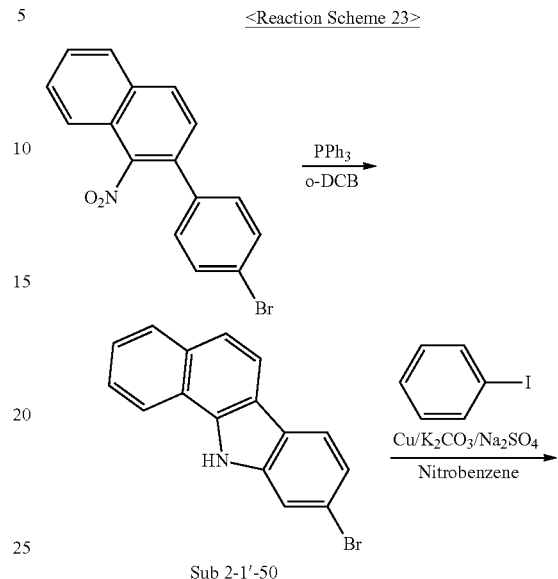

Sub 2-1'-50

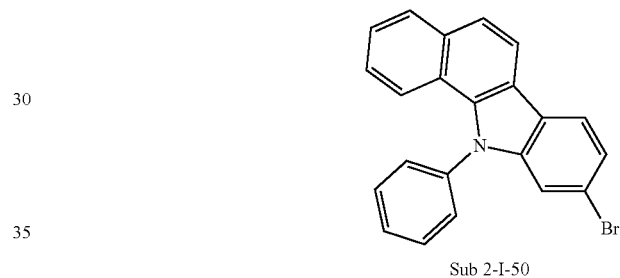

Sub 2-I-50

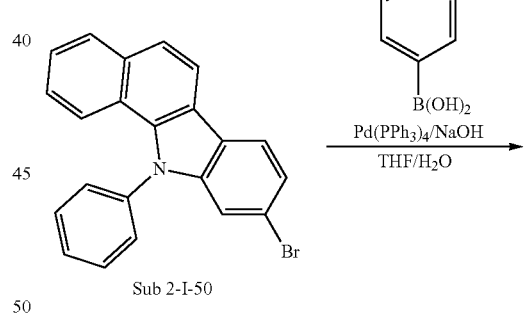

Sub 2-I-50

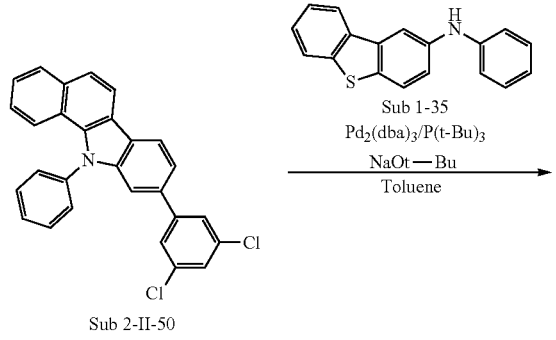

Sub 2-II-50

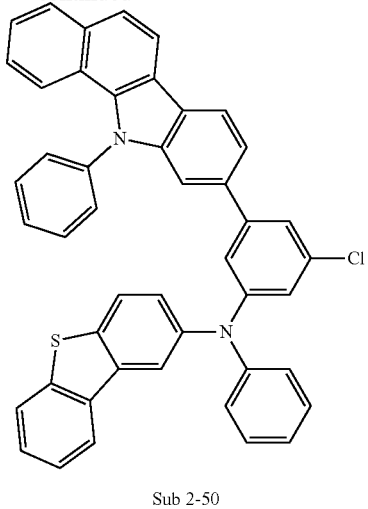

Sub 2-50

(1) Synthesis of Sub 2-I'-50

The starting material 2-(4-bromophenyl)-1-nitronaphthalene (30.18 g, 91.97 mmol) was dissolved in o-dichlorobenzene (805 ml) in a round bottom flask, and then triphenylphosphine (60.31 g, 229.92 mmol) was added and stirred at 200° C. When the reaction was completed, o-dichlorobenzene was removed by distillation and extracting with $CH_2Cl_2$ and water was followed. Then, the organic layer was dried with $MgSO_4$ and concentrated and the concentrate was passed through silica gel column and recrystallized to obtain 19.07 g (yield: 70%) of the product.

(2) Synthesis of Sub 2-I-50

Sub 2-I'-50 (19.07 g, 64.39 mmol) obtained in the above synthesis was dissolved in nitrobenzene (400 ml) in a round bottom flask, and then iodobenzene (19.70 g, 96.59 mmol), $Na_2SO_4$ (9.15 g, 64.39 mmol), $K_2CO_3$ (8.90 g, 64.39 mmol), Cu (1.23 g, 19.32 mmol) were added and stirred at 200° C. When the reaction was completed, nitrobenzene was removed by distillation and extracting with $CH_2Cl_2$ and water was followed. Then, the organic layer was dried with $MgSO_4$ and concentrated and the concentrate was passed through silica gel column and recrystallized to obtain 17.98 g (yield: 75%) of the product.

(3) Synthesis of Sub 2-II-50

(3,5-dichlorophenyl)boronic acid (8.68 g, 45.48 mmol), $Pd(PPh_3)_4$ (1.58 g, 1.36 mmol), NaOH (5.46 g, 136.44 mmol), THF (150 ml), water (75 ml) were added to Sub 2-I-50 (16.93 g, 45.48 mmol) obtained in the above synthesis, and then 16.55 g (yield: 83%) of the product was obtained by using the same manner as described above for the synthesis of Sub 2-II-1.

(4) Synthesis of Sub 2-50

Sub 2-II-50 (16.55 g, 37.75 mmol), $Pd_2(dba)_3$ (0.69 g, 0.75 mmol), 50% $P(t-Bu)_3$ (1.0 ml, 2.01 mmol), NaOt-Bu (7.26 g, 75.50 mmol), toluene (210 ml) were added to Sub 1-35 (6.93 g, 25.17 mmol) obtained in the above synthesis, and then 11.25 g (yield: 66%) of the product was obtained by using the same manner as described above for the synthesis of Sub 2-1.

7. Synthesis Example of Sub 2-73

<Reaction Scheme 24>

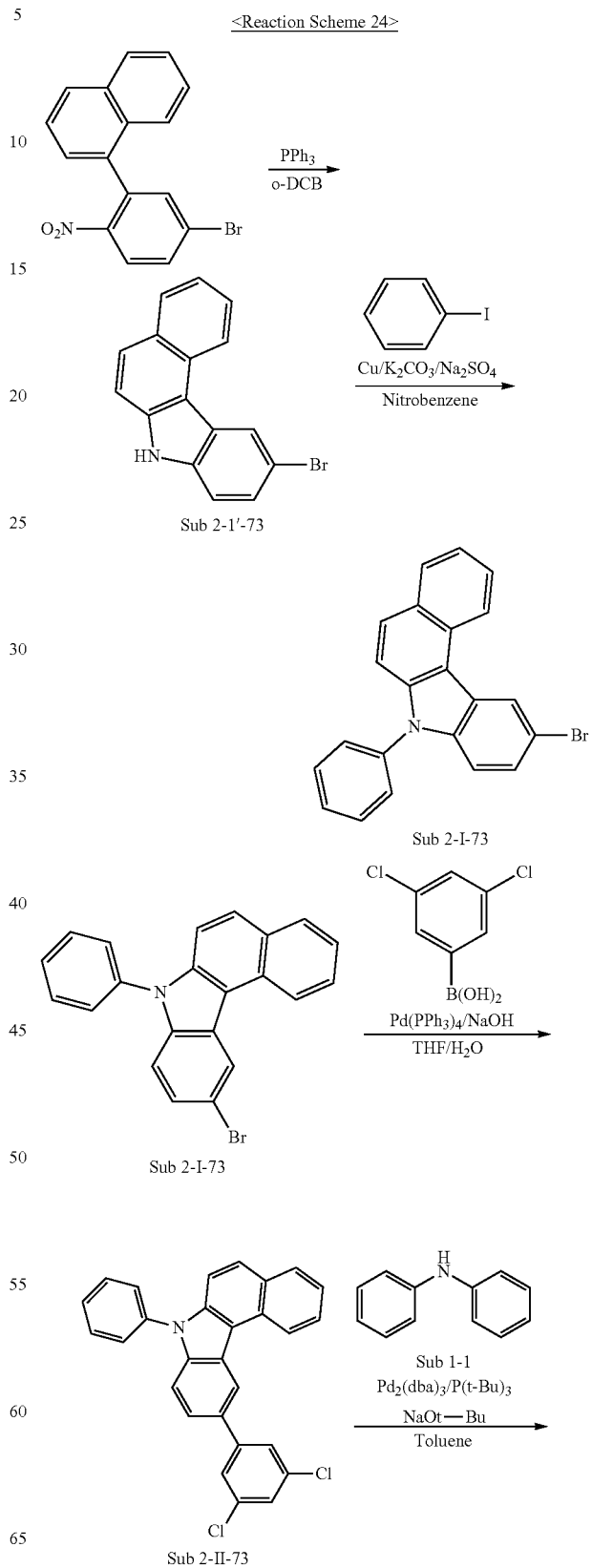

-continued

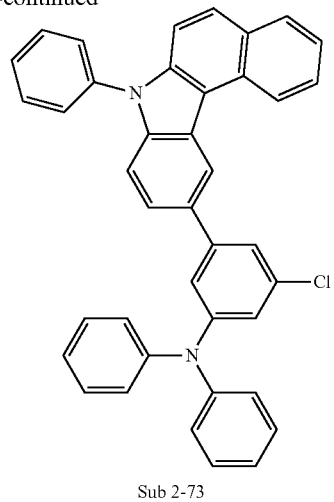

Sub 2-73

(1) Synthesis of Sub 2-I'-73

Triphenylphosphine (131.96 g, 503.11 mmol), o-dichlorobenzene (1760 ml) were added to the starting material 1-(5-bromo-2-nitrophenyl)naphthalene (66.04 g, 201.24 mmol), and then 43.51 g (yield: 73%) of the product was obtained by using the same manner as described above for the synthesis of Sub 2-I'-50.

(2) Synthesis of Sub 2-I-73

1-iodobenzene (44.96 g, 220.37 mmol), Na$_2$SO$_4$ (20.87 g, 146.91 mmol), K$_2$CO$_3$ (20.30 g, 146.91 mmol), Cu (2.80 g, 44.07 mmol), nitrobenzene (920 ml) were added to Sub 2-I'-73 (43.51 g, 146.91 mmol) obtained in the above synthesis, and then 42.66 g (yield: 78%) of the product was obtained by using the same manner as described above for the synthesis of Sub 2-I-50.

(3) Synthesis of Sub 2-II-73

(3,5-dichlorophenyl)boronic acid (21.72 g, 113.85 mmol), Pd(PPh$_3$)$_4$ (3.95 g, 3.42 mmol), NaOH (13.66 g, 341.54 mmol), THF (380 ml), water (190 ml) were added to Sub 2-I-73 (42.38 g, 113.85 mmol) obtained in the above synthesis, and then 40.92 g (yield: 82%) of the product was obtained by using the same manner as described above for the synthesis of Sub 2-II-1.

(4) Synthesis of Sub 2-73

Sub 2-II-73 (21.45 g, 48.93 mmol), Pd$_2$(dba)$_3$ (0.90 g, 0.98 mmol), 50% P(t-Bu)$_3$ (1.3 ml, 2.61 mmol), NaOt-Bu (9.41 g, 97.86 mmol), toluene (270 ml) were added to Sub 1-1 (5.52 g, 32.62 mmol) obtained in the above synthesis, and then 11.18 g (yield: 60%) of the product was obtained by using the same manner as described above for the synthesis of Sub 2-1.

8. Synthesis Example of Sub 2-74

<Reaction Scheme 25>

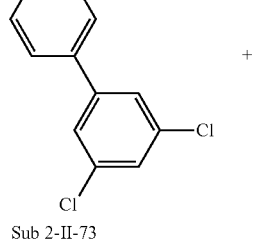

Sub 2-II-73

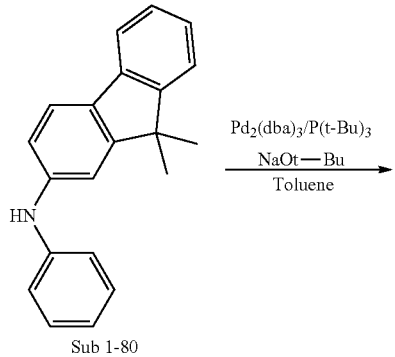

Sub 1-80

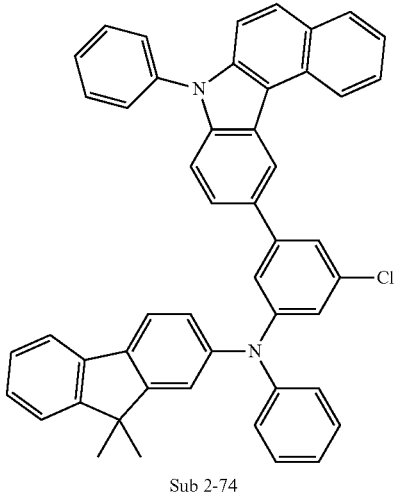

Sub 2-74

Sub 2-II-73 (18.13 g, 41.37 mmol), Pd$_2$(dba)$_3$ (0.76 g, 0.83 mmol), 50% P(t-Bu)$_3$ (1.1 ml, 2.21 mmol), NaOt-Bu (7.95 g, 82.73 mmol), toluene (230 ml) were added to Sub 1-80 (7.87 g, 27.58 mmol) obtained in the above synthesis, and then 11.75 g (yield: 62%) of the product was obtained by using the same manner as described above for the synthesis of Sub 2-1.

9. Synthesis Example of Sub 2-80

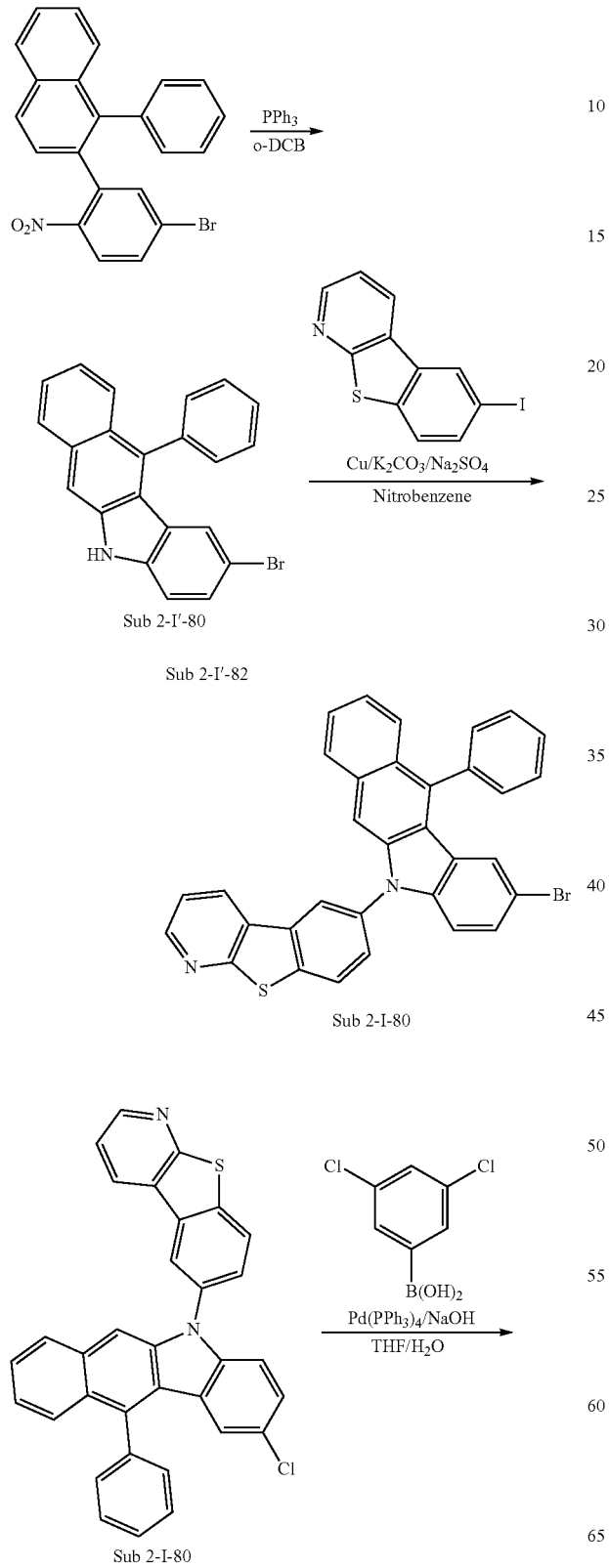

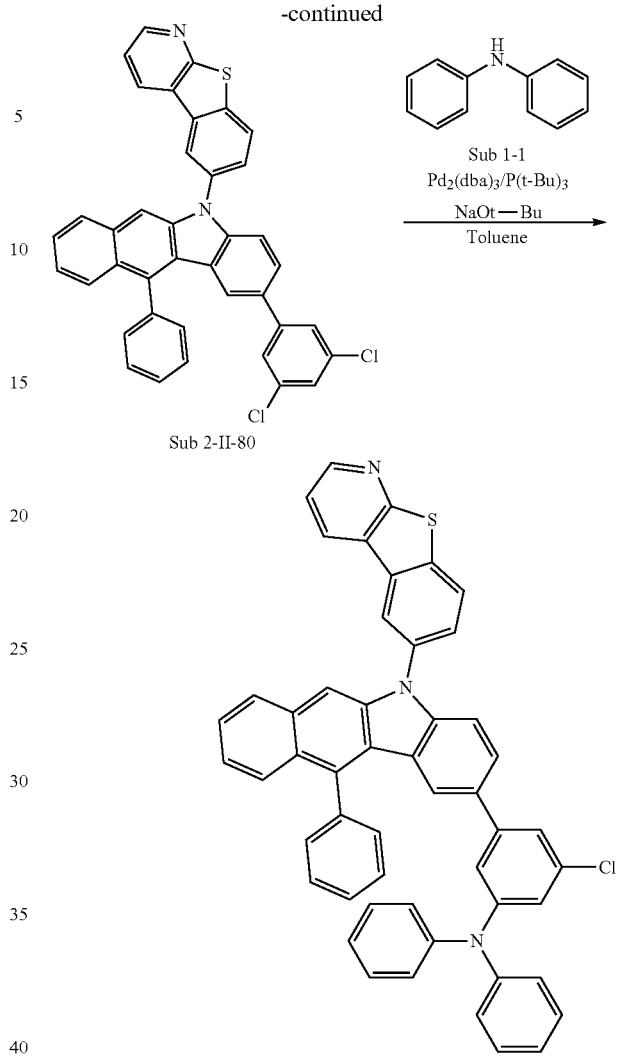

(1) Synthesis of Sub 2-I'-80

Triphenylphosphine (120.60 g, 459.79 mmol), o-dichlorobenzene (1600 ml) were added to the starting material 2-(5-bromo-2-nitrophenyl)-1-phenylnaphthalene (74.35 g, 183.92 mmol), and then 41.08 g (yield: 60%) of the product was obtained by using the same manner as described above for the synthesis of Sub 2-I'-50.

(2) Synthesis of Sub 2-I-80

6-iodobenzo[4,5]thieno[2,3-b]pyridine (51.50 g, 165.53 mmol), $Na_2SO_4$ (15.67 g, 110.35 mmol), $K_2CO_3$ (15.25 g, 110.35 mmol), Cu (2.10 g, 33.11 mmol), nitrobenzene (690 ml) were added to Sub 2-I'-80 (41.08 g, 110.35 mmol) obtained in the above synthesis, and then 38.01 g (yield: 62%) of the product was obtained by using the same manner as described above for the synthesis of Sub 2-I-50.

(3) Synthesis of Sub 2-II-80

(3,5-dichlorophenyl)boronic acid (13.98 g, 73.28 mmol), $Pd(PPh_3)_4$ (2.54 g, 2.20 mmol), NaOH (8.79 g, 219.85 mmol), THF (240 ml), water (120 ml) were added to Sub 2-I-80 (37.45 g, 73.28 mmol) obtained in the above synthesis, and then 29.15 g (yield: 64%) of the product was obtained by using the same manner as described above for the synthesis of Sub 2-II-1.

(4) Synthesis of Sub 2-80

Sub 2-II-80 (29.15 g, 46.89 mmol), $Pd_2(dba)_3$ (0.86 g, 0.94 mmol), 50% $P(t\text{-}Bu)_3$ (1.2 ml, 2.50 mmol), NaOt-Bu (9.01 g, 93.78 mmol), toluene (260 ml) were added to Sub 1-1 (5.29 g, 31.26 mmol) obtained in the above synthesis, and then 11.79 g (yield: 50%) of the product was obtained by using the same manner as described above for the synthesis of Sub 2-1.

10. Synthesis Example of Sub 2-82

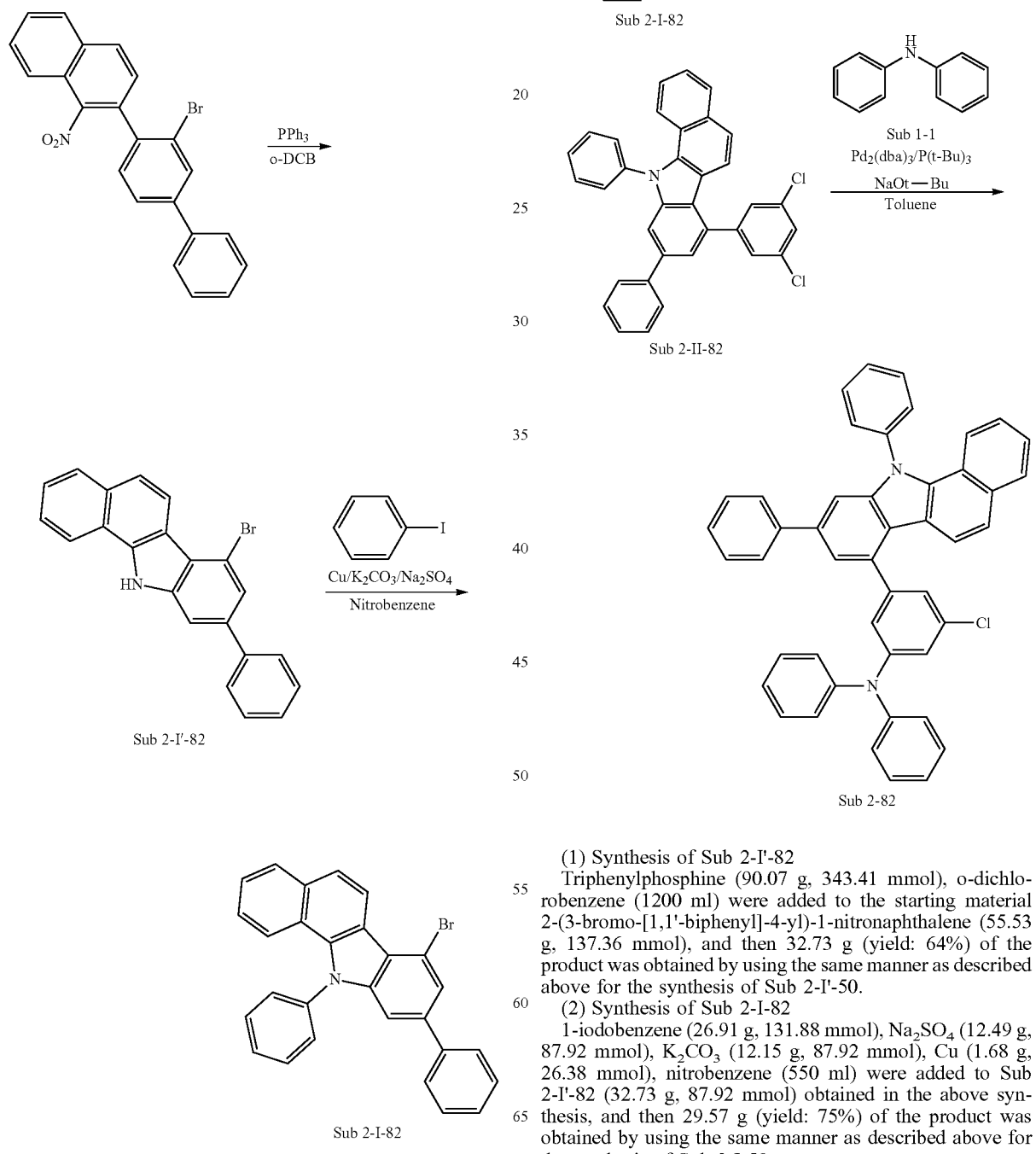

(1) Synthesis of Sub 2-I'-82

Triphenylphosphine (90.07 g, 343.41 mmol), o-dichlorobenzene (1200 ml) were added to the starting material 2-(3-bromo-[1,1'-biphenyl]-4-yl)-1-nitronaphthalene (55.53 g, 137.36 mmol), and then 32.73 g (yield: 64%) of the product was obtained by using the same manner as described above for the synthesis of Sub 2-I'-50.

(2) Synthesis of Sub 2-I-82

1-iodobenzene (26.91 g, 131.88 mmol), $Na_2SO_4$ (12.49 g, 87.92 mmol), $K_2CO_3$ (12.15 g, 87.92 mmol), Cu (1.68 g, 26.38 mmol), nitrobenzene (550 ml) were added to Sub 2-I'-82 (32.73 g, 87.92 mmol) obtained in the above synthesis, and then 29.57 g (yield: 75%) of the product was obtained by using the same manner as described above for the synthesis of Sub 2-I-50.

125

(3) Synthesis of Sub 2-II-82

(3,5-dichlorophenyl)boronic acid (12.11 g, 63.48 mmol), Pd(PPh$_3$)$_4$ (2.20 g, 1.90 mmol), NaOH (7.62 g, 190.43 mmol), THF (210 ml), water (105 ml) were added to Sub 2-I-82 (28.46 g, 63.48 mmol) obtained in the above synthesis, and then 22.53 g (yield: 69%) of the product was obtained by using the same manner as described above for the synthesis of Sub 2-II-1.

(4) Synthesis of Sub 2-82

Sub 2-II-82 (22.53 g, 43.79 mmol), Pd$_2$(dba)$_3$ (0.80 g, 0.88 mmol), 50% P(t-Bu)$_3$ (1.1 ml, 2.34 mmol), NaOt-Bu (8.42 g, 87.58 mmol), toluene (240 ml) were added to Sub 1-1 (4.94 g, 29.19 mmol) obtained in the above synthesis, and then 10.58 g (yield: 56%) of the product was obtained by using the same manner as described above for the synthesis of Sub 2-1.

11. Synthesis Example of Sub 2-92

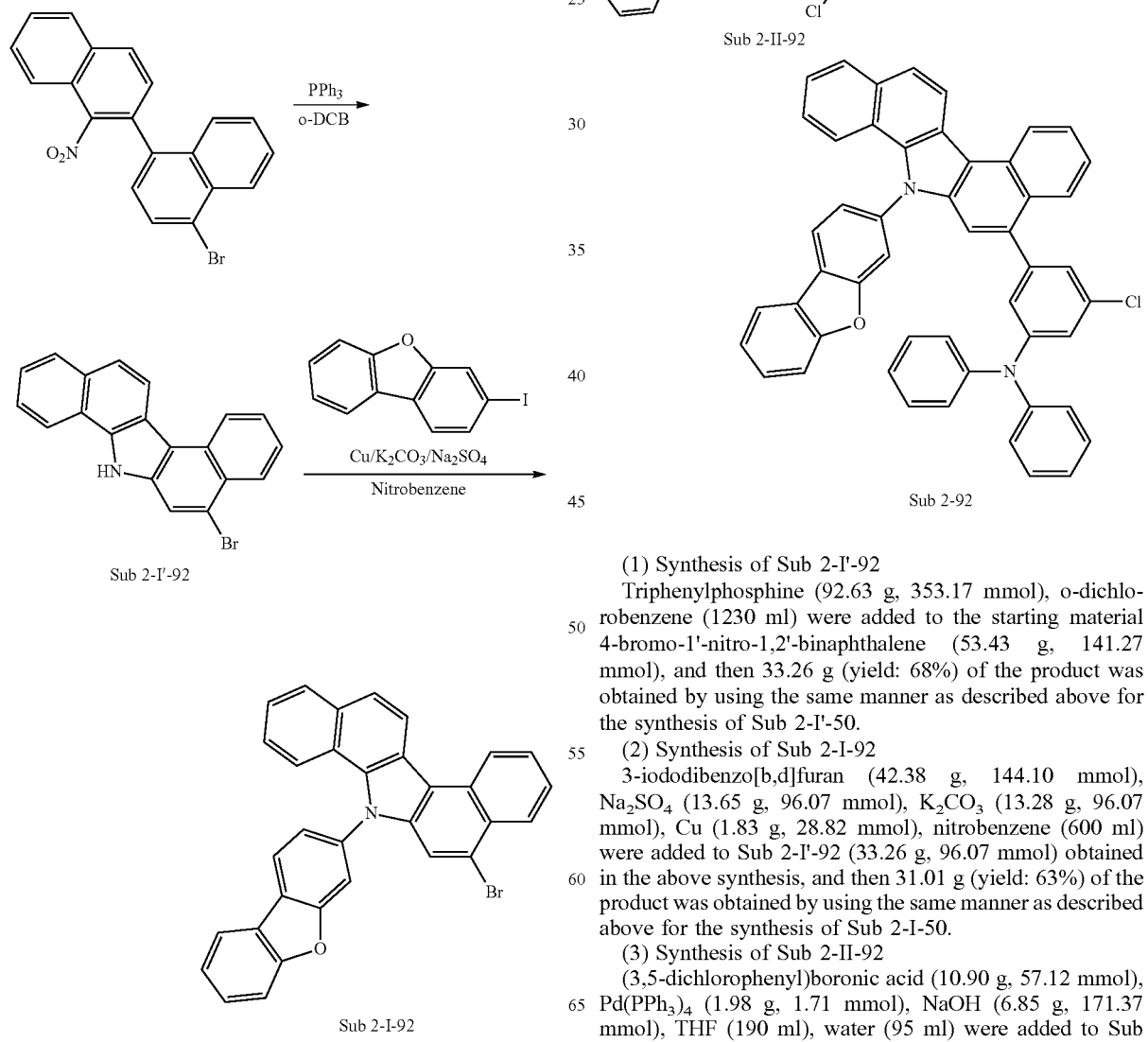

(1) Synthesis of Sub 2-I'-92

Triphenylphosphine (92.63 g, 353.17 mmol), o-dichlorobenzene (1230 ml) were added to the starting material 4-bromo-1'-nitro-1,2'-binaphthalene (53.43 g, 141.27 mmol), and then 33.26 g (yield: 68%) of the product was obtained by using the same manner as described above for the synthesis of Sub 2-I'-50.

(2) Synthesis of Sub 2-I-92

3-iododibenzo[b,d]furan (42.38 g, 144.10 mmol), Na$_2$SO$_4$ (13.65 g, 96.07 mmol), K$_2$CO$_3$ (13.28 g, 96.07 mmol), Cu (1.83 g, 28.82 mmol), nitrobenzene (600 ml) were added to Sub 2-I'-92 (33.26 g, 96.07 mmol) obtained in the above synthesis, and then 31.01 g (yield: 63%) of the product was obtained by using the same manner as described above for the synthesis of Sub 2-I-50.

(3) Synthesis of Sub 2-II-92

(3,5-dichlorophenyl)boronic acid (10.90 g, 57.12 mmol), Pd(PPh$_3$)$_4$ (1.98 g, 1.71 mmol), NaOH (6.85 g, 171.37 mmol), THF (190 ml), water (95 ml) were added to Sub 2-I-92 (29.27 g, 57.12 mmol) obtained in the above synthesis, and then 23.13 g (yield: 70%) of the product was obtained by using the same manner as described above for the synthesis of Sub 2-II-1.

(4) Synthesis of Sub 2-92

Sub 2-II-92 (23.13 g, 39.98 mmol), Pd$_2$(dba)$_3$ (0.73 g, 0.80 mmol), 50% P(t-Bu)$_3$ (1.0 ml, 2.13 mmol), NaOt-Bu (7.68 g, 79.96 mmol), toluene (220 ml) were added to Sub 1-1 (4.51 g, 26.65 mmol) obtained in the above synthesis, and then 10.43 g (yield: 55%) of the product was obtained by using the same manner as described above for the synthesis of Sub 2-1.

12. Synthesis Example of Sub 2-93

<Reaction Scheme 29>

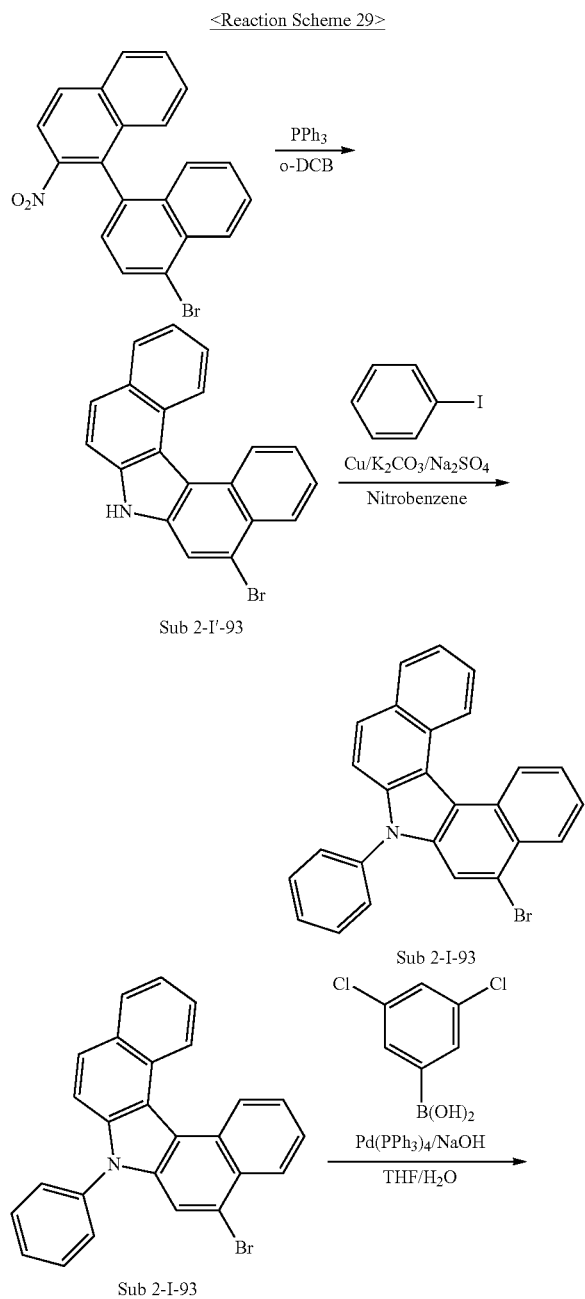

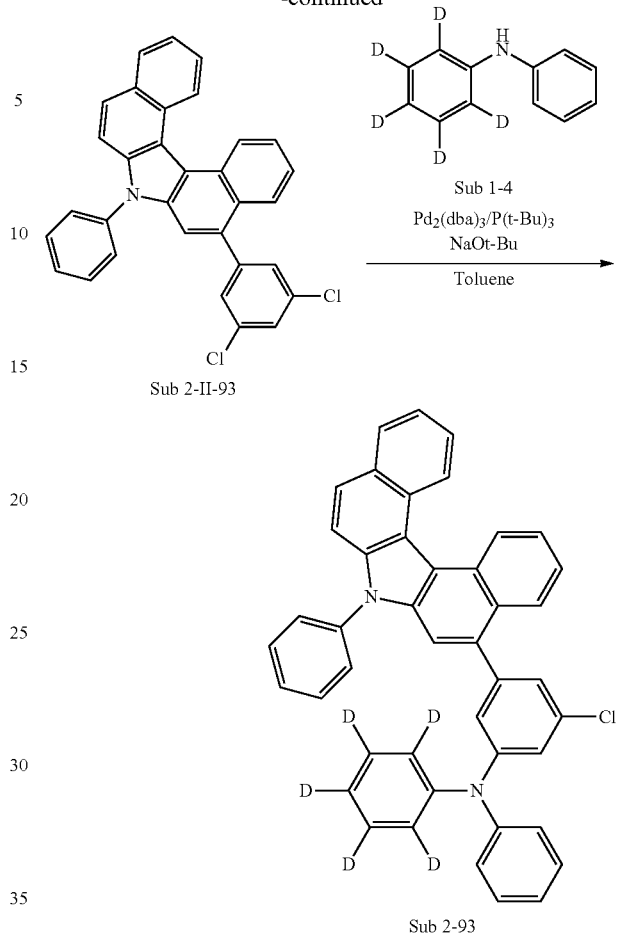

(1) Synthesis of Sub 2-I'-93

Triphenylphosphine (104.16 g, 397.12 mmol), o-dichlorobenzene (1390 ml) were added to the starting material 4'-bromo-2-nitro-1,1'-binaphthalene (60.08 g, 158.85 mmol), and then 35.75 g (yield: 65%) of the product was obtained by using the same manner as described above for the synthesis of Sub 2-I'-50.

(2) Synthesis of Sub 2-I-93

1-iodobenzene (31.60 g, 154.89 mmol), Na$_2$SO$_4$ (14.67 g, 103.26 mmol), K$_2$CO$_3$ (14.27 g, 103.26 mmol), Cu (1.97 g, 30.98 mmol), nitrobenzene (645 ml) were added to Sub 2-I'-93 (35.75 g, 103.26 mmol) obtained in the above synthesis, and then 30.09 g (yield: 69%) of the product was obtained by using the same manner as described above for the synthesis of Sub 2-1-50.

(3) Synthesis of Sub 2-II-93

(3,5-dichlorophenyl)boronic acid (12.79 g, 67.03 mmol), Pd(PPh$_3$)$_4$ (2.32 g, 2.01 mmol), NaOH (8.04 g, 201.10 mmol), THF (220 ml), water (110 ml) were added to Sub 2-I-93 (28.31 g, 67.03 mmol) obtained in the above synthesis, and then 23.25 g (yield: 71%) of the product was obtained by using the same manner as described above for the synthesis of Sub 2-II-1.

(4) Synthesis of Sub 2-93

Sub 2-II-93 (23.25 g, 47.60 mmol), Pd$_2$(dba)$_3$ (0.87 g, 0.95 mmol), 50% P(t-Bu)$_3$ (1.2 ml, 2.54 mmol), NaOt-Bu (9.15 g, 95.21 mmol), toluene (260 ml) were added to Sub 1-4 (5.53 g, 31.74 mmol) obtained in the above synthesis, and then 10.53 g (yield: 53%) of the product was obtained by using the same manner as described above for the synthesis of Sub 2-1.
The compound belonging to Sub 2 may be, but not limited to, the following compounds, and Table 2 shows FD-MS values of compounds belonging to Sub 2.
Sub 2-1
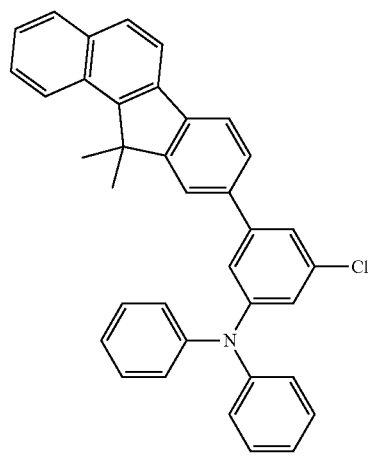
Sub 2-2
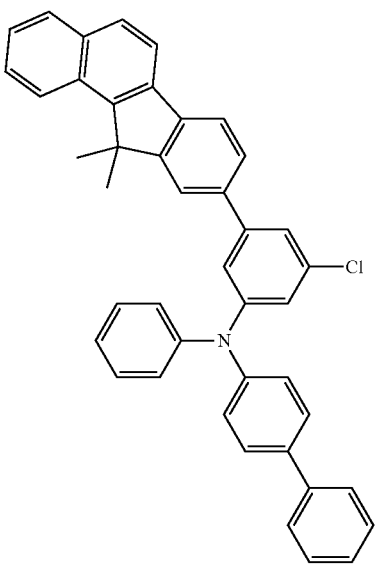
Sub 2-3
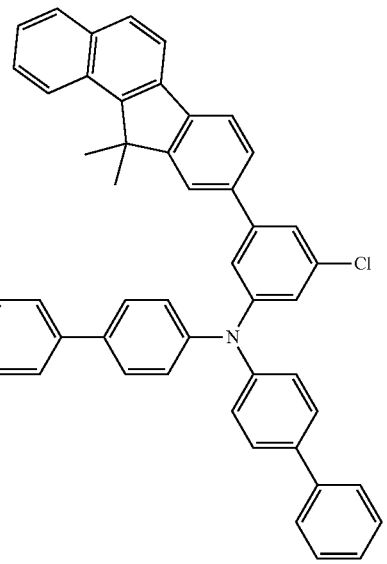
Sub 2-4
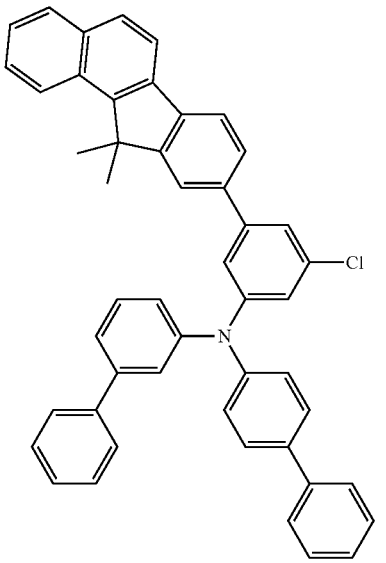
Sub 2-5
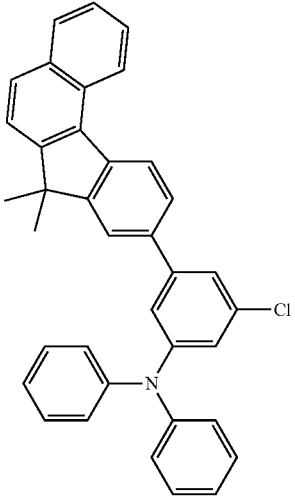

Sub 2-6
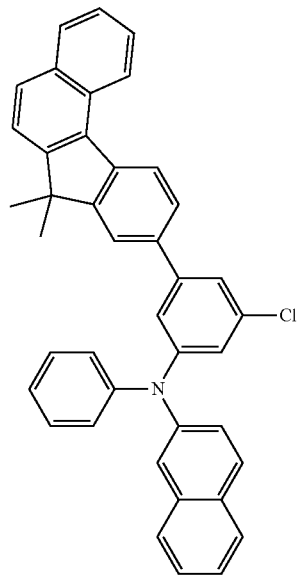
Sub 2-7
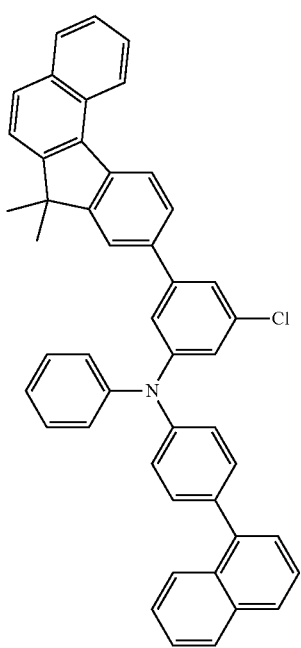
Sub 2-8
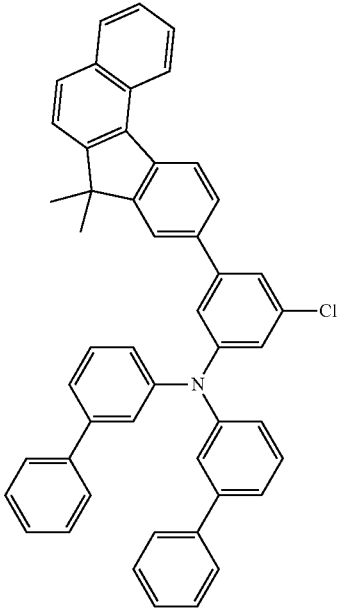
Sub 2-9
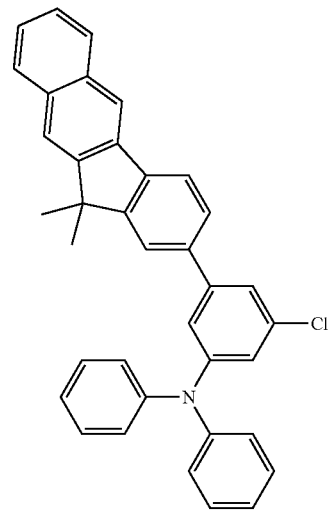
Sub 2-10
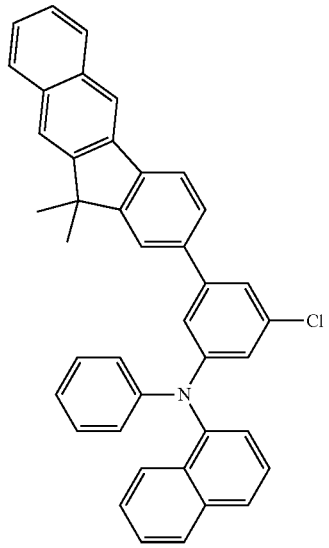

Sub 2-11
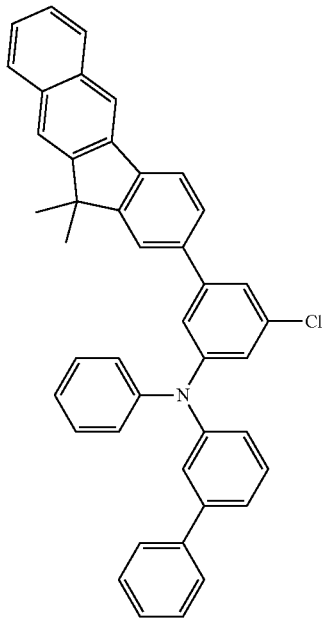
Sub 2-12
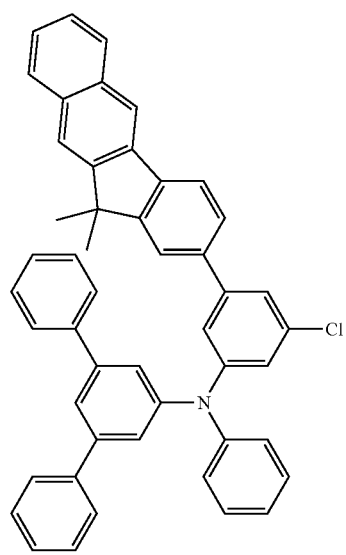
Sub 2-13
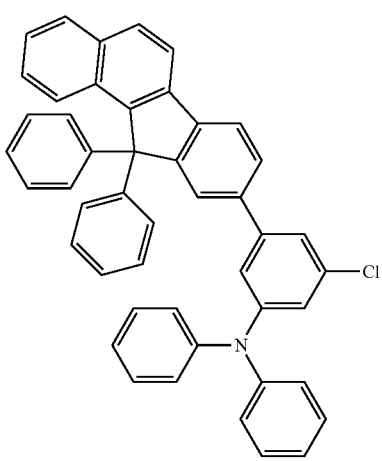
Sub 2-14
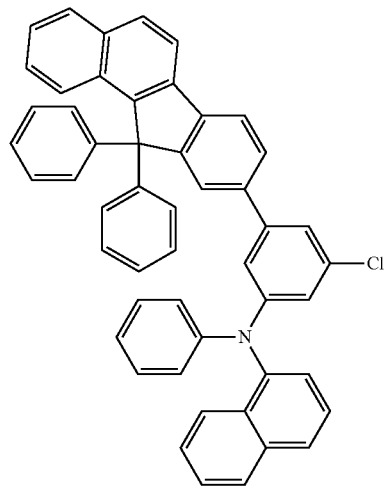
Sub 2-15
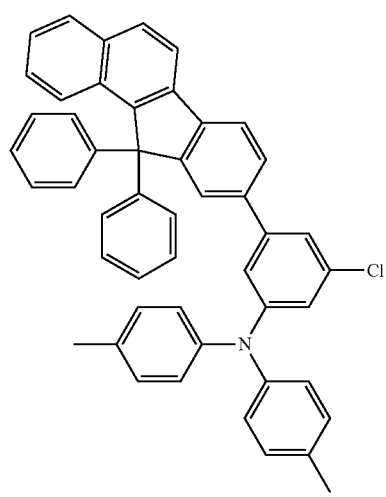
Sub 2-16
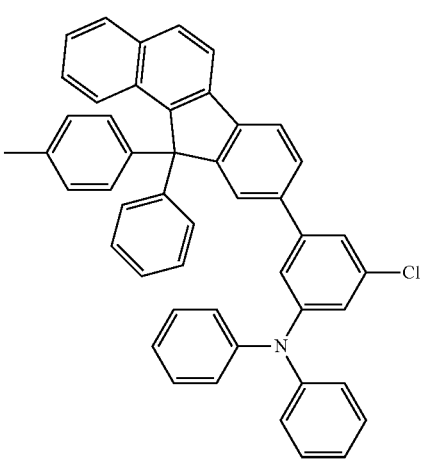

Sub 2-17
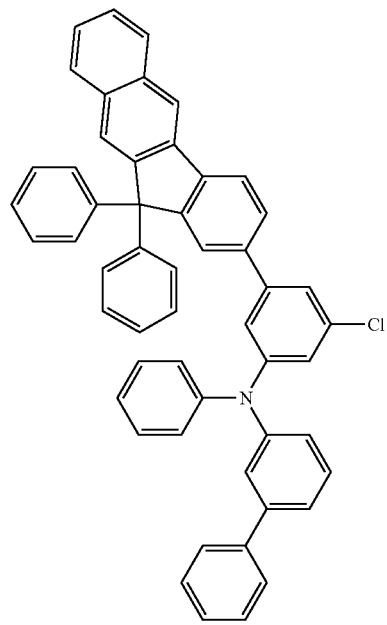
Sub 2-18
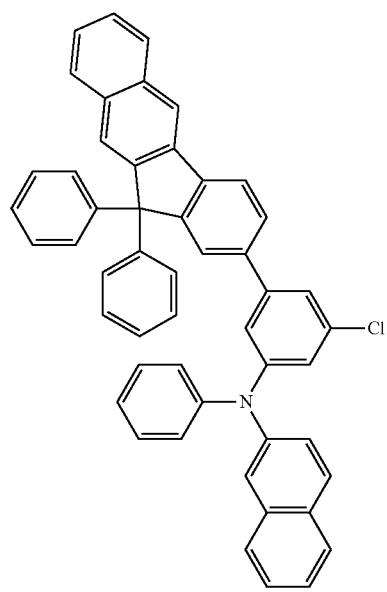
Sub 2-19
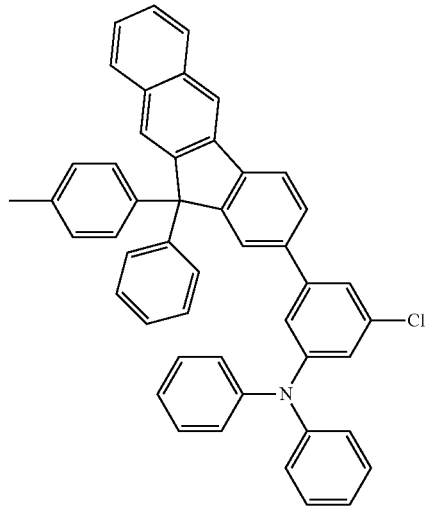
Sub 2-20
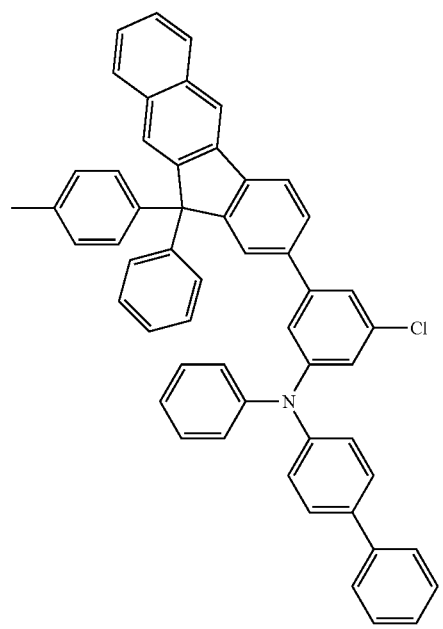
Sub 2-21
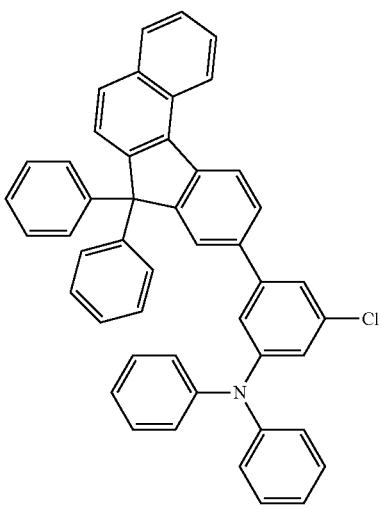

Sub 2-22
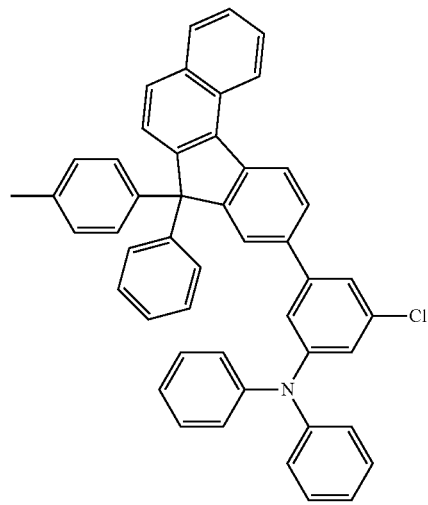
Sub 2-23
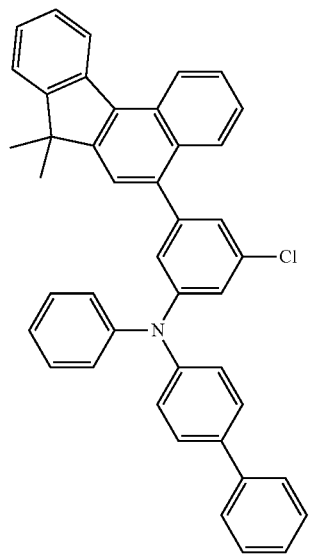
Sub 2-24
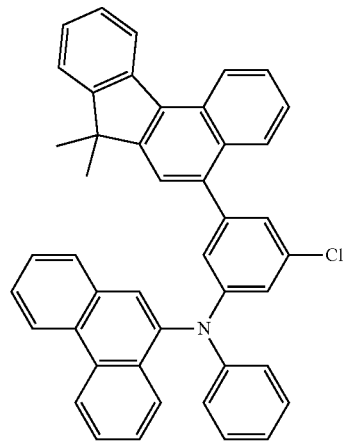
Sub 2-25
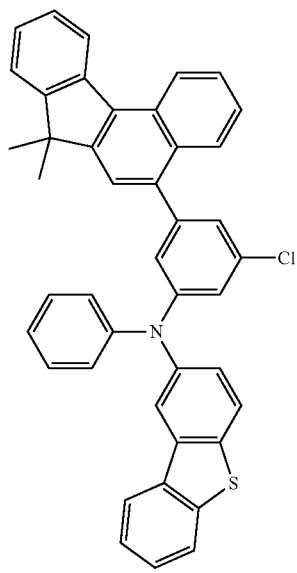
Sub 2-26
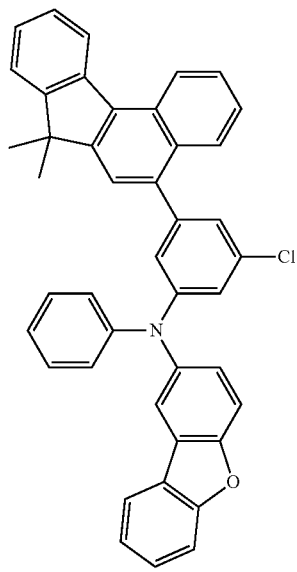
Sub 2-27
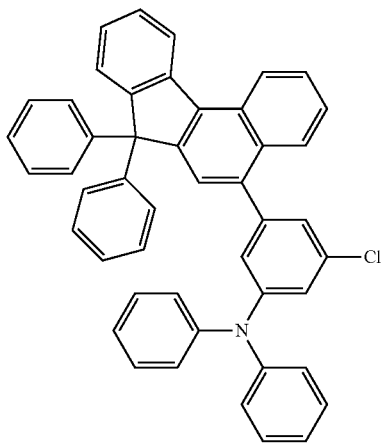

Sub 2-28
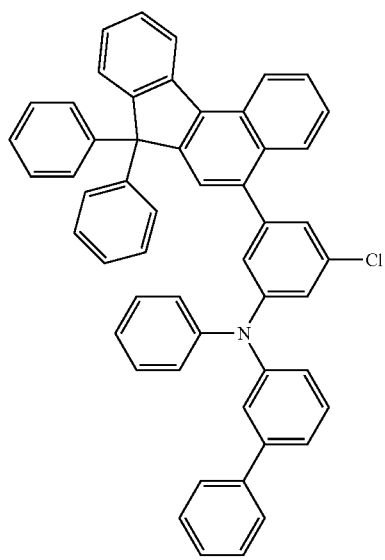
Sub 2-29
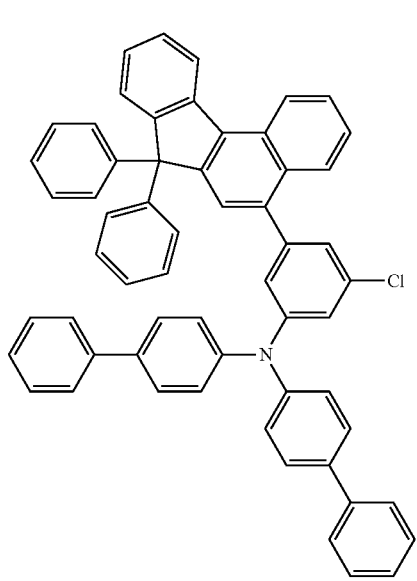
Sub 2-30
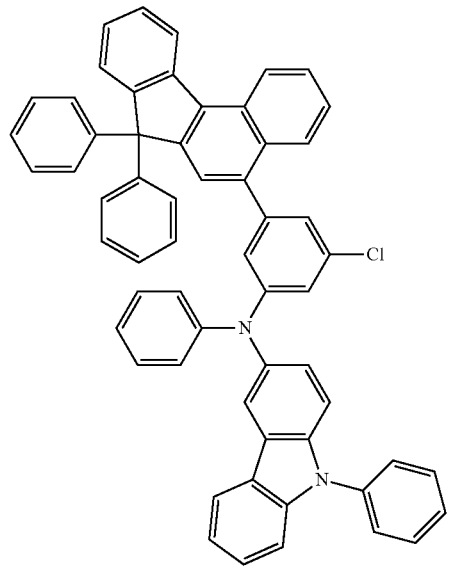
Sub 2-31
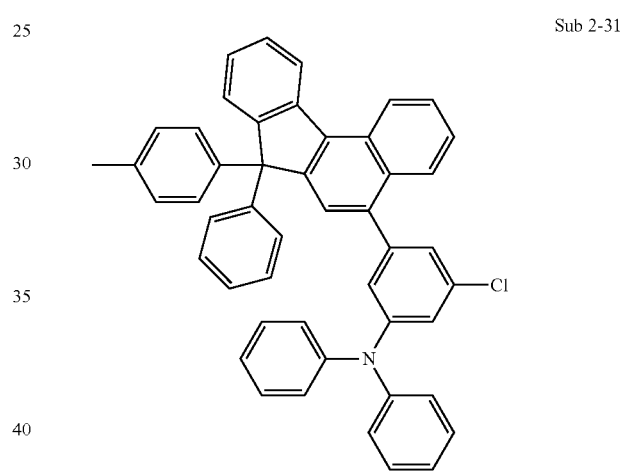
Sub 2-32
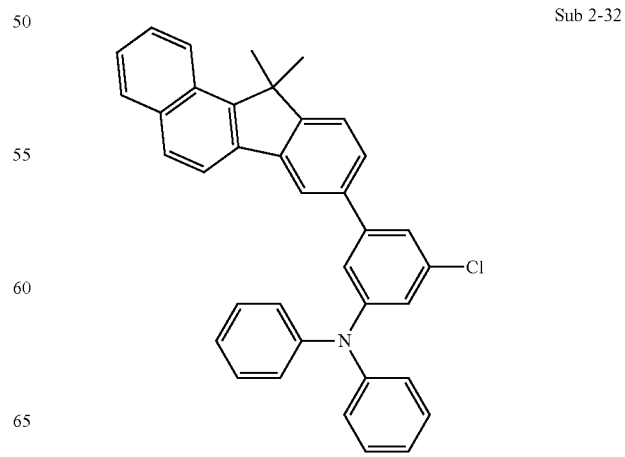

Sub 2-33
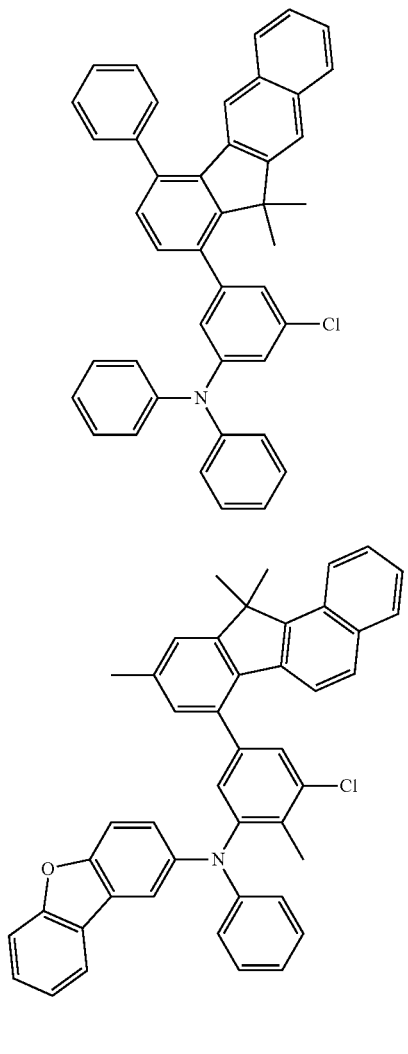
Sub 2-34
Sub 2-35
Sub 2-36
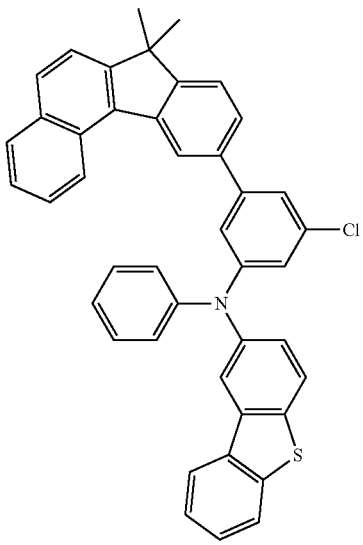
Sub 2-37
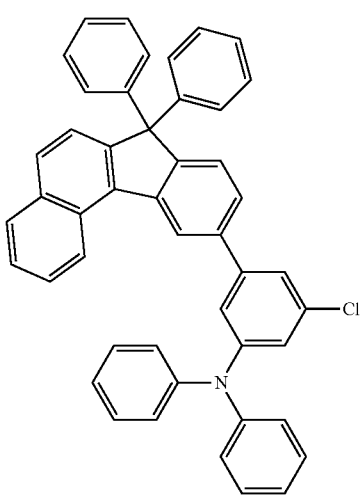
Sub 2-38
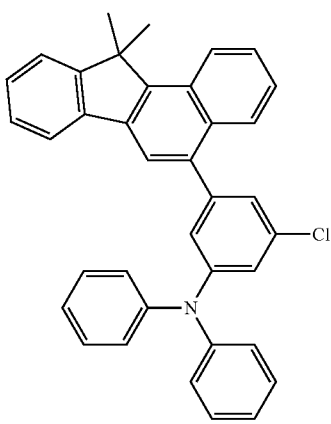
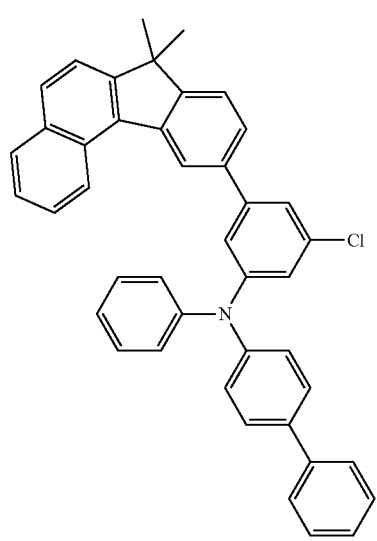

Sub 2-39
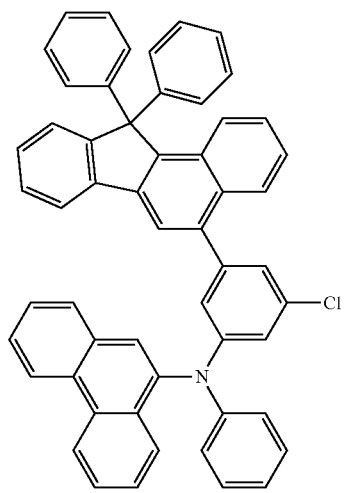
Sub 2-40
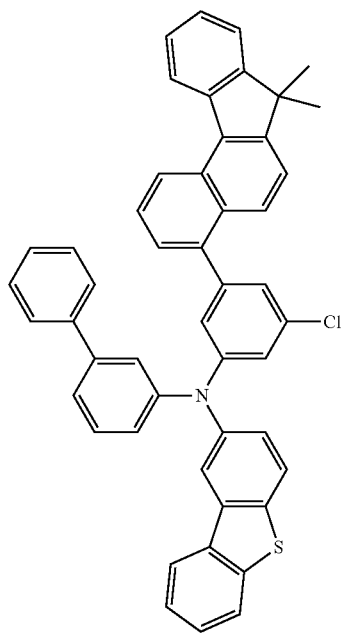
Sub 2-41
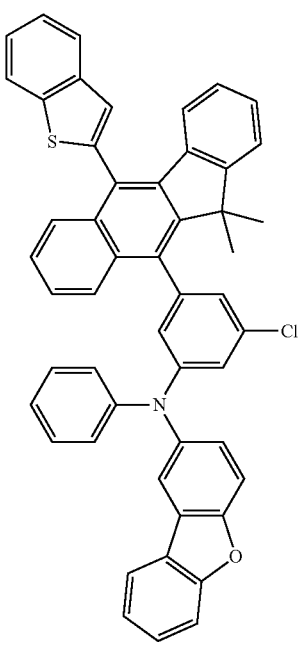
Sub 2-42

Sub 2-43
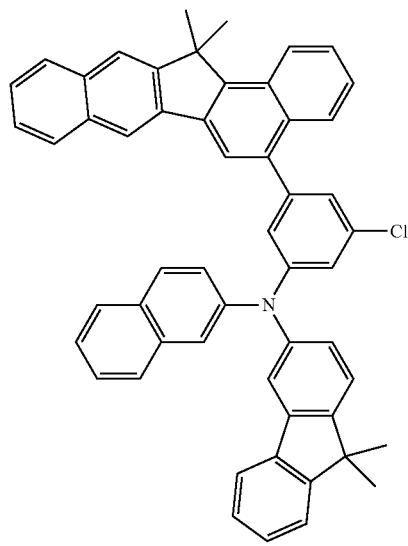
Sub 2-44
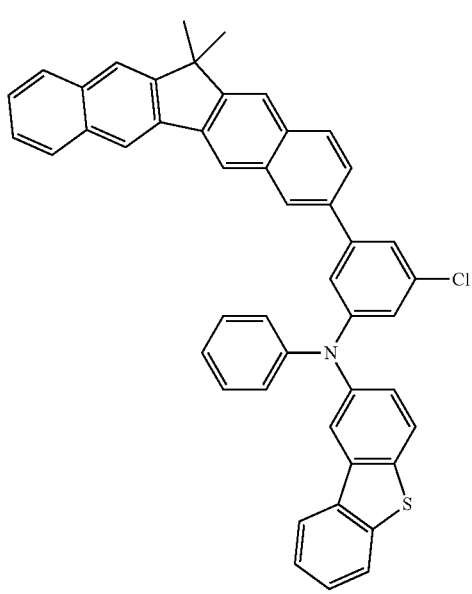
Sub 2-45
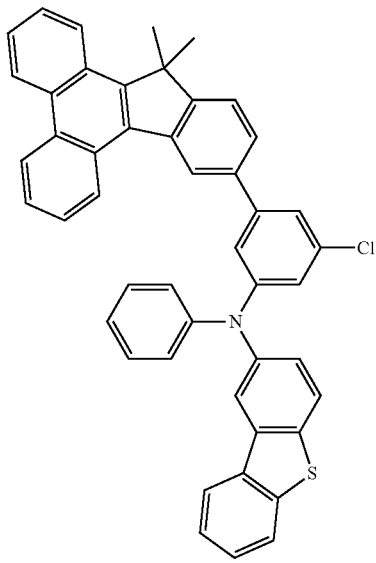
Sub 2-46
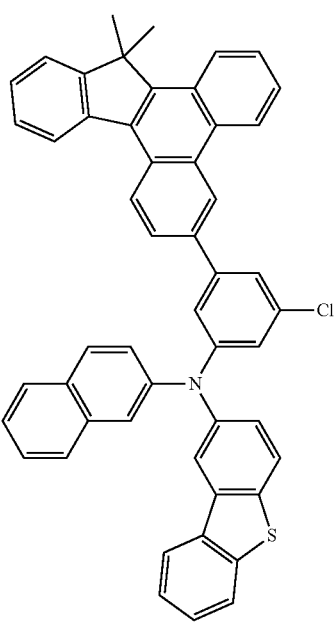
Sub 2-47
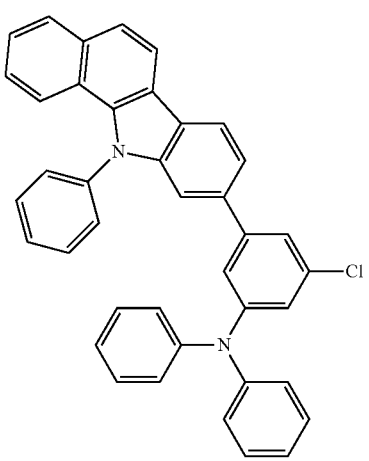

Sub 2-48
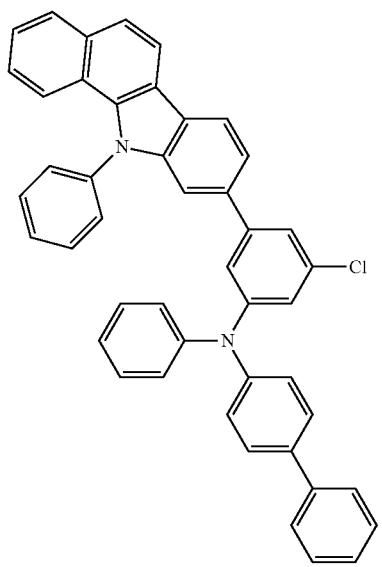
Sub 2-50
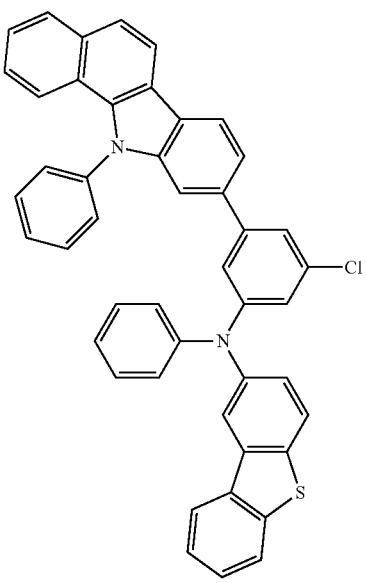
Sub 2-51
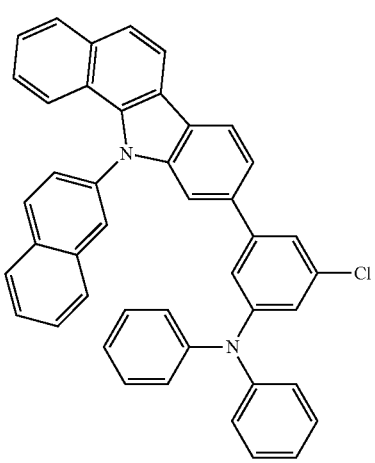
Sub 2-49
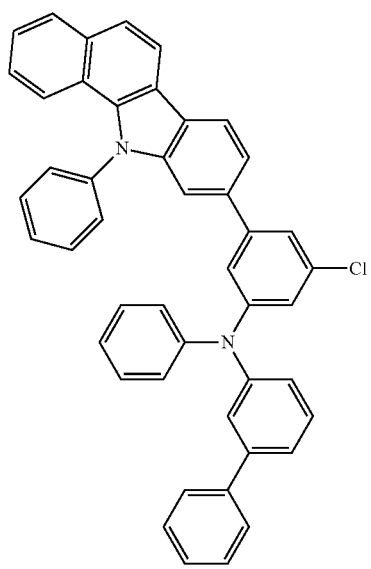
Sub 2-52
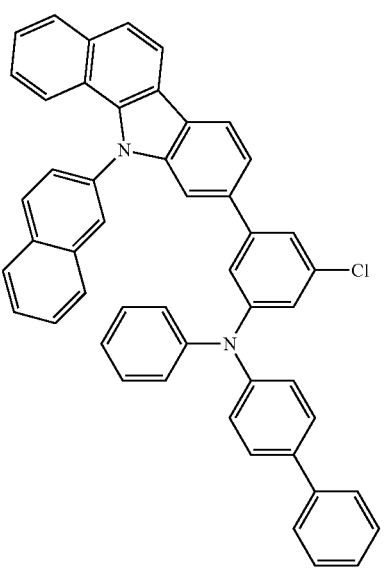

Sub 2-53
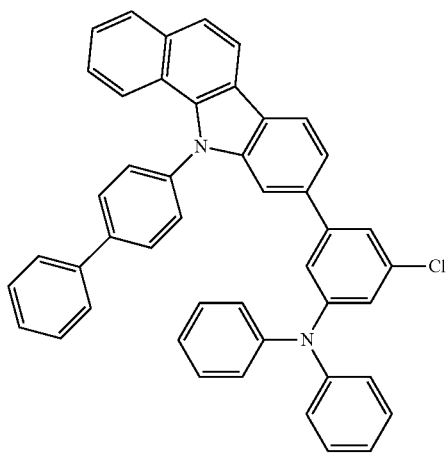
Sub 2-54
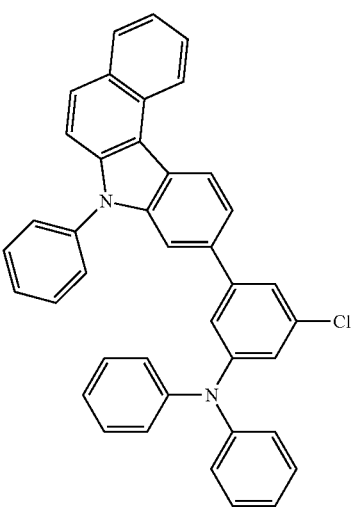
Sub 2-55
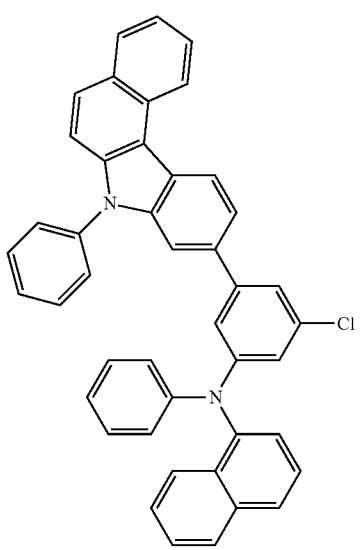
Sub 2-56
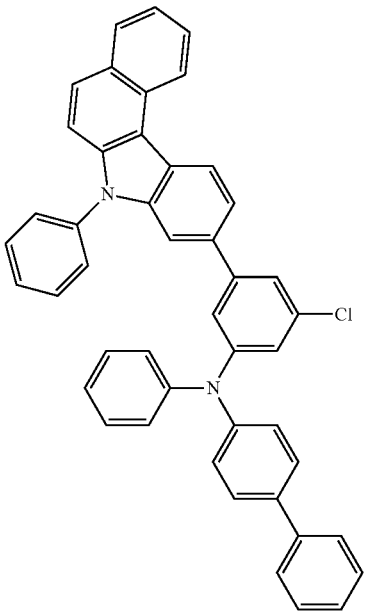
Sub 2-57
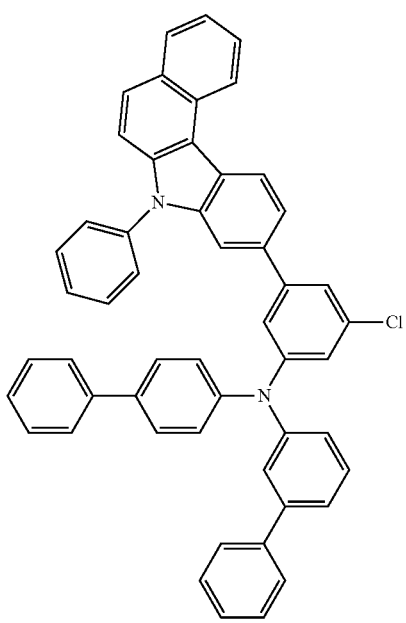

Sub 2-58
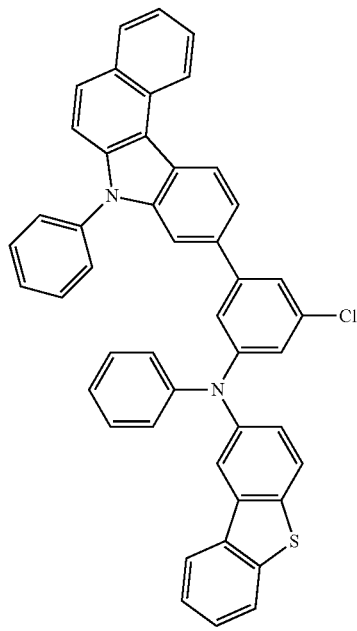
Sub 2-60
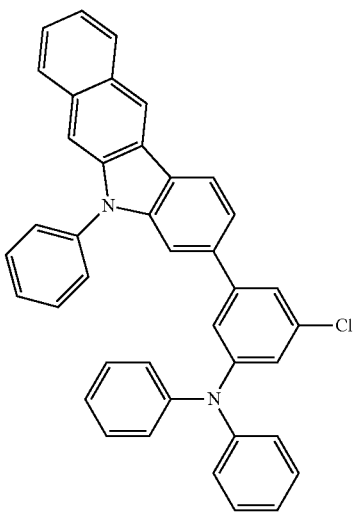
Sub 2-59
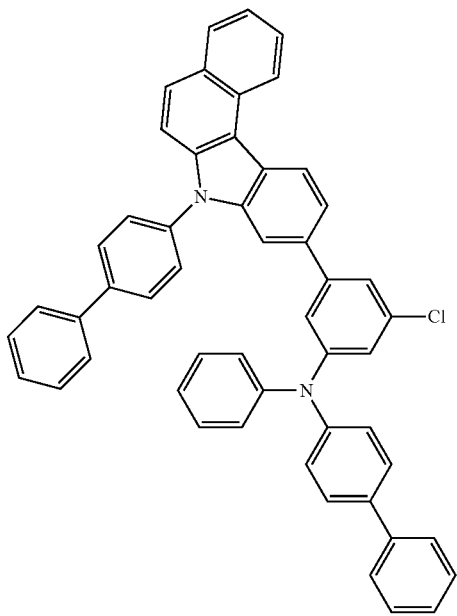
Sub 2-61
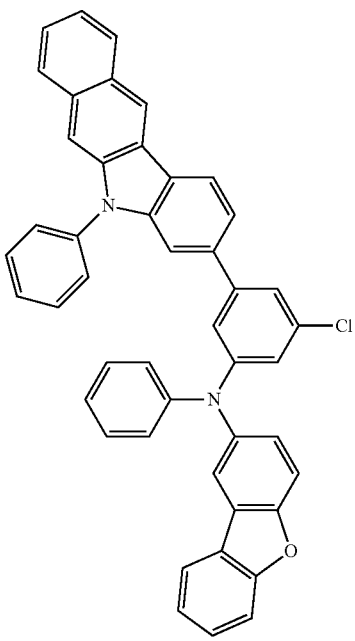

Sub 2-62
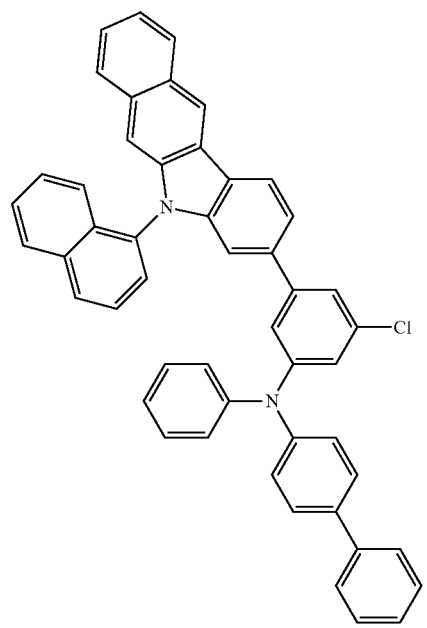
Sub 2-63
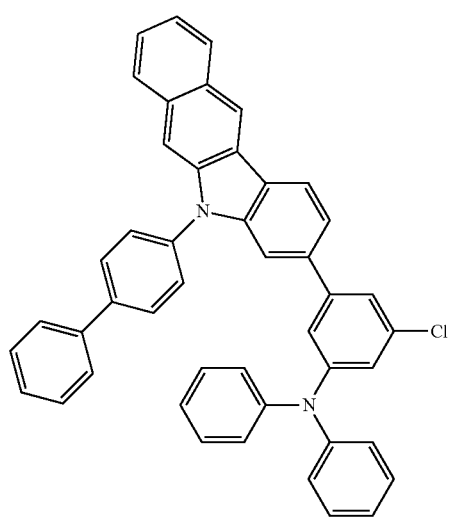
Sub 2-64
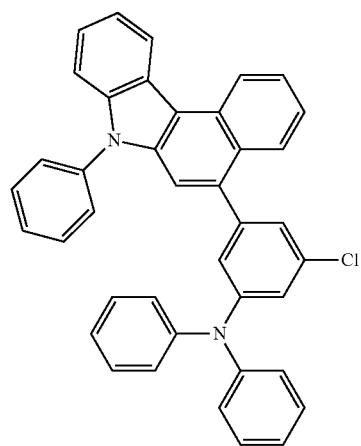
Sub 2-65
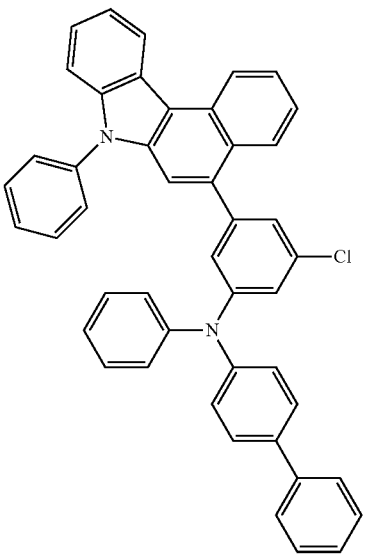
Sub 2-66
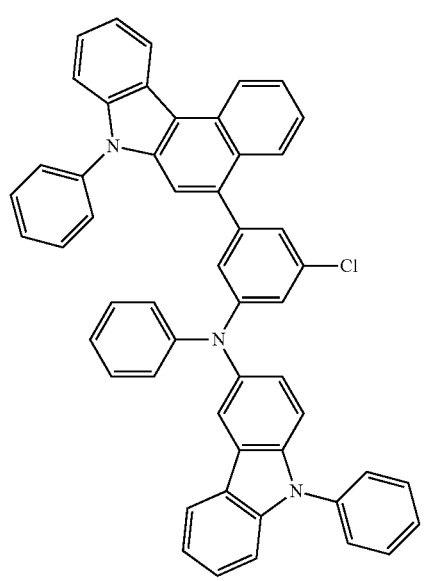
Sub 2-67
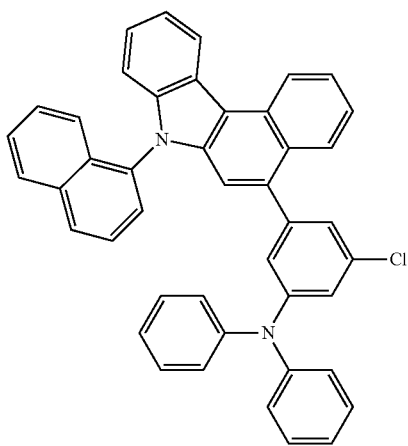

-continued
Sub 2-68
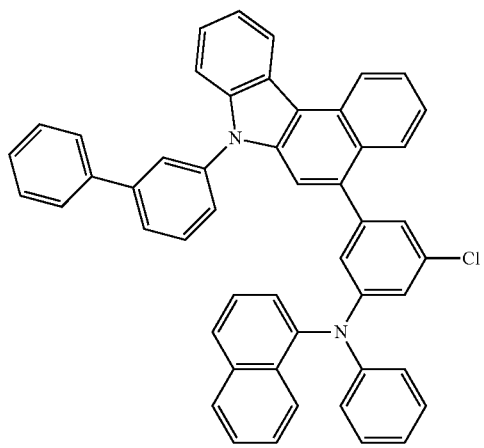
Sub 2-69
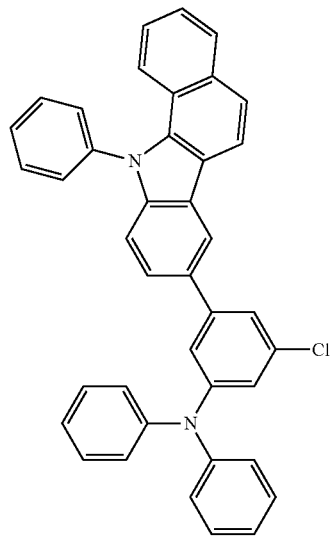
Sub 2-70
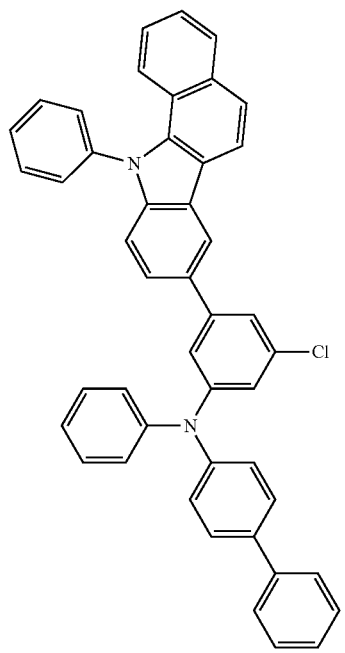
-continued
Sub 2-71
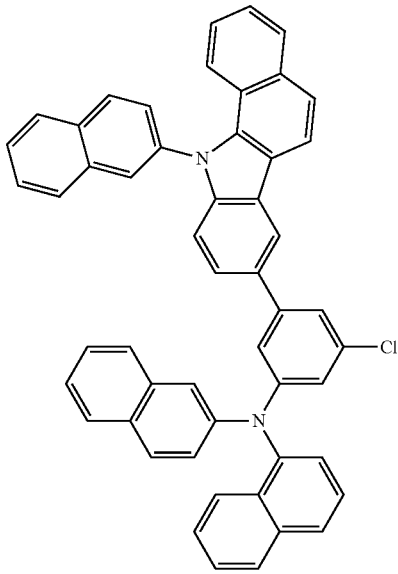
Sub 2-72
Sub 2-73

-continued
Sub 2-74
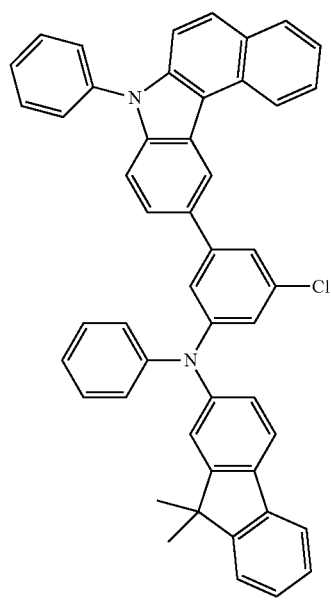
Sub 2-75
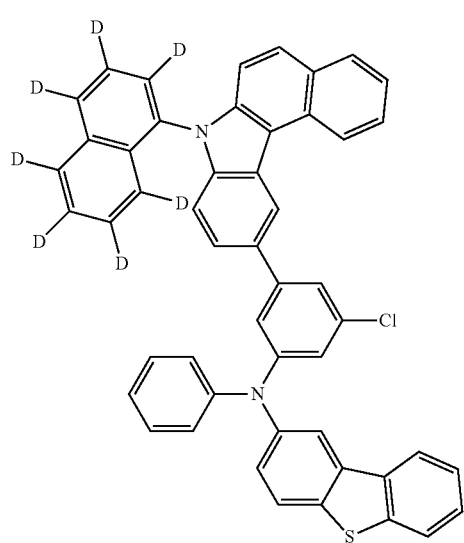
Sub 2-76
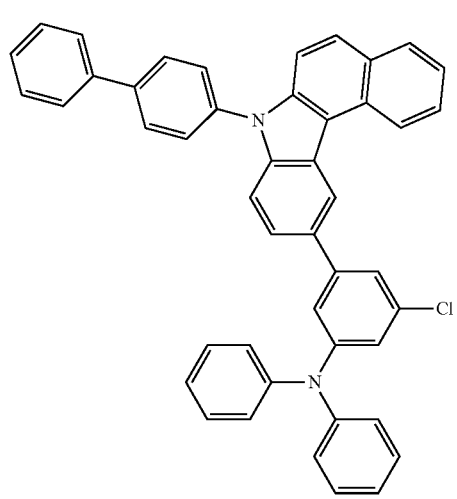
-continued
Sub 2-77
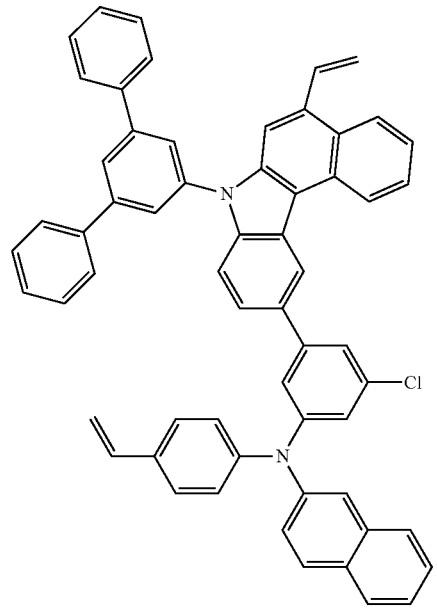
Sub 2-78
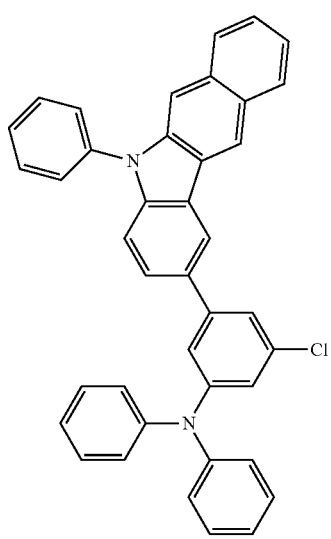
Sub 2-79
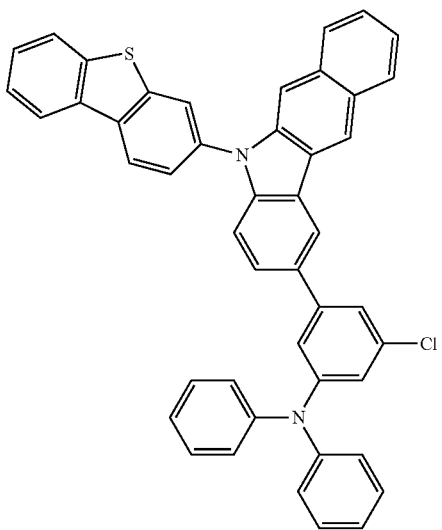

Sub 2-80
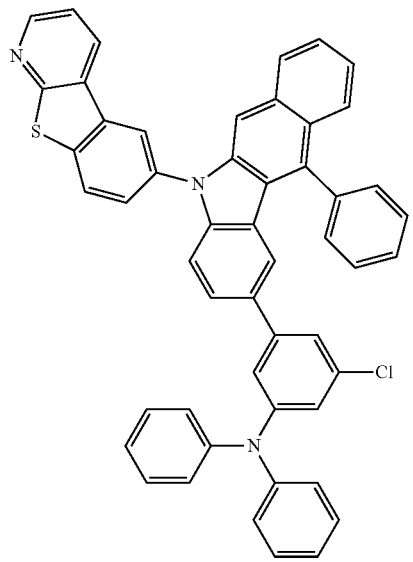
Sub 2-82
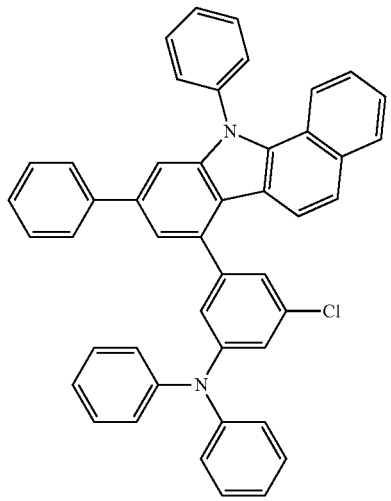
Sub 2-81
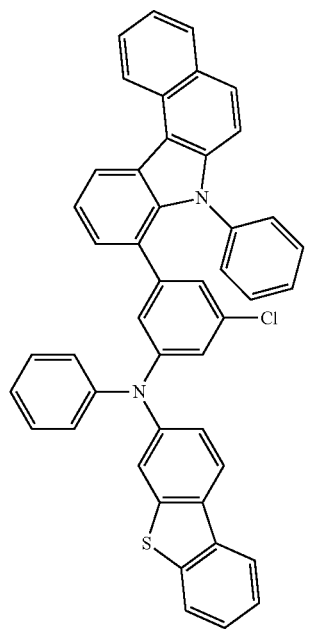
Sub 2-83
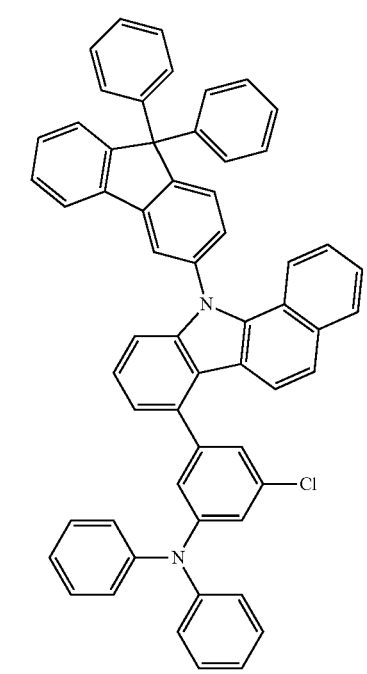

Sub 2-84
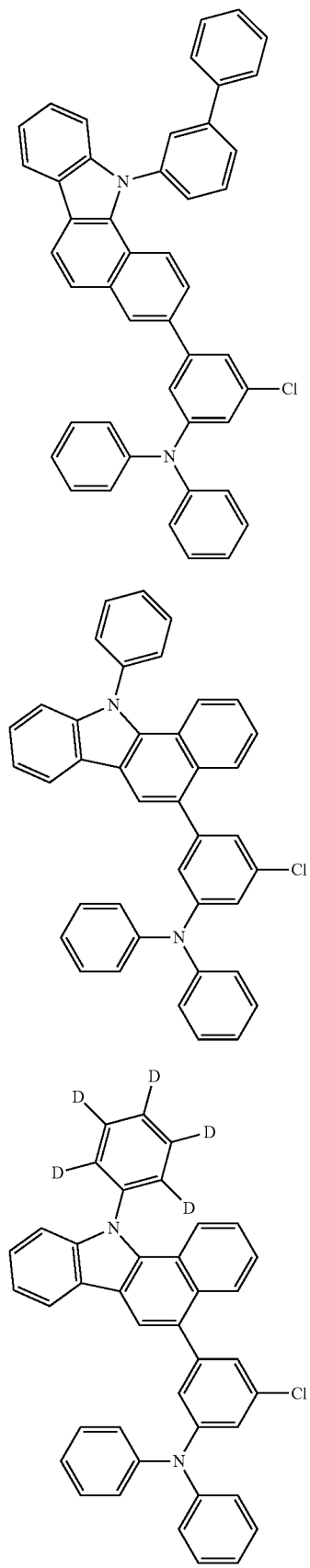
Sub 2-85
Sub 2-86
Sub 2-87
Sub 2-88

Sub 2-89
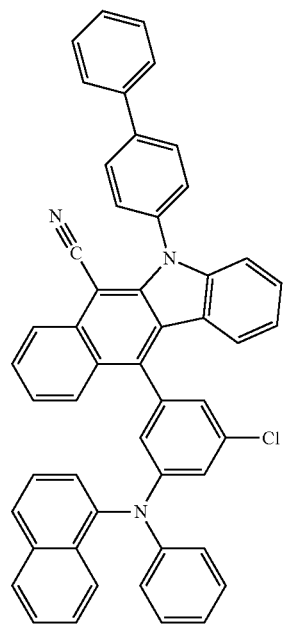
Sub 2-91
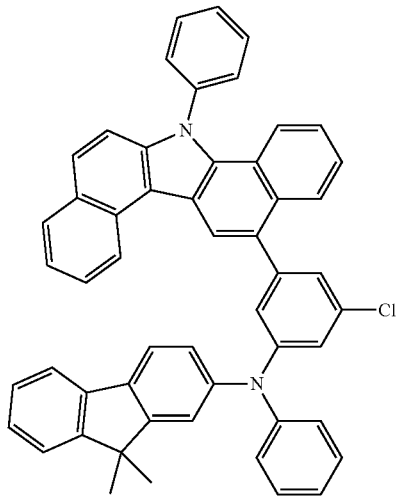
Sub 2-90
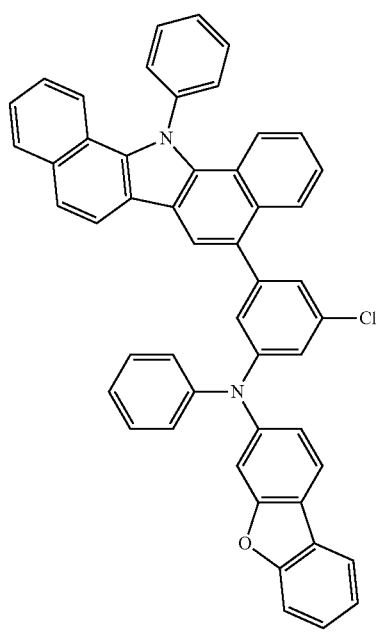
Sub 2-92
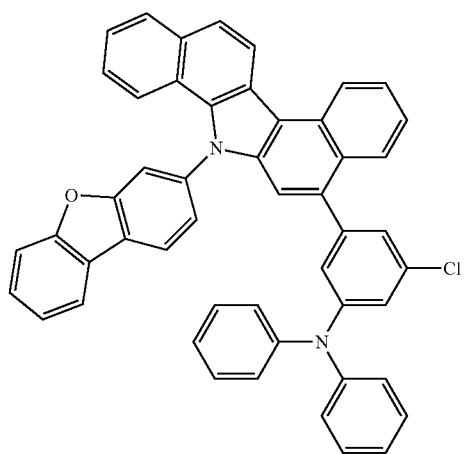

Sub 2-93
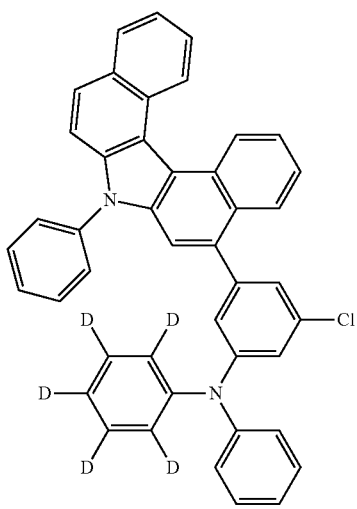

Sub 2-94
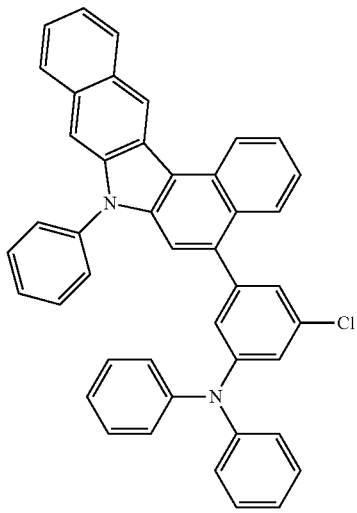

Sub 2-95
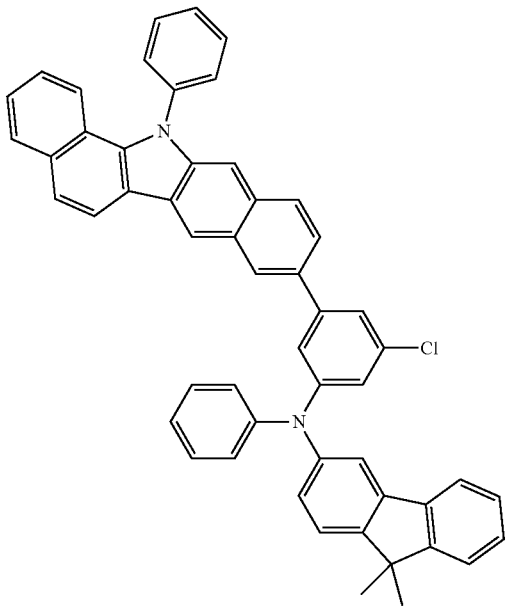

Sub 2-96
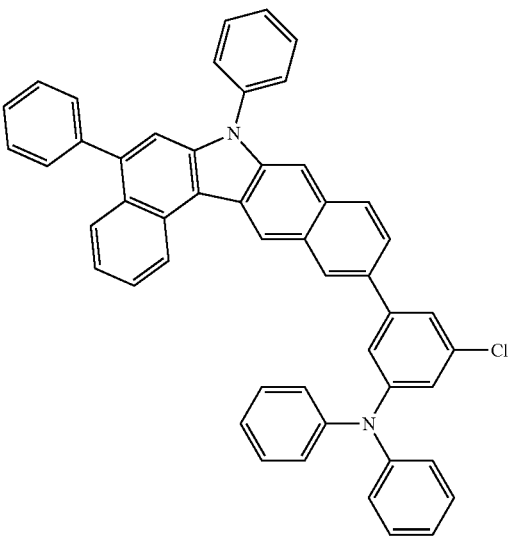

TABLE 2

| compound | FD-MS | compound | FD-MS |
|---|---|---|---|
| Sub 2-1 | m/z = 521.19($C_{37}H_{28}ClN$ = 522.08) | Sub 2-2 | m/z = 597.22($C_{43}H_{32}ClN$ = 598.17) |
| Sub 2-3 | m/z = 673.25($C_{49}H_{36}ClN$ = 674.27) | Sub 2-4 | m/z = 673.25($C_{49}H_{36}ClN$ = 674.27) |
| Sub 2-5 | m/z = 521.19($C_{37}H_{28}ClN$ = 522.08) | Sub 2-6 | m/z = 571.21($C_{41}H_{30}ClN$ = 572.14) |
| Sub 2-7 | m/z = 647.24($C_{47}H_{34}ClN$ = 648.23) | Sub 2-8 | m/z = 673.25($C_{49}H_{36}ClN$ = 674.27) |
| Sub 2-9 | m/z = 521.19($C_{37}H_{28}ClN$ = 522.08) | Sub 2-10 | m/z = 571.21($C_{41}H_{30}ClN$ = 572.14) |
| Sub 2-11 | m/z = 597.22($C_{43}H_{32}ClN$ = 598.17) | Sub 2-12 | m/z = 673.25($C_{49}H_{36}ClN$ = 674.27) |
| Sub 2-13 | m/z = 645.22($C_{47}H_{32}ClN$ = 646.22) | Sub 2-14 | m/z = 695.24($C_{51}H_{34}ClN$ = 696.28) |
| Sub 2-15 | m/z = 673.25($C_{49}H_{36}ClN$ = 674.27) | Sub 2-16 | m/z = 659.24($C_{48}H_{34}ClN$ = 660.24) |
| Sub 2-17 | m/z = 721.25($C_{53}H_{36}ClN$ = 722.31) | Sub 2-18 | m/z = 695.24($C_{51}H_{34}ClN$ = 696.28) |
| Sub 2-19 | m/z = 659.24($C_{48}H_{34}ClN$ = 660.24) | Sub 2-20 | m/z = 735.27($C_{54}H_{38}ClN$ = 736.34) |
| Sub 2-21 | m/z = 645.22($C_{47}H_{32}ClN$ = 646.22) | Sub 2-22 | m/z = 659.24($C_{48}H_{34}ClN$ = 660.24) |
| Sub 2-23 | m/z = 597.22($C_{43}H_{32}ClN$ = 598.17) | Sub 2-24 | m/z = 621.22($C_{45}H_{32}ClN$ = 622.20) |
| Sub 2-25 | m/z = 627.18($C_{43}H_{30}ClNS$ = 628.22) | Sub 2-26 | m/z = 611.20($C_{43}H_{30}ClNO$ = 612.16) |
| Sub 2-27 | m/z = 645.22($C_{47}H_{32}ClN$ = 646.22) | Sub 2-28 | m/z = 721.25($C_{53}H_{36}ClN$ = 722.31) |
| Sub 2-29 | m/z = 797.28($C_{59}H_{40}ClN$ = 798.41) | Sub 2-30 | m/z = 810.28($C_{59}H_{39}ClN_2$ = 811.41) |
| Sub 2-31 | m/z = 659.24($C_{48}H_{34}ClN$ = 660.24) | Sub 2-32 | m/z = 521.19($C_{37}H_{28}ClN$ = 522.08) |

TABLE 2-continued

| compound | FD-MS | compound | FD-MS |
|---|---|---|---|
| Sub 2-33 | m/z = 597.22($C_{43}H_{32}ClN$ = 598.17) | Sub 2-34 | m/z = 639.23($C_{45}H_{34}ClNO$ = 640.21) |
| Sub 2-35 | m/z = 597.22($C_{43}H_{32}ClN$ = 598.17) | Sub 2-36 | m/z = 627.18($C_{43}H_{30}ClNS$ = 628.22) |
| Sub 2-37 | m/z = 645.22($C_{47}H_{32}ClN$ = 646.22) | Sub 2-38 | m/z = 521.19($C_{37}H_{28}ClN$ = 522.08) |
| Sub 2-39 | m/z = 745.25($C_{55}H_{36}ClN$ = 746.33) | Sub 2-40 | m/z = 703.21($C_{49}H_{34}ClNS$ = 704.32) |
| Sub 2-41 | m/z = 743.20($C_{51}H_{34}ClNOS$ = 744.34) | Sub 2-42 | m/z = 743.24($C_{52}H_{38}ClNS$ = 744.38) |
| Sub 2-43 | m/z = 737.28($C_{54}H_{40}ClN$ = 738.36) | Sub 2-44 | m/z = 677.19($C_{47}H_{32}ClNS$ = 678.28) |
| Sub 2-45 | m/z = 677.19($C_{47}H_{32}ClNS$ = 678.28) | Sub 2-46 | m/z = 727.21($C_{51}H_{34}ClNS$ = 728.34) |
| Sub 2-47 | m/z = 570.19($C_{40}H_{27}ClN_2$ = 571.11) | Sub 2-48 | m/z = 646.22($C_{46}H_{31}ClN_2$ = 647.20) |
| Sub 2-49 | m/z = 646.22($C_{46}H_{31}ClN_2$ = 647.20) | Sub 2-50 | m/z = 676.17($C_{46}H_{29}ClN_2S$ = 677.25) |
| Sub 2-51 | m/z = 620.20($C_{44}H_{29}ClN_2$ = 621.17) | Sub 2-52 | m/z = 696.23($C_{50}H_{33}ClN_2$ = 697.26) |
| Sub 2-53 | m/z = 646.22($C_{46}H_{31}ClN_2$ = 647.20) | Sub 2-54 | m/z = 570.19($C_{40}H_{27}ClN_2$ = 571.11) |
| Sub 2-55 | m/z = 620.20($C_{44}H_{29}ClN_2$ = 621.17) | Sub 2-56 | m/z = 646.22($C_{46}H_{31}ClN_2$ = 647.20) |
| Sub 2-57 | m/z = 722.25($C_{52}H_{35}ClN_2$ = 723.30) | Sub 2-58 | m/z = 676.17($C_{46}H_{29}ClN_2S$ = 677.25) |
| Sub 2-59 | m/z = 722.25($C_{52}H_{35}ClN_2$ = 723.30) | Sub 2-60 | m/z = 570.19($C_{40}H_{27}ClN_2$ = 571.11) |
| Sub 2-61 | m/z = 660.20($C_{46}H_{29}ClN_2O$ = 661.19) | Sub 2-62 | m/z = 696.23($C_{50}H_{33}ClN_2$ = 697.26) |
| Sub 2-63 | m/z = 646.22($C_{46}H_{31}ClN_2$ = 647.20) | Sub 2-64 | m/z = 570.19($C_{40}H_{27}ClN_2$ = 571.11) |
| Sub 2-65 | m/z = 646.22($C_{46}H_{31}ClN_2$ = 647.20) | Sub 2-66 | m/z = 735.24($C_{52}H_{34}ClN_3$ = 736.30) |
| Sub 2-67 | m/z = 620.20($C_{44}H_{29}ClN_2$ = 621.17) | Sub 2-68 | m/z = 696.23($C_{50}H_{33}ClN_2$ = 697.26) |
| Sub 2-69 | m/z = 570.19($C_{40}H_{27}ClN_2$ = 571.11) | Sub 2-70 | m/z = 646.22($C_{46}H_{31}ClN_2$ = 647.20) |
| Sub 2-71 | m/z = 720.23($C_{52}H_{33}ClN_2$ = 721.28) | Sub 2-72 | m/z = 686.25($C_{49}H_{35}ClN_2$ = 687.27) |
| Sub 2-73 | m/z = 570.19($C_{40}H_{27}ClN_2$ = 571.11) | Sub 2-74 | m/z = 686.25($C_{49}H_{35}ClN_2$ = 687.27) |
| Sub 2-75 | m/z = 733.23($C_{50}H_{24}D_7ClN_2S$ = 734.36) | Sub 2-76 | m/z = 646.22($C_{46}H_{31}ClN_2$ = 647.20) |
| Sub 2-77 | m/z = 824.30($C_{60}H_{41}ClN_2$ = 825.43) | Sub 2-78 | m/z = 570.19($C_{40}H_{27}ClN_2$ = 571.11) |
| Sub 2-79 | m/z = 676.17($C_{46}H_{29}ClN_2S$ = 677.25) | Sub 2-80 | m/z = 753.20($C_{51}H_{32}ClN_3S$ = 754.34) |
| Sub 2-81 | m/z = 676.17($C_{46}H_{29}ClN_2S$ = 677.25) | Sub 2-82 | m/z = 646.22($C_{46}H_{31}ClN_2$ = 647.20) |
| Sub 2-83 | m/z = 810.28($C_{59}H_{39}ClN_2$ = 811.41) | Sub 2-84 | m/z = 646.22($C_{46}H_{31}ClN_2$ = 647.20) |
| Sub 2-85 | m/z = 570.19($C_{40}H_{27}ClN_2$ = 571.11) | Sub 2-86 | m/z = 575.22($C_{40}H_{22}D_5ClN_2$ = 576.14) |
| Sub 2-87 | m/z = 570.19($C_{40}H_{27}ClN_2$ = 571.11) | Sub 2-88 | m/z = 722.25($C_{52}H_{35}ClN_2$ = 723.30) |
| Sub 2-89 | m/z = 721.23($C_{51}H_{32}ClN_3$ = 722.27) | Sub 2-90 | m/z = 710.21($C_{50}H_{31}ClN_2O$ = 711.25) |
| Sub 2-91 | m/z = 736.26($C_{53}H_{37}ClN_2$ = 737.33) | Sub 2-92 | m/z = 710.21($C_{50}H_{31}ClN_2O$ = 711.25) |
| Sub 2-93 | m/z = 625.23($C_{44}H_{24}D_5ClN_2$ = 626.20) | Sub 2-94 | m/z = 620.20($C_{44}H_{29}ClN_2$ = 621.17) |
| Sub 2-95 | m/z = 736.26($C_{53}H_{37}ClN_2$ = 737.33) | Sub 2-96 | m/z = 696.23($C_{50}H_{33}ClN_2$ = 697.26) |

III. Synthesis of Final Products

Sub 2 (1 eq.) was dissolved in toluene in a round bottom flask, and Sub 1 (1 eq.), $Pd_2(dba)_3$ (0.03 eq.), $P(t\text{-}Bu)_3$ (0.08 eq.) and NaOt-Bu (3 eq.) were added, then, stirring at 100° C. was followed. When the reaction was completed, the reaction product was extracted with $CH_2Cl_2$ and water, and then the organic layer was dried with $MgSO_4$ and concentrated. Then, the concentrate was passed through silica gel column and recrystallized to obtain final product.

1. Synthesis Example of P-1

<Reaction Scheme 30>

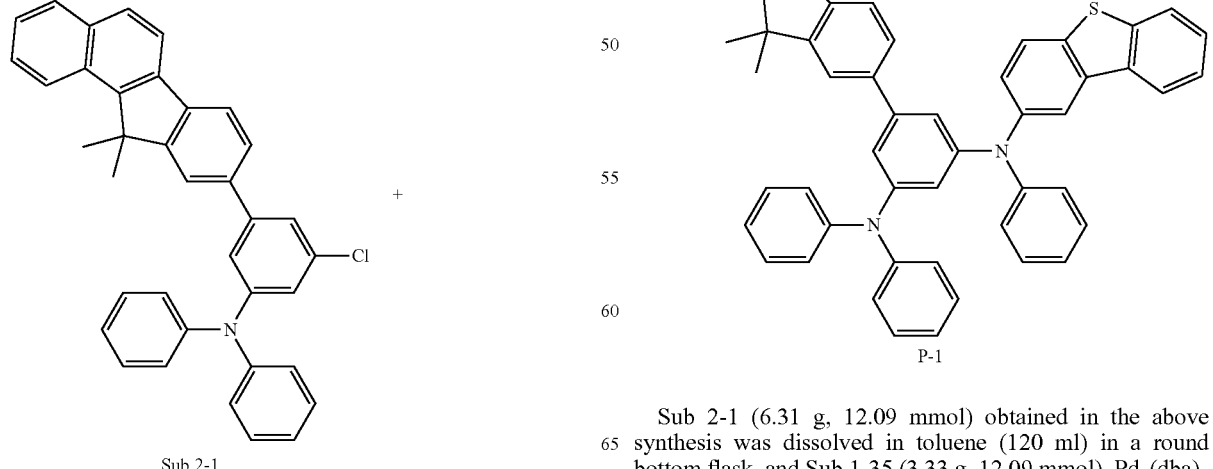

Sub 2-1 (6.31 g, 12.09 mmol) obtained in the above synthesis was dissolved in toluene (120 ml) in a round bottom flask, and Sub 1-35 (3.33 g, 12.09 mmol), $Pd_2(dba)_3$ (0.33 g, 0.36 mmol), 50% $P(t\text{-}Bu)_3$ (0.5 ml, 0.97 mmol), NaOt-Bu (3.48 g, 36.26 mmol) were added, then, stirring at 100° C. was followed. When the reaction was completed, the reaction product was extracted with $CH_2Cl_2$ and water, and then the organic layer was dried with $MgSO_4$ and concentrated. Then, the concentrate was passed through silica gel column and recrystallized to obtain 7.63 g (yield: 83%) of product.

2. Synthesis Example of P-19

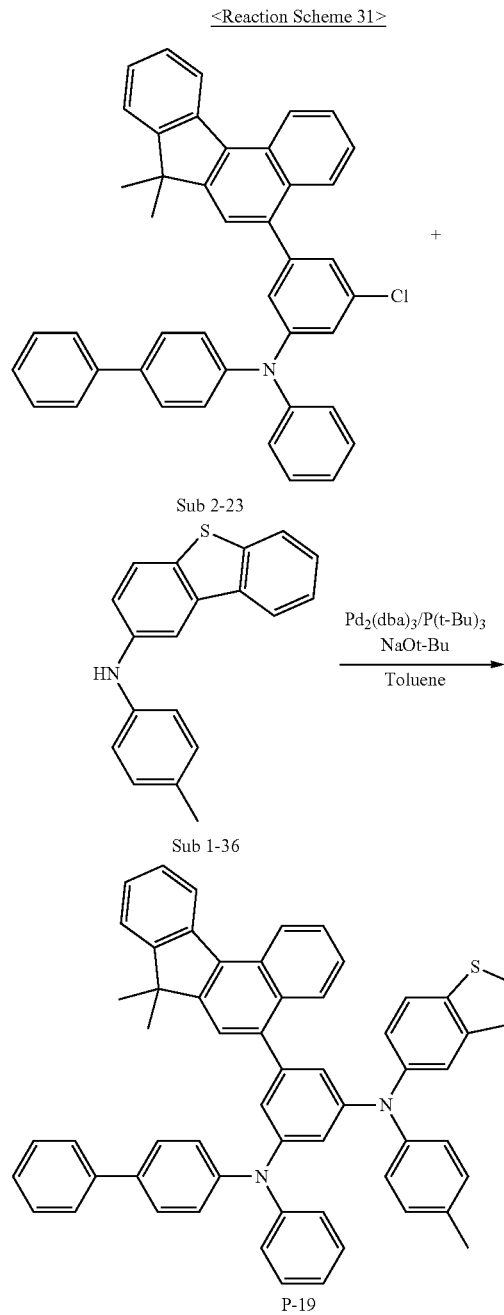

Sub 1-36 (3.41 g, 11.79 mmol), $Pd_2(dba)_3$ (0.32 g, 0.35 mmol), 50% P(t-Bu)$_3$ (0.5 ml, 0.94 mmol), NaOt-Bu (3.40 g, 35.36 mmol), toluene (120 ml) were added to Sub 2-23 (7.05 g, 11.79 mmol) obtained in the above synthesis, and then 7.52 g (yield: 75%) of the product was obtained by using the same manner as described above for the synthesis of the compound P-1.

3. Synthesis Example of P-44

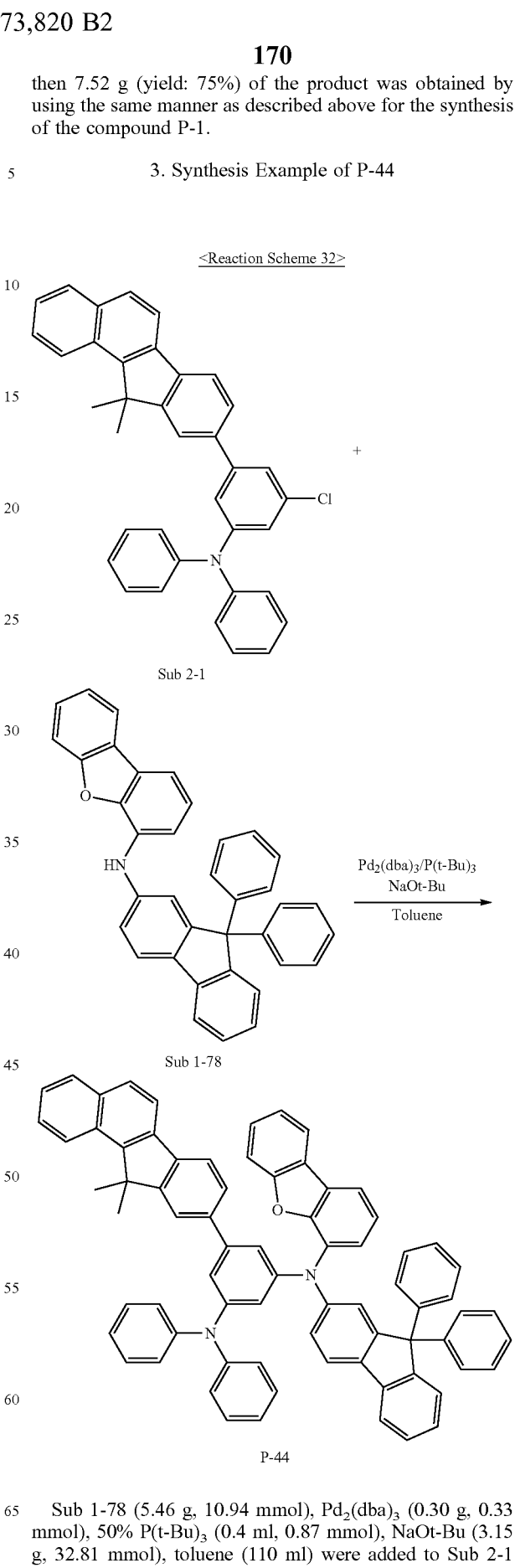

Sub 1-78 (5.46 g, 10.94 mmol), $Pd_2(dba)_3$ (0.30 g, 0.33 mmol), 50% P(t-Bu)$_3$ (0.4 ml, 0.87 mmol), NaOt-Bu (3.15 g, 32.81 mmol), toluene (110 ml) were added to Sub 2-1

(5.71 g, 10.94 mmol) obtained in the above synthesis, and then 7.76 g (yield: 72%) of the product was obtained by using the same manner as described above for the synthesis of the compound P-1.

4. Synthesis Example of P-50

<Reaction Scheme 33>

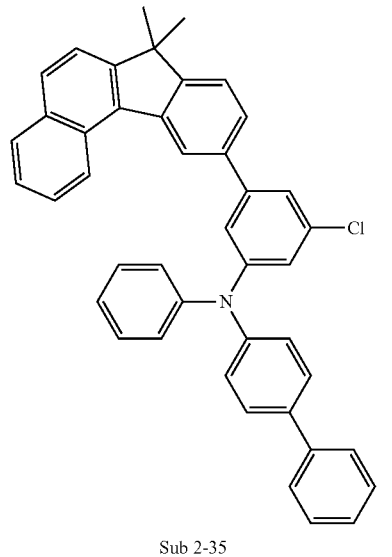

Sub 2-35

+

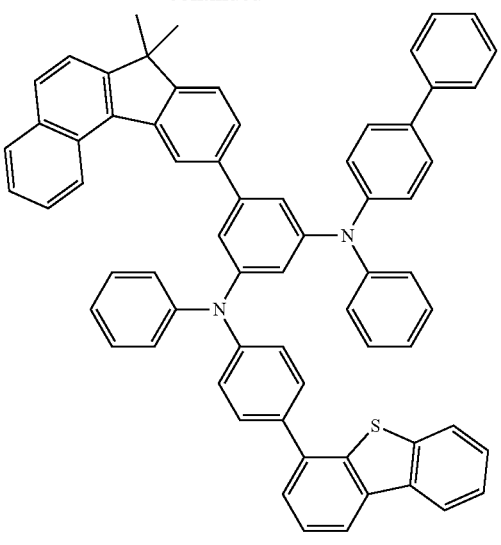

P-50

Sub 1-25 (3.54 g, 10.06 mmol), Pd$_2$(dba)$_3$ (0.28 g, 0.30 mmol), 50% P(t-Bu)$_3$ (0.4 ml, 0.81 mmol), NaOt-Bu (2.90 g, 30.19 mmol), toluene (100 ml) were added to Sub 2-35 (6.02 g, 10.06 mmol) obtained in the above synthesis, and then 7.26 g (yield: 79%) of the product was obtained by using the same manner as described above for the synthesis of the compound P-1.

5. Synthesis Example of P-51

<Reaction Scheme 34>

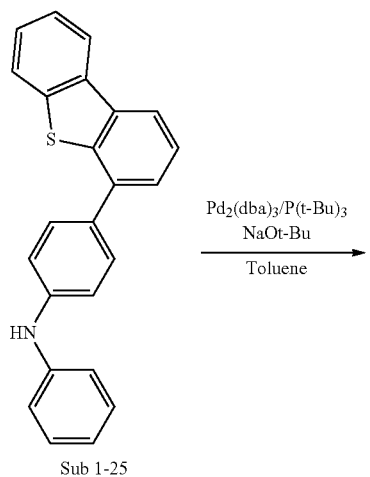

Sub 1-25

Pd$_2$(dba)$_3$/P(t-Bu)$_3$
NaOt-Bu
———————→
Toluene

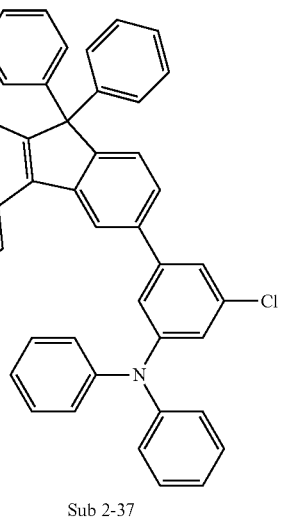

+

Sub 2-37

-continued

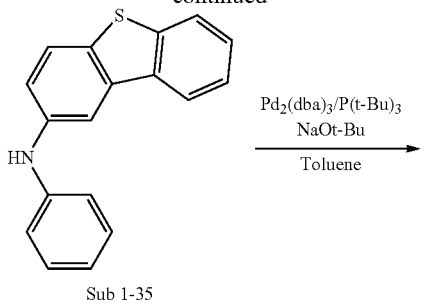
Sub 1-35

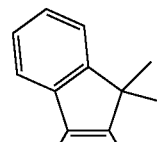
Pd₂(dba)₃/P(t-Bu)₃
NaOt-Bu
Toluene
→

6. Synthesis Example of P-56

<Reaction Scheme 33>

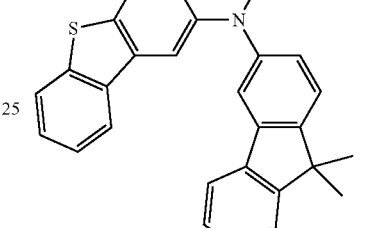
Sub 2-42

+

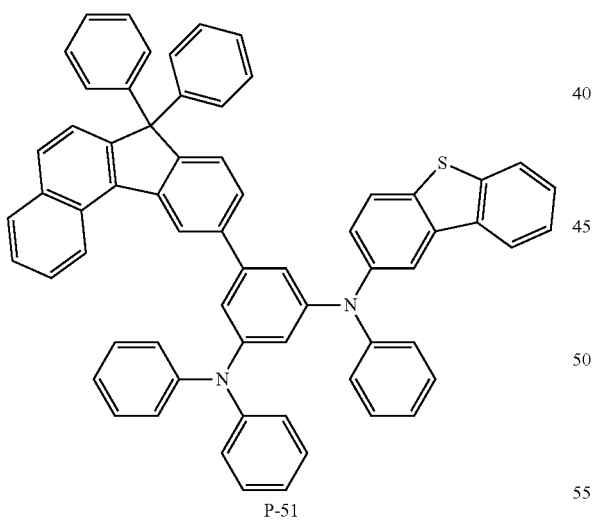
P-51

Sub 1-35 (3.00 g, 10.88 mmol), Pd₂(dba)₃ (0.30 g, 0.33 mmol), 50% P(t-Bu)₃ (0.4 ml, 0.87 mmol), NaOt-Bu (3.14 g, 32.64 mmol), toluene (110 ml) were added to Sub 2-37 (7.03 g, 10.88 mmol) obtained in the above synthesis, and then 7.41 g (yield: 77%) of the product was obtained by using the same manner as described above for the synthesis of the compound P-1.

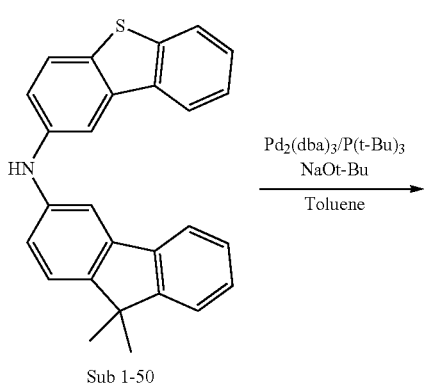
Sub 1-50

Pd₂(dba)₃/P(t-Bu)₃
NaOt-Bu
Toluene
→

-continued

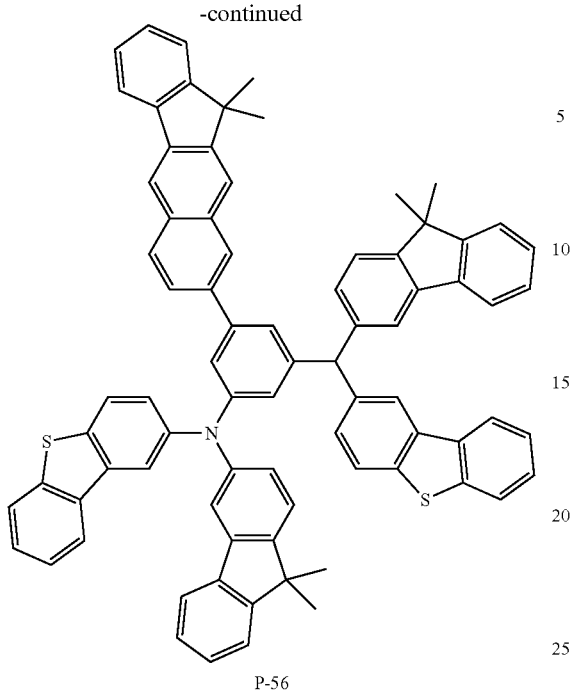

P-56

Sub 1-50 (3.92 g, 10.01 mmol), Pd$_2$(dba)$_3$ (0.27 g, 0.30 mmol), 50% P(t-Bu)$_3$ (0.4 ml, 0.80 mmol), NaOt-Bu (2.89 g, 30.02 mmol), toluene (100 ml) were added to Sub 2-42 (7.45 g, 10.01 mmol) obtained in the above synthesis, and then 7.48 g (yield: 68%) of the product was obtained by using the same manner as described above for the synthesis of the compound P-1.

7. Synthesis Example of P-66

<Reaction Scheme 36>

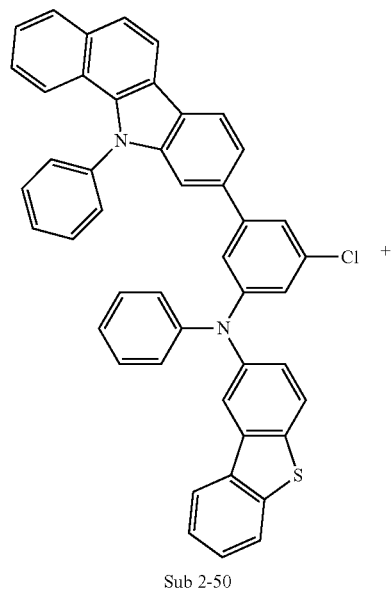

Sub 2-50

-continued

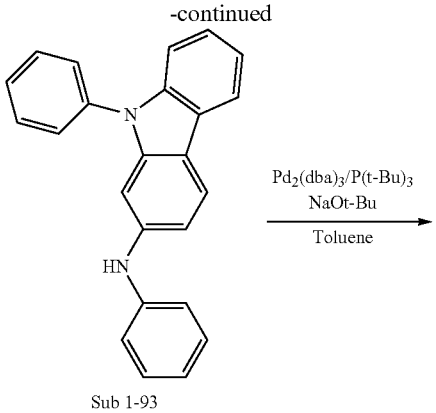

Sub 1-93

P-66

Sub 1-93 (3.34 g, 9.98 mmol), Pd$_2$(dba)$_3$ (0.27 g, 0.30 mmol), 50% P(t-Bu)$_3$ (0.4 ml, 0.80 mmol), NaOt-Bu (2.88 g, 29.94 mmol), toluene (100 ml) were added to Sub 2-50 (6.76 g, 9.98 mmol) obtained in the above synthesis, and then 7.88 g (yield: 81%) of the product was obtained by using the same manner as described above for the synthesis of the compound P-1.

8. Synthesis Example of P-112

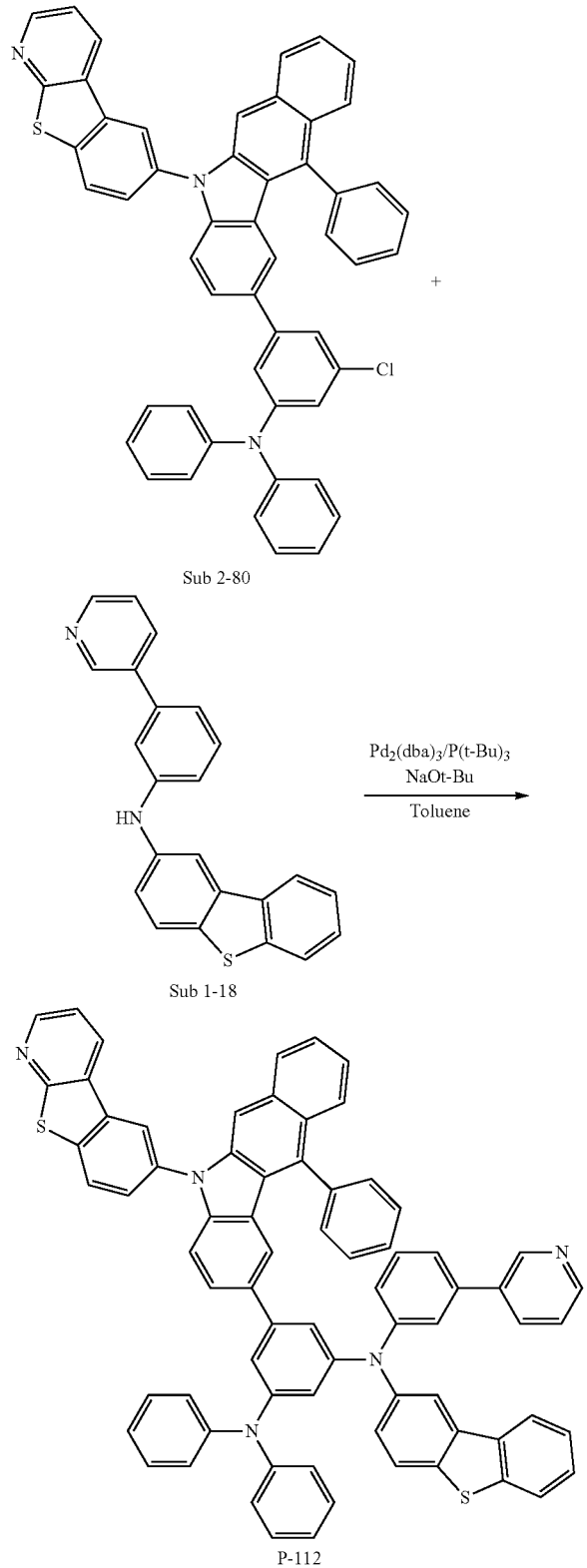

<Reaction Scheme 37>

Sub 1-18 (3.89 g, 11.03 mmol), Pd₂(dba)₃ (0.30 g, 0.33 mmol), 50% P(t-Bu)₃ (0.4 ml, 0.88 mmol), NaOt-Bu (3.18 g, 33.09 mmol), toluene (110 ml) were added to Sub 2-80 (8.32 g, 11.03 mmol) obtained in the above synthesis, and then 7.08 g (yield: 60%) of the product was obtained by using the same manner as described above for the synthesis of the compound P-1.

9. Synthesis Example of P-113

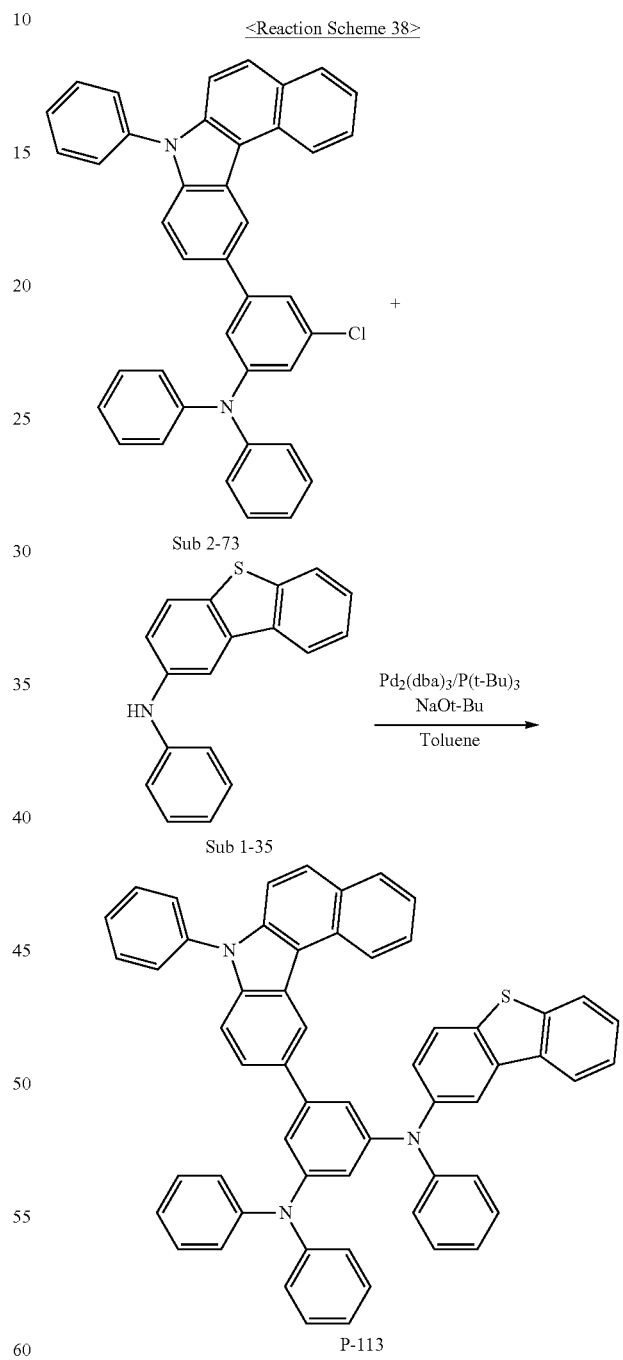

<Reaction Scheme 38>

Sub 1-35 (2.98 g, 10.82 mmol), Pd₂(dba)₃ (0.30 g, 0.32 mmol), 50% P(t-Bu)₃ (0.4 ml, 0.87 mmol), NaOt-Bu (3.12 g, 32.46 mmol), toluene (110 ml) were added to Sub 2-73 (6.18 g, 10.82 mmol) obtained in the above synthesis, and then 7.36 g (yield: 84%) of the product was obtained by using the same manner as described above for the synthesis of the compound P-1.

10. Synthesis Example of P-120

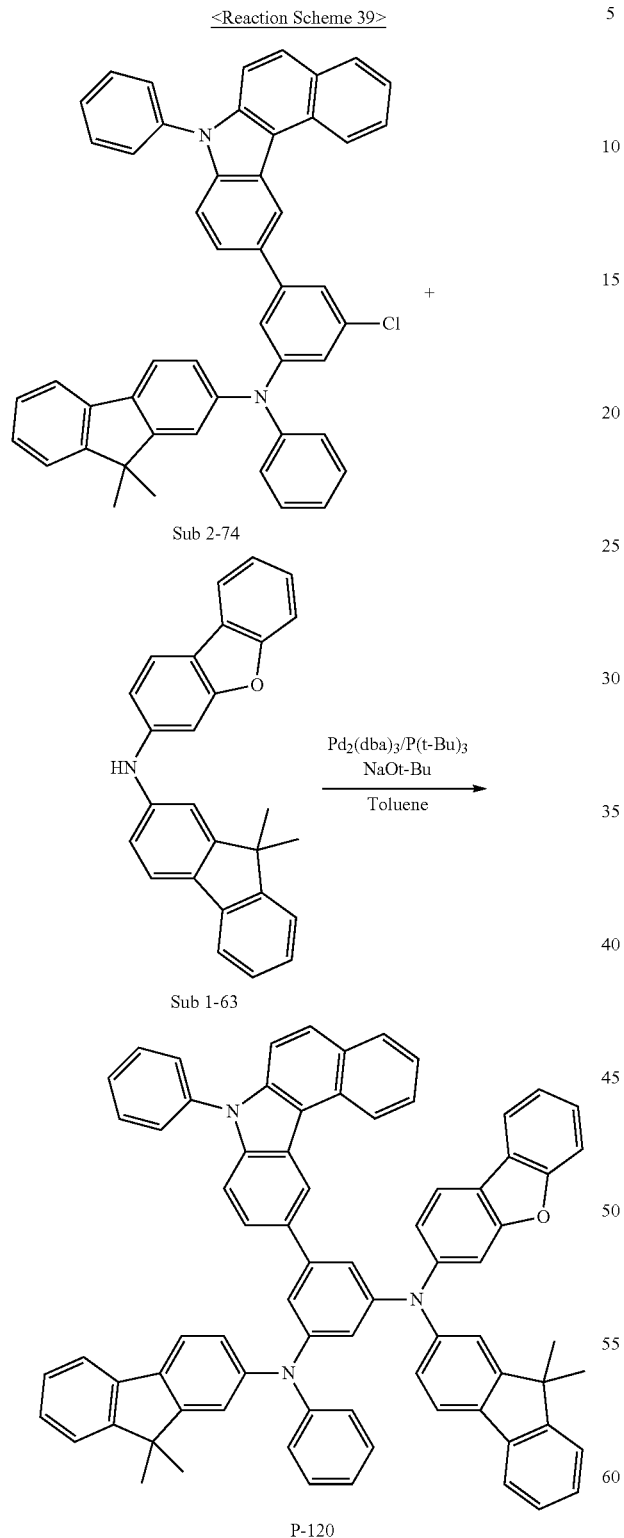

Sub 1-63 (3.89 g, 10.36 mmol), Pd$_2$(dba)$_3$ (0.28 g, 0.31 mmol), 50% P(t-Bu)$_3$ (0.4 ml, 0.83 mmol), NaOt-Bu (2.99 g, 31.08 mmol), toluene (105 ml) were added to Sub 2-74 (7.12 g, 10.36 mmol) obtained in the above synthesis, and then 7.55 g (yield: 71%) of the product was obtained by using the same manner as described above for the synthesis of the compound P-1.

11. Synthesis Example of P-122

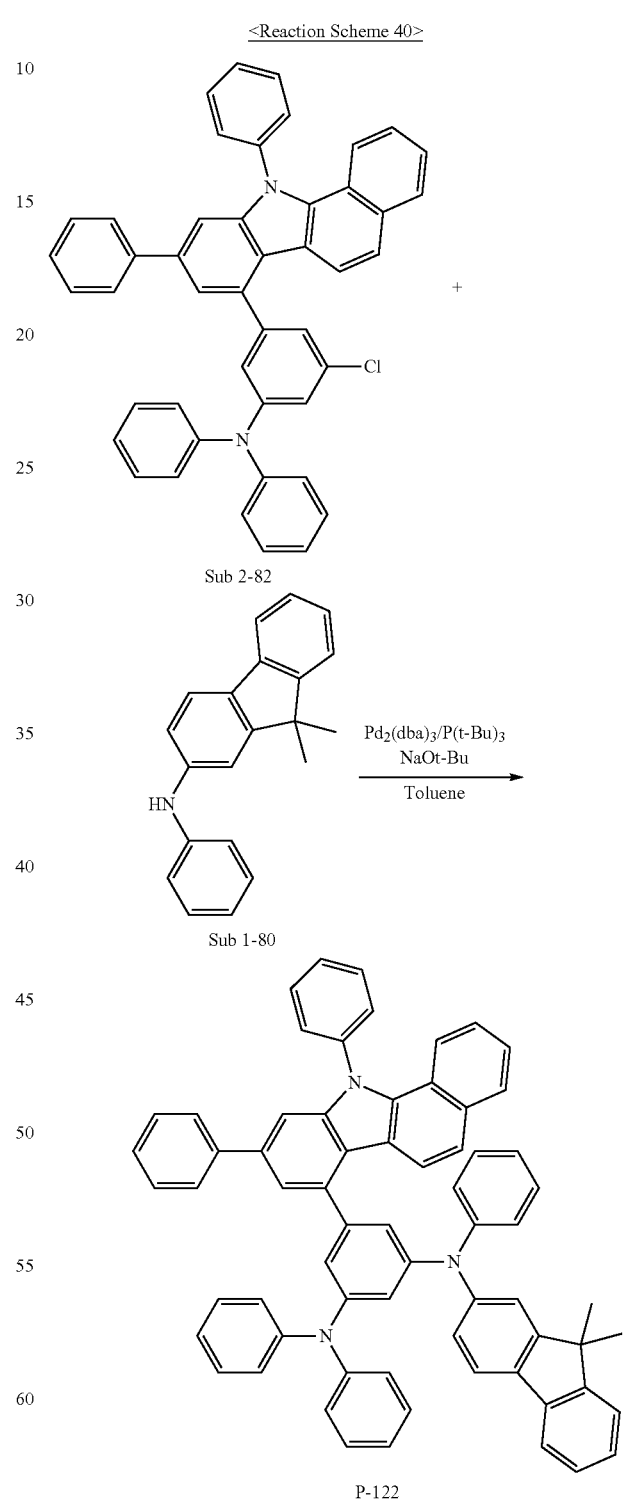

Sub 1-80 (3.10 g, 10.88 mmol), Pd$_2$(dba)$_3$ (0.30 g, 0.33 mmol), 50% P(t-Bu)$_3$ (0.4 ml, 0.87 mmol), NaOt-Bu (3.14 g, 32.63 mmol), toluene (110 ml) were added to Sub 2-82

(7.04 g, 10.88 mmol) obtained in the above synthesis, and then 7.41 g (yield: 76%) of the product was obtained by using the same manner as described above for the synthesis of the compound P-1.

12. Synthesis Example of P-132

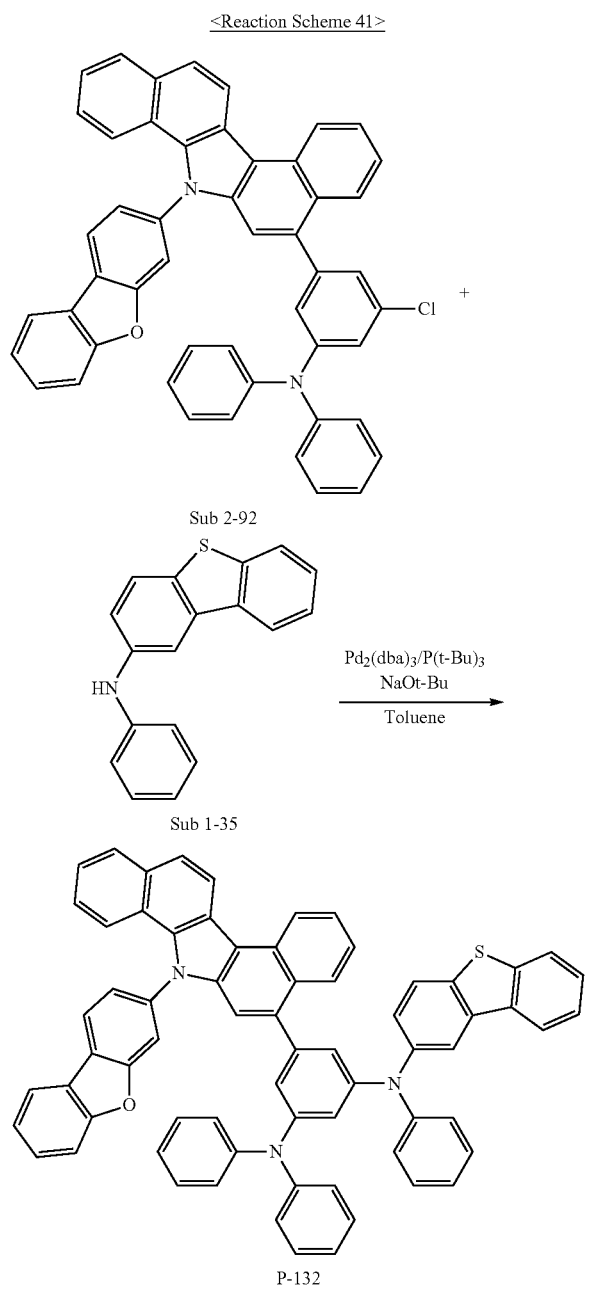

13. Synthesis Example of P-133

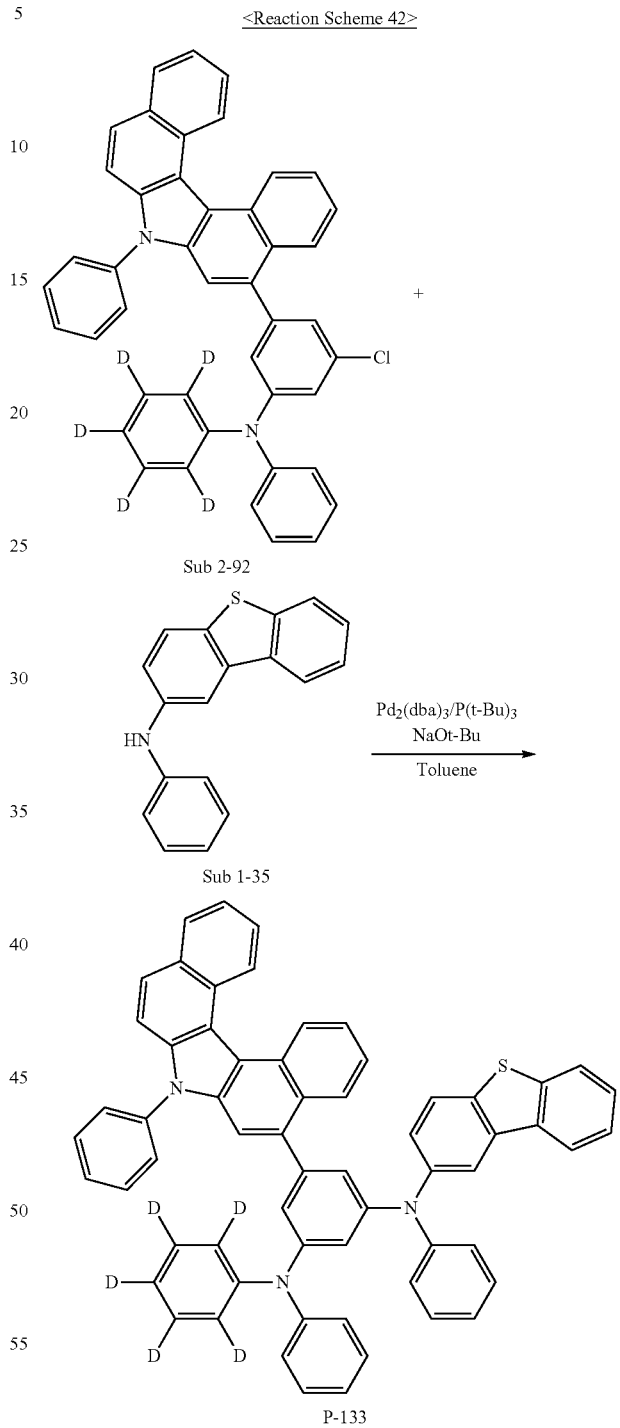

Sub 1-35 (3.28 g, 11.91 mmol), Pd$_2$(dba)$_3$ (0.33 g, 0.36 mmol), 50% P(t-Bu)$_3$ (0.5 ml, 0.95 mmol), NaOt-Bu (3.43 g, 35.73 mmol), toluene (120 ml) were added to Sub 2-92 (8.47 g, 11.91 mmol) obtained in the above synthesis, and then 7.35 g (yield: 65%) of the product was obtained by using the same manner as described above for the synthesis of the compound P-1.

Sub 1-35 (3.37 g, 12.23 mmol), Pd$_2$(dba)$_3$ (0.34 g, 0.37 mmol), 50% P(t-Bu)$_3$ (0.5 ml, 0.98 mmol), NaOt-Bu (3.53 g, 36.70 mmol), toluene (120 ml) were added to Sub 2-93 (7.66 g, 12.23 mmol) obtained in the above synthesis, and then 7.09 g (yield: 67%) of the product was obtained by using the same manner as described above for the synthesis of the compound P-1.

The FD-MS values of compounds P-1 to P-136 of the present invention prepared according to the above synthesis examples are shown in Table 3 below.

TABLE 3

| compound | FD-MS | compound | FD-MS |
|---|---|---|---|
| P-1 | m/z = 760.29($C_{55}H_{40}N_2S$ = 760.98) | P-2 | m/z = 886.34($C_{65}H_{46}N_2S$ = 887.14) |
| P-3 | m/z = 962.37($C_{71}H_{50}N_2S$ = 963.24) | P-4 | m/z = 912.35($C_{67}H_{48}N_2S$ = 913.18) |
| P-5 | m/z = 988.39($C_{73}H_{52}N_2S$ = 989.27) | P-6 | m/z = 962.37($C_{71}H_{50}N_2S$ = 963.24) |
| P-7 | m/z = 916.29($C_{65}H_{44}N_2S_2$ = 917.19) | P-8 | m/z = 1051.40($C_{77}H_{53}N_3S$ = 1052.33) |
| P-9 | m/z = 1002.36($C_{73}H_{50}N_2OS$ = 1003.26) | P-10 | m/z = 896.38($C_{67}H_{48}N_2O$ = 897.11) |
| P-11 | m/z = 984.35($C_{73}H_{48}N_2S$ = 985.24) | P-12 | m/z = 910.39($C_{68}H_{50}N_2O$ = 911.14) |
| P-13 | m/z = 1125.41($C_{83}H_{55}N_3S$ = 1126.41) | P-14 | m/z = 994.39($C_{75}H_{50}N_2O$ = 995.21) |
| P-15 | m/z = 970.43($C_{74}H_{54}N_2$ = 971.23) | P-16 | m/z = 1018.43($C_{78}H_{54}N_2$ = 1019.28) |
| P-17 | m/z = 896.38($C_{67}H_{48}N_2O$ = 897.11) | P-18 | m/z = 946.43($C_{72}H_{54}N_2$ = 947.21) |
| P-19 | m/z = 850.34($C_{62}H_{46}N_2S$ = 851.11) | P-20 | m/z = 1036.39($C_{77}H_{52}N_2S$ = 1037.32) |
| P-21 | m/z = 866.28($C_{61}H_{42}N_2S_2$ = 867.13) | P-22 | m/z = 850.30($C_{61}H_{42}N_2OS$ = 851.06) |
| P-23 | m/z = 834.32($C_{61}H_{42}N_2O_2$ = 835.00) | P-24 | m/z = 1033.40($C_{77}H_{51}N_3O$ = 1034.25) |
| P-25 | m/z = 1046.46($C_{80}H_{58}N_2$ = 1047.33) | P-26 | m/z = 1018.43($C_{78}H_{54}N_2$ = 1019.28) |
| P-27 | m/z = 898.34($C_{66}H_{46}N_2S$ = 899.15) | P-28 | m/z = 974.37($C_{72}H_{50}N_2S$ = 975.25) |
| P-29 | m/z = 1004.33($C_{72}H_{48}N_2S_2$ = 1005.29) | P-30 | m/z = 972.37($C_{72}H_{48}N_2O_2$ = 973.16) |
| P-31 | m/z = 988.35($C_{72}H_{48}N_2OS$ = 989.23) | P-32 | m/z = 972.37($C_{72}H_{48}N_2O_2$ = 973.16) |
| P-33 | m/z = 1004.33($C_{72}H_{48}N_2S_2$ = 1005.29) | P-34 | m/z = 1000.39($C_{74}H_{52}N_2S$ = 1001.28) |
| P-35 | m/z = 1010.46($C_{77}H_{58}N_2$ = 1011.30) | P-36 | m/z = 886.43($C_{67}H_{54}N_2$ = 887.16) |
| P-37 | m/z = 1000.39($C_{74}H_{52}N_2S$ = 1001.28) | P-38 | m/z = 984.41($C_{74}H_{52}N_2O$ = 985.22) |
| P-39 | m/z = 1000.39($C_{74}H_{52}N_2S$ = 1001.28) | P-40 | m/z = 984.41($C_{74}H_{52}N_2O$ = 985.22) |
| P-41 | m/z = 820.35($C_{61}H_{44}N_2O$ = 821.01) | P-42 | m/z = 925.35($C_{67}H_{47}N_3S$ = 926.18) |
| P-43 | m/z = 952.39($C_{70}H_{52}N_2S$ = 953.24) | P-44 | m/z = 984.41($C_{74}H_{52}N_2O$ = 985.22) |
| P-45 | m/z = 892.38($C_{68}H_{48}N_2$ = 893.12) | P-46 | m/z = 945.41($C_{71}H_{51}N_3$ = 946.18) |
| P-47 | m/z = 978.42($C_{72}H_{54}N_2O_2$ = 979.21) | P-48 | m/z = 820.35($C_{61}H_{44}N_2O$ = 821.01) |
| P-49 | m/z = 841.35($C_{61}H_{39}D_5N_2S$ = 842.11) | P-50 | m/z = 912.35($C_{67}H_{48}N_2S$ = 913.18) |
| P-51 | m/z = 884.32($C_{65}H_{44}N_2S$ = 885.12) | P-52 | m/z = 968.38($C_{73}H_{48}N_2O$ = 969.18) |
| P-53 | m/z = 935.42($C_{70}H_{53}N_3$ = 936.19) | P-54 | m/z = 960.35($C_{71}H_{48}N_2S$ = 961.22) |
| P-55 | m/z = 912.30($C_{63}H_{42}F_2N_2OS$ = 913.08) | P-56 | m/z = 1098.40($C_{79}H_{58}N_2S_2$ = 1099.45) |
| P-57 | m/z = 921.41($C_{69}H_{51}N_3$ = 922.16) | P-58 | m/z = 870.33($C_{61}H_{46}N_2O_2S$ = 871.10) |
| P-59 | m/z = 916.29($C_{65}H_{44}N_2S_2$ = 917.19) | P-60 | m/z = 932.36($C_{66}H_{52}N_2SSi$ = 933.28) |
| P-61 | m/z = 809.29($C_{58}H_{39}N_3S$ = 810.02) | P-62 | m/z = 809.29($C_{58}H_{39}N_3S$ = 810.02) |
| P-63 | m/z = 809.29($C_{58}H_{39}N_3S$ = 810.02) | P-64 | m/z = 915.27($C_{64}H_{41}N_3S_2$ = 916.16) |
| P-65 | m/z = 915.27($C_{64}H_{41}N_3S_2$ = 916.16) | P-66 | m/z = 974.34($C_{70}H_{46}N_4S$ = 975.21) |
| P-67 | m/z = 869.34($C_{64}H_{43}N_3O$ = 870.05) | P-68 | m/z = 919.36($C_{68}H_{45}N_3O$ = 920.10) |
| P-69 | m/z = 971.42($C_{73}H_{53}N_3$ = 972.22) | P-70 | m/z = 1069.44($C_{81}H_{55}N_3$ = 1070.32) |
| P-71 | m/z = 1049.38($C_{77}H_{51}N_3S$ = 1050.31) | P-72 | m/z = 959.39($C_{71}H_{49}N_3O$ = 960.17) |
| P-73 | m/z = 984.42($C_{73}H_{52}N_4$ = 985.22) | P-74 | m/z = 1108.45($C_{83}H_{56}N_4$ = 1109.36) |
| P-75 | m/z = 935.33($C_{68}H_{45}N_3S$ = 936.17) | P-76 | m/z = 965.29($C_{68}H_{43}N_3S_2$ = 966.22) |
| P-77 | m/z = 899.30($C_{64}H_{41}N_3OS$ = 900.09) | P-78 | m/z = 991.31($C_{70}H_{45}N_3S_2$ = 992.26) |
| P-79 | m/z = 949.31($C_{68}H_{43}N_3OS$ = 950.15) | P-80 | m/z = 991.31($C_{70}H_{45}N_3S_2$ = 992.26) |
| P-81 | m/z = 899.30($C_{64}H_{41}N_3OS$ = 900.09) | P-82 | m/z = 915.27($C_{64}H_{41}N_3S_2$ = 916.16) |
| P-83 | m/z = 899.30($C_{64}H_{41}N_3OS$ = 900.09) | P-84 | m/z = 933.34($C_{68}H_{43}N_3O_2$ = 934.09) |
| P-85 | m/z = 965.29($C_{68}H_{43}N_3S_2$ = 966.22) | P-86 | m/z = 1025.34($C_{74}H_{47}N_3OS$ = 1026.25) |
| P-87 | m/z = 991.31($C_{70}H_{45}N_3S_2$ = 992.26) | P-88 | m/z = 975.33($C_{70}H_{45}N_3OS$ = 976.19) |
| P-89 | m/z = 959.35($C_{70}H_{45}N_3O_2$ = 960.13) | P-90 | m/z = 925.35($C_{67}H_{47}N_3S$ = 926.18) |
| P-91 | m/z = 909.37($C_{67}H_{47}N_3O$ = 910.11) | P-92 | m/z = 925.35($C_{67}H_{47}N_3S$ = 926.18) |
| P-93 | m/z = 1061.43($C_{79}H_{55}N_3O$ = 1062.30) | P-94 | m/z = 925.35($C_{67}H_{47}N_3S$ = 926.18) |
| P-95 | m/z = 909.37($C_{67}H_{47}N_3O$ = 910.11) | P-96 | m/z = 1011.46($C_{76}H_{57}N_3$ = 1012.29) |
| P-97 | m/z = 1049.38($C_{77}H_{51}N_3S$ = 1050.31) | P-98 | m/z = 1083.42($C_{81}H_{53}N_3O$ = 1034.25) |
| P-99 | m/z = 1049.38($C_{77}H_{51}N_3S$ = 1050.31) | P-100 | m/z = 1033.40($C_{77}H_{51}N_3O$ = 1034.25) |
| P-101 | m/z = 1049.38($C_{77}H_{51}N_3S$ = 1050.31) | P-102 | m/z = 1033.40($C_{77}H_{51}N_3O$ = 1034.25) |
| P-103 | m/z = 1108.45($C_{83}H_{56}N_4$ = 1109.36) | P-104 | m/z = 1060.45($C_{79}H_{56}N_4$ = 1061.32) |
| P-105 | m/z = 885.32($C_{64}H_{43}N_3S$ = 886.11) | P-106 | m/z = 991.31($C_{70}H_{45}N_3S_2$ = 992.26) |
| P-107 | m/z = 943.36($C_{70}H_{45}N_3O$ = 944.13) | P-108 | m/z = 984.42($C_{73}H_{52}N_4$ = 985.22) |
| P-109 | m/z = 935.33($C_{68}H_{45}N_3S$ = 936.17) | P-110 | m/z = 919.36($C_{68}H_{45}N_3O$ = 920.10) |
| P-111 | m/z = 925.35($C_{67}H_{47}N_3S$ = 926.18) | P-112 | m/z = 963.34($C_{68}H_{45}N_5S$ = 964.18) |
| P-113 | m/z = 809.29($C_{58}H_{39}N_3S$ = 810.02) | P-114 | m/z = 974.34($C_{70}H_{46}N_4S$ = 975.21) |
| P-115 | m/z = 975.33($C_{70}H_{45}N_3OS$ = 976.19) | P-116 | m/z = 909.37($C_{67}H_{47}N_3O$ = 910.11) |
| P-117 | m/z = 991.39($C_{75}H_{49}N_3$ = 992.21) | P-118 | m/z = 972.33($C_{68}H_{36}D_7N_3S_2$ = 973.26) |
| P-119 | m/z = 1099.49($C_{83}H_{61}N_3$ = 1100.39) | P-120 | m/z = 1025.43($C_{76}H_{55}N_3O$ = 1026.27) |
| P-121 | m/z = 933.32($C_{68}H_{43}N_3S$ = 934.15) | P-122 | m/z = 895.39($C_{67}H_{49}N_3$ = 896.13) |
| P-123 | m/z = 1033.40($C_{77}H_{51}N_3O$ = 1034.25) | P-124 | m/z = 1019.42($C_{77}H_{53}N_3$ = 1020.26) |
| P-125 | m/z = 918.37($C_{68}H_{46}N_4$ = 919.12) | P-126 | m/z = 989.45($C_{73}H_{47}D_5N_4$ = 990.25) |
| P-127 | m/z = 974.34($C_{70}H_{46}N_4S$ = 975.21) | P-128 | m/z = 995.39($C_{74}H_{49}N_3O$ = 996.20) |
| P-129 | m/z = 960.33($C_{69}H_{44}N_4S$ = 961.18) | P-130 | m/z = 949.31($C_{68}H_{43}N_3OS$ = 950.15) |
| P-131 | m/z = 999.45($C_{75}H_{49}D_4N_3$ = 1000.27) | P-132 | m/z = 949.31($C_{68}H_{43}N_3OS$ = 950.15) |
| P-133 | m/z = 864.33($C_{62}H_{36}D_5N_3S$ = 865.10) | P-134 | m/z = 919.36($C_{68}H_{45}N_3O$ = 920.10) |
| P-135 | m/z = 920.39($C_{68}H_{48}N_4$ = 921.14) | P-136 | m/z = 935.33($C_{68}H_{45}N_3S$ = 936.17) |

In the above, even though an exemplary synthesis example of the present invention represented by the Formula 1 are described, all of them are based on Buchwald-Hartwig cross coupling reaction, Suzuki cross-coupling reaction, Grignard reaction, Cyclic Dehydration reaction, PPh$_3$-mediated reductive cyclization reaction (*J. Org. Chem.* 2005, 70, 5014.) and Ullmann reaction. It will be understood by those skilled in the art that the above reaction proceeds even when other substituents (substituents of A ring, B ring, X, $R^3$, $Ar^1$ to $Ar^4$, $L^1$ to $L^4$, a and the like) defined in Formula 1 are bonded, in addition to the substituents described in the specific synthesis example.

For example, the reaction of Sub 1 and Sub 2->Final Product in Reaction Scheme 1, and the reaction of the starting material->Sub 1 in Reaction Scheme 2 are based on Buchwald-Hartwig cross coupling reaction, the reaction of Sub 2-I ->Sub 2-II in Reaction Scheme 15 is based on Suzuki cross-coupling reaction, and the reaction of the starting material->Sub 2-I in Reaction Scheme 16 is based on Grignard reaction/Cyclic Dehydration reaction. Further, the reaction of the starting material->Sub 2-I' in Reaction Scheme 17 is based on $PPh_3$-mediated reductive cyclization reaction, and the reaction of Sub 2-I'->Sub 2-I in Reaction Scheme 17 is based on Ullmann reaction. The above reactions will proceed even if a substituent not specifically mentioned is attached.

Fabrication and Evaluation of Organic Electronic Element

[Example I-1] Green OLED (A Hole Transport Layer)

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, compound P-1 of the present invention was vacuum-deposited with a thickness of 60 nm on the hole injection layer to form a hole transport layer.

Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 90:10.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example I-2] to [Example I-70] Green OLED (A Hole Transport Layer)

The OLEDs were fabricated in the same manner as described in Example I-1 except that the compounds P-2 to P-136 of the present invention described in Table 4 instead of the compound P-1 of the present invention were used as the hole transport layer material.

[Comparative Example I-1] to [Comparative Example I-6]

The OLEDs were fabricated in the same manner as described in Example 1 except that the following Comparative Compounds 1 to 6 instead of the compound P-1 of the present invention were each used as the hole transport layer material.

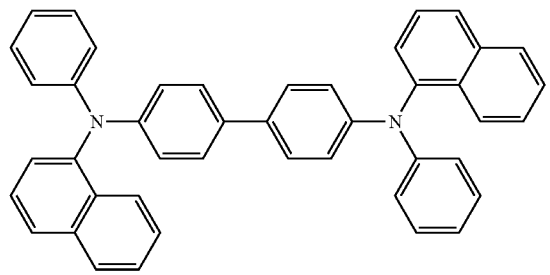

<Comp. compd 1>

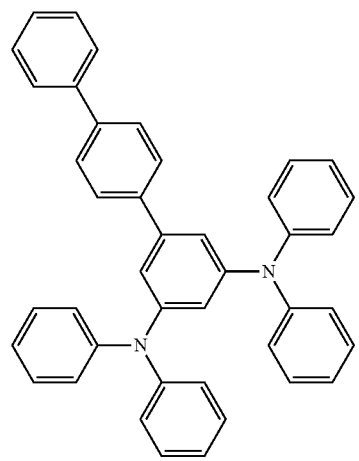

<Comp.compd 2>

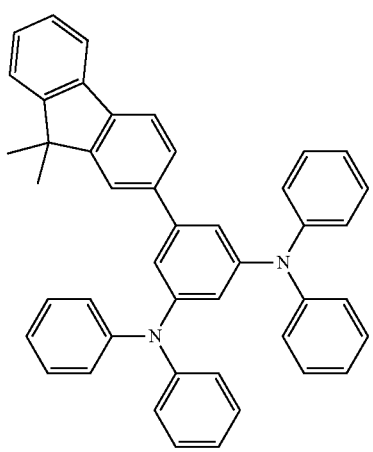

<Comp.compd 3>

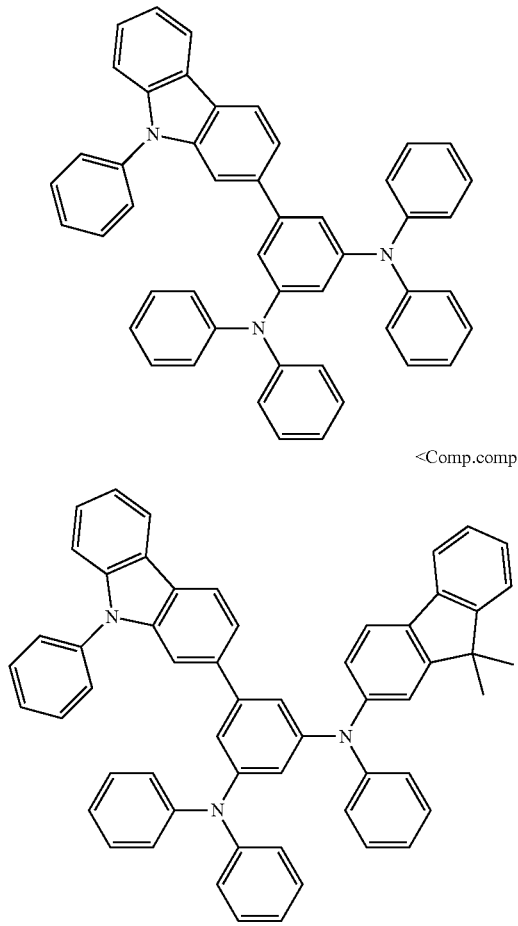

<Comp.compd 4>

<Comp.compd 5>

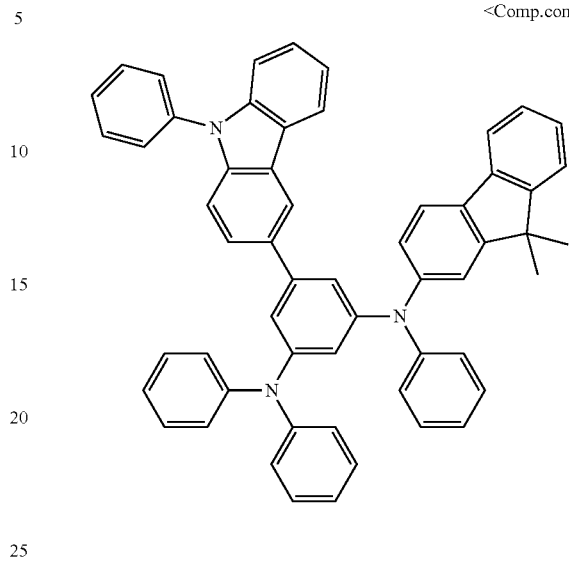

<Comp.compd 6>

Electroluminescence (EL) characteristics were measured with a PR-650(Photoresearch) by applying a forward bias DC voltage to the OLEDs prepared in Examples I-1 to I-70 of the present invention and Comparative Examples I-1 to I-6. And, the T95 life time was measured using a life time measuring apparatus manufactured by Macscience Inc. at reference brightness of 5000 cd/m$^2$. The measurement results are shown in Table 4 below.

TABLE 4

|  | compound | Voltage (V) | Current Density (mA/cm$^2$) | Brightness (cd/m$^2$) | Efficiency (cd/A) | Lifetime T(95) | CIE x | CIE y |
| --- | --- | --- | --- | --- | --- | --- | --- | --- |
| comp. Ex(I-1) | comp. Com1 | 6.0 | 21.5 | 5000 | 23.3 | 57.3 | 0.32 | 0.61 |
| comp. Ex(I-2) | comp. Com2 | 5.9 | 19.8 | 5000 | 25.3 | 67.9 | 0.32 | 0.62 |
| comp. Ex(I-3) | comp. Com3 | 5.9 | 18.4 | 5000 | 27.2 | 76.5 | 0.33 | 0.61 |
| comp. Ex(I-4) | comp. Com4 | 5.9 | 17.6 | 5000 | 28.4 | 79.3 | 0.33 | 0.62 |
| comp. Ex(I-5) | comp. Com5 | 5.8 | 17.1 | 5000 | 29.2 | 83.4 | 0.33 | 0.61 |
| comp. Ex(I-6) | comp. Com6 | 5.8 | 17.4 | 5000 | 28.7 | 82.6 | 0.33 | 0.61 |
| Ex.(I-1) | Com.(P-1) | 5.5 | 12.4 | 5000 | 40.2 | 132.7 | 0.33 | 0.62 |
| Ex.(I-2) | Com.(P-2) | 5.6 | 12.3 | 5000 | 40.6 | 126.1 | 0.33 | 0.61 |
| Ex.(I-3) | Com.(P-3) | 5.6 | 12.5 | 5000 | 40.0 | 128.1 | 0.33 | 0.61 |
| Ex.(I-4) | Com.(P-4) | 5.7 | 13.2 | 5000 | 37.8 | 122.7 | 0.33 | 0.62 |
| Ex.(I-5) | Com.(P-7) | 5.5 | 12.8 | 5000 | 39.2 | 129.7 | 0.33 | 0.61 |
| Ex.(I-6) | Com.(P-8) | 5.6 | 12.7 | 5000 | 39.5 | 127.4 | 0.33 | 0.62 |
| Ex.(I-7) | Com.(P-10) | 5.6 | 12.6 | 5000 | 39.6 | 125.5 | 0.33 | 0.62 |
| Ex.(I-8) | Com.(P-11) | 5.7 | 13.1 | 5000 | 38.2 | 121.3 | 0.33 | 0.62 |
| Ex.(I-9) | Com.(P-14) | 5.7 | 13.6 | 5000 | 36.7 | 120.5 | 0.33 | 0.62 |
| Ex.(I-10) | Com.(P-15) | 5.5 | 12.5 | 5000 | 40.0 | 125.2 | 0.33 | 0.61 |
| Ex.(I-11) | Com.(P-16) | 5.6 | 13.1 | 5000 | 38.1 | 121.6 | 0.33 | 0.62 |
| Ex.(I-12) | Com.(P-19) | 5.7 | 13.5 | 5000 | 36.9 | 118.4 | 0.33 | 0.62 |
| Ex.(I-13) | Com.(P-21) | 5.7 | 13.1 | 5000 | 38.0 | 122.8 | 0.33 | 0.61 |
| Ex.(I-14) | Com.(P-22) | 5.7 | 12.9 | 5000 | 38.9 | 121.2 | 0.33 | 0.62 |
| Ex.(I-15) | Com.(P-24) | 5.6 | 13.3 | 5000 | 37.5 | 123.0 | 0.33 | 0.61 |
| Ex.(I-16) | Com.(P-25) | 5.7 | 13.4 | 5000 | 37.2 | 118.6 | 0.33 | 0.61 |
| Ex.(I-17) | Com.(P-34) | 5.6 | 13.0 | 5000 | 38.4 | 119.3 | 0.33 | 0.61 |
| Ex.(I-18) | Com.(P-40) | 5.6 | 13.7 | 5000 | 36.5 | 120.2 | 0.33 | 0.62 |
| Ex.(I-19) | Com.(P-41) | 5.6 | 12.8 | 5000 | 39.1 | 128.3 | 0.33 | 0.61 |
| Ex.(I-20) | Com.(P-42) | 5.5 | 12.5 | 5000 | 40.0 | 124.5 | 0.33 | 0.62 |

TABLE 4-continued

|  | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex.(I-21) | Com.(P-43) | 5.5 | 12.7 | 5000 | 39.4 | 129.1 | 0.33 | 0.62 |
| Ex.(I-22) | Com.(P-45) | 5.7 | 13.2 | 5000 | 37.7 | 122.4 | 0.33 | 0.62 |
| Ex.(I-23) | Com.(P-46) | 5.5 | 12.6 | 5000 | 39.7 | 129.9 | 0.33 | 0.62 |
| Ex.(I-24) | Com.(P-48) | 5.6 | 14.8 | 5000 | 33.8 | 115.8 | 0.33 | 0.62 |
| Ex.(I-25) | Com.(P-49) | 5.6 | 12.6 | 5000 | 39.8 | 128.4 | 0.33 | 0.62 |
| Ex.(I-26) | Com.(P-50) | 5.6 | 13.3 | 5000 | 37.6 | 122.1 | 0.33 | 0.62 |
| Ex.(I-27) | Com.(P-51) | 5.6 | 12.6 | 5000 | 39.7 | 128.2 | 0.33 | 0.61 |
| Ex.(I-28) | Com.(P-53) | 5.6 | 13.3 | 5000 | 37.5 | 119.7 | 0.33 | 0.61 |
| Ex.(I-29) | Com.(P-59) | 5.7 | 14.3 | 5000 | 34.8 | 111.7 | 0.33 | 0.61 |
| Ex.(I-30) | Com.(P-61) | 5.5 | 11.6 | 5000 | 43.3 | 153.7 | 0.33 | 0.61 |
| Ex.(I-31) | Com.(P-62) | 5.6 | 11.7 | 5000 | 42.8 | 148.8 | 0.33 | 0.61 |
| Ex.(I-32) | Com.(P-63) | 5.6 | 11.7 | 5000 | 42.7 | 148.1 | 0.33 | 0.61 |
| Ex.(I-33) | Com.(P-64) | 5.5 | 11.6 | 5000 | 43.3 | 150.4 | 0.33 | 0.61 |
| Ex.(I-34) | Com.(P-65) | 5.5 | 11.7 | 5000 | 42.8 | 147.4 | 0.33 | 0.62 |
| Ex.(I-35) | Com.(P-66) | 5.6 | 11.6 | 5000 | 43.0 | 147.3 | 0.33 | 0.61 |
| Ex.(I-36) | Com.(P-67) | 5.6 | 12.7 | 5000 | 39.3 | 133.9 | 0.33 | 0.61 |
| Ex.(I-37) | Com.(P-69) | 5.6 | 11.9 | 5000 | 41.9 | 142.8 | 0.33 | 0.61 |
| Ex.(I-38) | Com.(P-70) | 5.6 | 12.0 | 5000 | 41.6 | 142.8 | 0.33 | 0.61 |
| Ex.(I-39) | Com.(P-71) | 5.6 | 12.1 | 5000 | 41.5 | 142.0 | 0.33 | 0.62 |
| Ex.(I-40) | Com.(P-72) | 5.5 | 12.6 | 5000 | 39.6 | 137.8 | 0.33 | 0.62 |
| Ex.(I-41) | Com.(P-73) | 5.6 | 12.7 | 5000 | 39.3 | 133.4 | 0.33 | 0.62 |
| Ex.(I-42) | Com.(P-74) | 5.6 | 13.3 | 5000 | 37.7 | 126.7 | 0.33 | 0.61 |
| Ex.(I-43) | Com.(P-75) | 5.5 | 11.7 | 5000 | 42.8 | 149.1 | 0.33 | 0.61 |
| Ex.(I-44) | Com.(P-76) | 5.5 | 12.1 | 5000 | 41.2 | 141.3 | 0.33 | 0.61 |
| Ex.(I-45) | Com.(P-77) | 5.5 | 12.1 | 5000 | 41.3 | 141.1 | 0.33 | 0.61 |
| Ex.(I-46) | Com.(P-83) | 5.6 | 12.8 | 5000 | 39.1 | 134.7 | 0.33 | 0.61 |
| Ex.(I-47) | Com.(P-89) | 5.5 | 12.0 | 5000 | 41.6 | 142.0 | 0.33 | 0.62 |
| Ex.(I-48) | Com.(P-92) | 5.6 | 12.1 | 5000 | 41.2 | 142.0 | 0.33 | 0.62 |
| Ex.(I-49) | Com.(P-95) | 5.5 | 12.7 | 5000 | 39.2 | 138.0 | 0.33 | 0.62 |
| Ex.(I-50) | Com.(P-99) | 5.5 | 12.3 | 5000 | 40.5 | 137.8 | 0.33 | 0.61 |
| Ex.(I-51) | Com.(P-103) | 5.5 | 12.4 | 5000 | 40.3 | 138.0 | 0.33 | 0.62 |
| Ex.(I-52) | Com.(P-104) | 5.7 | 13.3 | 5000 | 37.7 | 126.1 | 0.33 | 0.62 |
| Ex.(I-53) | Com.(P-105) | 5.5 | 12.1 | 5000 | 41.3 | 143.3 | 0.33 | 0.62 |
| Ex.(I-54) | Com.(P-106) | 5.5 | 12.5 | 5000 | 40.1 | 137.7 | 0.33 | 0.62 |
| Ex.(I-55) | Com.(P-108) | 5.5 | 12.5 | 5000 | 40.0 | 138.4 | 0.33 | 0.62 |
| Ex.(I-56) | Com.(P-109) | 5.6 | 12.5 | 5000 | 39.9 | 138.7 | 0.33 | 0.61 |
| Ex.(I-57) | Com.(P-111) | 5.7 | 13.0 | 5000 | 38.4 | 124.6 | 0.33 | 0.61 |
| Ex.(I-58) | Com.(P-113) | 5.6 | 12.0 | 5000 | 41.5 | 144.3 | 0.33 | 0.62 |
| Ex.(I-59) | Com.(P-114) | 5.6 | 12.4 | 5000 | 40.4 | 138.6 | 0.33 | 0.62 |
| Ex.(I-60) | Com.(P-115) | 5.6 | 12.4 | 5000 | 40.3 | 136.6 | 0.33 | 0.62 |
| Ex.(I-61) | Com.(P-116) | 5.6 | 12.3 | 5000 | 40.8 | 138.4 | 0.33 | 0.62 |
| Ex.(I-62) | Com.(P-118) | 5.6 | 11.9 | 5000 | 42.2 | 143.9 | 0.33 | 0.61 |
| Ex.(I-63) | Com.(P-120) | 5.6 | 12.8 | 5000 | 39.2 | 138.8 | 0.33 | 0.61 |
| Ex.(I-64) | Com.(P-122) | 5.6 | 12.6 | 5000 | 39.7 | 138.7 | 0.33 | 0.61 |
| Ex.(I-65) | Com.(P-124) | 5.6 | 12.9 | 5000 | 38.8 | 125.0 | 0.33 | 0.62 |
| Ex.(I-66) | Com.(P-125) | 5.5 | 12.8 | 5000 | 39.1 | 138.2 | 0.33 | 0.62 |
| Ex.(I-67) | Com.(P-126) | 5.7 | 13.1 | 5000 | 38.2 | 127.6 | 0.33 | 0.62 |
| Ex.(I-68) | Com.(P-132) | 5.6 | 13.4 | 5000 | 37.3 | 126.1 | 0.33 | 0.62 |
| Ex.(I-69) | Com.(P-133) | 5.6 | 13.1 | 5000 | 38.3 | 127.6 | 0.33 | 0.61 |
| Ex.(I-70) | Com.(P-136) | 5.6 | 13.6 | 5000 | 36.7 | 127.9 | 0.33 | 0.62 |

From the results of the above table 4, it is found that luminous efficiency and lifetime of OLED are improved when the compound of the present invention is used as material of a hole transport layer.

Particularly, Comparative Example I-3 to Comparative Example I-6 using Comparative compounds 2 to 6, wherein two amine groups are bonded on both sides of the linkage phenyl substituted with fluorene core or carbazol core, exhibited higher luminous efficiency than Comparative Example I-1 using Comparative compound 1 and Comparative compound 2, wherein Comparative compound 1 is NPB widely used and Comparative compound 2 has the linkage phenyl which is substituted with aryl group two amine groups are bonded on both sides of the linkage phenyl. Further, Example I-1 to Example I-70 of the present invention using the compound, wherein two amine groups are bonded on both sides of the linkage phenyl substituted with fluorene core or carbazol core fused with an aromatic ring and at least one substituent bonded to the amine groups is a form having a fluorene, dibenzofuran, dibenzothiophene or carbazole not aryl group, exhibited lower driving voltage, higher luminous efficiency and improved lifetime than Comparative Example I-3 to Comparative Example I-6.

These results are considered to be due to the fact that the compound of the present invention has more substituents that increase the planarity of the molecules than Comparative Compounds 1 to 6.

The introduction of a substituent which enhances the planarity of the molecule is intended to increase the π-π orbital overlap between the molecules by increasing the intermolecular π-π stacking, so that the lone pair electron of the π orbital facilitates intermolecular transport, thereby improving the hole transporting ability.

Therefore, as the hole transfer ability becomes better, the deterioration of the interface between ITO and HTL is reduced, as a result, the lifetime of the device is improved, and the charge balance between the holes and the electrons in the light emitting layer is well-balanced because the hole can be easily transported to the light emitting layer, and thus the luminous efficiency and lifetime are improved.

Therefore, it can be confirmed that the life span of the present invention is remarkably increased as compared to the comparative compounds 3 to 6 because the compound of the present invention has the increased planarity of the molecule and the packing density, and thus the driving voltage of the device is lowered and the Joule heat generated when the device is driven is reduced, so that the device has high thermal stability, wherein the compound of the present invention has a fluorene or carbazole fused with an aromatic ring as core, at least one substituent substituted in two amine groups (bonded to the linkage phenyl) has a form having a fluorene, dibenzofuran, dibenzothiophene or carbazole not aryl group.

Taking all the above described properties (high hole-transporting ability and thermal stability), it can be seen that electrical properties and interface characteristics can be greatly changed depending on whether or not a substituent increasing the planarity of the molecule is introduced and this acts as a major factor in improving the performance of the device.

In addition, even though similar core is used, it will be very difficult for those skilled in the art to infer the properties showing in a transport layer formed by the inventive compound because it is necessary to grasp interrelation between hole transport layer and a light emitting layer (host).

[Example II-1] Green OLED (An Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine (hereinafter, NPB) was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 90:10.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example II-2] to [Example II-72] Green OLED (An Emission-Auxiliary Layer)

The OLEDs were fabricated in the same manner as described in Example II-1 except that the compounds P-2 to P-136 of the present invention described in Table 5, instead of the compound P-1 of the present invention, were used as an emission-auxiliary layer material.

Comparative Example II-1

The OLED was fabricated in the same manner as described in Example II-1 except that an emission-auxiliary layer was not formed.

[Comparative Example II-2] to [Comparative Example II-5]

The OLEDs were fabricated in the same manner as described in Example II-1 except that the Comparative compounds 3 to 6, instead of the compound P-1 of the present invention, were used as an emission-auxiliary layer material.

Electroluminescence (EL) characteristics were measured with a PR-650(Photoresearch) by applying a forward bias DC voltage to the OLEDs prepared in Examples II-1 to II-72 of the present invention and Comparative Examples II-1 to II-5. And, the T95 life time was measured using a life time measuring apparatus manufactured by Macscience Inc. at reference brightness of 5000 cd/m$^2$. The measurement results are shown in Tables 5 below.

TABLE 5

| | compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| comp. Ex(II-1) | — | 6.0 | 21.5 | 5000 | 23.3 | 57.3 | 0.32 | 0.61 |
| comp. Ex(II-2) | comp. Com3 | 6.6 | 13.6 | 5000 | 36.9 | 99.8 | 0.33 | 0.62 |
| comp. Ex(II-3) | comp. Com4 | 6.6 | 13.0 | 5000 | 38.5 | 109.7 | 0.33 | 0.61 |
| comp. Ex(II-4) | comp. Com5 | 6.5 | 12.5 | 5000 | 40.0 | 112.4 | 0.33 | 0.62 |
| comp. Ex(II-5) | comp. Com6 | 6.5 | 12.6 | 5000 | 39.7 | 106.7 | 0.33 | 0.62 |
| Ex.(II-1) | Com.(P-1) | 6.3 | 9.8 | 5000 | 50.8 | 164.1 | 0.33 | 0.62 |
| Ex.(II-2) | Com.(P-2) | 6.3 | 10.0 | 5000 | 49.8 | 156.0 | 0.33 | 0.61 |
| Ex.(II-3) | Com.(P-3) | 6.3 | 10.0 | 5000 | 50.0 | 160.0 | 0.33 | 0.61 |
| Ex.(II-4) | Com.(P-4) | 6.3 | 10.4 | 5000 | 48.2 | 153.6 | 0.33 | 0.62 |
| Ex.(II-5) | Com.(P-7) | 6.3 | 10.2 | 5000 | 49.2 | 161.1 | 0.33 | 0.62 |
| Ex.(II-6) | Com.(P-8) | 6.3 | 10.1 | 5000 | 49.3 | 159.0 | 0.33 | 0.62 |
| Ex.(II-7) | Com.(P-10) | 6.3 | 10.2 | 5000 | 49.1 | 160.9 | 0.33 | 0.61 |
| Ex.(II-8) | Com.(P-11) | 6.4 | 10.3 | 5000 | 48.4 | 152.1 | 0.33 | 0.61 |
| Ex.(II-9) | Com.(P-14) | 6.4 | 10.5 | 5000 | 47.5 | 155.6 | 0.33 | 0.62 |
| Ex.(II-10) | Com.(P-19) | 6.4 | 10.6 | 5000 | 47.3 | 154.3 | 0.33 | 0.62 |
| Ex.(II-11) | Com.(P-21) | 6.3 | 10.3 | 5000 | 48.6 | 153.5 | 0.33 | 0.61 |
| Ex.(II-12) | Com.(P-22) | 6.4 | 10.3 | 5000 | 48.7 | 155.9 | 0.33 | 0.62 |
| Ex.(II-13) | Com.(P-24) | 6.4 | 10.6 | 5000 | 47.3 | 151.2 | 0.33 | 0.62 |
| Ex.(II-14) | Com.(P-25) | 6.3 | 10.5 | 5000 | 47.6 | 150.6 | 0.33 | 0.62 |

TABLE 5-continued

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex.(II-15) | Com.(P-34) | 6.4 | 10.3 | 5000 | 48.3 | 154.0 | 0.33 | 0.61 |
| Ex.(II-16) | Com.(P-40) | 6.3 | 10.5 | 5000 | 47.6 | 155.7 | 0.33 | 0.61 |
| Ex.(II-17) | Com.(P-41) | 6.3 | 10.2 | 5000 | 48.9 | 160.3 | 0.33 | 0.61 |
| Ex.(II-18) | Com.(P-42) | 6.4 | 10.2 | 5000 | 49.0 | 160.7 | 0.33 | 0.62 |
| Ex.(II-19) | Com.(P-43) | 6.3 | 10.1 | 5000 | 49.5 | 158.6 | 0.33 | 0.62 |
| Ex.(II-20) | Com.(P-45) | 6.3 | 10.3 | 5000 | 48.3 | 150.1 | 0.33 | 0.61 |
| Ex.(II-21) | Com.(P-46) | 6.4 | 10.1 | 5000 | 49.4 | 161.5 | 0.33 | 0.61 |
| Ex.(II-22) | Com.(P-48) | 6.3 | 10.7 | 5000 | 46.6 | 155.2 | 0.33 | 0.61 |
| Ex.(II-23) | Com.(P-49) | 6.4 | 10.1 | 5000 | 49.4 | 156.0 | 0.33 | 0.62 |
| Ex.(II-24) | Com.(P-50) | 6.3 | 10.3 | 5000 | 48.4 | 154.8 | 0.33 | 0.62 |
| Ex.(II-25) | Com.(P-51) | 6.4 | 10.2 | 5000 | 49.1 | 158.5 | 0.33 | 0.62 |
| Ex.(II-26) | Com.(P-52) | 6.3 | 10.7 | 5000 | 46.6 | 154.9 | 0.33 | 0.62 |
| Ex.(II-27) | Com.(P-53) | 6.3 | 10.4 | 5000 | 47.9 | 154.1 | 0.33 | 0.62 |
| Ex.(II-28) | Com.(P-59) | 6.4 | 10.7 | 5000 | 46.6 | 154.6 | 0.33 | 0.61 |
| Ex.(II-29) | Com.(P-61) | 6.2 | 9.1 | 5000 | 54.7 | 184.4 | 0.33 | 0.61 |
| Ex.(II-30) | Com.(P-62) | 6.2 | 9.3 | 5000 | 53.9 | 176.4 | 0.33 | 0.61 |
| Ex.(II-31) | Com.(P-63) | 6.2 | 9.3 | 5000 | 53.6 | 178.6 | 0.33 | 0.62 |
| Ex.(II-32) | Com.(P-64) | 6.3 | 9.2 | 5000 | 54.6 | 183.4 | 0.33 | 0.61 |
| Ex.(II-33) | Com.(P-65) | 6.2 | 9.4 | 5000 | 53.5 | 178.4 | 0.33 | 0.61 |
| Ex.(II-34) | Com.(P-66) | 6.2 | 9.4 | 5000 | 53.3 | 177.1 | 0.33 | 0.61 |
| Ex.(II-35) | Com.(P-67) | 6.3 | 10.0 | 5000 | 50.2 | 169.6 | 0.33 | 0.62 |
| Ex.(II-36) | Com.(P-68) | 6.2 | 9.9 | 5000 | 50.3 | 172.3 | 0.33 | 0.62 |
| Ex.(II-37) | Com.(P-69) | 6.2 | 9.5 | 5000 | 52.6 | 177.3 | 0.33 | 0.62 |
| Ex.(II-38) | Com.(P-71) | 6.3 | 9.6 | 5000 | 52.3 | 177.1 | 0.33 | 0.62 |
| Ex.(II-39) | Com.(P-72) | 6.3 | 9.9 | 5000 | 50.4 | 172.8 | 0.33 | 0.61 |
| Ex.(II-40) | Com.(P-73) | 6.2 | 10.0 | 5000 | 50.2 | 174.2 | 0.33 | 0.62 |
| Ex.(II-41) | Com.(P-74) | 6.4 | 10.0 | 5000 | 49.8 | 168.8 | 0.33 | 0.61 |
| Ex.(II-42) | Com.(P-75) | 6.3 | 9.3 | 5000 | 53.5 | 179.9 | 0.33 | 0.62 |
| Ex.(II-43) | Com.(P-76) | 6.2 | 9.4 | 5000 | 53.0 | 179.6 | 0.33 | 0.61 |
| Ex.(II-44) | Com.(P-77) | 6.3 | 9.5 | 5000 | 52.8 | 178.0 | 0.33 | 0.61 |
| Ex.(II-45) | Com.(P-82) | 6.2 | 9.9 | 5000 | 50.5 | 170.7 | 0.33 | 0.61 |
| Ex.(II-46) | Com.(P-86) | 6.3 | 9.9 | 5000 | 50.6 | 171.2 | 0.33 | 0.61 |
| Ex.(II-47) | Com.(P-89) | 6.3 | 9.4 | 5000 | 53.0 | 179.3 | 0.33 | 0.62 |
| Ex.(II-48) | Com.(P-92) | 6.2 | 9.4 | 5000 | 53.0 | 177.9 | 0.33 | 0.62 |
| Ex.(II-49) | Com.(P-95) | 6.3 | 9.9 | 5000 | 50.7 | 171.2 | 0.33 | 0.61 |
| Ex.(II-50) | Com.(P-99) | 6.3 | 9.7 | 5000 | 51.4 | 171.8 | 0.33 | 0.61 |
| Ex.(II-51) | Com.(P-104) | 6.3 | 10.0 | 5000 | 49.8 | 168.9 | 0.33 | 0.62 |
| Ex.(II-52) | Com.(P-105) | 6.3 | 9.6 | 5000 | 52.3 | 179.0 | 0.33 | 0.62 |
| Ex.(II-53) | Com.(P-106) | 6.2 | 9.7 | 5000 | 51.5 | 173.9 | 0.33 | 0.62 |
| Ex.(II-54) | Com.(P-108) | 6.2 | 9.7 | 5000 | 51.7 | 170.6 | 0.33 | 0.61 |
| Ex.(II-55) | Com.(P-109) | 6.2 | 9.9 | 5000 | 50.5 | 169.6 | 0.33 | 0.62 |
| Ex.(II-56) | Com.(P-110) | 6.3 | 10.0 | 5000 | 50.0 | 167.3 | 0.33 | 0.61 |
| Ex.(II-57) | Com.(P-111) | 6.4 | 10.0 | 5000 | 49.9 | 167.7 | 0.33 | 0.62 |
| Ex.(II-58) | Com.(P-112) | 6.4 | 10.5 | 5000 | 47.5 | 167.9 | 0.33 | 0.62 |
| Ex.(II-59) | Com.(P-113) | 6.3 | 9.4 | 5000 | 53.2 | 178.6 | 0.33 | 0.61 |
| Ex.(II-60) | Com.(P-114) | 6.3 | 9.8 | 5000 | 51.3 | 174.0 | 0.33 | 0.61 |
| Ex.(II-61) | Com.(P-115) | 6.3 | 9.7 | 5000 | 51.7 | 171.1 | 0.33 | 0.62 |
| Ex.(II-62) | Com.(P-116) | 6.2 | 9.7 | 5000 | 51.7 | 172.0 | 0.33 | 0.62 |
| Ex.(II-63) | Com.(P-117) | 6.3 | 9.8 | 5000 | 50.9 | 174.9 | 0.33 | 0.62 |
| Ex.(II-64) | Com.(P-118) | 6.2 | 9.5 | 5000 | 52.5 | 179.8 | 0.33 | 0.62 |
| Ex.(II-65) | Com.(P-124) | 6.3 | 10.1 | 5000 | 49.3 | 167.8 | 0.33 | 0.62 |
| Ex.(II-66) | Com.(P-125) | 6.3 | 9.8 | 5000 | 51.0 | 171.0 | 0.33 | 0.62 |
| Ex.(II-67) | Com.(P-127) | 6.4 | 10.1 | 5000 | 49.6 | 167.8 | 0.33 | 0.62 |
| Ex.(II-68) | Com.(P-128) | 6.3 | 10.1 | 5000 | 49.7 | 167.6 | 0.33 | 0.62 |
| Ex.(II-69) | Com.(P-132) | 6.3 | 10.2 | 5000 | 48.9 | 168.5 | 0.33 | 0.61 |
| Ex.(II-70) | Com.(P-133) | 6.3 | 10.1 | 5000 | 49.7 | 167.8 | 0.33 | 0.62 |
| Ex.(II-71) | Com.(P-134) | 6.3 | 10.2 | 5000 | 49.2 | 167.2 | 0.33 | 0.62 |
| Ex.(II-72) | Com.(P-136) | 6.3 | 10.2 | 5000 | 49.0 | 167.7 | 0.33 | 0.62 |

[Example III-1] Red OLED (An Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm.

Subsequently, NPB was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and bis-(1-phenylisoquinolyl)iridium(III) acetylacetonate (hereinafter, "(piq)$_2$Ir(acac)") as a dopant material in a weight ratio of 95:5.

Next, a film of BAlq was vacuum-deposited with a thickness of 10 nm on the light emitting layer to form a hole blocking layer, and a film of $Alq_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode.

In this way, the OLED was completed.

[Example III-2] to [Example III-40] Red OLED (An Emission-Auxiliary Layer)

The OLEDs were fabricated in the same manner as described in Example III-1 except that the compounds P-2 to P-136 of the present invention described in Table 6, instead of the compound P-1 of the present invention, were used as an emission-auxiliary layer material.

Comparative Example III-1

The OLED was fabricated in the same manner as described in Example III-1 except that an emission-auxiliary layer was not formed.

[Comparative Example III-2] to [Comparative Example III-5]

The OLEDs were fabricated in the same manner as described in Example III-1 except that the Comparative compounds 3 to 6, instead of the compound P-1 of the present invention, were used as an emission-auxiliary layer material.

Electroluminescence (EL) characteristics were measured with a PR-650(Photoresearch) by applying a forward bias DC voltage to the OLEDs prepared in Examples III-1 to III-40 of the present invention and Comparative Examples III-1 to III-5. And, the T95 life time was measured using a life time measuring apparatus manufactured by Macscience Inc. at reference brightness of 2500 $cd/m^2$. The measurement results are shown in Tables 6 below.

TABLE 6

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(III-1) | — | 6.5 | 33.8 | 2500 | 7.4 | 63.9 | 0.66 | 0.32 |
| comp. Ex(III-2) | comp. Com3 | 6.9 | 28.0 | 2500 | 8.9 | 86.6 | 0.66 | 0.33 |
| comp. Ex(III-3) | comp. Com4 | 6.9 | 26.6 | 2500 | 9.4 | 93.1 | 0.66 | 0.32 |
| comp. Ex(III-4) | comp. Com5 | 6.8 | 25.3 | 2500 | 9.9 | 97.2 | 0.66 | 0.33 |
| comp. Ex(III-5) | comp. Com6 | 6.8 | 26.0 | 2500 | 9.6 | 95.0 | 0.66 | 0.32 |
| Ex.(III-1) | Com.(P-1) | 6.7 | 16.1 | 2500 | 15.5 | 161.5 | 0.66 | 0.32 |
| Ex.(III-2) | Com.(P-2) | 6.6 | 16.3 | 2500 | 15.4 | 155.8 | 0.66 | 0.32 |
| Ex.(III-3) | Com.(P-7) | 6.6 | 17.0 | 2500 | 14.7 | 149.7 | 0.66 | 0.33 |
| Ex.(III-4) | Com.(P-8) | 6.6 | 16.7 | 2500 | 15.0 | 152.5 | 0.66 | 0.32 |
| Ex.(III-5) | Com.(P-11) | 6.7 | 17.3 | 2500 | 14.4 | 149.9 | 0.66 | 0.32 |
| Ex.(III-6) | Com.(P-14) | 6.7 | 18.0 | 2500 | 13.9 | 147.4 | 0.66 | 0.32 |
| Ex.(III-7) | Com.(P-21) | 6.7 | 17.4 | 2500 | 14.4 | 147.5 | 0.66 | 0.33 |
| Ex.(III-8) | Com.(P-22) | 6.8 | 17.6 | 2500 | 14.2 | 149.8 | 0.66 | 0.32 |
| Ex.(III-9) | Com.(P-24) | 6.8 | 17.5 | 2500 | 14.3 | 151.4 | 0.66 | 0.33 |
| Ex.(III-10) | Com.(P-34) | 6.7 | 17.4 | 2500 | 14.4 | 149.8 | 0.66 | 0.33 |
| Ex.(III-11) | Com.(P-40) | 6.7 | 17.9 | 2500 | 14.0 | 146.8 | 0.66 | 0.33 |
| Ex.(III-12) | Com.(P-43) | 6.6 | 16.8 | 2500 | 14.9 | 150.1 | 0.66 | 0.33 |
| Ex.(III-13) | Com.(P-45) | 6.8 | 18.0 | 2500 | 13.9 | 147.1 | 0.66 | 0.33 |
| Ex.(III-14) | Com.(P-46) | 6.6 | 17.2 | 2500 | 14.5 | 147.5 | 0.66 | 0.33 |
| Ex.(III-15) | Com.(P-49) | 6.6 | 16.9 | 2500 | 14.8 | 147.8 | 0.66 | 0.33 |
| Ex.(III-16) | Com.(P-50) | 6.8 | 17.7 | 2500 | 14.1 | 152.2 | 0.66 | 0.33 |
| Ex.(III-17) | Com.(P-51) | 6.6 | 16.8 | 2500 | 14.9 | 147.8 | 0.66 | 0.33 |
| Ex.(III-18) | Com.(P-52) | 6.8 | 17.8 | 2500 | 14.1 | 149.5 | 0.66 | 0.32 |
| Ex.(III-19) | Com.(P-53) | 6.8 | 17.5 | 2500 | 14.3 | 147.4 | 0.66 | 0.32 |
| Ex.(III-20) | Com.(P-59) | 6.8 | 17.7 | 2500 | 14.1 | 150.5 | 0.66 | 0.32 |
| Ex.(III-21) | Com.(P-61) | 6.6 | 14.6 | 2500 | 17.2 | 176.5 | 0.66 | 0.32 |
| Ex.(III-22) | Com.(P-64) | 6.6 | 14.6 | 2500 | 17.1 | 178.6 | 0.66 | 0.33 |
| Ex.(III-23) | Com.(P-65) | 6.6 | 15.0 | 2500 | 16.6 | 173.5 | 0.66 | 0.32 |
| Ex.(III-24) | Com.(P-66) | 6.6 | 14.7 | 2500 | 17.0 | 169.0 | 0.66 | 0.33 |
| Ex.(III-25) | Com.(P-71) | 6.7 | 15.5 | 2500 | 16.2 | 170.9 | 0.66 | 0.33 |
| Ex.(III-26) | Com.(P-75) | 6.6 | 14.7 | 2500 | 17.0 | 173.8 | 0.66 | 0.32 |
| Ex.(III-27) | Com.(P-76) | 6.6 | 15.5 | 2500 | 16.1 | 173.5 | 0.66 | 0.33 |
| Ex.(III-28) | Com.(P-86) | 6.7 | 16.1 | 2500 | 15.5 | 161.5 | 0.66 | 0.32 |
| Ex.(III-29) | Com.(P-99) | 6.6 | 16.0 | 2500 | 15.6 | 161.5 | 0.66 | 0.32 |
| Ex.(III-30) | Com.(P-106) | 6.6 | 16.1 | 2500 | 15.5 | 163.9 | 0.66 | 0.32 |
| Ex.(III-31) | Com.(P-108) | 6.7 | 15.8 | 2500 | 15.8 | 159.1 | 0.66 | 0.33 |
| Ex.(III-32) | Com.(P-113) | 6.6 | 15.3 | 2500 | 16.4 | 173.2 | 0.66 | 0.33 |
| Ex.(III-33) | Com.(P-114) | 6.6 | 16.0 | 2500 | 15.6 | 162.3 | 0.66 | 0.33 |
| Ex.(III-34) | Com.(P-115) | 6.7 | 15.8 | 2500 | 15.8 | 162.5 | 0.66 | 0.32 |
| Ex.(III-35) | Com.(P-116) | 6.7 | 16.0 | 2500 | 15.7 | 161.4 | 0.66 | 0.33 |
| Ex.(III-36) | Com.(P-117) | 6.7 | 16.0 | 2500 | 15.6 | 161.8 | 0.66 | 0.32 |
| Ex.(III-37) | Com.(P-118) | 6.6 | 15.5 | 2500 | 16.1 | 173.7 | 0.66 | 0.33 |
| Ex.(III-38) | Com.(P-132) | 6.6 | 16.4 | 2500 | 15.3 | 166.4 | 0.66 | 0.33 |
| Ex.(III-39) | Com.(P-133) | 6.6 | 16.4 | 2500 | 15.3 | 161.6 | 0.66 | 0.32 |
| Ex.(III-40) | Com.(P-136) | 6.7 | 16.3 | 2500 | 15.3 | 161.6 | 0.66 | 0.32 |

From the results shown in Tables 5 and 6, it can be seen that the luminous efficiency and lifetime of the organic electroluminescent device are remarkably improved when compounds of the present invention were used as an emission-auxiliary layer material, compared with the organic electroluminescent device of Comparative Example II-1 to Comparative Example III-5.

From these results, it is confirmed that luminescent efficiency and lifetime of device are improved when Comparative Compounds 3 to 6 and the compound of the present invention are used as an emission-auxiliary layer material, among them, particularly the compound of the present invention, compared with device not having an emission-auxiliary layer.

It is confirmed that in terms of introduction of substituents increasing a planarity of molecule, the structure, wherein core of the structure is the aromatic ring-condensed fluorine and carbazole and the structure has at least one substituent in two amine groups (bonded to a linking phenyl group) being a fluorene group, an dibenzofuran, dibenzothiophene or carbazole not aryl group, acts as a major factor in improving the performance of the device in the light-emitting auxiliary layer (green phosphorescence, blue fluorescence) as well as in the hole transport layer. Also, it is confirmed that the compound of the present invention used as the light emitting auxiliary layer material has a deep HOMO energy level and a high T1 value, thereby maintaining the charge balance in the light emitting layer and performing an effective electronic blocking function, as a result, the light emitting efficiency and lifetime are improved.

According to the embodiments of the present invention, by using a specific compound having a substituent which enhances the planity of a molecule, the limited type of an amine group bonded to the linking group, and the limited bonding position and number of amine groups as a material of the organic electric device, hole transport ability and thermal In addition, in the evaluation results of the device fabrication described above, even though the characteristics of devise have been described when the compound of the present invention is used as material of only one layer of the hole transport layer and an emission-auxiliary layer, the compound of the present invention can be used as material of both the hole transport layer and an emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:
1. A compound of Formula 1 below:

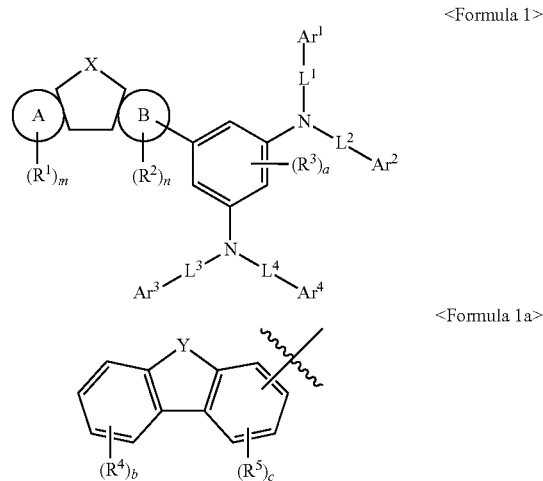

<Formula 1>

<Formula 1a> wherein,

X is $C(R^a)(R^b)$ or $N(R^c)$, $R^a$ to $R^c$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, A ring and B ring are each independently a $C_6$-$C_{18}$ aryl group, and the case where A ring and B ring are simultaneously $C_6$ aryl groups is excluded, when X is $N(R^c)$, at least one of A ring and B ring is $C_{10}$ aryl group, $Ar^1$ to $Ar^4$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, wherein at least one of $Ar^1$ to $Ar^4$ is Formula 1a, $L^1$ to $L^4$ are each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; and $C_2$-$C_{60}$ aliphatic hydrocarbon group, they (except for a single bond) may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, R¹ to R³ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, m is an integer of 0 to 8, n is an integer of 0 to 7, a is an integer of 0 to 3 when m, n and a are each an integer of 2 or more, a plurality of R¹ to a plurality of R³ are each the same or different from each other, in the above Formula 1a, Y is independently S, O, C(R$^d$)(R$^e$), or N(R$^f$), R$^d$ to R$^f$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and R$^d$ and R$^e$ may be linked to each other to form a spiro-compound together with carbon they bond to, i) R⁴ and R⁵ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, or ii) neighboring R⁴s or neighboring R⁵ may be linked to each other to form at least one of a ring, wherein R⁴ and R⁵ not forming a ring are each the same as defined in i) above, b is an integer of 0 to 4, c is an integer of 0 to 3, and when b and c are each an integer of 2 or more, a plurality of R⁴s and a plurality of R⁵s may be each the same or different from each other, when Ar¹ to Ar⁴, and R¹ to R⁵ are each the aryl group, fluorenyl group, heterocyclic group, fused ring group, alkyl group, alkenyl group, alkynyl group, alkoxyl group, or aryloxy group, they may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when these substituents are adjacent, they may be linked each other to form a ring.

2. The compound of claim 1, wherein A ring and B ring of Formula 1 above are each any one of Formulas below:

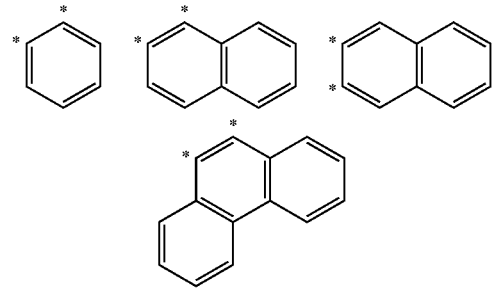

Wherein "*" indicates the position to be bonded.

3. The compound of claim 1, wherein Formula 1 above is represented by any one of Formulas 2 to 6 below:

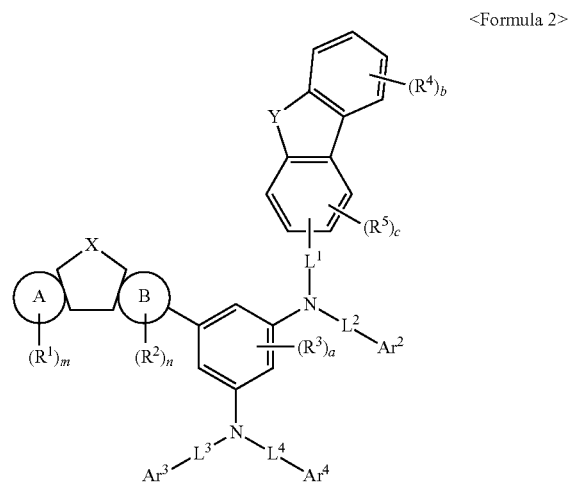

<Formula 2>

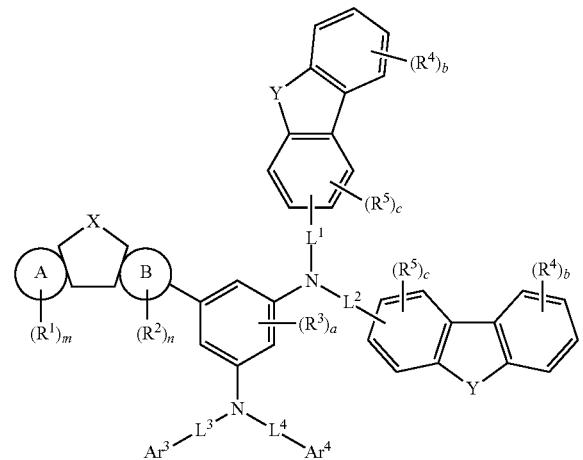

<Formula 3>

201
-continued
<Formula 4>
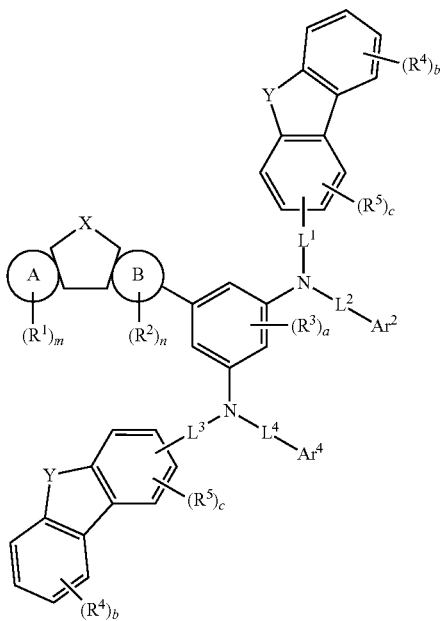
<Formula 5>
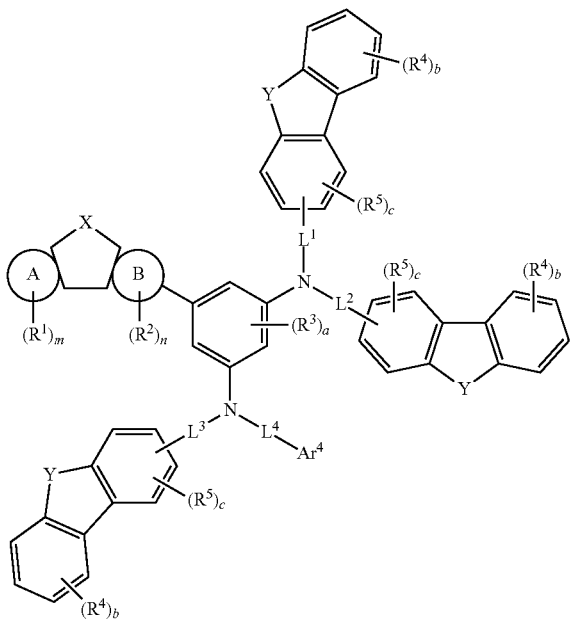
202
-continued
<Formula 6>
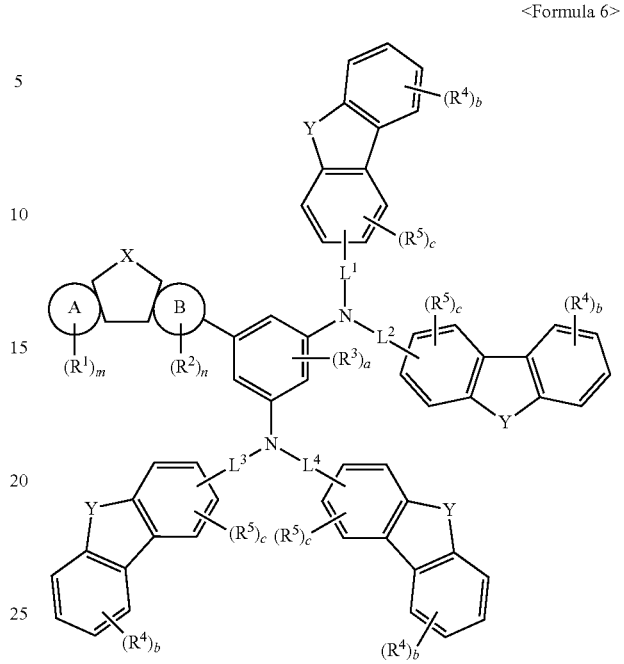
in Formulas 2 to 6, A ring, B ring, X, Y, $R^1$ to $R^5$, $Ar^2$ to $Ar^4$, $L^1$ to $L^4$, m, n, a, b and c are the same as defined in claim 1.
4. The compound of claim 1, wherein Formula 1 is any one of the compounds below:
P-1
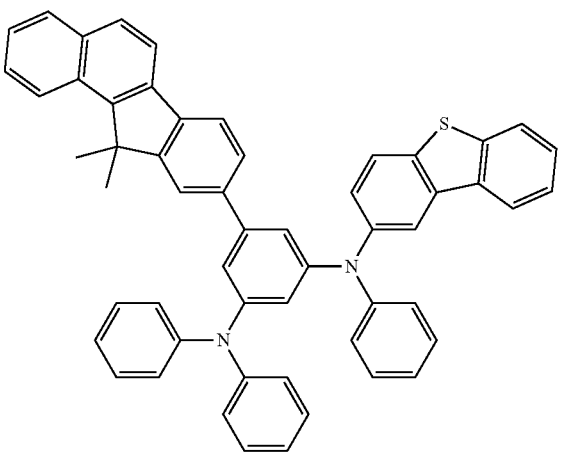

P-2
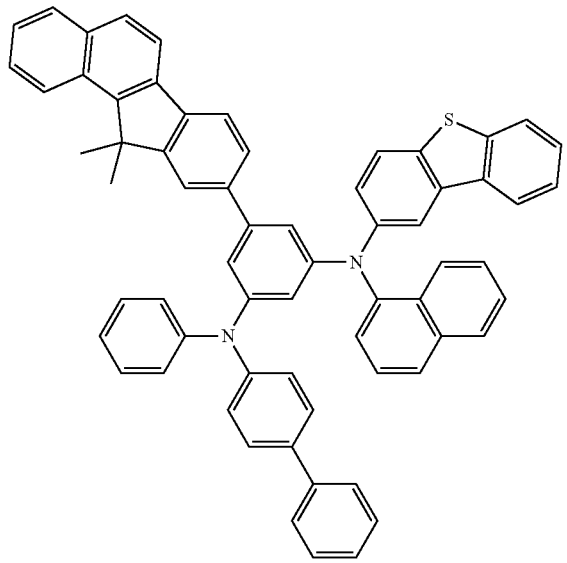
P-4
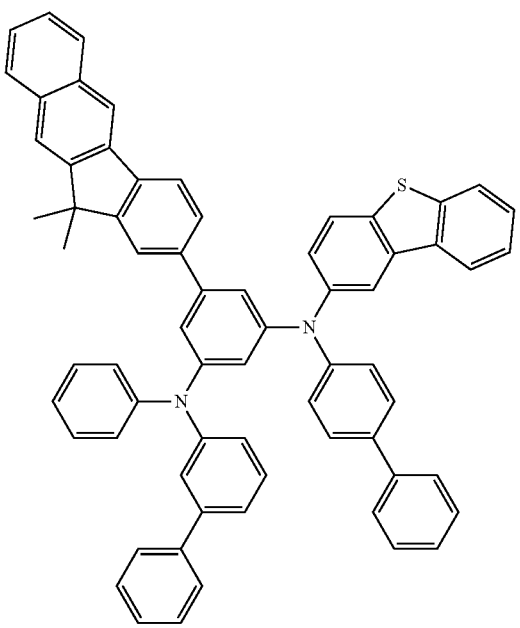
P-3
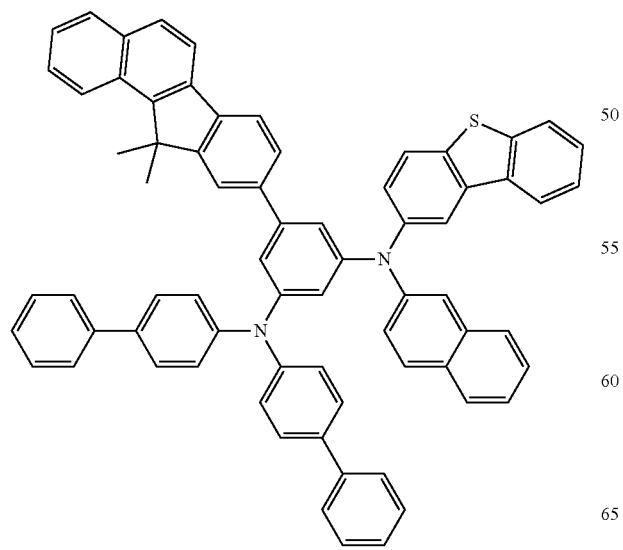
P-5
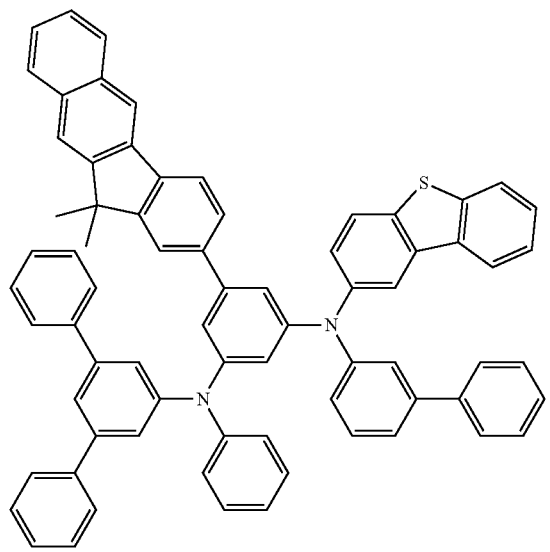

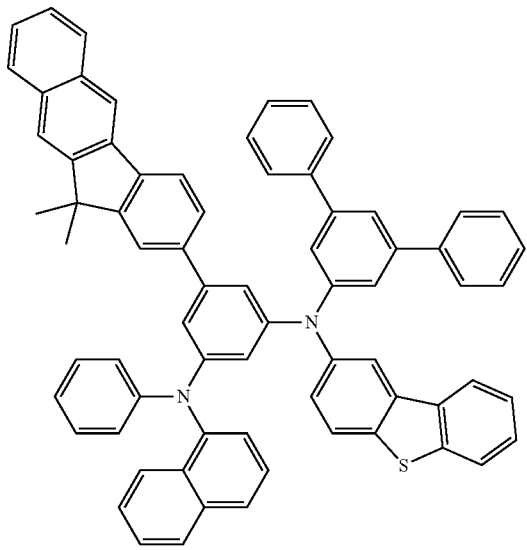
P-6
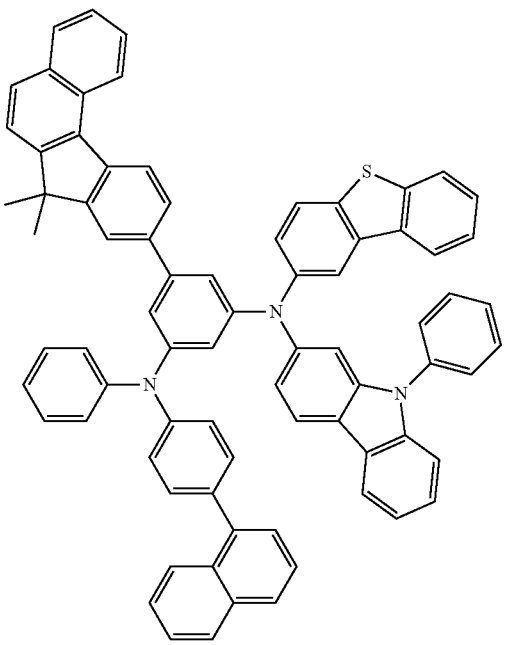
P-8
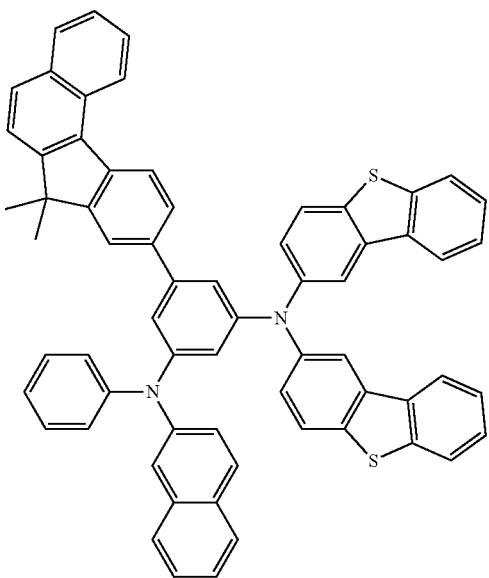
P-7
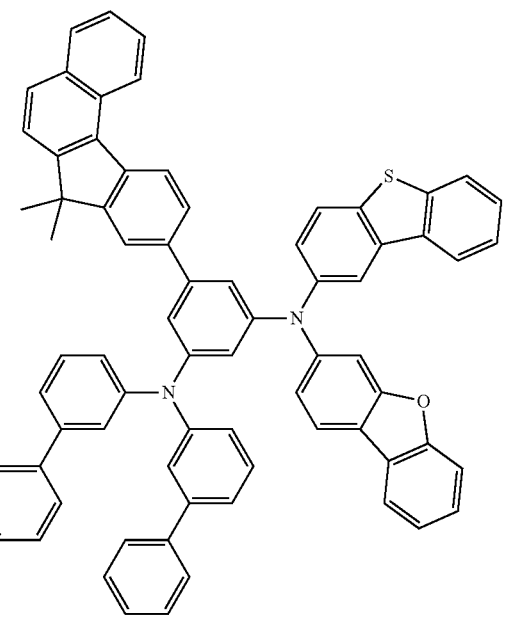
P-9

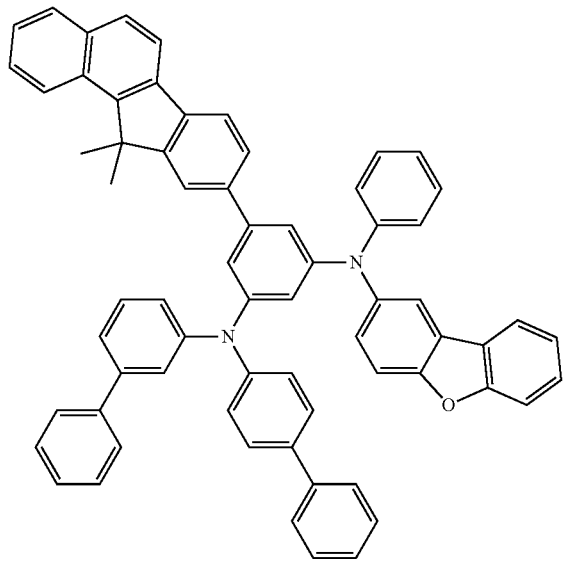
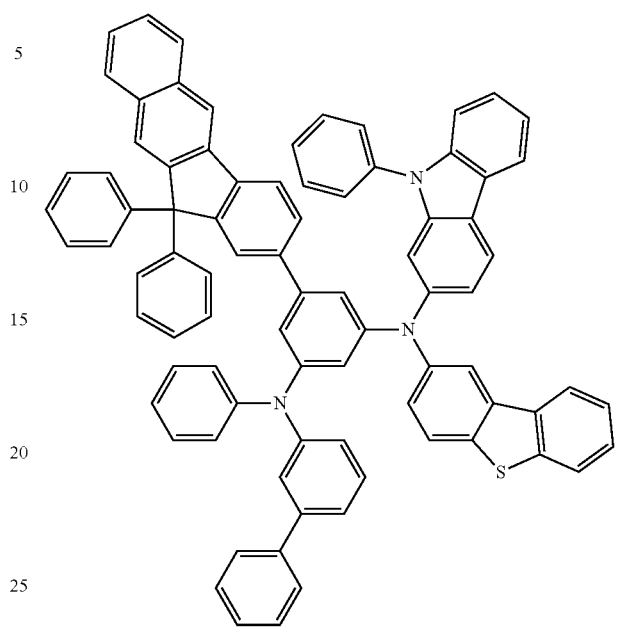

-continued
P-15
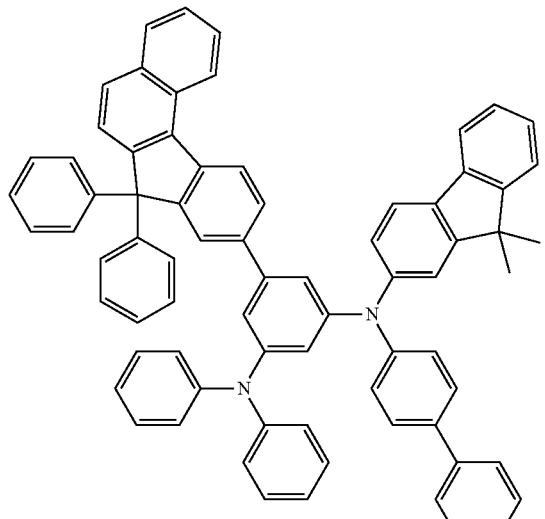
P-16
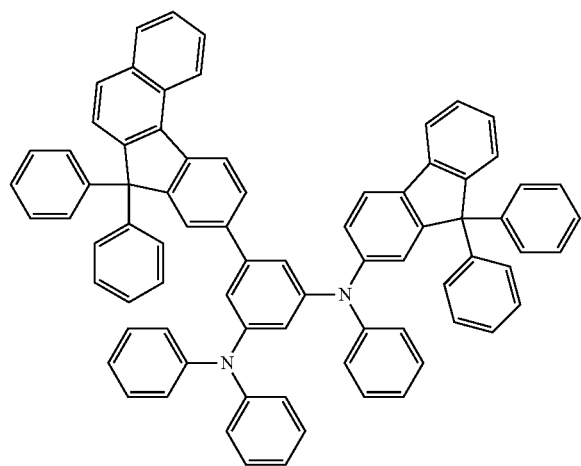
P-17
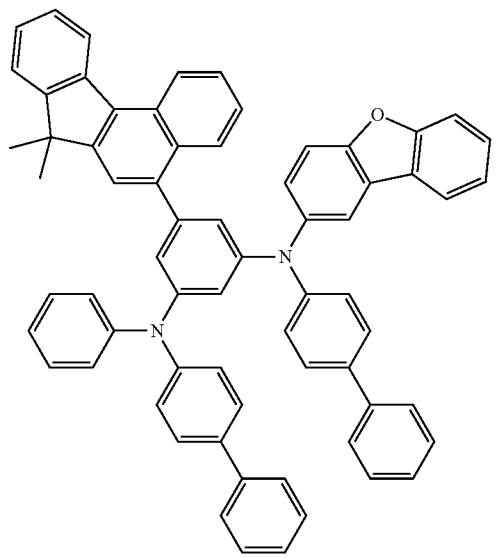
-continued
P-18
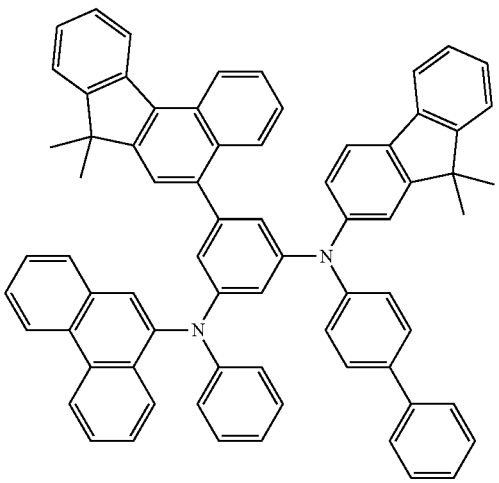
P-19
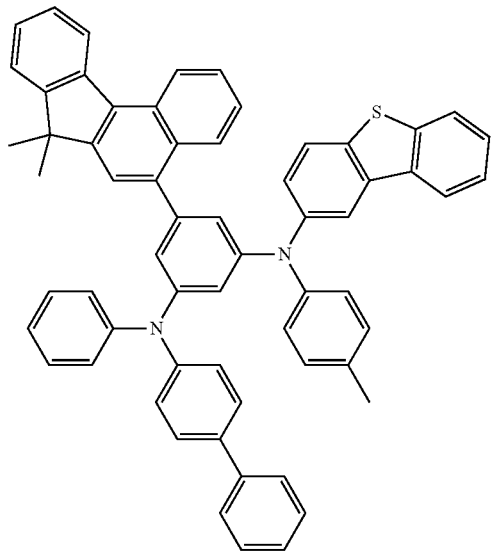
P-20
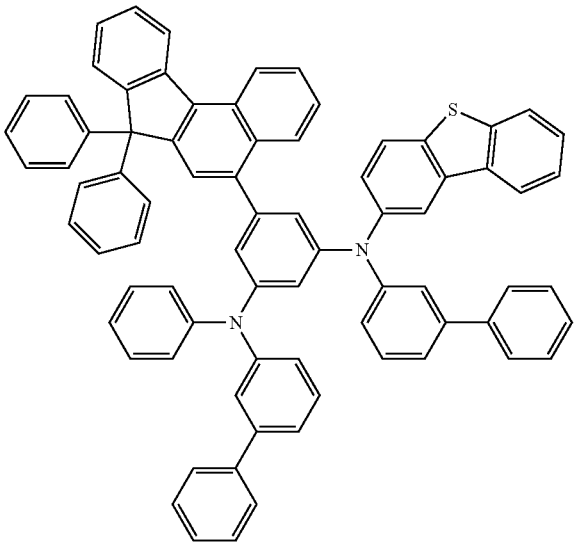

P-21
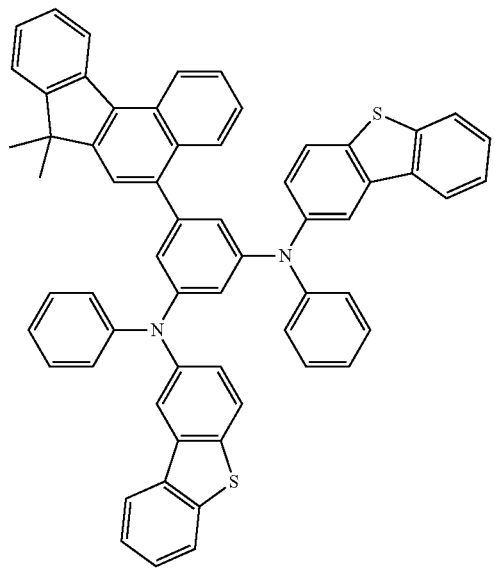
P-22
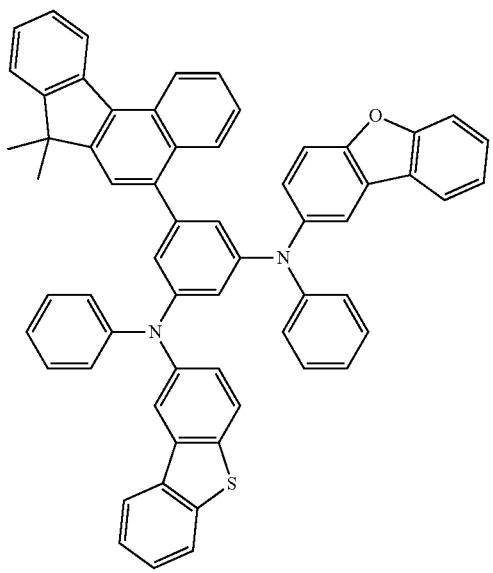
P-23
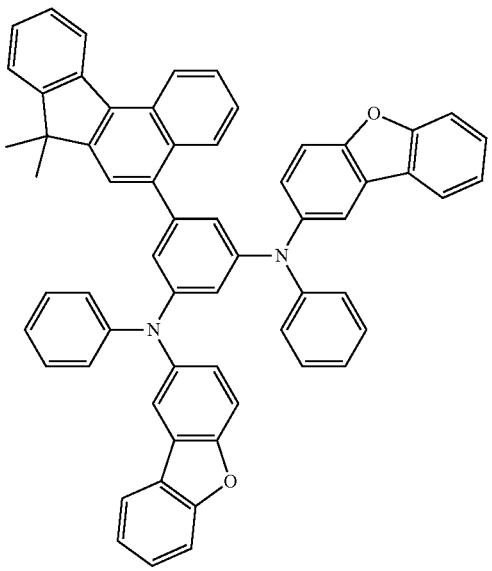
P-24
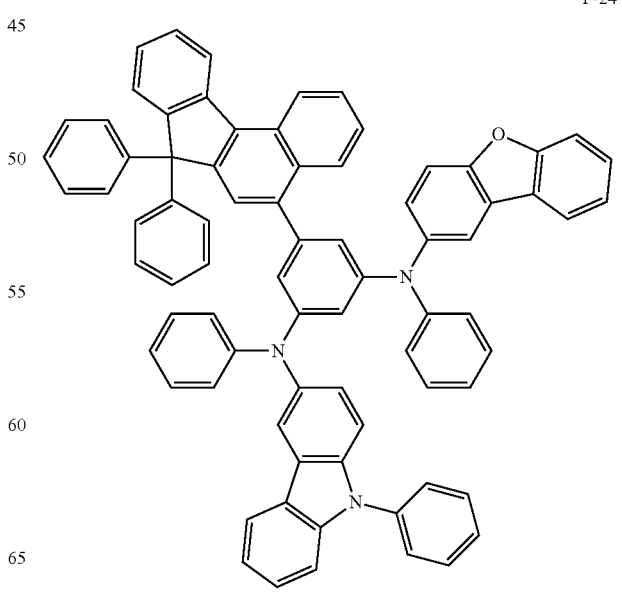

P-25
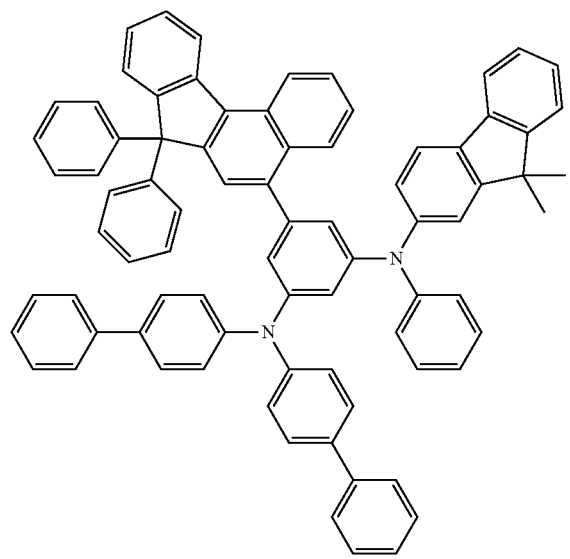
P-28
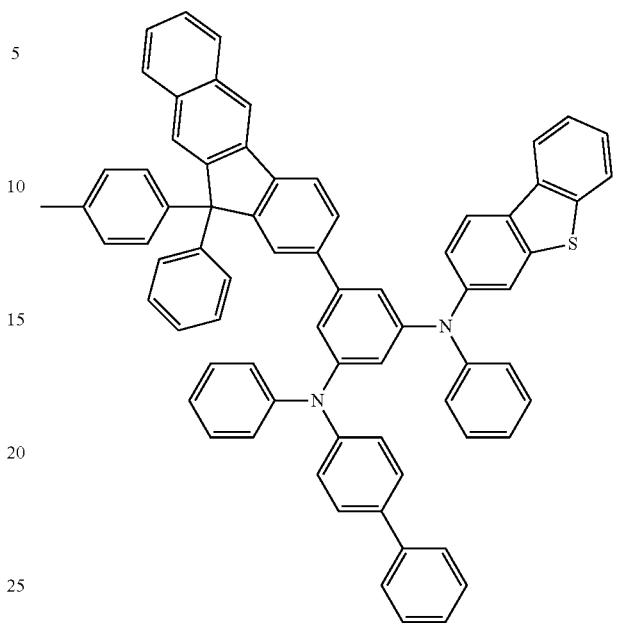
P-26
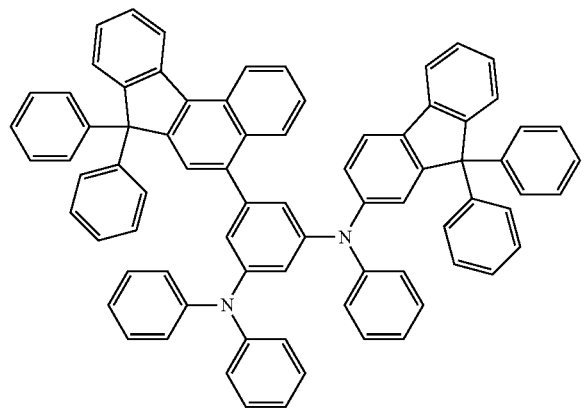
P-29
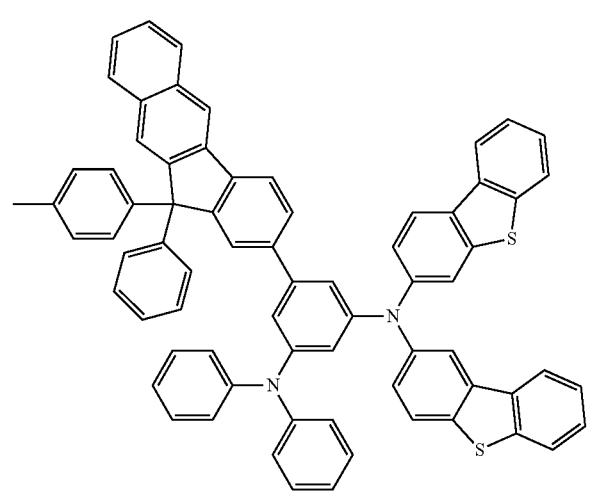
P-27
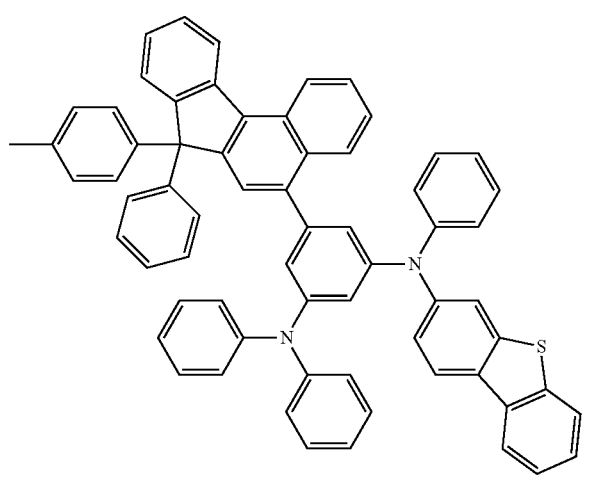
P-30
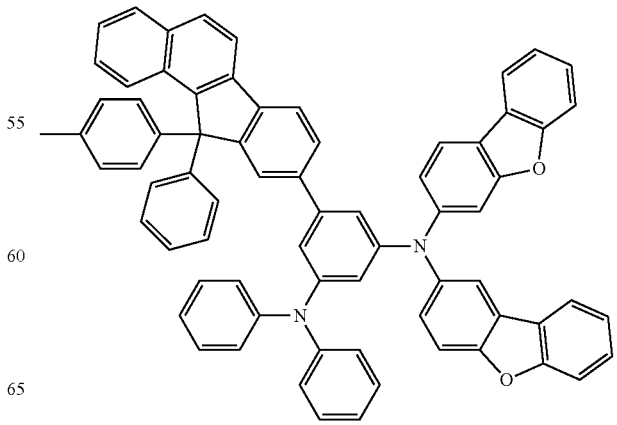

P-31
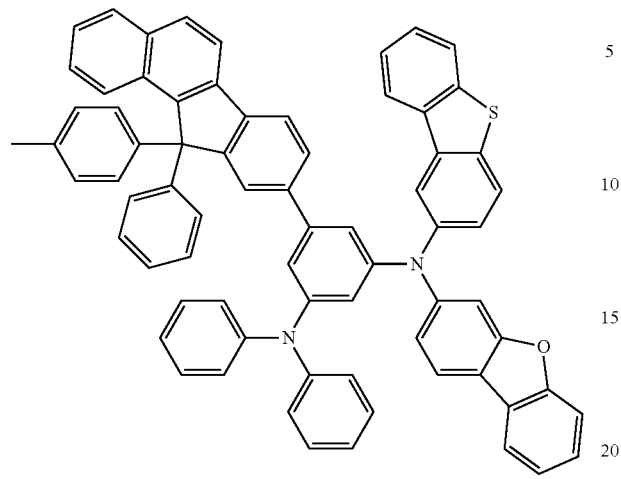
P-34
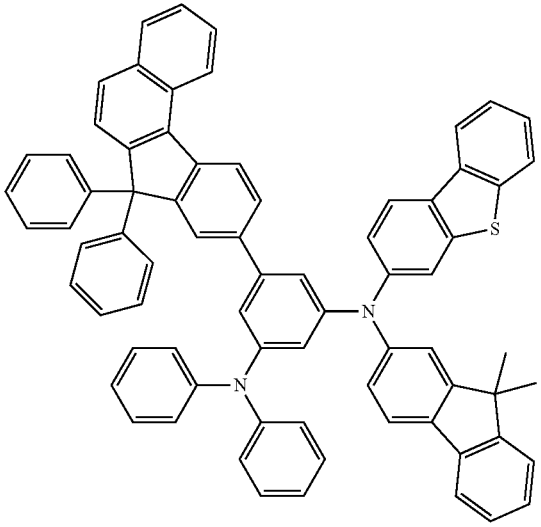
P-32
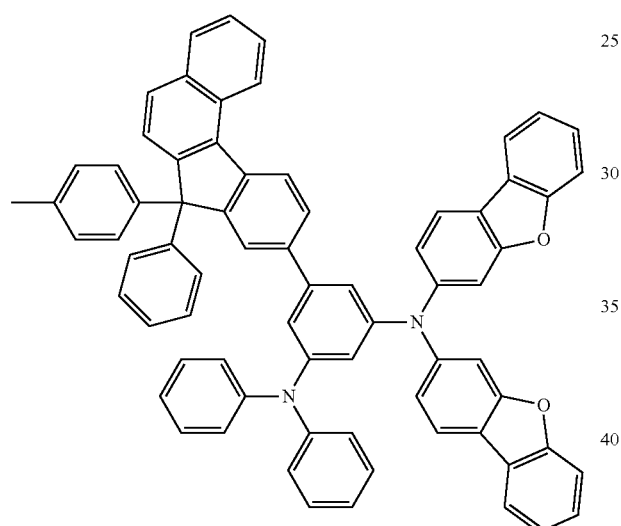
P-35
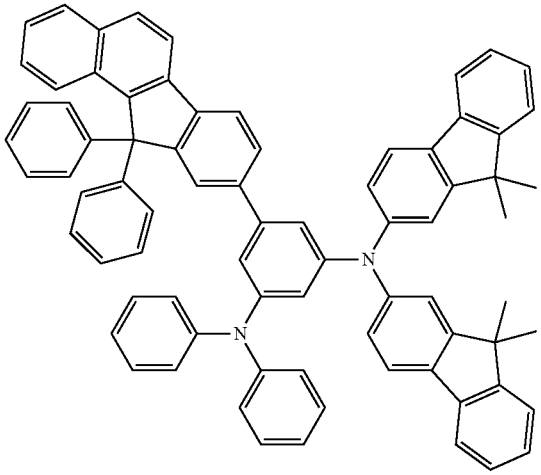
P-33
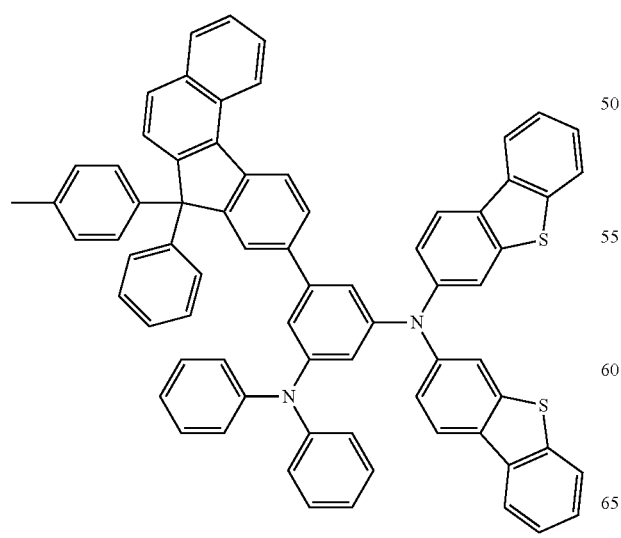
P-36
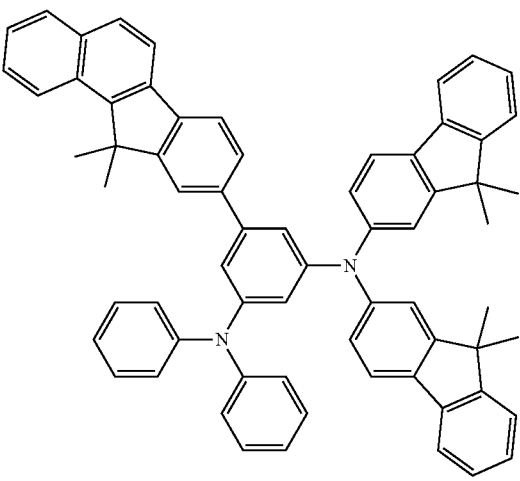

-continued
P-37
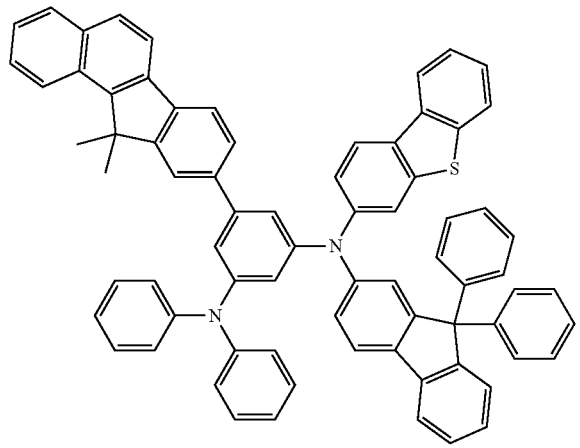
P-38
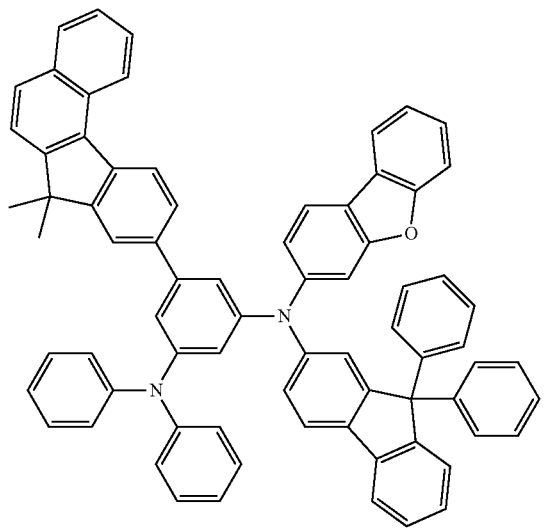
P-39
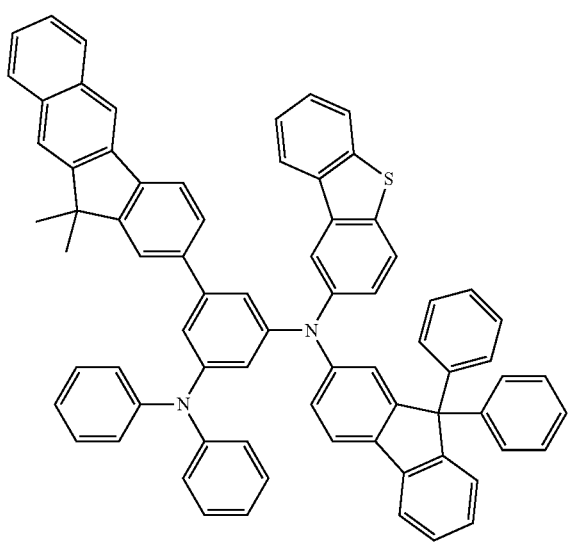
P-40
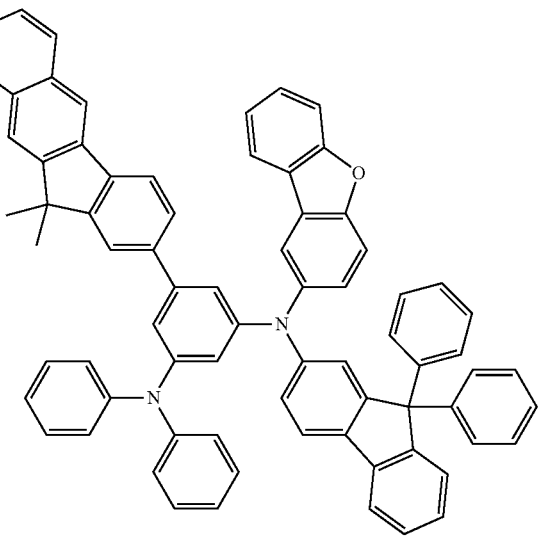
P-41
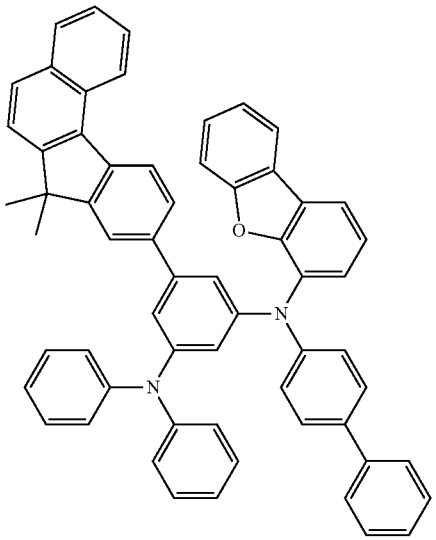
P-42
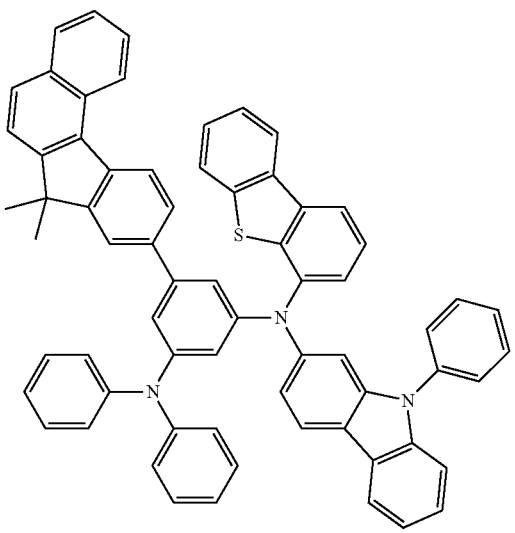

P-43
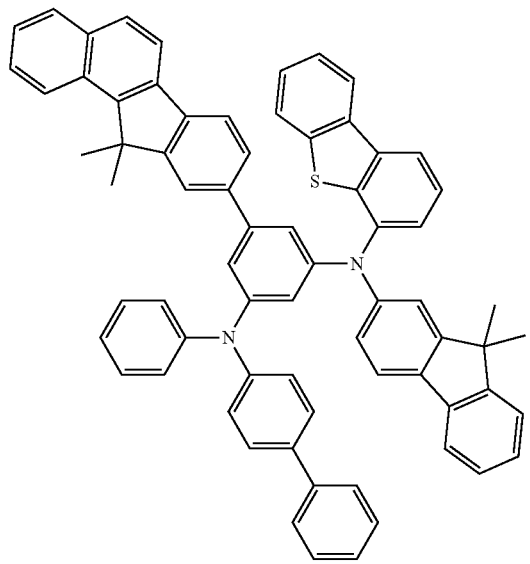
P-46
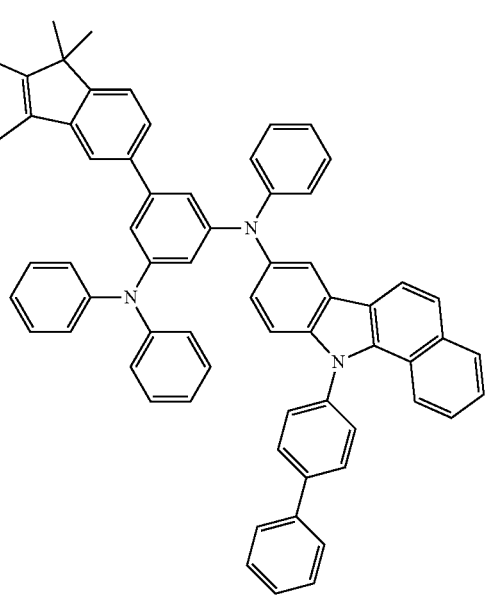
P-44
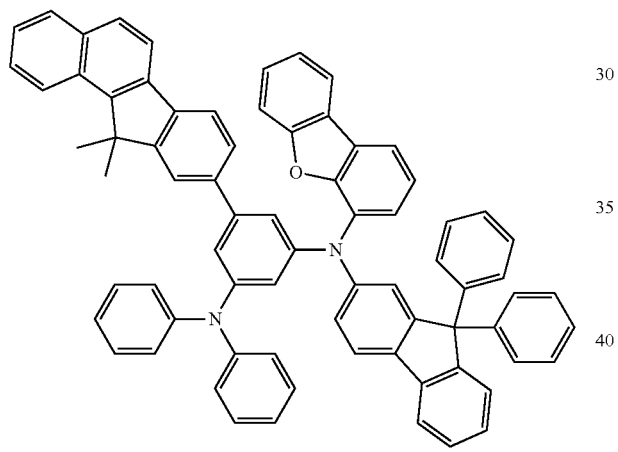
P-45
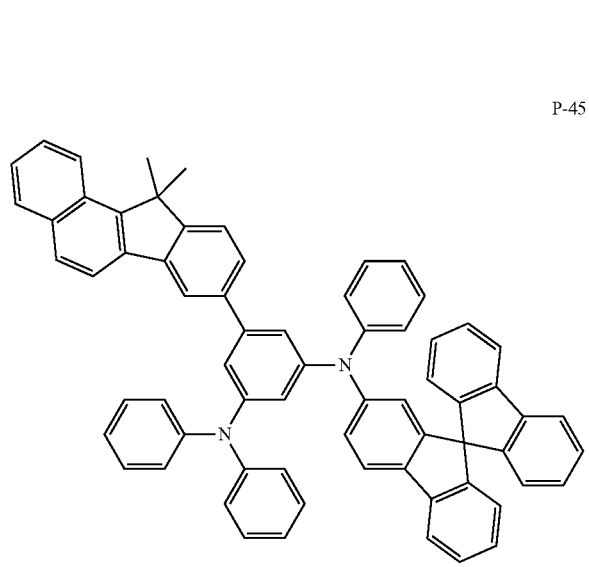
P-47
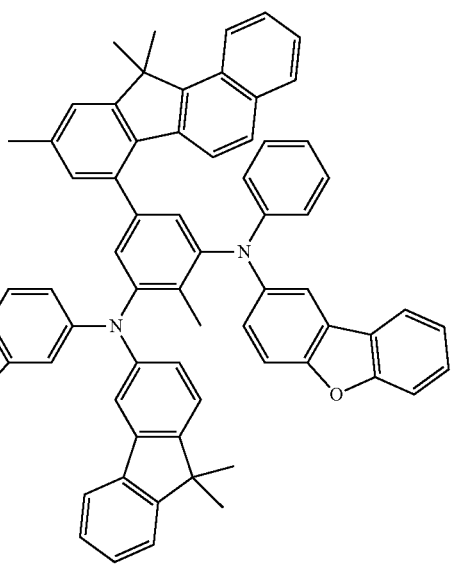

-continued
P-48
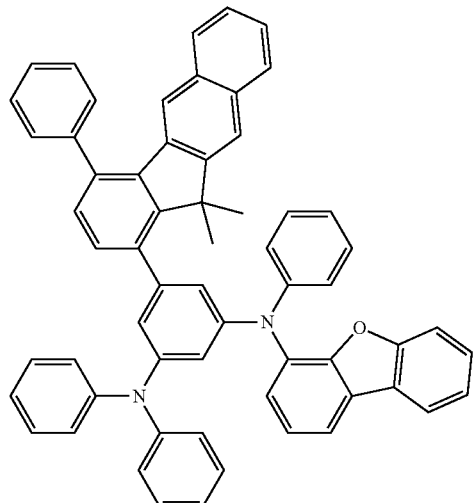
P-49
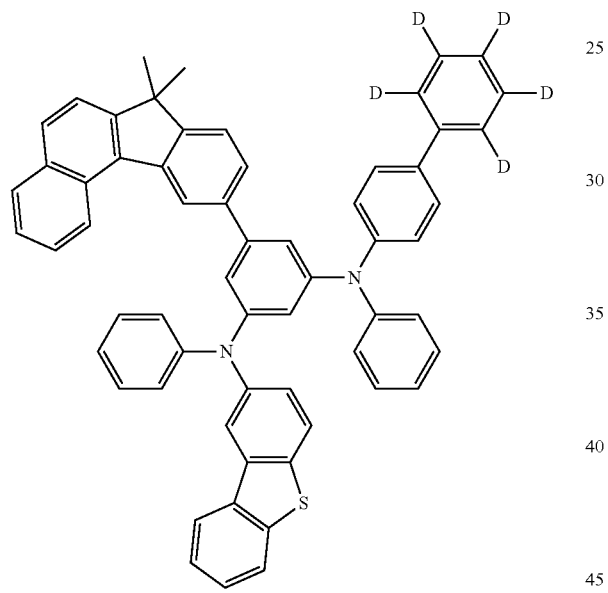
P-50
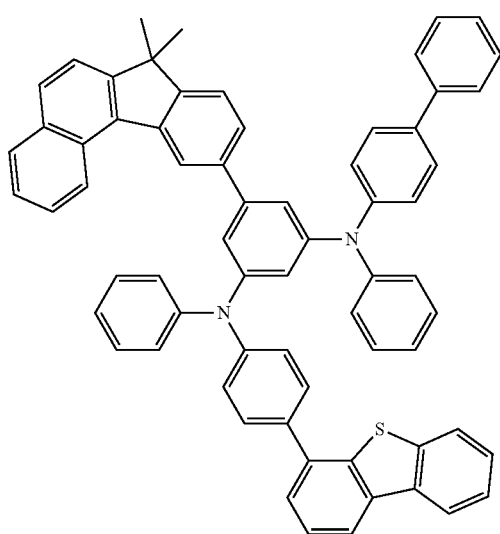
-continued
P-51
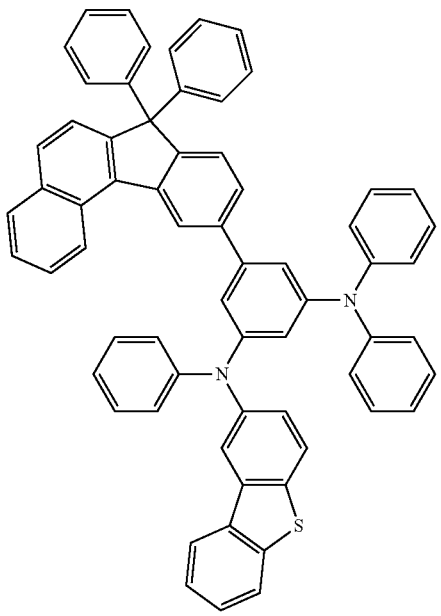
P-52
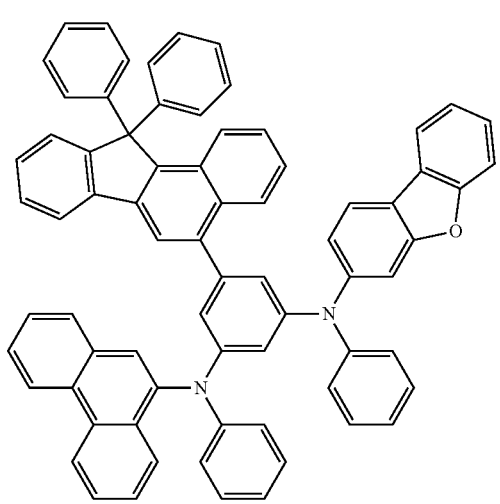

P-53
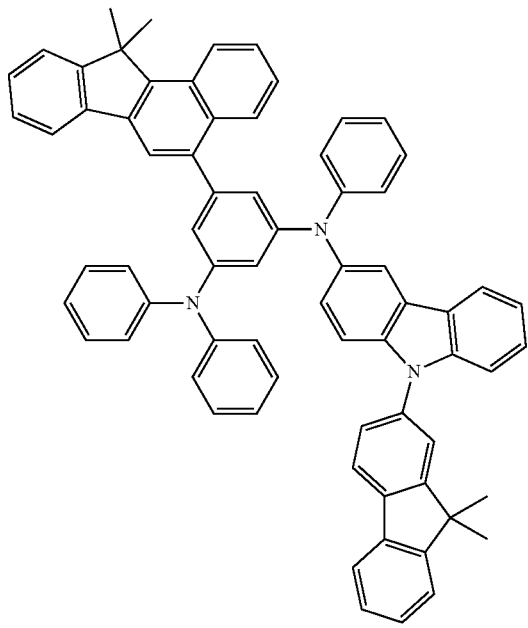
P-55
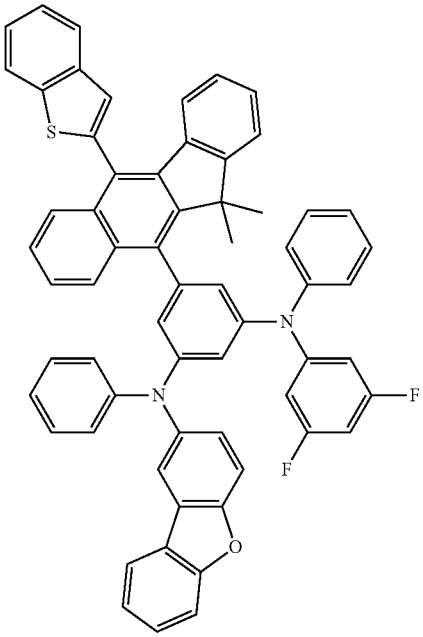
P-54
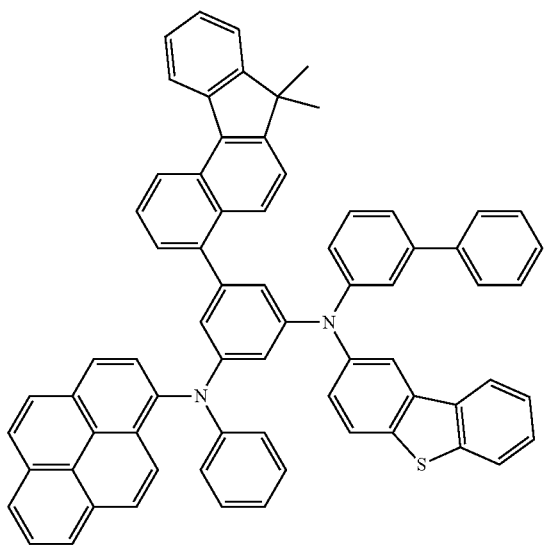
P-56
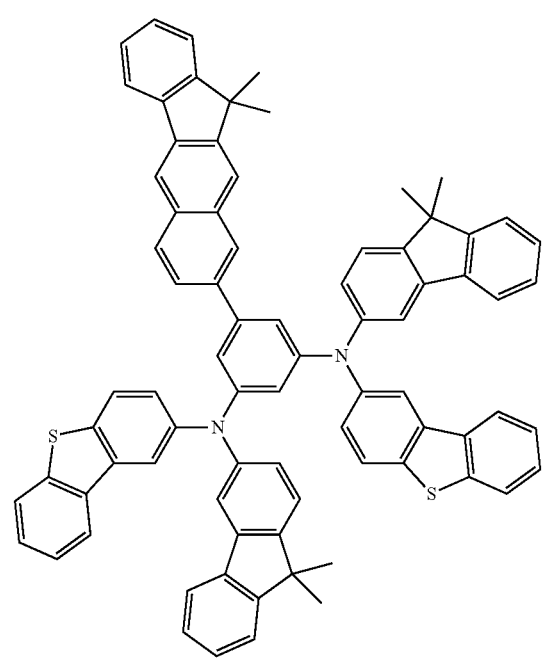

-continued
P-57
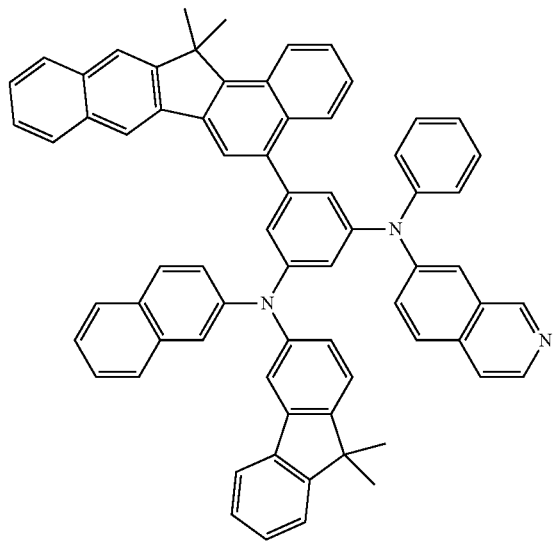
P-58
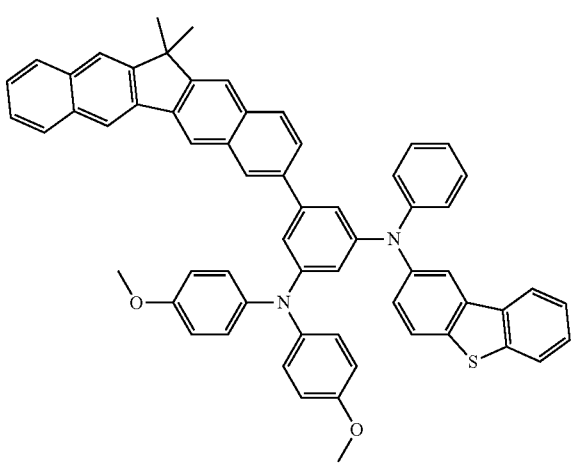
P-59
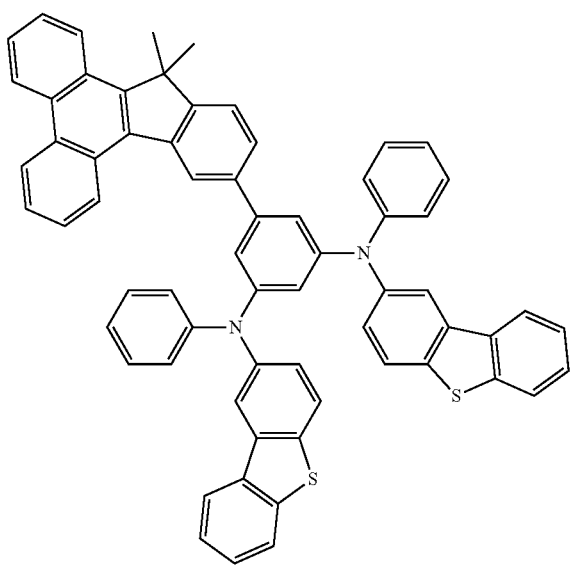
-continued
P-60
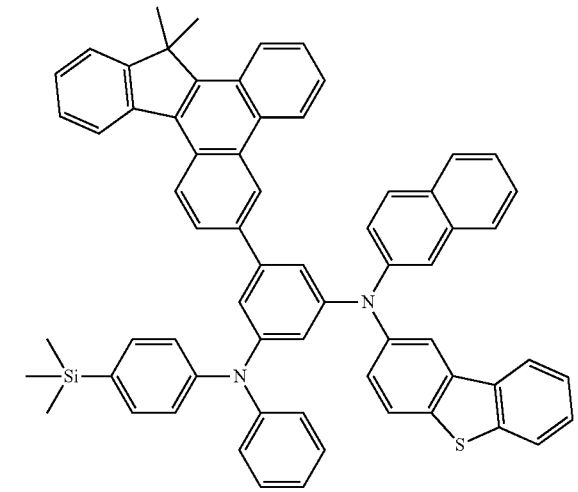
P-61
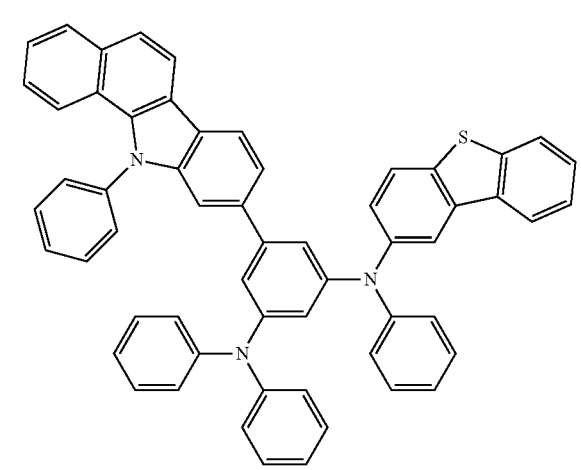
P-62

-continued
P-63
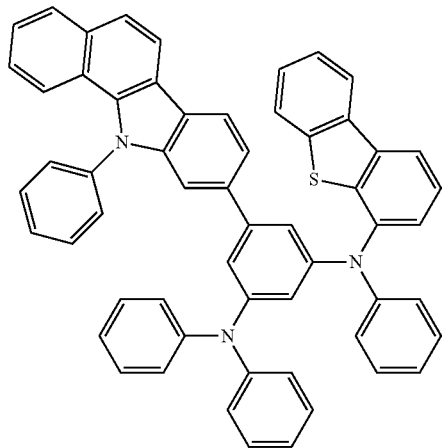
P-64
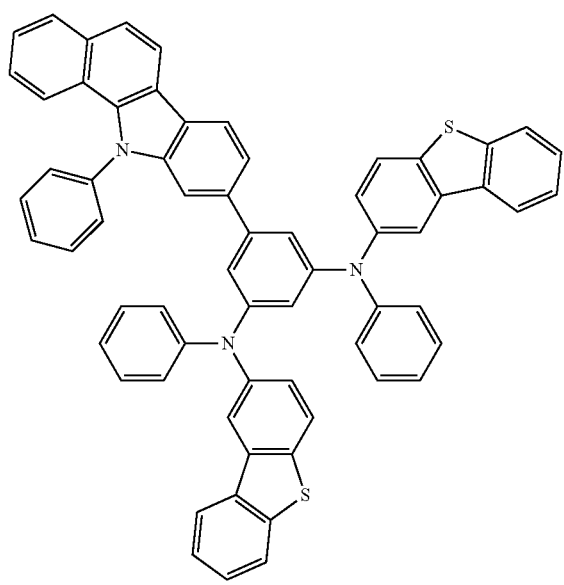
P-65
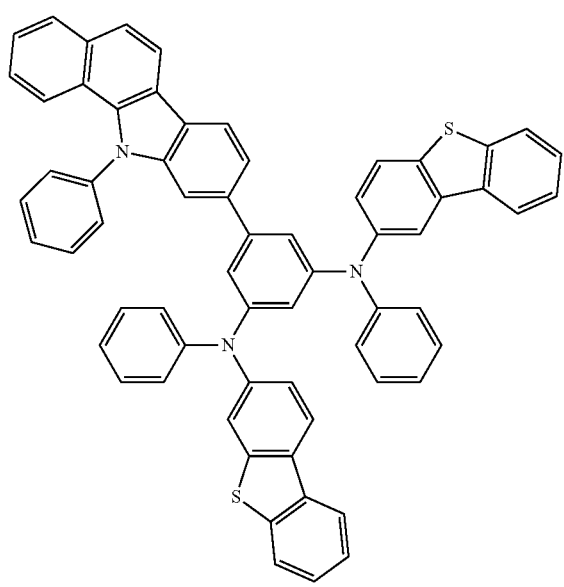
-continued
P-66
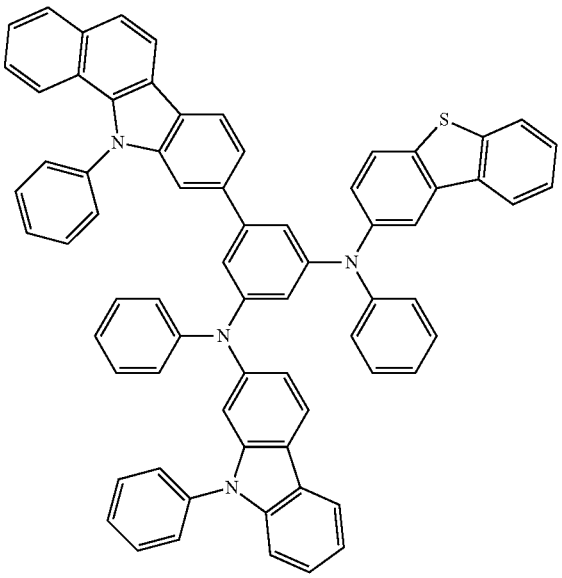
P-67
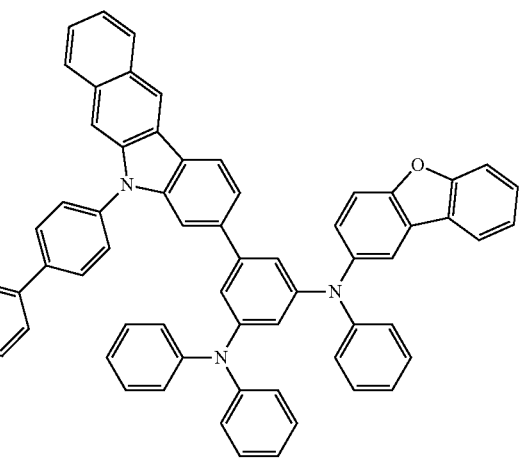

P-68
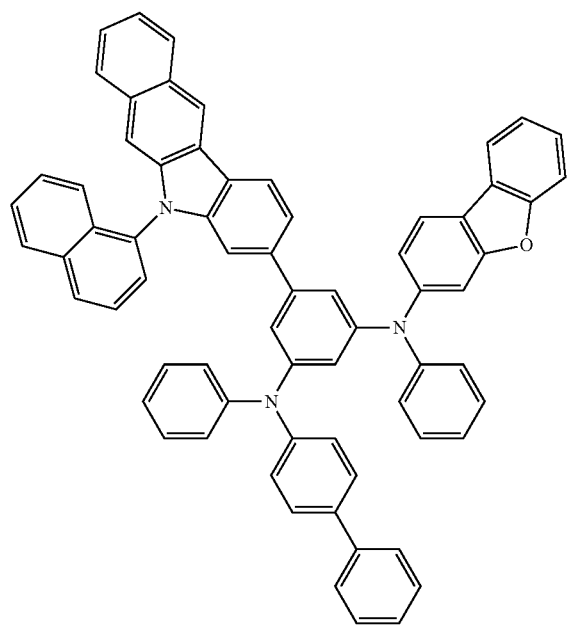
P-70
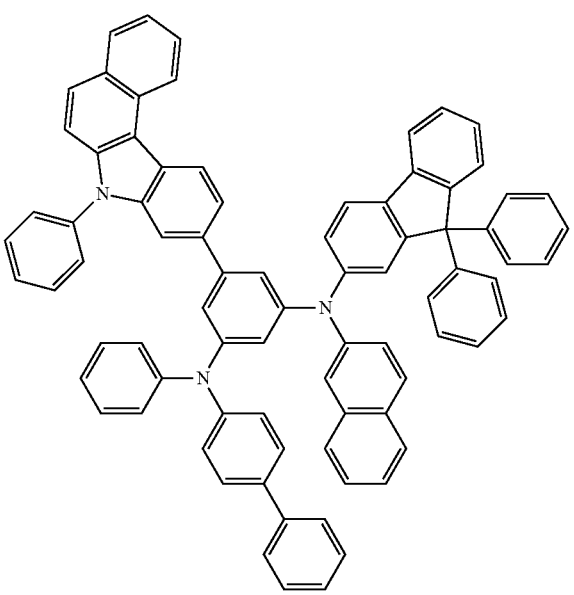
P-69
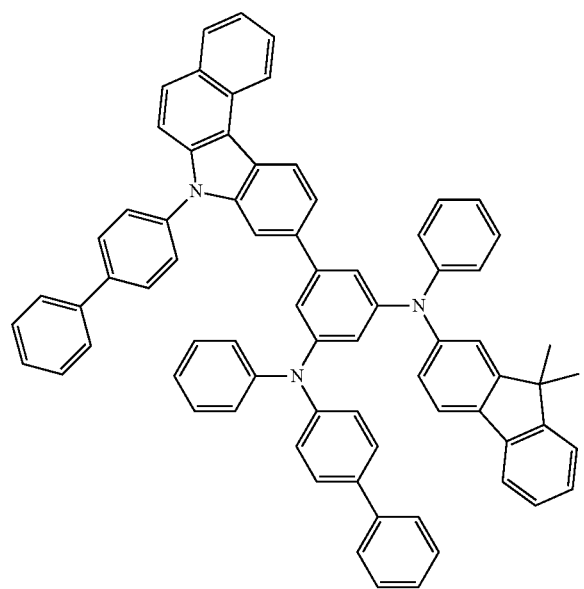
P-71
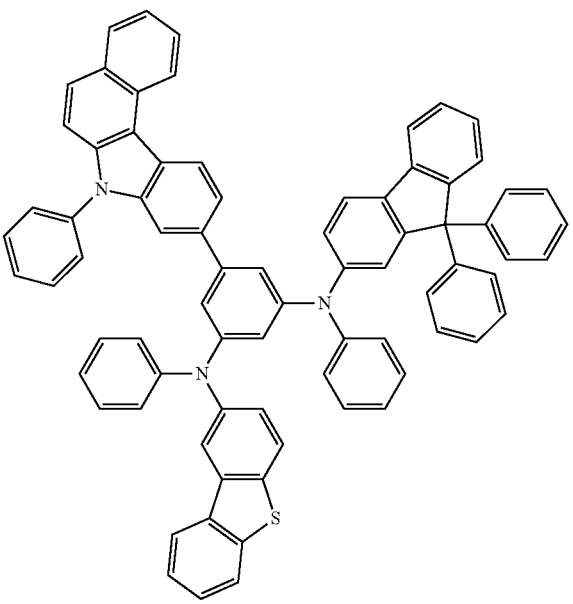

-continued
P-72
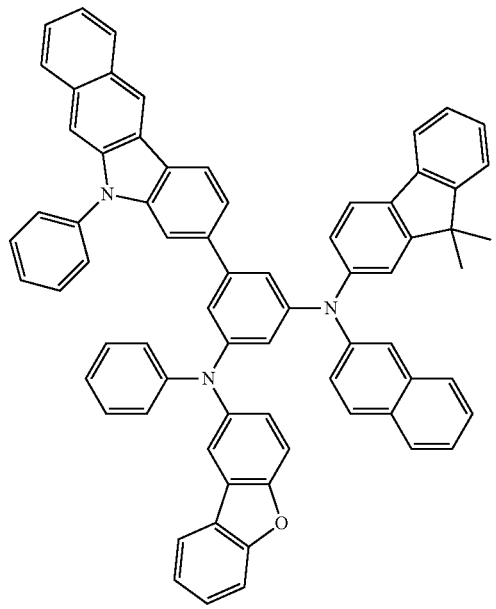
P-73
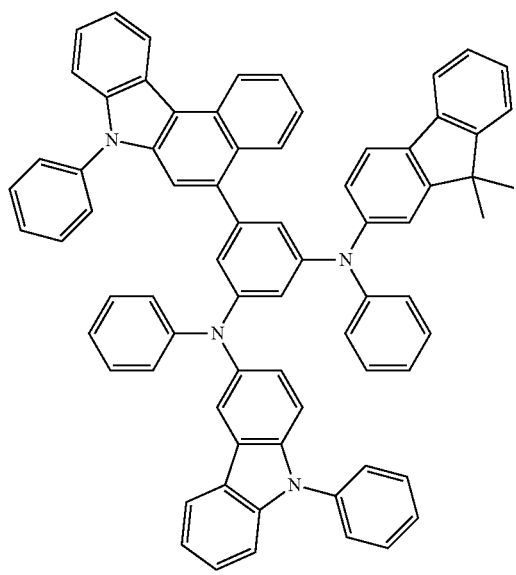
P-74
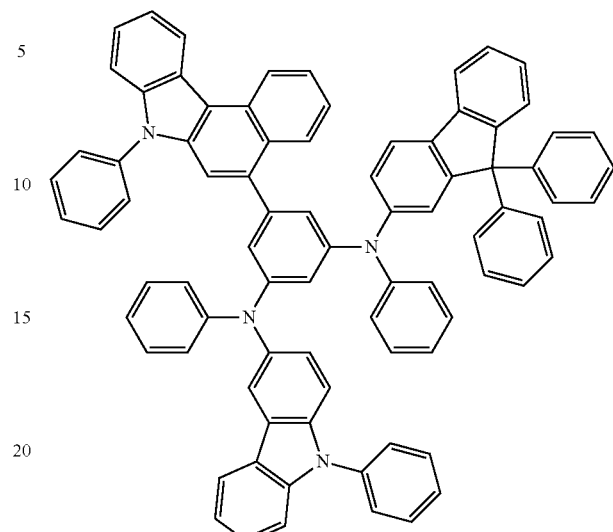
P-75
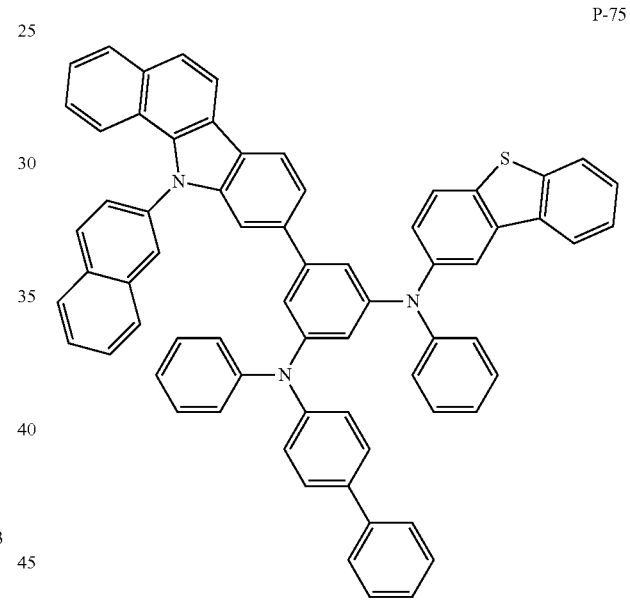
P-76
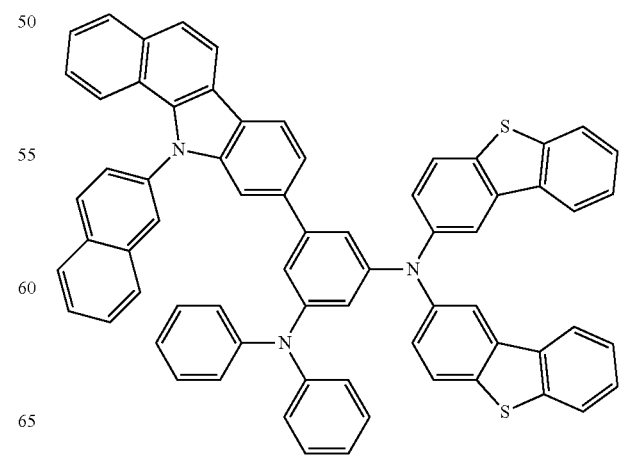

-continued
P-77
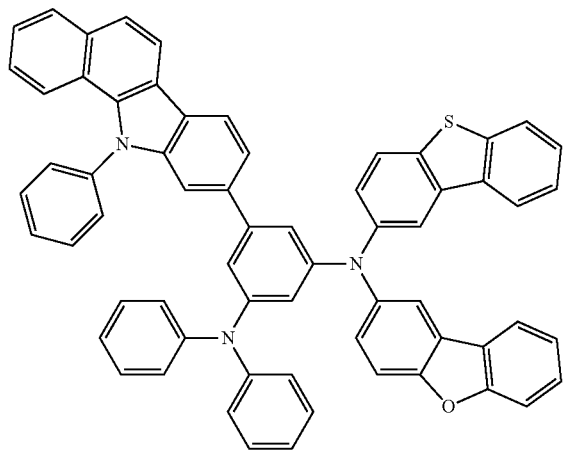
P-78
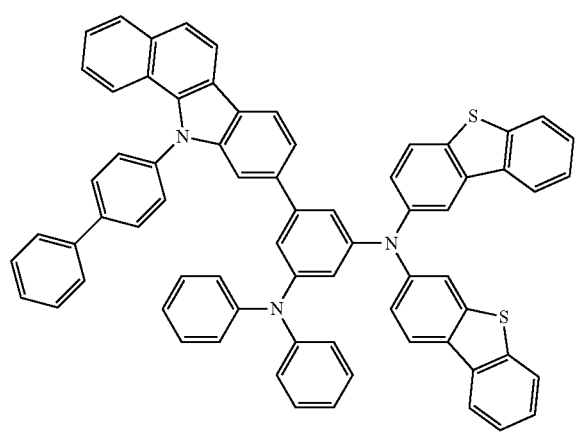
P-79
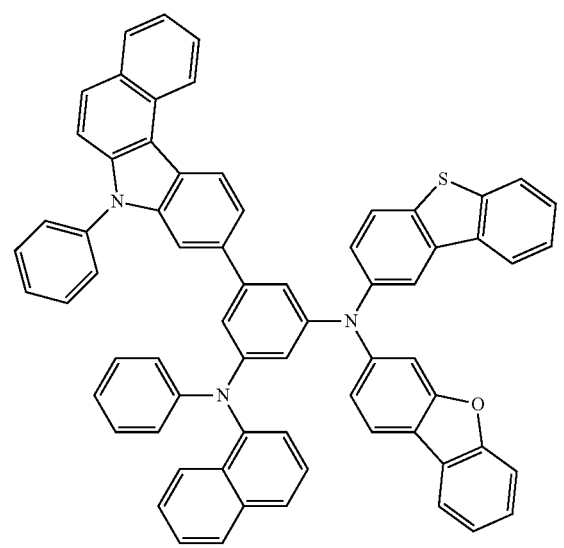
-continued
P-80
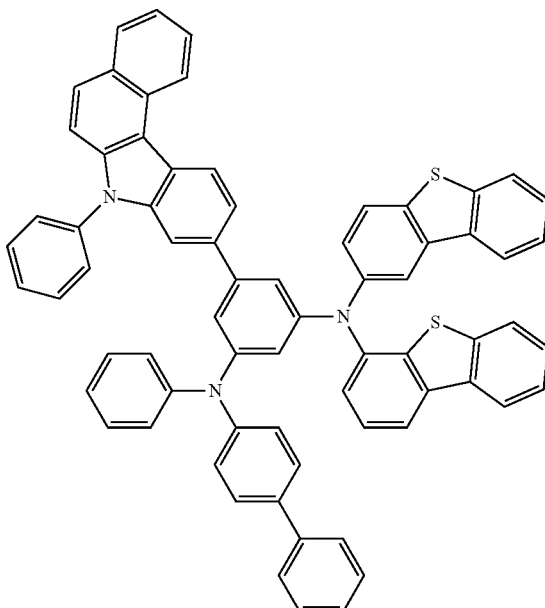
P-81
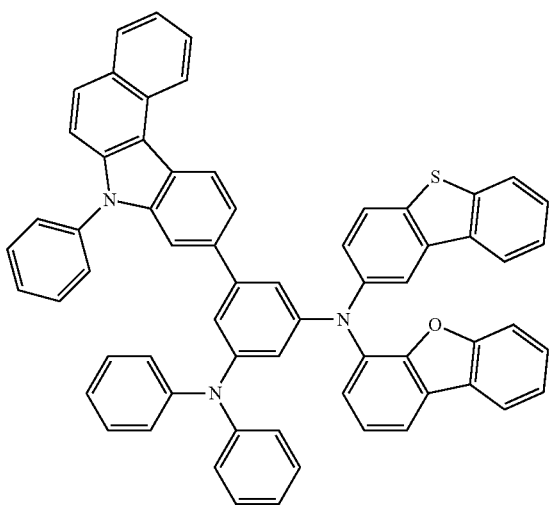

P-82
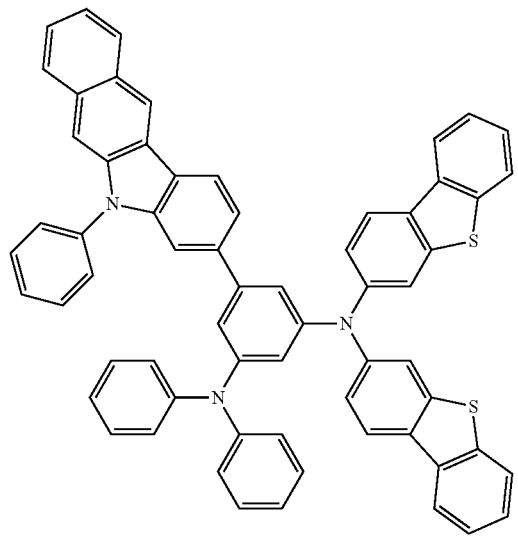
P-83
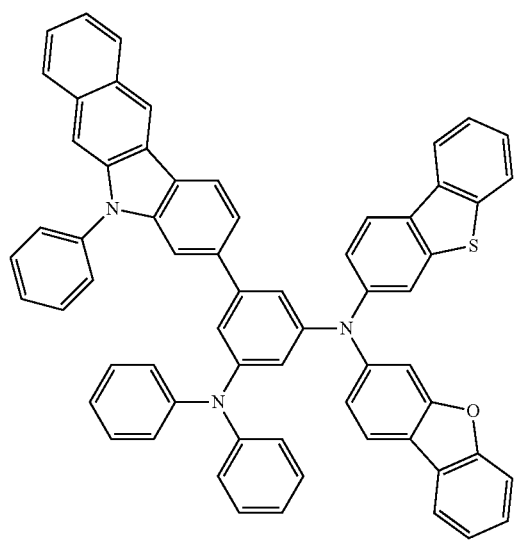
P-84
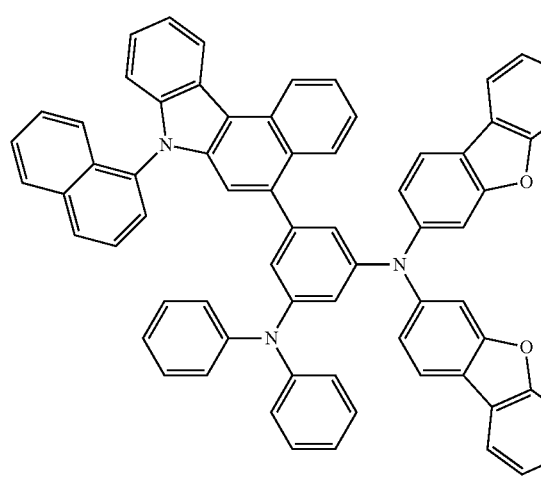
P-85
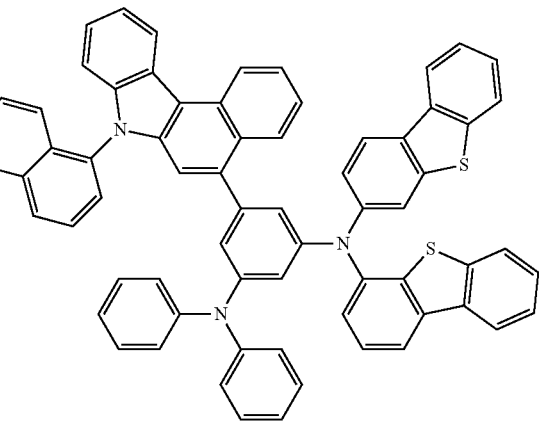
P-86
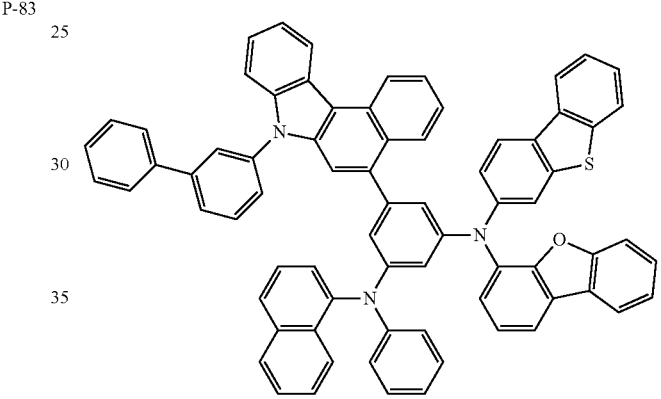
P-87
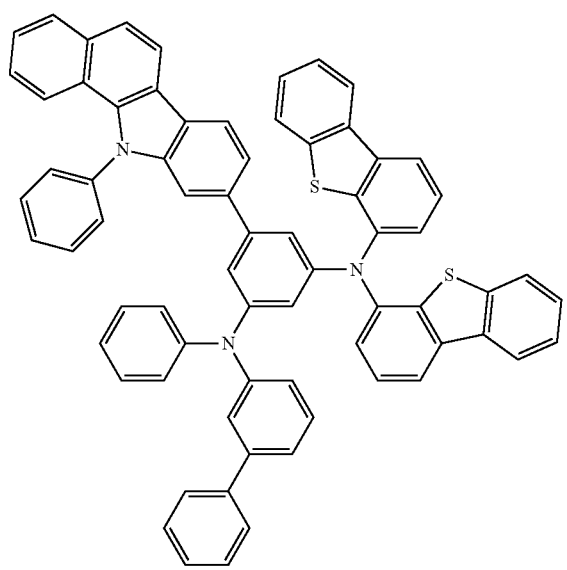

P-88
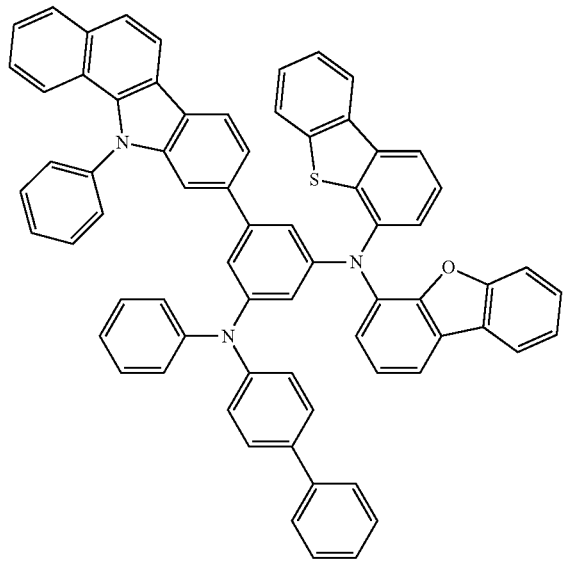
P-89
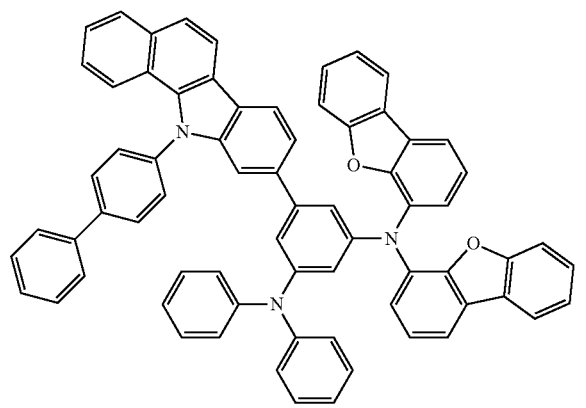
P-90
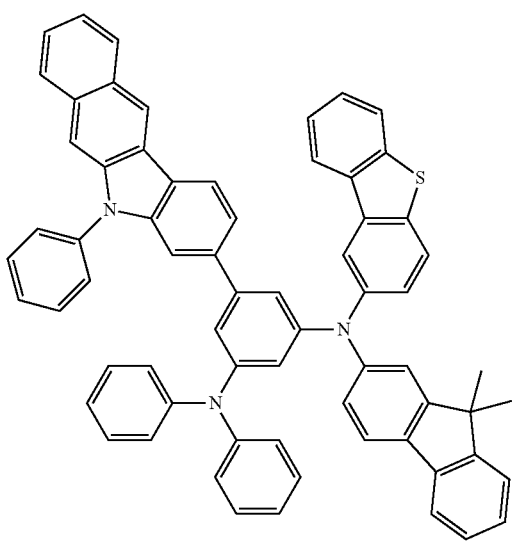
P-91
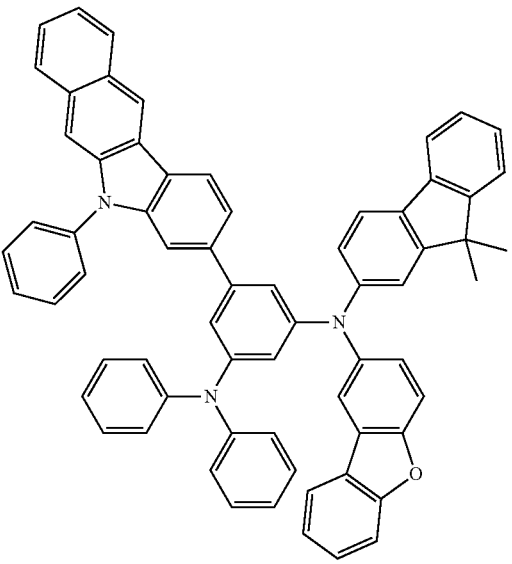
P-92
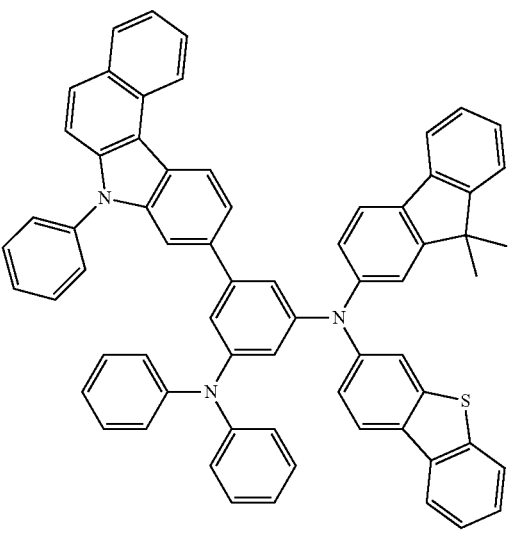

P-93
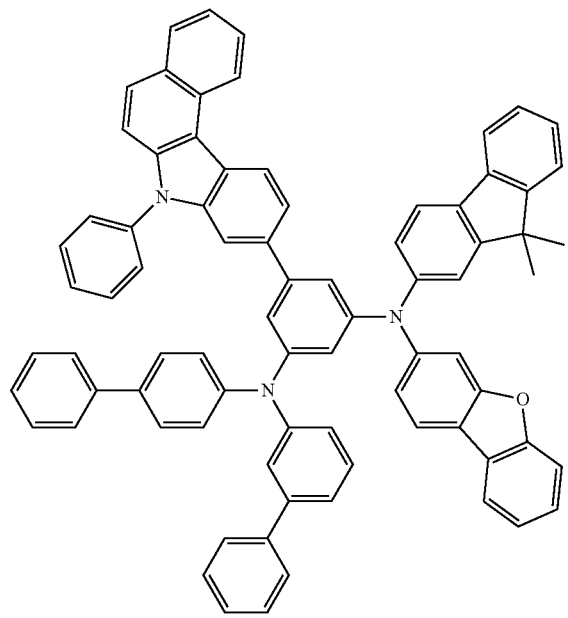
P-96
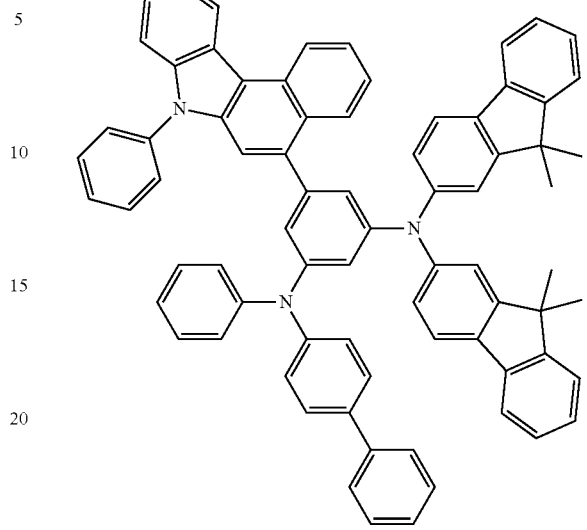
P-94
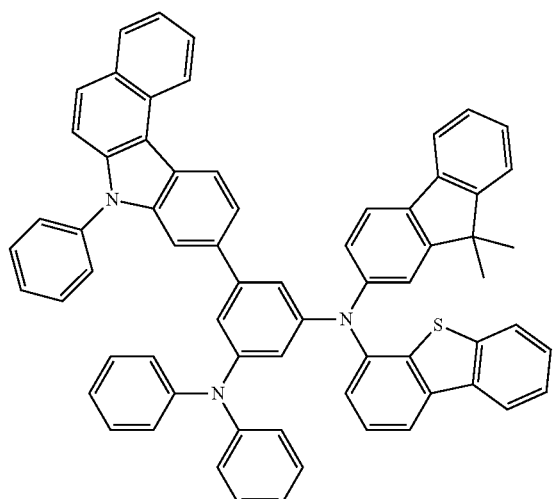
P-97
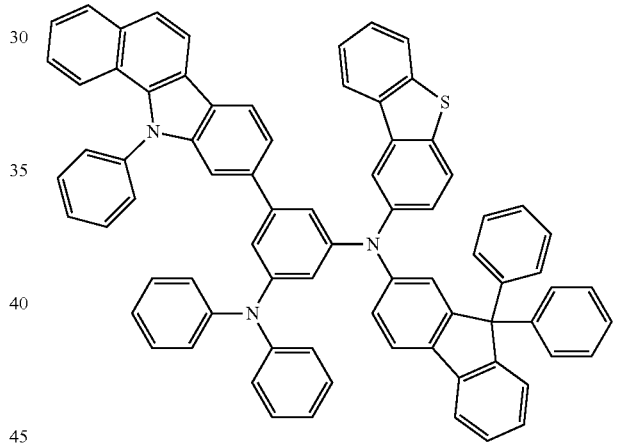
P-95
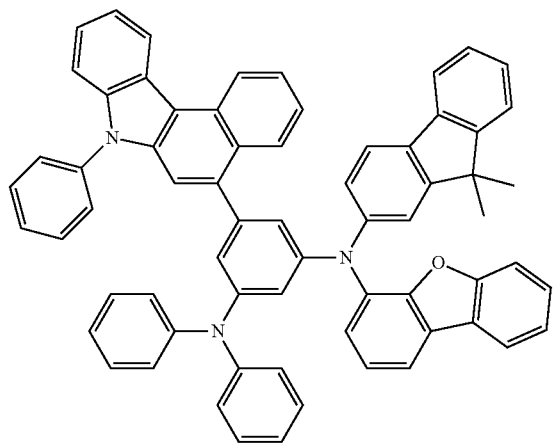
P-98
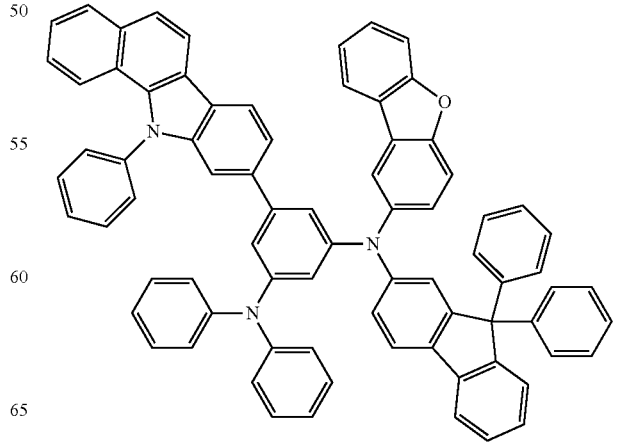

P-99
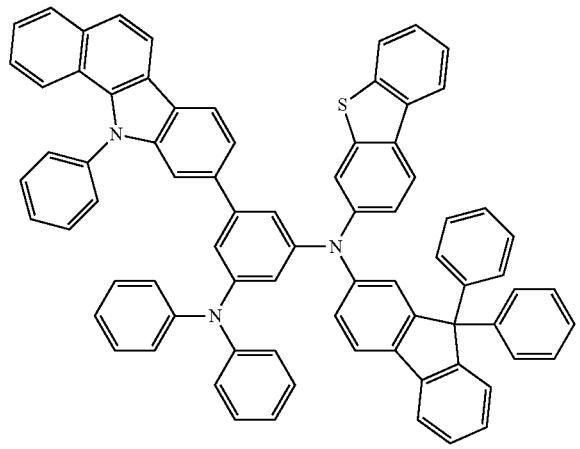
P-100
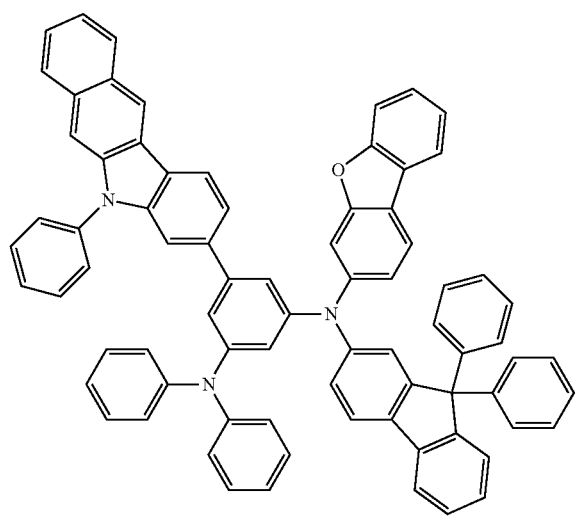
P-101
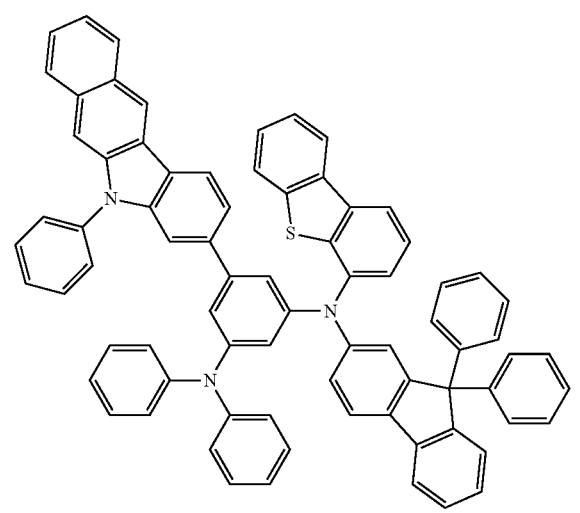
P-102
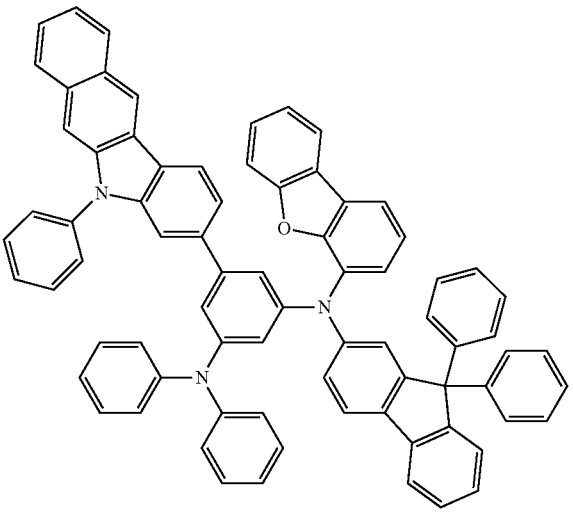
P-103
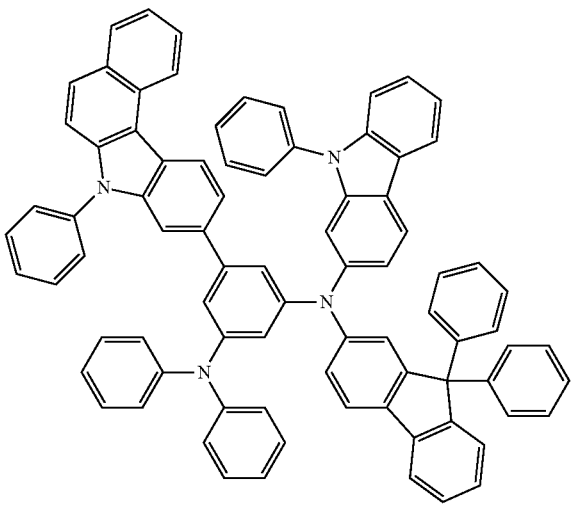
P-104
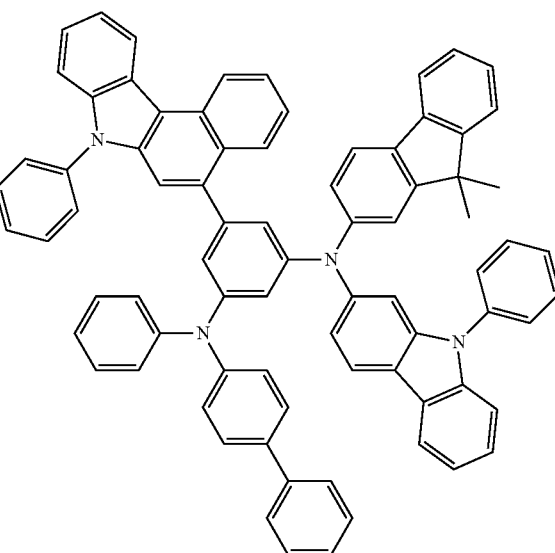

-continued
P-105
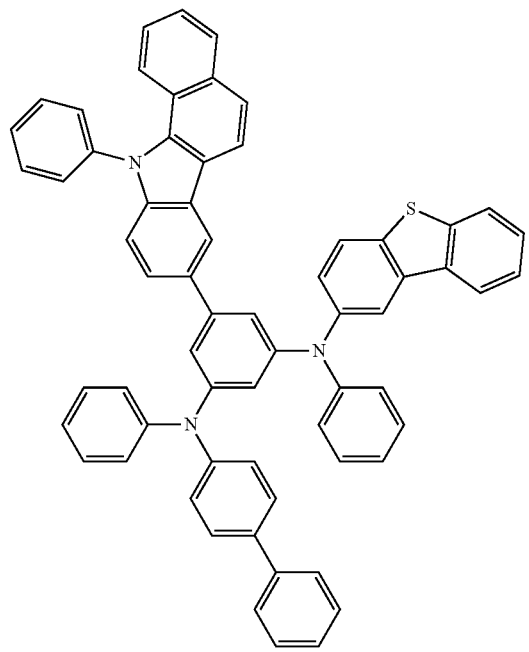
P-106
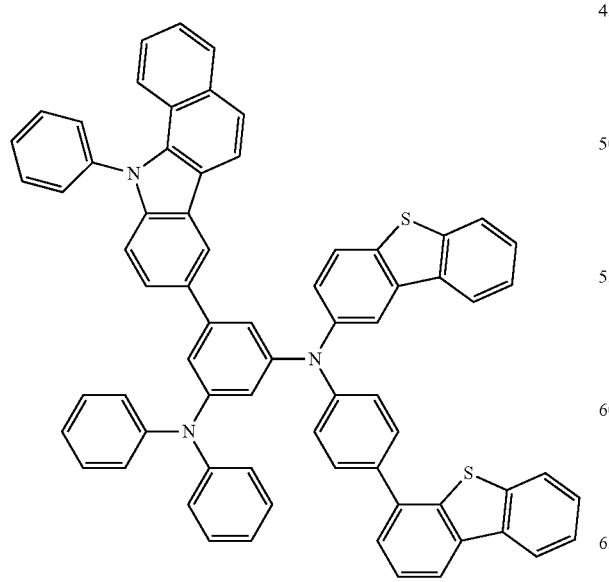
P-107
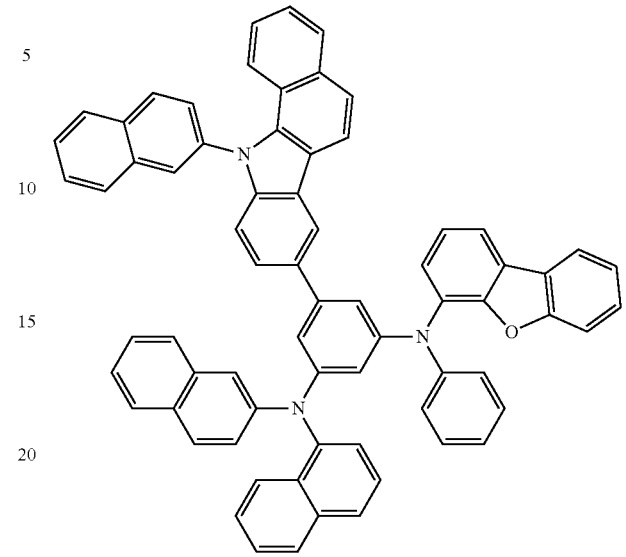
P-108
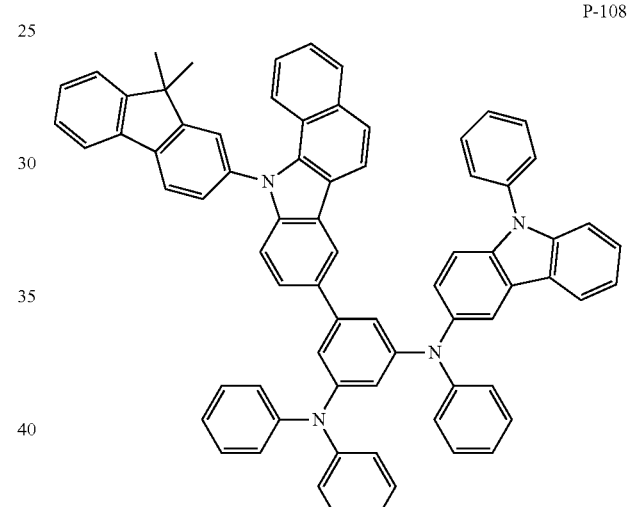
P-109
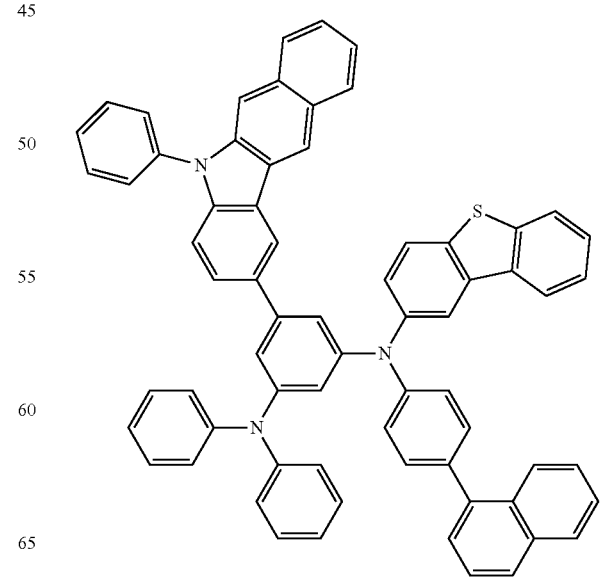

P-110
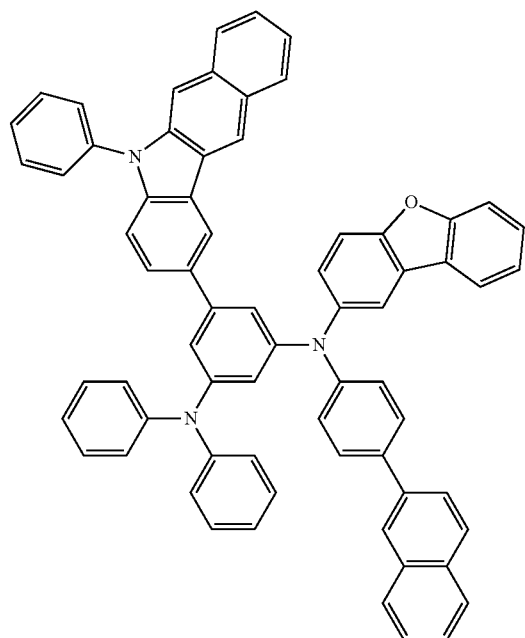
P-111
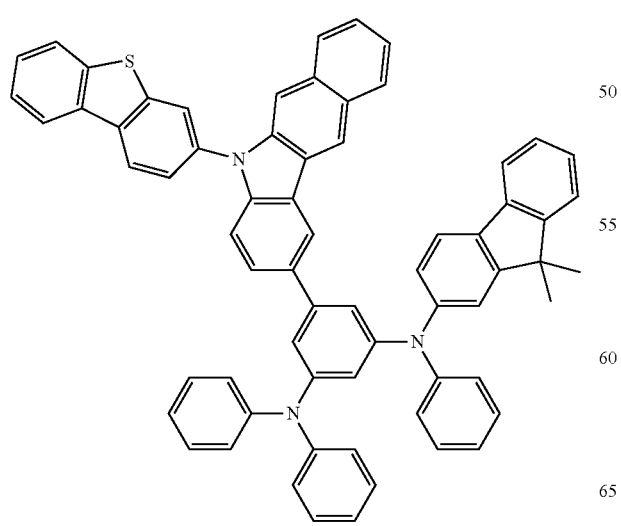
P-112
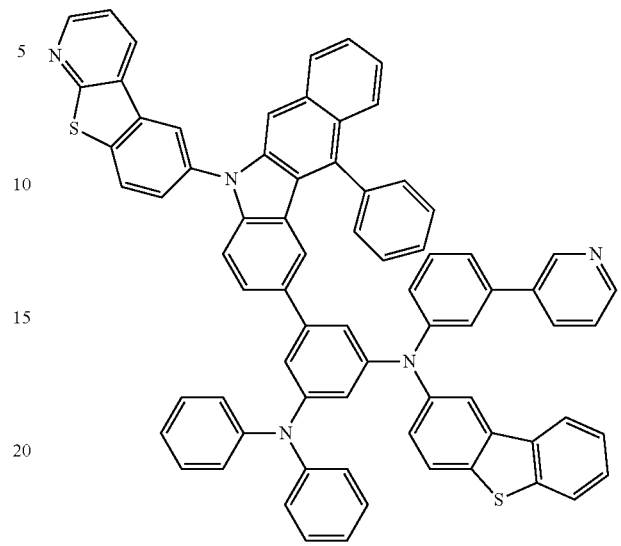
P-113
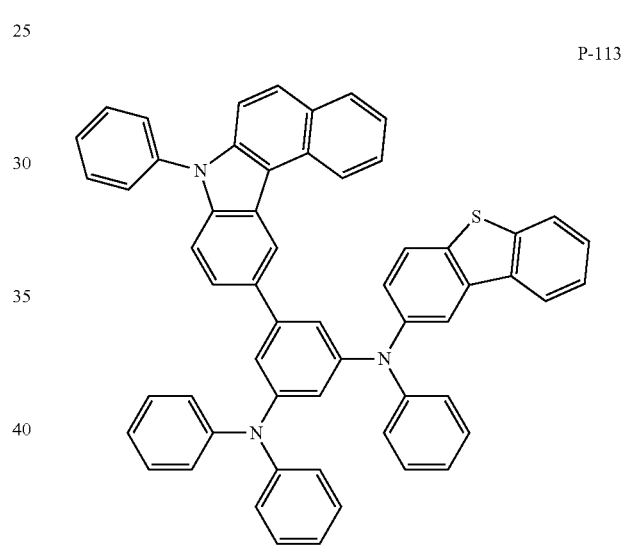
P-114
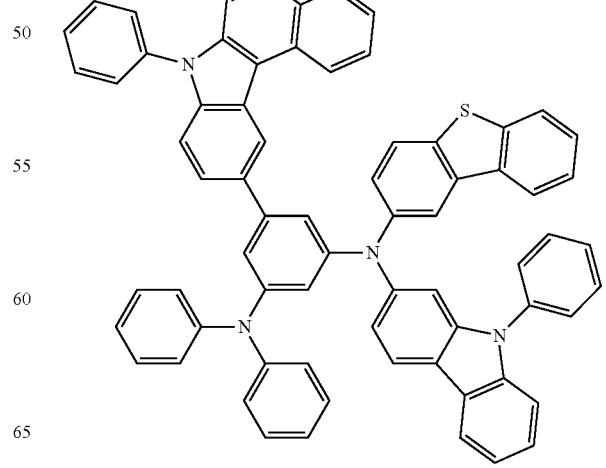

P-115
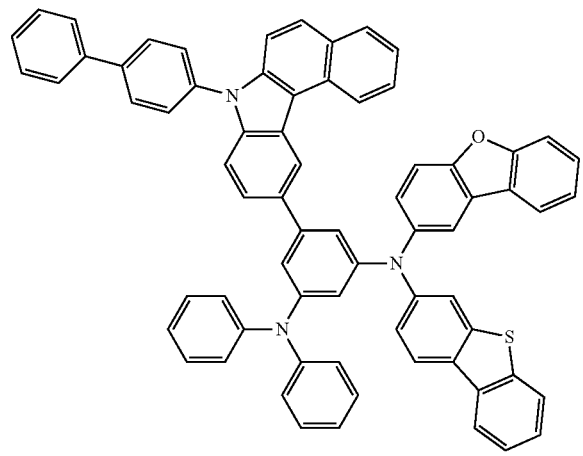
P-116
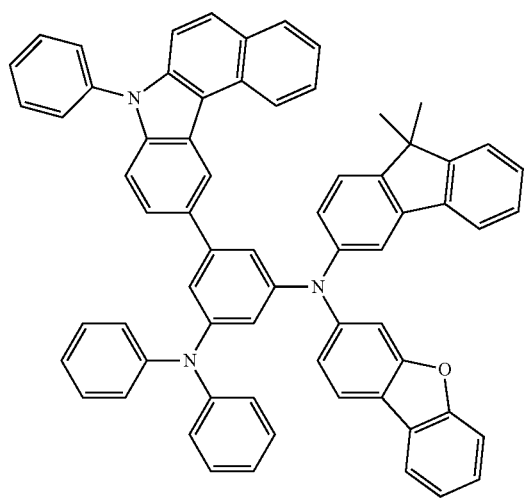
P-117
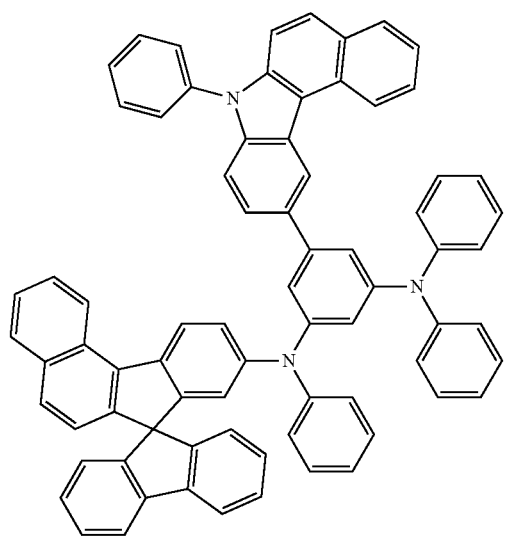
P-118
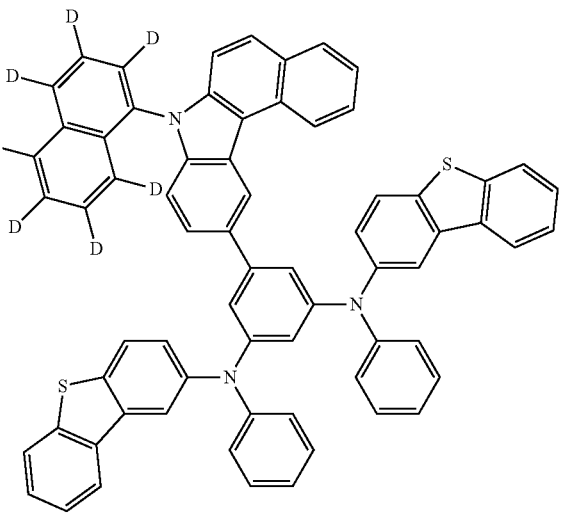
P-119
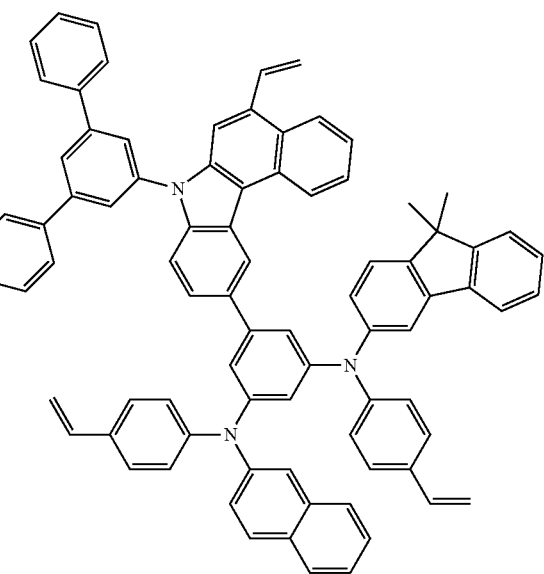

P-120
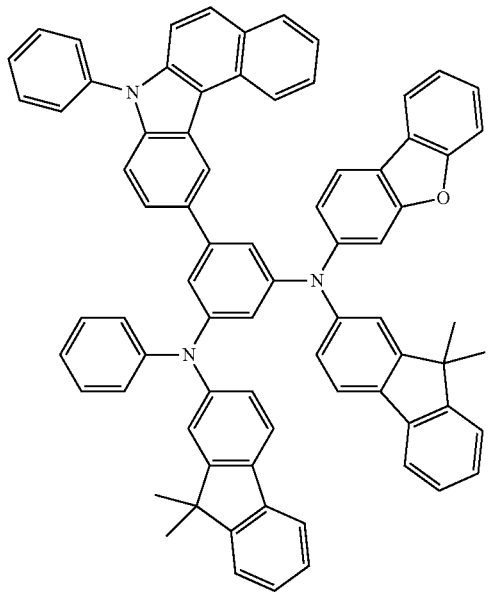
P-122
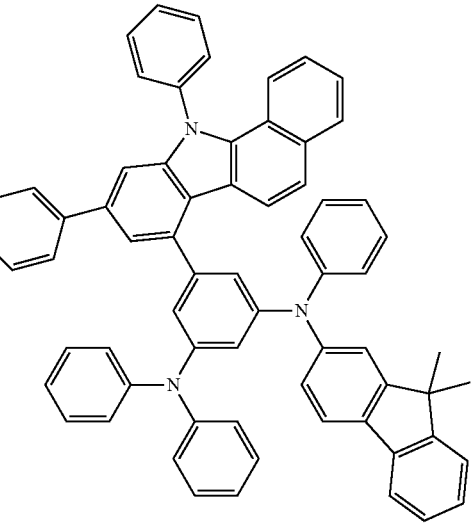
P-121
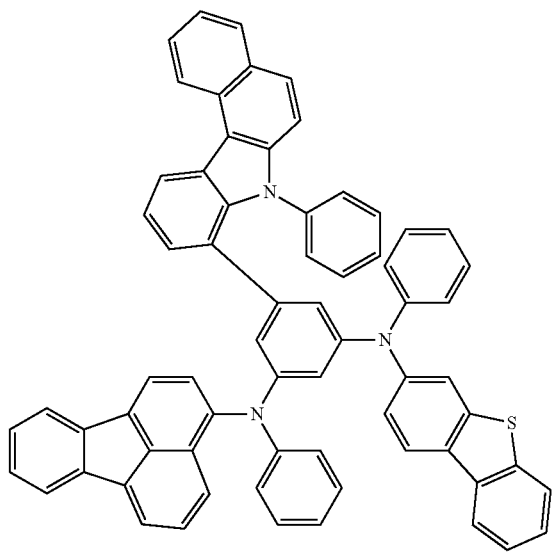
P-123
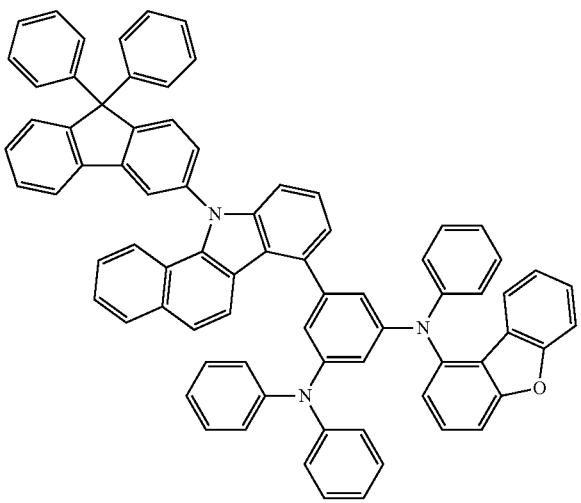

P-124
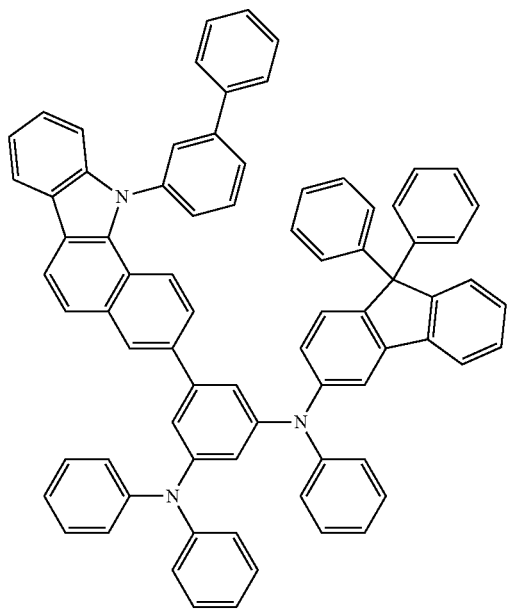
P-125
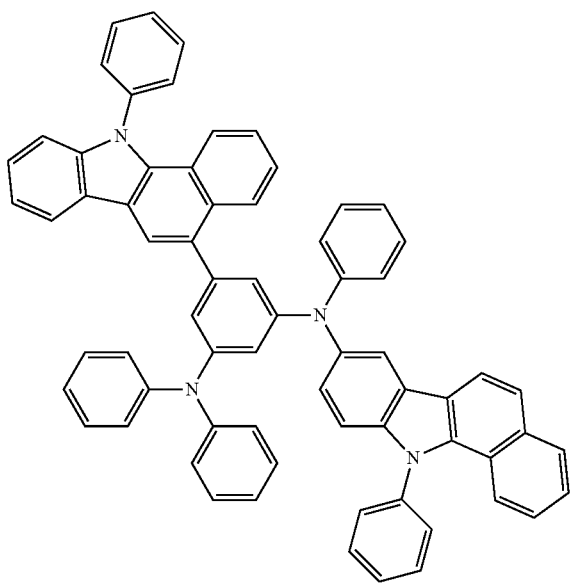
P-126
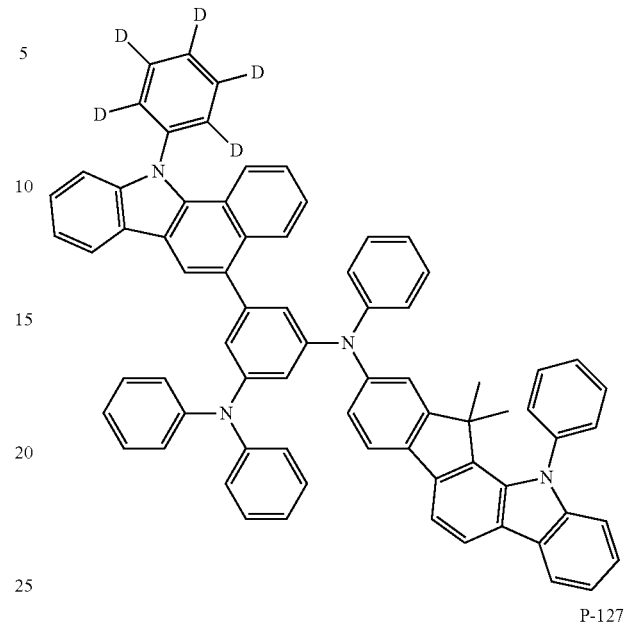
P-127
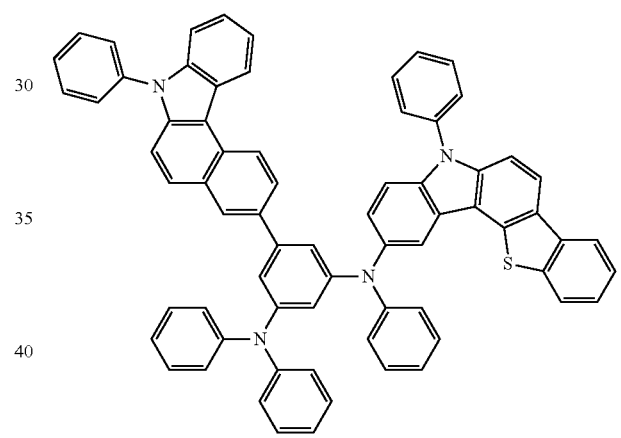
P-128

P-129
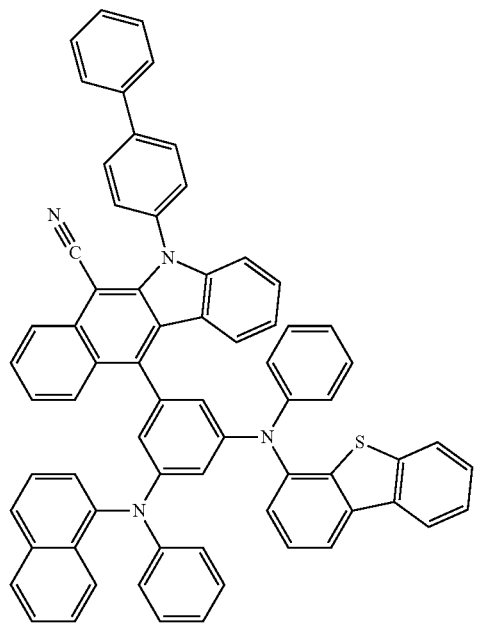
P-130
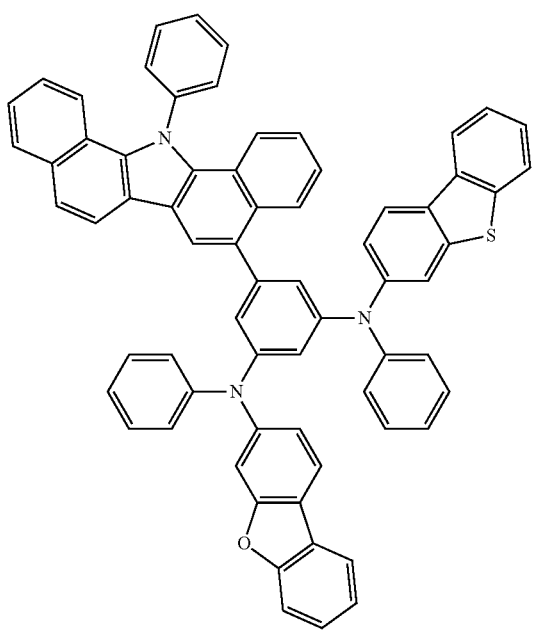
P-131
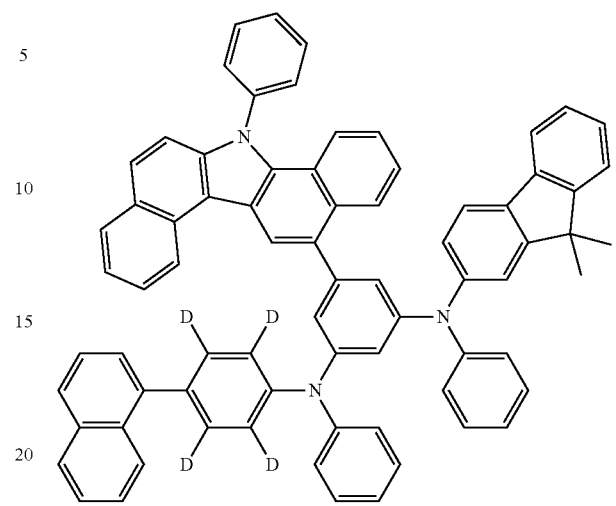
P-132
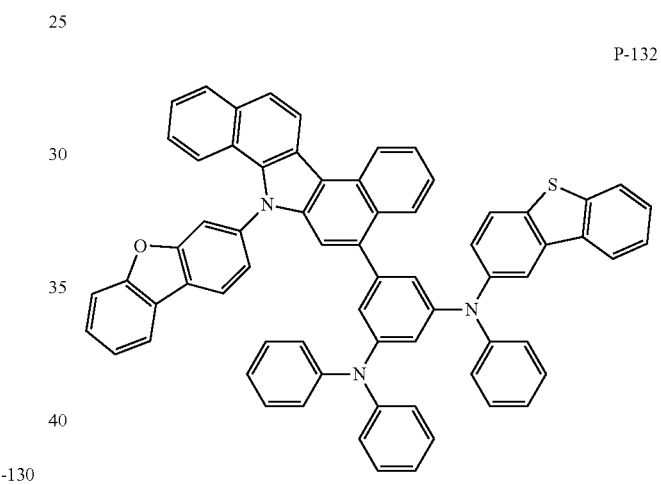
P-133
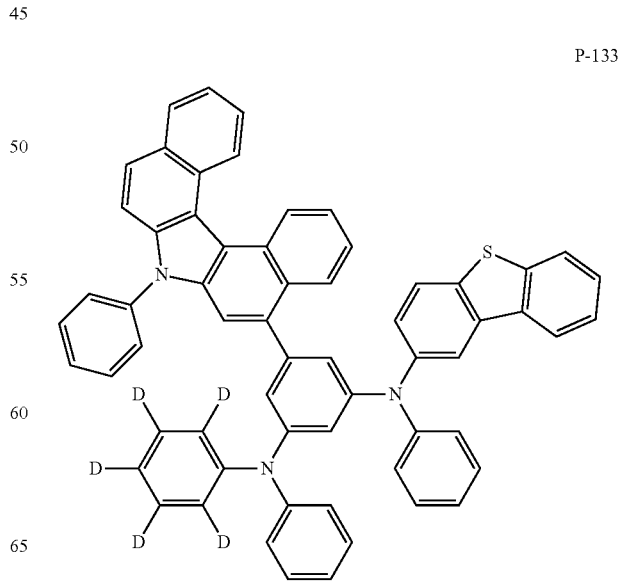

P-134

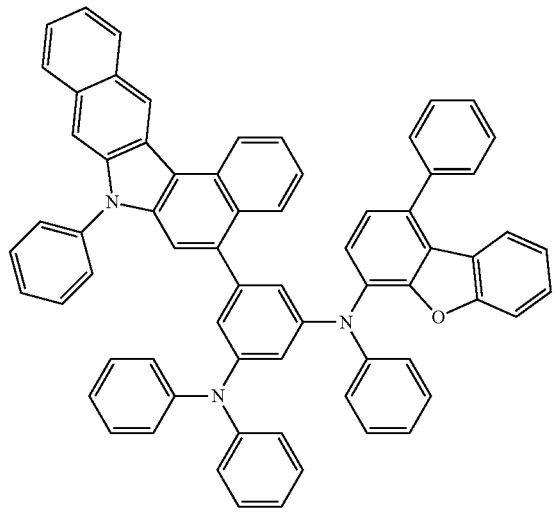

P-135

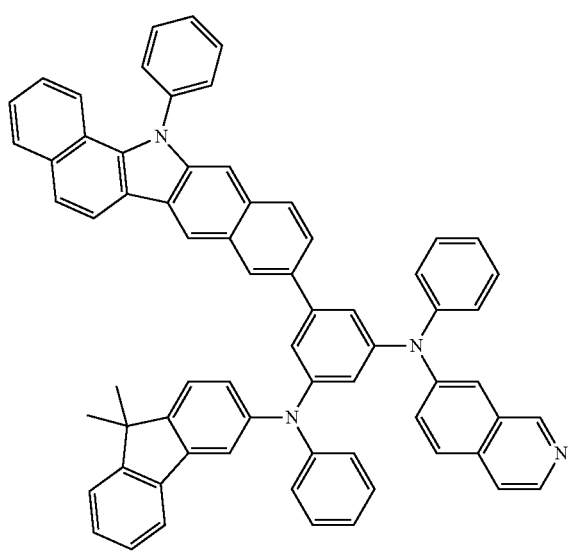

P-136

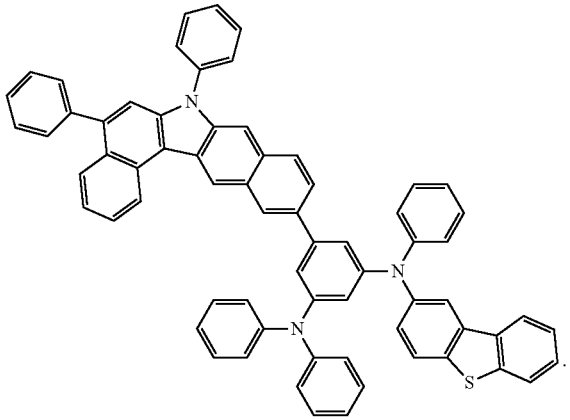

5. An organic electric element comprising a first electrode, a second electrode, and an organic material layer formed between the first electrode and the second electrode, wherein the organic material layer comprises the compound of claim 1.

6. The organic electric element of claim 5, wherein the compound is comprised in at least one layer of a hole injection layer, a hole transport layer, an emission-auxiliary layer, a light emitting layer, an electron transport-auxiliary layer, an electron transport layer and an electron injection layer, and the compound is comprised as a single compound or a mixture of two or more different kinds.

7. The organic electric element of claim 5, wherein the organic material layer is formed by any one of the processes of spin coating, nozzle printing, inkjet printing, slot coating, dip coating or roll-to-roll.

8. An electronic device comprising a display device and a control unit for driving the display device, wherein the display device comprises the organic electric element of claim 5.

9. The electronic device of claim 8, wherein the organic electric element is an organic light emitting diode, an organic solar cell, an organic photo conductor, an organic transistor, or an element for monochromatic or white illumination.

\* \* \* \* \*